US012735709B2

(12) United States Patent
Geng et al.

(10) Patent No.: US 12,735,709 B2
(45) Date of Patent: Sep. 15, 2026

(54) SMALL INTERFERING RNA TARGETING CFB AND USES THEREOF

(71) Applicant: Sanegene Bio USA Inc., Woburn, MA (US)

(72) Inventors: Xin Geng, Oklahoma City, OK (US); Chunyang Zhang, Burlington, MA (US); Shiyu Wang, Belmont, MA (US); Weimin Wang, Winchester, MA (US)

(73) Assignee: Sanegene Bio USA Inc., Woburn, MA (US)

( * ) Notice: Subject to any disclaimer, the term of this patent is extended or adjusted under 35 U.S.C. 154(b) by 0 days.

(21) Appl. No.: 19/572,773

(22) Filed: Mar. 19, 2026

(65) Prior Publication Data

US 2026/0209764 A1 Jul. 23, 2026

Related U.S. Application Data

(63) Continuation of application No. 19/240,198, filed on Jun. 17, 2025.

(60) Provisional application No. 63/661,546, filed on Jun. 18, 2024.

(51) Int. Cl.
*C12N 15/113* (2010.01)
*A61P 37/06* (2006.01)

(52) U.S. Cl.
CPC ............ *C12N 15/113* (2013.01); *A61P 37/06* (2018.01); *C12N 2310/11* (2013.01); *C12N 2310/14* (2013.01); *C12N 2310/315* (2013.01); *C12N 2310/321* (2013.01); *C12N 2310/322* (2013.01); *C12N 2310/351* (2013.01); *C12N 2320/30* (2013.01)

(58) Field of Classification Search
CPC .............. C12N 15/113; C12N 2310/11; C12N 2310/14; C12N 2310/315; C12N 2310/321; C12N 2310/322; C12N 2310/351; C12N 2320/30; A61P 37/06
See application file for complete search history.

(56) References Cited

U.S. PATENT DOCUMENTS 4,522,811 A 6/1985 Eppstein
8,703,136 B2 4/2014 Baas et al.
10,155,983 B2 12/2018 Ero et al.
10,280,423 B2 5/2019 Prakash et al.
10,465,194 B2 11/2019 Borodovsky et al.
11,186,842 B2 11/2021 Borodovsky et al.
11,732,265 B2 8/2023 Prakash et al.
11,965,166 B2 * 4/2024 McIninch ............... A61P 43/00
2005/0244858 A1 11/2005 Rossi et al.
2009/0023673 A1 1/2009 Manoharan et al.
2009/0239814 A1 9/2009 Manoharan
2009/0247608 A1 10/2009 Manoharan et al.
2012/0136042 A1 5/2012 Manoharan et al.
2013/0158824 A1 6/2013 Nassouri et al.
2015/0337377 A1 11/2015 Ero et al.
2016/0298124 A1 10/2016 Borodovsky et al.
2017/0159055 A1 6/2017 Prakash et al.
2020/0263183 A1 8/2020 Borodovsky et al.
2020/0339998 A1 10/2020 Borodovsky et al.
2022/0213486 A1 7/2022 Borodovsky et al.
2023/0135763 A1 5/2023 Samarsky
2023/0138928 A1 * 5/2023 Wang .................. A61K 47/549
514/44 A
2023/0257749 A1 8/2023 Mcininch et al.
2024/0002857 A1 1/2024 Zhang et al.
2024/0018515 A1 1/2024 Mcininch et al.
2024/0043836 A1 2/2024 Li et al.
2024/0052348 A1 2/2024 Zhang et al.
2024/0175026 A1 5/2024 Zhang et al.
2024/0218363 A1 7/2024 Wang et al.
2024/0294916 A1 9/2024 Zhang et al.
2024/0301421 A1 9/2024 Zhang et al.
2024/0309380 A1 9/2024 Zhou et al.
2024/0309383 A1 9/2024 Zhang et al.
2025/0136977 A1 5/2025 Dames et al.
2025/0327070 A1 10/2025 Lasaro et al.
2025/0382616 A1 12/2025 Geng et al.
2026/0022381 A1 1/2026 Li et al.

FOREIGN PATENT DOCUMENTS

WO 198902439 A1 3/1989
WO 9506731 A2 3/1995
WO 9511910 A1 5/1995
WO 9802439 A1 1/1998
WO 199914226 A2 3/1999
WO 0056746 A2 9/2000

(Continued)

OTHER PUBLICATIONS

Zhou, J. et al. "Deep sequencing analyses of DsiRNAs reveal the influence of 3' terminal overhang on dicing polarity, strand selectivity, and RNA editing of siRNAs". Molecular Therapy—Nucleic Acids, vol. 1 (2012), p. e5. (Year: 2012).*
Albazli, K. et al. (Jun. 2, 2020). "Complement Inhibitor Therapy for Myasthenia Gravis". Frontiers in Immunology 11(917):1-11.
Altschul, S.F. et al. (1990). "Basic Local Alignment Search Tool," J. Mol. Biol. 215:403-410, 11 pages.
Altschul, S.F. et al. (Sep. 1, 1997). "Gapped BLAST and PSI-BLAST: A New Generation of Protein Database Search Programs," Nucleic Acids Res. 25(17):3389-3402.
Beecher, G. et al. (2019, e-pub. Feb. 19, 2019). "Therapies Directed Against B-Cells and Downstream Effectors in Generalized Autoimmune Myasthenia Gravis: Current Status" Drugs 79: 353-364.

(Continued)

*Primary Examiner* — Nancy J Leith
*Assistant Examiner* — Alexandra Geraldine Dace Denito
(74) *Attorney, Agent, or Firm* — Morrison & Foerster LLP

(57) ABSTRACT

This disclosure relates to isolated oligonucleotides comprising duplex regions targeting human CFB mRNA, and delivery systems, and compositions comprising the same, and methods of using the same for inhibiting or downregulating CFB gene expression.

12 Claims, 10 Drawing Sheets

Specification includes a Sequence Listing.

(56) References Cited

FOREIGN PATENT DOCUMENTS

| | | | | |
|---|---|---|---|---|
| WO | 200056748 | A1 | 9/2000 | |
| WO | 200066604 | A2 | 11/2000 | |
| WO | 2009082607 | A2 | 7/2009 | |
| WO | 2011005860 | A2 | 1/2011 | |
| WO | 2012089352 | A1 | 7/2012 | |
| WO | 2015006740 | A2 | 1/2015 | |
| WO | 2015089368 | A2 | 6/2015 | |
| WO | 2016100401 | A1 | 6/2016 | |
| WO | 2017214112 | A1 | 12/2017 | |
| WO | 2018039364 | A1 | 3/2018 | |
| WO | 2018045317 | A1 | 3/2018 | |
| WO | 2018117253 | A1 | 6/2018 | |
| WO | 2019027015 | A1 | 2/2019 | |
| WO | 2021222549 | A1 | 11/2021 | |
| WO | 2023014938 | A1 | 2/2023 | |
| WO | 2023031359 | A1 | 3/2023 | |
| WO | 2023076451 | A1 | 5/2023 | |
| WO | 2023097291 | A1 | 6/2023 | |
| WO | 2023141247 | A2 | 7/2023 | |
| WO | 2024008114 | A1 | 1/2024 | |
| WO | WO-2024031101 | A1 * | 2/2024 | ........... A61K 31/713 |
| WO | 2024059873 | A2 | 3/2024 | |
| WO | 2024081954 | A2 | 4/2024 | |
| WO | 2024137590 | A2 | 6/2024 | |
| WO | 2024175111 | A2 | 8/2024 | |
| WO | 2024197017 | A2 | 9/2024 | |
| WO | 2024245424 | A1 | 12/2024 | |
| WO | 2025002401 | A1 | 1/2025 | |
| WO | 2025026228 | A1 | 2/2025 | |
| WO | 2025113592 | A1 | 6/2025 | |
| WO | 2025140402 | A1 | 7/2025 | |
| WO | 2025256564 | A1 | 12/2025 | |
| WO | 2026052075 | A1 | 3/2026 | |

OTHER PUBLICATIONS

Beltrame, M.H. et al. (Jan. 21, 2015). "The Lectin Pathway of Complement and Rheumatic Heart Disease," Front. Pediatr. 2(148):1-14.
Brodsky, R.A. et al. (Feb. 2008). "Multicenter Phase 3 Study of the Complement Inhibitor Eculizumab for the Treatment of Patients with Paroxysmal Nocturnal Hemoglobinuria," Blood Clinical Trials & Observations 111(4):1840-1847.
Carrillo, H. et al. (1988). "The Multiple Sequence Alignment Problem in Biology," SIAM Journal on Applied Mathematics 48(5):1073-1082.
Cload, S.T. et al. (1991). "Polyether Tethered Oligonucleotide Probes," Journal of the American Chemical Society 113(16):6324-6326.
Dhillon, S. (Mar. 2018). "Eculizumab: A Review in Generalized Myasthenia Gravis," Drugs 78: 16:367-376.
Felice, K.M. et al. (2009). "The 5' Terminal Uracil of let-7a is Critical for the Recruitment of mRNA to Argonaute 2," Biochemical Journal 422:329-341.
Ferentz, A.E. et al. (1991). "Disulfide-Cross-Linked Oligonucleotides," Journal of the American Chemical Society 113(10):4000-4002.
Garred, P. et al. (Apr. 2021). "Therapeutic Targeting of the Complement System: From Rare Diseases to Pandemics," Pharmacological Reviews 73(2):792-827.
GENBANK Accession No. NM_001710.5 "*Homo sapiens* Complement Factor B (CFB), mRNA" entered Aug. 21, 2019, 6 pages.
GENBANK Accession No. NM_001710.6 "*Homo sapiens* Complement Factor B (CFB), mRNA" entered Apr. 7, 2024, 6 pages.
Howard, J.F. et al. (2020). "Clinical Effects of the Self-Administered Subcutaneous Complement Inhibitor Zilucoplan in Patients with Moderate to Severe Generalized Myasthenia Gravis. Results of a Phase 2 Randomized Double-Blind Placebo-Controlled Multicenter Clinical Trial," JAMA Neurology Original Investigation 77(5):582-592.
Hu, B. et al. (2020). "Therapeutic siRNA: State of the Art," Signal Transduction and Targeted Therapy 5:101, 25 pages.
International Preliminary Report on Patentability, issued Jun. 24, 2025, for PCT Application No. PCT/US2023/084763, filed Dec. 19, 2023, 18 pages.
International Search Report and Written Opinion mailed on Oct. 20, 2025, for PCT/US2025/033895, filed on Jun. 17, 2025, 14 pages.
International Search Report and Written Opinion, mailed Aug. 7, 2024, for PCT Application No. PCT/US2023/084763, filed Dec. 19, 2023, 26 pages.
Jaschke, A. et al. (1993). "Automated Incorporation of Polyethylene Glycol into Synthetic Oligonucleotides," Tetrahedron Letters 34(2):301-304.
Karlin, S. et al. (Jun. 1993). "Applications and Statistics for Multiple High-Scoring Segments in Molecular Sequences," Proc. Natl. Acad. Sci. USA 90:5873-5877.
Keshari, R.S. et al. (Jul. 18, 2017). "Inhibition of Complement C5 Protects Against Organ Failure and Reduces Mortality in a Baboon Model of *Escherichia coli* Sepsis," PNAS E6390-E6399.
Kulasekararaj, A.G. et al. (Feb. 2019). "Ravulizumab (ALXN1210) vs Eculizumab in C5-Inhibitor Experienced Adult Patients with PNH: the 302 Study," Blood Clinical Trials & Observations 133(6):540-549.
Lee, J.W. et al. "Ravulizumab (ALXN1210) vs Eculizumab in Adult Patients with PNH Naïve to Complement Inhibitors: the 301 Study," Blood Clinical Trials & Observations 133(6):530-539, 2019.
Lee, J.W. et al. (Feb. 14, 2020). "Ravulizumab for the Treatment of Paroxysmal Nocturnal Hemoglobinuria," Expert Opinion on Biological Therapy 20(3):227-237.
Loirat, C. et al. (Apr. 2015). "An International Consensus Approach to the Management of Atypical Hemolytic Uremic Syndrome in Children," Pediatr Nephrol 31:15-39.
McKeage, K. (2019). "Ravulizumab: First Global Approval," Drugs 79:347-352.
Parker, C. (Feb. 2009). "Eculizumab for Paroxysmal Nocturnal Haemoglobinuria," New Drug Class 373(9665): 759-767.
Ravon, M. et al. (Jan. 1, 2012). "Single Base Mismatches in the mRNA Target Site Allow Specific Seed Region-Mediated off-Target Binding of siRNA Targeting Human Coagulation Factor 7," RNA Biol. 9(1):87-97.
Seela, F. et al. (1987). "Oligodeoxyribonucleotides Containing 1 3-Propanediol as Nucleoside Substitute," Nucleic Acids Research 15(7):3113-3129.
Selmaj, K. et al. (2019). "Novel Emerging Treatments for NMOSD," Neuroglia Neurochirurgia Polska 53(5):317-326.
Stern, R.M. et al. (Dec. 2019). "Ravulizumab: a Novel C5 Inhibitor for the Treatment of Paroxysmal Nocturnal Hemoglobinuria," Therapeutic Advances in Hematology 10:1-11.
Takagi, M. et al. (1997). "Comparison of Different Hepatocyte Cell Lines for Use in a Hybrid Artificial Liver Model," Cytotechnology, 24(1):39-45.
Tschumi, S. et al. (2011). "Eculizumab in Atypical Hemolytic Uremic Syndrome: Long-Term Clinical Course and Histological Findings," Pediatric Nephrology Brief Report 26:2085-2088.
Winkler, J. (2013). "Oligonucleotide Conjugates for Therapeutic Applications," Therapeutic Delivery 4(7):791-809.
Yuan, W. et al. (2021). "Transcriptomic Characterization Reveals Prognostic Molecular Signatures of Sorafenib Resistance in Hepatocellular Carcinoma," Aging (Albany NY). 13(3):3969-3993.
U.S. Appl. No. 19/381,593, filed Nov. 6, 2025, by Zhang et al. (A copy of U.S. Patent Application is not submitted herewith pursuant to the waiver of 37 C.F.R § 1.98(a)(2)(iii) issued by the Office on Sep. 21, 2004.).

* cited by examiner

Huh7

SMALL INTERFERING RNA TARGETING CFB AND USES THEREOF

RELATED APPLICATIONS

This application is a continuation of U.S. patent application Ser. No. 19/240,198, filed Jun. 17, 2025, and claims priority to, and the benefit of, U.S. Provisional Application No. 63/661,546, filed Jun. 18, 2024, the contents of each of which are incorporated herein by reference in their entirety.

REFERENCE TO SEQUENCE LISTING

The content of the electronic sequence listing (146392074501seglist.xml; Size: 545,732 bytes; and Date of Creation: Mar. 19, 2026) is herein incorporated by reference in its entirety.

BACKGROUND

The complement system is a part of the innate immune system consisting of multiple soluble proteins that are present in the serum as inactive precursors. Upon activation, these complement components form an amplifying cascade that leads to the generation of bioactive effector compounds. This cascade plays a central role in maintaining cellular integrity and tissue homeostasis via the removal of damaged or dying cells, immune complexes, and cell debris. It also plays a role in immunomodulation, metabolism, inflammation, and host defense against pathogens. The complement system has three activation pathways, all of which revolve around the proteolytic cleavage of C3, a central component that serves as a convergence point for downstream effector function. Upon cleavage, the active subunit of complement factor B, Bb, combines with complement factor 3b component of C3 to form the alternative pathway C3 or C5 convertase. The central role of complement factor B (CFB) in the functioning of the alternative complement cascade makes it an ideal target for therapeutic modulation of the complement system.

Deficiencies or loss-of-function mutations of the ordinary complement components may lead to dysregulation of normal complement system function and possible overproduction of complement components. Excessive production and/or dysregulation is linked to an increasing number of ailments, for example, but not limited to, type 2 diabetes mellitus, cardiovascular, neurological, hematological, eye, kidney, and autoimmune diseases and/or disorders, and infections. Accordingly, there is a need for therapies for subject having diseases, disorders and symptoms associated with elevated complement CFB expression levels. The present disclosure provides compositions targeting CFB and methods of reducing CFB expression for treatment of subjects having a complement-associated disease, disorder or symptom.

SUMMARY

The present disclosure provides an isolated oligonucleotide comprising a sense strand and an antisense strand, wherein the sense strand comprises a nucleotide sequence that is substantially identical to a region comprising 19-25 nucleotides between the nucleotide positions from 1821 to 1881 from the 5' end of a human CFB mRNA sequence according to SEQ ID NO:1, and the antisense strand is substantially complementary to the sense strand such that the sense strand and the antisense strand together form a double stranded region.

In some embodiments, the sense strand comprises a nucleotide sequence that is at least 70%, at least 80%, at least 90%, at least 95%, or at least 99% identical to a region comprising 19-25 nucleotides between the nucleotide positions from 1821 to 1881 from the 5' end of a human CFB mRNA sequence according to SEQ ID NO:1.

In some embodiments, the sense strand comprises a nucleotide sequence that is identical to a region comprising 19-25 nucleotides between the nucleotide positions from 1821 to 1881 from the 5' end of a human CFB mRNA sequence according to SEQ ID NO:1.

In some embodiments, both the sense strand and the antisense strand are single stranded RNA molecules.

In some embodiments, the antisense strand comprises a 3' overhang.

In some embodiments, the 3' overhang comprises at least one nucleotide.

In some embodiments, the sense strand comprises an RNA sequence of at least 20 nucleotides in length.

In some embodiments, the antisense strand comprises an RNA sequence of at least 22 nucleotides in length.

In some embodiments, the double stranded region is between 19 and 21 nucleotides in length.

In some embodiments, the double stranded region comprises (i) an antisense strand of nucleic acid sequence according to SEQ ID NO: 20 (5' UAUUCAGGAAUUCCUGCUUCUU 3'), and a sense strand of nucleic acid sequence according to SEQ ID NO: 54 (5' GAAGCAGGAAUUCCUGAAUA 3'); (ii) an antisense strand of nucleic acid sequence according to SEQ ID NO: 21 (5' UAAUUCAGGAAUUCCUGCUUCU 3'), and a sense strand of nucleic acid sequence according to SEQ ID NO: 55 (5' AAGCAGGAAUUCCUGAAUUA 3'); (iii) an antisense strand of nucleic acid sequence according to SEQ ID NO: 22 (5' UUAAAAUUCAGGAAUUCCUGCU 3'), and a sense strand of nucleic acid sequence according to SEQ ID NO: 56 (5' CAGGAAUUCCUGAAUUUUAA 3'); (iv) an antisense strand of nucleic acid sequence according to SEQ ID NO: 23 (5' UAUAAAAUUCAGGAAUUCCUGC 3'), and a sense strand of nucleic acid sequence according to SEQ ID NO: 57 (5' AGGAAUUCCUGAAUUUUAUA 3'); (v) an antisense strand of nucleic acid sequence according to SEQ ID NO: 24 (5' UGUCAUAAAAUUCAGGAAUUCC 3'), and a sense strand of nucleic acid sequence according to SEQ ID NO: 58 (5' AAUUCCUGAAUUUUAUGACA 3'); (vi) an antisense strand of nucleic acid sequence according to SEQ ID NO:25 (5' UUAUUCUUGAGCUUGAUCAGGG 3'), and a sense strand of nucleic acid sequence according to SEQ ID NO: 59 (5' CUGAUCAAGCUCAAGAAUAA 3'); or (vii) an antisense strand of nucleic acid sequence according to SEQ ID NO: 26 (5' UUUAUUCUUGAGCUUGAUCAGG 3'), and a sense strand of nucleic acid sequence according to SEQ ID NO: 60 (5' UGAUCAAGCUCAAGAAUAAA 3').

In some embodiments, the sense strand or the antisense strand or both comprise one or more modified nucleotide(s).

In some embodiments, in the sense strand or the antisense strand or both, a terminal or internal nucleotide is linked to a targeting ligand.

In some embodiments, the targeting ligand comprises at least one GalNAc G1b moiety.

In some embodiments, the antisense strand comprises a nucleic acid sequence according to SEQ ID NO: 377 (5' [mUs][fGs][fU][mC][fA][mU][fA][mA][mA][fA][mU][mU][mC][fA][mG][fG][mA][mA][mU][mUs][mCs][mC]

3'), wherein "m" is a 2'-O-methyl modified nucleotide, "f" is a 2'-F modified nucleotide, and "s" is a phosphorothioate internucleotide linkage.

In some embodiments, the sense strand comprises a nucleic acid sequence according to SEQ ID NO: 388 (5' [mAs][mAs][mU][mU][mC][fC][mU][fG][fA][fA][fU][mU][mU][mU][mA][mU][mG][mA][m C][mA][G1b][G1b][G1b]3'), wherein "m" is a 2'-O-methyl modified nucleotide, "f" is a 2'-F modified nucleotide, "s" is a phosphorothioate internucleotide linkage, and "G1b" is a GalNAc G1b moiety.

The present disclosure also provides an isolated oligonucleotide comprising a sense strand and an antisense strand, wherein the sense strand and the antisense strand together form a double stranded region, wherein the double stranded region comprises (i) an antisense strand of nucleic acid sequence according to SEQ ID NO: 370 (5' [MeEP-mUs][fGs][fU][mC][fA][mU][fA][mA][mA][fA][mU][mU][mC][fA][mG][fG][mA][mA][mU][mUs][mCs][mC] 3'), and a sense strand of nucleic acid sequence according to SEQ ID NO: 388 (5' [mAs][mAs][mU][mU][mC][fC][mU][fG][fA][fA][fU][mU][mU][mU][mA][mU][mG][mA][m C][mA][G1b][G1b][G1b]3'); or (ii) an antisense strand of nucleic acid sequence according to SEQ ID NO: 377 (5' [mUs][fGs][fU][mC][fA][mU][fA][mA][mA][fA][mU][mU][mC][fA][mG][fG][mA][mA][mU][mUs][mCs][mC] 3'), and a sense strand of nucleic acid sequence according to SEQ ID NO: 388 (5' [mAs][mAs][mU][mU][mC][fC][mU][fG][fA][fA][fU][mU][mU][mU][mA][mU][mG][mA][m C][mA][G1b][G1b][G1b]3').

In some embodiments, the double stranded region comprising of an antisense strand of nucleic acid sequence according to SEQ ID NO: 377 (5' [mUs][fGs][fU][mC][fA][mU][fA][mA][mA][fA][mU][mU][mC][fA][mG][fG][mA][mA][mU][mUs][mCs][mC]3'), and a sense strand of nucleic acid sequence according to SEQ ID NO: 388 (5' [mAs][mAs][mU][mU][mC][fC][mU][fG][fA][fA][fU][mU][mU][mU][mA][mU][mG][mA][m C][mA][G1b][G1b][G1b]3').

In some embodiments, the double stranded region comprising of an antisense strand of nucleic acid sequence according to SEQ ID NO: 370 (5' [MeEPmUs][fGs][fU][mC][fA][mU][fA][mA][mA][fA][mU][mU][mC][fA][mG][fG][mA][mA][mU][mUs][mCs][mC]3'), and a sense strand of nucleic acid sequence according to SEQ ID NO: 388 (5' [mAs][mAs][mU][mU][mC][fC][mU][fG][fA][fA][fU][mU][mU][mU][mA][mU][mG][mA][m C][mA][G1b][G1b][G1b]3').

The present disclosure also provides a pharmaceutical composition comprising at least one isolated oligonucleotide disclosed herein, and a pharmaceutically acceptable excipient.

The present disclosure also provides a method of treating or preventing a disease or disorder associated with aberrant or increased expression of activity of CFB or a disease or disorder where CFB plays a role in a subject in need thereof, wherein the method comprises administering to the subject an effective amount of at least one isolated oligonucleotide described herein or the pharmaceutical composition described herein.

DETAILED DESCRIPTION

Figure 1:
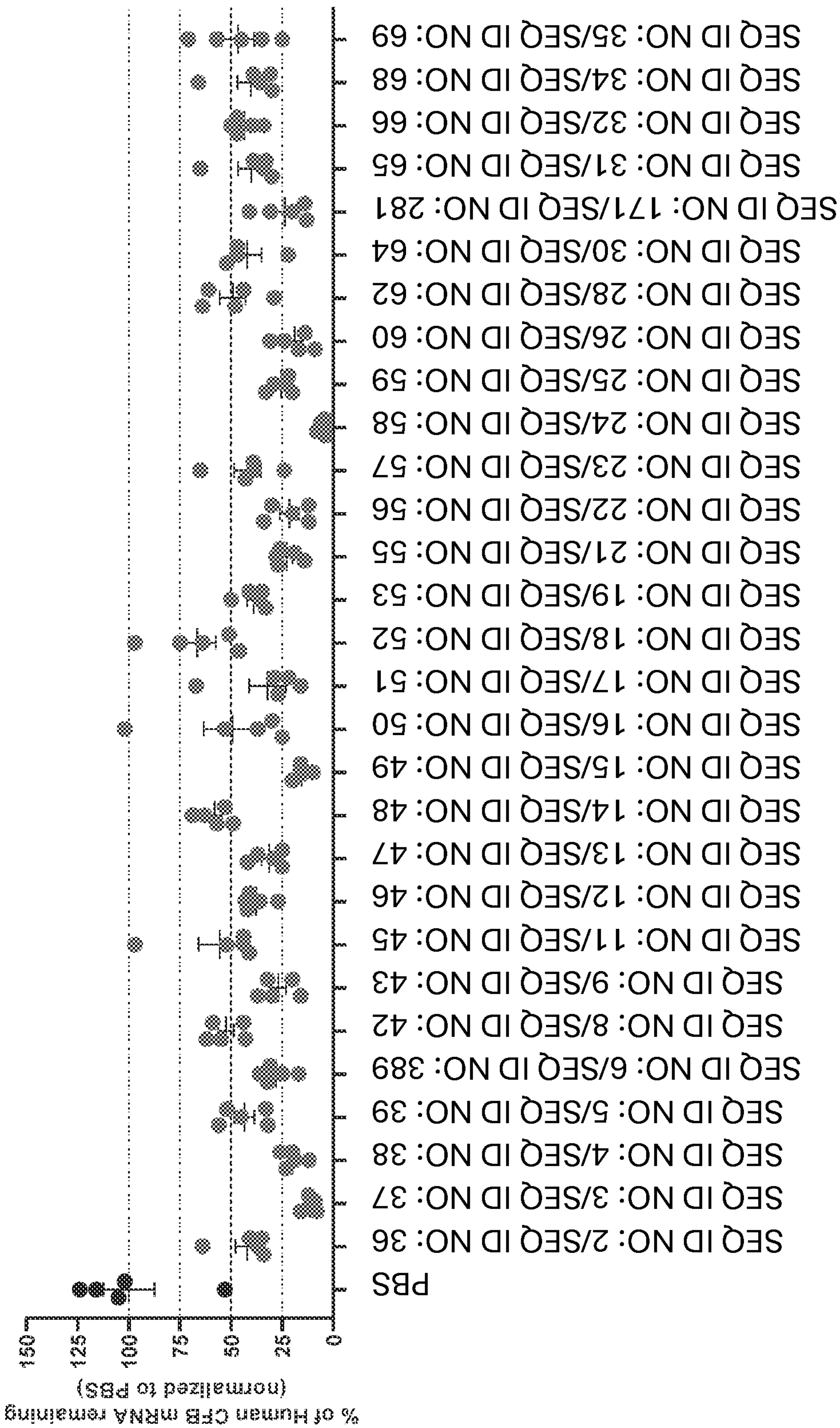
FIG. 1 is a graph showing the in vivo potency of a subset of compounds listed in Table 2 in mouse HDI liver at 1 mg/kg at day 4 post-dosing. Data is presented as % of human CFB mRNA remaining relative to PBS when normalized to NeoR mRNA levels (Mean, +/−SEM).

The present disclosure provides isolated oligonucleotides (oligonucleotide(s)) that form a double stranded region, preferably small interfering RNAs (siRNAs), that can decrease complement CFB mRNA expression, in turn leading to a decrease in the degree of CFB protein expression in target cells. The oligonucleotides disclosed herein can have therapeutic application in regulating the expression of CFB, for treatment of diseases involving a complement component-associated disease such as, but not limited to Paroxysmal Nocturnal Hemoglobinuria (PNH), rheumatoid arthritis, ischemia-reperfusion injuries, Multiple Sclerosis (MS), Guillain-Barre syndrome, Systemic lupus erythmatosis, C3 Glomerulonephritis, atypical Hemolytic Uremic Syndrome (aHUS), Myasthenia Gravis (MG), Neuromyelistis Optic nerve and Spinal Cord (NMOSD), Dense Deposit Disease (DDD), Age-related Macular Degeneration (AMD), IgA nephropathy, Multifocal Motor Neuropathy (MMN), organ transplantation and neurodegenerative diseases.

In some aspects, the present invention provides compositions and methods of treating a subject having a disorder that would benefit from the reduction in complement CFB expression. In some aspects, the methods disclosed herein prevent at least one symptom in a subject having a disease or disorder that would benefit from reduction in complement CFB expression.

The present disclosure has identified specific regions within the CFB mRNA, that provide targets for binding double stranded oligonucleotides, e.g., siRNA, leading to reduction in level of expression of the CFB mRNA.

The complement factor B (CFB) mRNA sequence described herein, is an mRNA sequence encoded by a CFB gene according to GenBank Accession No. NM_001710.6:

```
                                          (SEQ ID NO: 1)
GGGAAGGGAATGTGACCAGGTCTAGGTCTGGAGTTTCAGCTTGGAC

ACTGAGCCAAGCAGACAAGCAAAGCAAGCCAGGACACACCATCCT

GCCCCAGGCCCAGCTTCTCTCCTGCCTTCCAACGCCATGGGGAGC

AATCTCAGCCCCCAACTCTGCCTGATGCCCTTTATCTTGGGCCTC

TTGTCTGGAGGTGTGACCACCACTCCATGGTCTTTGGCCCGGCCC

CAGGGATCCTGCTCTCTGGAGGGGGTAGAGATCAAAGGCGGCTCC
```

-continued

```
TTCCGACTTCTCCAAGAGGGCCAGGCACTGGAGTACGTGTGTCCT
TCTGGCTTCTACCCGTACCCTGTGCAGACACGTACCTGCAGATCT
ACGGGGTCCTGGAGCACCCTGAAGACTCAAGACCAAAAGACTGTC
AGGAAGGCAGAGTGCAGAGCAATCCACTGTCCAAGACCACACGAC
TTCGAGAACGGGGAATACTGGCCCCGGTCTCCCTACTACAATGTG
AGTGATGAGATCTCTTTCCACTGCTATGACGGTTACACTCTCCGG
GGCTCTGCCAATCGCACCTGCCAAGTGAATGGCCGATGGAGTGGG
CAGACAGCGATCTGTGACAACGGAGCGGGGTACTGCTCCAACCCG
GGCATCCCCATTGGCACAAGGAAGGTGGGCAGCCAGTACCGCCTT
GAAGACAGCGTCACCTACCACTGCAGCCGGGGGCTTACCCTGCGT
GGCTCCCAGCGGCGAACGTGTCAGGAAGGTGGCTCTTGGAGCGGG
ACGGAGCCTTCCTGCCAAGACTCCTTCATGTACGACACCCCTCAA
GAGGTGGCCGAAGCTTTCCTGTCTTCCCTGACAGAGACCATAGAA
GGAGTCGATGCTGAGGATGGGCACGGCCCAGGGGAACAACAGAAG
CGGAAGATCGTCCTGGACCCTTCAGGCTCCATGAACATCTACCTG
GTGCTAGATGGATCAGACAGCATTGGGGCCAGCAACTTCACAGGA
GCCAAAAAGTGTCTAGTCAACTTAATTGAGAAGGTGGCAAGTTAT
GGTGTGAAGCCAAGATATGGTCTAGTGACATATGCCACATACCCC
AAAATTTGGGTCAAAGTGTCTGAAGCAGACAGCAGTAATGCAGAC
TGGGTCACGAAGCAGCTCAATGAAATCAATTATGAAGACCACAAG
TTGAAGTCAGGGACTAACACCAAGAAGGCCCTCCAGGCAGTGTAC
AGCATGATGAGCTGGCCAGATGACGTCCCTCCTGAAGGCTGGAAC
CGCACCCGCCATGTCATCATCCTCATGACTGATGGATTGCACAAC
ATGGGCGGGGACCCAATTACTGTCATTGATGAGATCCGGGACTTG
CTATACATTGGCAAGGATCGCAAAAACCCAAGGGAGGATTATCTG
GATGTCTATGTGTTTGGGGTCGGGCCTTTGGTGAACCAAGTGAAC
ATCAATGCTTTGGCTTCCAAGAAAGACAATGAGCAACATGTGTTC
AAAGTCAAGGATATGGAAAACCTGGAAGATGTTTTCTACCAAATG
ATCGATGAAAGCCAGTCTCTGAGTCTCTGTGGCATGGTTTGGGAA
CACAGGAAGGGTACCGATTACCACAAGCAACCATGGCAGGCCAAG
ATCTCAGTCATTCGCCCTTCAAAGGGACACGAGAGCTGTATGGGG
GCTGTGGTGTCTGAGTACTTTGTGCTGACAGCAGCACATTGTTTC
ACTGTGGATGACAAGGAACACTCAATCAAGGTCAGCGTAGGAGGG
GAGAAGCGGGACCTGGAGATAGAAGTAGTCCTATTTCACCCCAAC
TACAACATTAATGGGAAAAAAGAAGCAGGAATTCCTGAATTTTAT
GACTATGACGTTGCCCTGATCAAGCTCAAGAATAAGCTGAAATAT
GGCCAGACTATCAGGCCCATTTGTCTCCCCTGCACCGAGGGAACA
ACTCGAGCTTTGAGGCTTCCTCCAACTACCACTTGCCAGCAACAA
AAGGAAGAGCTGCTCCCTGCACAGGATATCAAAGCTCTGTTTGTG
TCTGAGGAGGAGAAAAAGCTGACTCGGAAGGAGGTCTACATCAAG
```

-continued

```
AATGGGGATAAGAAAGGCAGCTGTGAGAGAGATGCTCAATATGCC
CCAGGCTATGACAAAGTCAAGGACATCTCAGAGGTGGTCACCCCT
CGGTTCCTTTGTACTGGAGGAGTGAGTCCCTATGCTGACCCCAAT
ACTTGCAGAGGTGATTCTGGCGGCCCCTTGATAGTTCACAAGAGA
AGTCGTTTCATTCAAGTTGGTGTAATCAGCTGGGGAGTAGTGGAT
GTCTGCAAAAACCAGAAGCGGCAAAAGCAGGTACCTGCTCACGCC
CGAGACTTTCACATCAACCTCTTTCAAGTGCTGCCCTGGCTGAAG
GAGAAACTCCAAGATGAGGATTTGGGTTTTCTATAAGGGGTTTCC
TGCTGGACAGGGGCGTGGGATTGAATTAAAACAGCTGCGACAACA.
```

The present disclosure provides an isolated oligonucleotide comprising a sense strand and an antisense strand, wherein the sense strand comprises a nucleotide sequence that is substantially identical to a region comprising 19-25 nucleotides between the nucleotide positions from 1821 to 1881 from the 5' end of a human CFB mRNA sequence according to SEQ ID NO: 1, and the antisense strand is substantially complementary to the sense strand such that the sense strand and the antisense strand together form a double stranded region.

In some embodiments of the isolated oligonucleotide of the present disclosure, the sense strand comprises a nucleotide sequence that is at least 70%, at least 80%, at least 90%, at least 95%, or at least 99% identical to a region comprising 19-25 nucleotides between the nucleotide positions from 1821 to 1881 from the 5' end of a human CFB mRNA sequence according to SEQ ID NO: 1.

In some embodiments of the isolated oligonucleotide of the present disclosure, the sense strand comprises a nucleotide sequence that is identical to a region comprising 19-25 nucleotides between the nucleotide positions from 1821 to 1881 from the 5' end of a human CFB mRNA sequence according to SEQ ID NO: 1.

In some embodiments of the isolated oligonucleotide of the present disclosure, the sense strand comprises a nucleotide sequence that is substantially identical to a region between the nucleotide positions from 1829 to 1850, from the 5' end of a human CFB mRNA sequence according to SEQ ID NO: 1.

In some embodiments of the isolated oligonucleotide of the present disclosure, the sense strand comprises a nucleotide sequence that is at least 70%, at least 80%, at least 90%, at least 95%, or at least 99% identical to a region between the nucleotide positions from 1829 to 1850, from the 5' end of a human CFB mRNA sequence according to SEQ ID NO: 1.

In some embodiments of the isolated oligonucleotide of the present disclosure, the sense strand comprises a nucleotide sequence that is identical to a region between the nucleotide positions from 1829 to 1850, from the 5' end of a human CFB mRNA sequence according to SEQ ID NO: 1.

The CFB mRNA sequence according to SEQ ID NO: 1, as described herein, is any heterologous mRNA sequence with sufficient identity to a CFB according to Accession No. NM_001710.6, as described herein, that allows binding to the antisense strand of the oligonucleotides of the present disclosure.

In some embodiments of the isolated oligonucleotide of the present disclosure, the isolated oligonucleotide is capable of inducing degradation of the CFB mRNA.

In some embodiments of the isolated oligonucleotide of the present disclosure, the sense strand is a single stranded RNA molecule. In some embodiments of the isolated oligonucleotide of the present disclosure, the antisense strand is a single stranded RNA molecule. In some embodiments of the isolated oligonucleotide of the present disclosure, both the sense strand and the antisense strand are single stranded RNA molecules.

In some embodiments, the isolated oligonucleotide of the present disclosure is a small interfering RNA (siRNA). Accordingly, the disclosure provides siRNAs, wherein the siRNA comprises a sense region and antisense region complementary to the sense region that together form an RNA duplex, and wherein the sense region comprises a sequence at least 70% to 100% identical to a CFB mRNA sequence.

DEFINITIONS

"RNAi" or "RNA interference" refers to the process of sequence-specific post-transcriptional gene silencing, mediated by double-stranded RNA (dsRNA). Duplex RNA siRNA (small interfering RNA), miRNA (micro RNA), shRNA (short hairpin RNA), ddRNA (DNA-directed RNA), piRNA (Piwi-interacting RNA), or rasiRNA (repeat associated siRNA) and modified forms thereof are all capable of mediating RNA interference. These dsRNA molecules may be commercially available or may be designed and prepared based on known sequence information, etc. The antisense strand of these molecules can include RNA, DNA, peptide nucleic acid (PNA), or a combination thereof. These DNA/RNA chimera polynucleotide includes, but is not limited to, a double-strand polynucleotide composed of DNA and RNA that inhibits the expression of a target gene. These dsRNA molecules can also include one or more modified nucleotides, as described herein, which can be incorporated on either strand.

In the RNAi gene silencing or knockdown process, dsRNA comprising a first (antisense) strand that is complementary to a portion of a target gene and a second (sense) strand that is fully or partially complementary to the first antisense strand is introduced into an organism. After introduction into the organism, the target gene-specific dsRNA is processed into relatively small fragments (siRNAs) and can subsequently become distributed throughout the organism, decrease messenger RNA of target gene, leading to a phenotype that may come to closely resemble the phenotype arising from a complete or partial deletion of the target gene.

Certain dsRNAs in cells can undergo the action of Dicer enzyme, a ribonuclease III enzyme. Dicer can process the dsRNA into shorter pieces of dsRNA, i.e. siRNAs. RNAi also involves an endonuclease complex known as the RNA induced silencing complex (RISC). Following cleavage by Dicer, siRNAs enter the RISC complex and direct cleavage of a single stranded RNA target having a sequence complementary to the antisense strand of the siRNA duplex. The other strand of the siRNA is the passenger strand. Cleavage of the target RNA takes place in the middle of the region complementary to the antisense strand of the siRNA duplex. siRNAs can thus down regulate or knock down gene expression by mediating RNA interference in a sequence-specific manner.

Alternatively, short oligonucleotides such as siRNAs can be specifically delivered into a cell. Once introduced into the cell, they are recognized by and loaded into RISC to cleave a target RNA.

As used herein, "target gene" or "target sequence" refers to a gene or gene sequence whose corresponding RNA is targeted for degradation through the RNAi pathway using dsRNAs or siRNAs as described herein. To target a gene, for example using an siRNA, the siRNA comprises an antisense region complementary to, or substantially complementary to, at least a portion of the target gene or sequence, and a sense strand complementary to the antisense strand. Once introduced into a cell, the siRNA directs the RISC complex to cleave an RNA comprising a target sequence, thereby degrading the RNA.

As used herein, "oligonucleotide", "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present disclosure further provides a nucleic acid that is the complement (which can be either a full complement or a partial complement) of a nucleic acid, nucleotide sequence, or polynucleotide of this disclosure. When dsRNA is produced synthetically, less common bases, such as inosine, 5-methylcytosine, 6-methyladenine, hypoxanthine and others can also be used for antisense, dsRNA, and ribozyme pairing. Other modifications, such as modification to the phosphodiester backbone, or the 2'-fluoro, the 2'-hydroxy or 2'O-methyl in the ribose sugar group of the RNA can also be made.

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

The term "region" or "fragment" is used interchangeably and as applied to an oligonucleotide.

The CFB mRNA sequence, as described herein, will be understood to mean a nucleotide sequence of reduced length relative to a reference nucleic acid or nucleotide sequence of the CFB mRNA sequence and comprising, consisting essentially of, and/or consisting of a nucleotide sequence of contiguous nucleotides identical or almost identical (e.g., 60%, 70%, 80%, 90%, 92%, 95%, 98% or 99% identical) to the reference nucleic acid or nucleotide sequence. Such a nucleic acid fragment according to the disclosure may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, or more consecutive nucleotides of a nucleic acid or nucleotide sequence according to the disclosure.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

As used herein, the term "substantially complementary" is at least 90% (e.g., 91, 92, 93, 94, 95, 96, 97, 98 or 99%) complementary to the sense strand that is substantially identical to the nucleotide sequence within the defined regions in SEQ ID NO: 1. As used herein, the term "substantially complementary" means that two nucleic acid sequences are complementary at least at about 90%, 95% or 99% of their nucleotides.

In some embodiments, the two nucleic acid sequences can be complementary at least at 90%, 95%, 96%, 97%, 98%, 99% or more of their nucleotides. In some embodiments, the two nucleic acid sequences can be between 90% to 95% complementary, between 70% to 100% complementary, between 95% and 96% complementary, between 90% and 100% complementary, between 96% to 97% complementary, between 60% to 80% complementary, between 97% and 98% complementary, between 70% and 90% complementary, between 98% and 99% complementary, between 80% and 100% complementary, or between 99% and 100% complementary.

The term "substantially complementary" can also mean that two nucleic acid sequences, sense strand and antisense strand have sufficient complementarity that allows binding between the sense strand and antisense strand to form a double stranded region comprising of between 19-25 nucleotides in length. The term "substantially complementary" can also mean that two nucleic acid sequences can hybridize under high stringency conditions, and such conditions are well known in the art.

As used herein, the term "substantially identical" or "sufficient identity" used interchangeably herein, is at least 70%, at least 80%, at least 90%, at least 95%, or at least 99% (e.g., between 70% to 805, 8-% to 90% or 90% to 95% or 95% to 99% or 99% to 100%) identical to the nucleotide sequence within the defined regions in SEQ ID NO: 1.

As used herein, the term "identity" means that sequences are compared with one another as follows. In order to determine the percentage identity of two nucleic acid sequences, the sequences can first be aligned with respect to one another in order to subsequently make a comparison of these sequences possible. For example, gaps can be inserted into the sequence of the first nucleic acid sequence to optimize alignment against the second nucleic acid sequence. If a position in the first nucleic acid sequence is occupied by the same nucleotide as is the case at a position in the second sequence, the two sequences are identical at this position. The percentage identity between two sequences is a function of the number of identical positions divided by the number of all the positions compared in the sequences investigated.

A "percent identity" or "% identity" as used interchangeably herein, for aligned segments of a test sequence and a reference sequence is the percent of identical components which are shared by the two aligned sequences divided by the total number of components in reference sequence segment, i.e., the entire reference sequence or a smaller defined part of the reference sequence.

The percentage identity of two sequences can be determined with the aid of a mathematical algorithm. A preferred, but not limiting, example of a mathematical algorithm which can be used for comparison of two sequences is the algorithm of Karlin et al. (1993), PNAS USA, 90:5873-5877. Such an algorithm is integrated in the NBLAST program, with which sequences which have a desired identity to the sequences of the present disclosure can be identified. In order to obtain a gapped alignment, as described here, the "Gapped BLAST" program can be used, as is described in Altschul et al. (1997), Nucleic Acids Res, 25:3389-3402. If BLAST and Gapped BLAST programs are used, the preset parameters of the particular program (e.g. NBLAST) can be used. The sequences can be aligned further using version 9 of GAP (global alignment program) of the "Genetic Computing Group" using the preset (BLOSUM62) matrix (values −4 to +11) with a gap open penalty of −12 (for the first zero of a gap) and a gap extension penalty of −4 (for each additional successive zero in the gap). After the alignment, the percentage identity is calculated by expressing the number of agreements as a percentage content of the nucleic acids in the sequence claimed. The methods described for determination of the percentage identity of two nucleic acid sequences can also be used correspondingly, if necessary, on the coded amino acid sequences.

Useful methods for determining sequence identity are also disclosed in Guide to Huge Computers (Martin J. Bishop, ed., Academic Press, San Diego (1994)), and Carillo, H., and Lipton, D., (Applied Math48:1073(1988)). More particularly, preferred computer programs for determining sequence identity include but are not limited to the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., J. Mol. Biol. 215:403-410 (1990)); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity. Percent identity can be 70% identity or greater, e.g., at least 70% identity, at least 75% identity, at least 80% identity, at least 85% identity, at least 90% identity, at least 95% identity, at least 98% identity, at least 99% identity or 100% identity.

As used herein, "heterologous" refers to a nucleic acid sequence that either originates from another species or is from the same species or organism but is modified from either its original form or the form primarily expressed in the cell. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g., a different copy number, and/or under the control of different regulatory sequences than that found in nature.

Double Stranded RNAs Targeting Human Complement Factor B (CFB)

The disclosure provides isolated oligonucleotides comprising a double stranded RNAs (dsRNAs) duplex region which targets a CFB mRNA sequence for degradation. The double stranded RNA molecule of the disclosure may be in the form of any type of RNA interference molecule known in the art. In some embodiments, the double stranded RNA molecule is a small interfering RNA (siRNA). In other embodiments, the double stranded RNA molecule is a short hairpin RNA (shRNA) molecule. In other embodiments, the double stranded RNA molecule is a Dicer substrate that is processed in a cell to produce an siRNA. In other embodiments the double stranded RNA molecule is part of a microRNA precursor molecule.

In some embodiments, the dsRNA is a small interfering RNA (siRNA) which targets a CFB mRNA sequence for degradation. In some embodiments, the siRNA targeting CFB is packaged in a delivery system described herein.

The isolated oligonucleotides of the present disclosure targeting CFB for degradation can comprise a sense strand at least 70% identical to any fragment of a CFB mRNA, for example the CFB mRNA of SEQ ID NO: 1. In some embodiments, the sense strand comprises or consists essentially of a sequence at least 70%, at least 80%, at least 90%, at least 95% or is 100% identical to any fragment of SEQ ID NO: 1. The siRNAs targeting CFB for degradation can comprise an antisense strand at least 70% identical to a sequence complementary to any fragment of a CFB mRNA, for example the CFB mRNA of SEQ ID NO: 1. In some embodiments, the antisense strand comprises or consists essentially of a sequence at least 70%, at least 80%, at least 90%, at least 95% or is 100% identical to a sequence complementary to any fragment of SEQ ID NO: 1. In some embodiments, the sense region and antisense regions are complementary, and base pair to form an RNA duplex structure. The fragment of the CFB mRNA that has percent identity to the sense region of the siRNA, and which is complementary to the antisense region of the siRNA, can be protein coding sequence of the mRNA, an untranslated region (UTR) of the mRNA (5' UTR or 3' UTR), or both.

In some embodiments, the isolated oligonucleotide of the present disclosure comprises a sense region and antisense region complementary to the sense region that together form an RNA duplex, and the sense region comprises a sequence at least 70% identical to a CFB mRNA sequence. In some embodiments, the sense region is identical to a CFB mRNA sequence.

As used herein, the term "sense strand" or "sense region" refers to a nucleotide sequence of an siRNA molecule that is partially or fully complementary to at least a portion of a corresponding antisense strand or antisense region of the siRNA molecule. The sense strand of an isolated oligonucleotides of the present disclosure molecule can include a nucleic acid sequence having some percentage identity with a target nucleic acid sequence such as a CFB mRNA sequence. In some cases, the sense region may have 100% identity, i.e., complete identity or homology, to the target nucleic acid sequence. In other cases, there may be one or more mismatches between the sense region and the target nucleic acid sequence. For example, there may be 1, 2, 3, 4, 5, 6, or 7 mismatches between the sense region and the target nucleic acid sequence.

As used herein, the term "antisense strand" or "antisense region" refers to a nucleotide sequence of the isolated oligonucleotides of the present disclosure, that is partially or fully complementary to at least a portion of a target nucleic acid sequence. The antisense strand of an isolated oligonucleotides of the present disclosure molecule can include a nucleic acid sequence that is complementary to at least a portion of a corresponding sense strand of the isolated oligonucleotides.

In some embodiments, the sense region comprises a sequence that is at least 70% identical, at least 75% identical, at least 80% identical, at least 85% identical, at least 90% identical, at least 95% identical, at least 97% identical, at least 99% identical or 100% identical to a sequence of SEQ ID NO: 1 or a region of SEQ ID NO: 1, as disclosed herein. In some embodiments, the sense region consists essentially of a sequence that is at least 70% identical, at least 75% identical, at least 80% identical, at least 85% identical, at least 90% identical, at least 95% identical, at least 97% identical, at least 99% identical or 100% identical to a sequence of SEQ ID NO: 1 or a region of SEQ ID NO: 1, as disclosed herein. In some embodiments, the sense region comprises a sequence that is identical to a sequence of SEQ ID NO: 1 or a region of SEQ ID NO: 1, as disclosed herein. In some embodiments, the sense region consists essentially of a sequence that is identical to a sequence of SEQ ID NO: 1 or a region of SEQ ID NO: 1, as disclosed herein.

In some embodiments, the sense region of the isolated oligonucleotides of the present disclosure targeting CFB has one or more mismatches between the sequence of the isolated oligonucleotides and the CFB sequence. For example, the sequence of the sense region may have 1, 2, 3, 4 or 5 mismatches between the sequence of the sense region of the isolated oligonucleotides and the CFB sequence. In some embodiments, the CFB sequence is a CFB 3' untranslated region sequence (3' UTR). Without wishing to be bound by theory, it is thought that siRNAs targeting the 3' UTR have elevated mismatch tolerance when compared to mismatches in the isolated oligonucleotides targeting coding regions of a gene. Further, the isolated oligonucleotides RNAs may be tolerant of mismatches outside the seed region. As used herein, the "seed region" of the isolated oligonucleotides refers to base pairs 2-8 of the antisense region of the isolated oligonucleotides, i.e., the strand of the isolated oligonucleotides that is complementary to and hybridizes to the target mRNA.

In some embodiments, the antisense region comprises a sequence that is at least 70% identical, at least 75% identical, at least 80% identical, at least 85% identical, at least 90% identical, at least 95% identical, at least 97% identical, at least 99% identical or 100% identical to a sequence complementary to a sequence of SEQ ID NO: 1 or a region of SEQ ID NO: 1, as disclosed herein. In some embodiments, the antisense region consists essentially of a sequence that is at least 70% identical, at least 75% identical, at least 80% identical, at least 85% identical, at least 90% identical, at least 95% identical, at least 97% identical, at least 99% or 100% identical to a sequence complementary to a sequence of SEQ ID NO: 1 or a region of SEQ ID NO: 1. In some embodiments, the antisense region comprises a sequence that is identical to a sequence complementary to a sequence of SEQ ID NO: 1 or a region of SEQ ID NO: 1. In some embodiments, the sense region consists essentially of a sequence that is complementary to a sequence of SEQ ID NO: 1 or a region of SEQ ID NO: 1.

The antisense region of the CFB targeting isolated oligonucleotide of the present disclosure is complementary to the sense region. In some embodiments, the sense region and the antisense region are fully complementary (no mismatches). In some embodiments the antisense region is partially complementary to the sense region, i.e., there are 1, 2, 3, 4 or 5 mismatches between the sense region and the antisense region.

In general, isolated oligonucleotide of the present disclosure comprises an RNA duplex that is about 16 to about 25 nucleotides in length. In some embodiments, the RNA duplex is between about 17 and about 24 nucleotides in length, between about 18 and about 23 nucleotides in length, or between about 19 and about 22 nucleotides in length. In some embodiments, the RNA duplex is 19 nucleotides in length. In some embodiments, the RNA duplex is 20 nucleotides in length.

In some embodiments of the isolated oligonucleotide of the present disclosure, the sense strand is a single stranded RNA molecule. In some embodiments of the isolated oligonucleotide of the present disclosure, the antisense strand is a single stranded RNA molecule. In some embodiments, both the sense strand and the antisense strand are single stranded RNA molecules. In some embodiments, the isolated oligonucleotide of the present disclosure is an siRNA targeting CFB that comprises two different single stranded RNAs, the first comprising the sense region and the second comprising the antisense region, which hybridize to form an RNA duplex.

In some embodiments, the isolated oligonucleotide of the present disclosure can have one or more overhangs from the duplex region. In some embodiments, the overhangs, which are non-base-paired, single strand regions, can be from one to eight nucleotides in length, or longer. In some embodiments, the overhang can be a 3' overhang, wherein the 3'-end of a strand has a single strand region of from one to eight nucleotides. In some embodiments, the overhang can be a 5' overhang, wherein the 5'-end of a strand has a single strand region of from one to eight nucleotides. In some embodiments, the overhangs of the isolated oligonucleotide are the same length. In some embodiments, the overhangs of the isolated oligonucleotide are different lengths.

In some embodiments of the isolated oligonucleotide of the present disclosure, the single stranded RNA molecule of the sense strand comprises a 3' overhang. In some embodiments, the 3' overhang of the single stranded RNA molecule of the sense strand comprises at least one nucleotide. In some embodiments, the 3' overhang of the single stranded RNA molecule of the sense strand comprises two nucleotides.

In some embodiments of the isolated oligonucleotide of the present disclosure, the single stranded RNA molecule of the antisense strand comprises a 3' overhang. In some embodiments, the 3' overhang of the single stranded RNA molecule of the antisense strand comprises at least one nucleotide. In some embodiments, the 3' overhang of the single stranded RNA molecule of the antisense strand comprises two nucleotides.

In some embodiments of the isolated oligonucleotide of the present disclosure, both ends of isolated oligonucleotide have an overhang, for example, a 3' dinucleotide overhang on each end. In some embodiments, the overhangs at the 5'- and 3'-ends are of different lengths. In some embodiments, the overhangs at the 5'- and 3'-ends are of the same length.

In some embodiments of the isolated oligonucleotide of the present disclosure, the overhang can contain one or more deoxyribonucleotides, one or more ribonucleotides, or a combination of deoxyribonucleotides and ribonucleotides. In some embodiments, one, or both, of the overhang nucleotides of an siRNA may be 2'-deoxyribonucleotides.

In some embodiments of the isolated oligonucleotide of the present disclosure, the first single stranded RNA molecule comprises a first 3' overhang. In some embodiments, the second single stranded RNA molecule comprises a second 3' overhang. In some embodiments, the first and second 3' overhangs comprise a dinucleotide.

In some embodiments of the isolated oligonucleotide of the present disclosure, the 3' overhang comprises any one of thymidine-thymidine (dTdT), Adenine-Adenine (AA), Cysteine-Cysteine (CC), Guanine-Guanine (GG) or Uracil-Uracil (UU). In some embodiments, the isolated oligonucleotide of the present disclosure, the 3' overhang comprises a thymidine-thymidine (dTdT) or a Uracil-Uracil (UU) overhang. In some embodiments, the 3' overhang comprises a Uracil-Uracil (UU) overhang. Without wishing to be bound by theory, it is thought that 3' overhangs, such as dinucleotide overhangs, enhance siRNA mediated mRNA degradation by enhancing siRNA-RISC complex formation, and/or rate of cleavage of the target mRNA by the siRNA-RISC complex.

In some embodiments, the isolated oligonucleotide of the present disclosure can have one or more blunt ends, in which the duplex region ends with no overhang, and the strands are base paired to the end of the duplex region. In some embodiments, the isolated oligonucleotide of the present disclosure can have one or more blunt ends, or can have one or more overhangs, or can have a combination of a blunt end and an overhang end. For example, the 5' end of the siRNA can be blunt and the 3' end of the same isolated oligonucleotide comprises an overhang, or vice versa.

In some embodiments, both ends of the isolated oligonucleotide of the present disclosure are blunt ends.

In some embodiments of the isolated oligonucleotide of the present disclosure, the double stranded region comprises an antisense strand and a sense strand, according to any one of the pairs of antisense strand and sense strand sequences in Table 1, as described below.

The Complement System

The complement system is a critical component of the innate immune system and comprises a group of proteins that are normally present in an inactive state. These proteins are organized in three activation pathways: the classical, the lectin, and the alternative pathways.

Molecules from microorganisms, antibodies or cellular components can activate these pathways resulting in the formation of protease complexes known as the C3-convertase and the C5-convertase. The first enzymatically activated cascade, known as classical pathway, is a calcium/magnesium-dependent cascade, which is normally activated by the formation of antigen-antibody complexes. It can also be activated in an antibody-independent manner by the binding of C-reactive protein complexed to ligand and by many pathogens including Gram-negative bacteria.

As described in U.S. Pat. No. 8,703,136, the classical pathway comprises several components, C1, C4, C2, C3 and C5 (listed by order in the pathway). Initiation of the classical pathway of the complement system occurs following binding and activation of the first complement component (C1) by both immune and non-immune activators. C1 comprises a calcium-dependent complex of components C1q, C1r and C1s, and is activated through binding of the C1q component. C1q contains six identical subunits and each subunit comprises three chains (the A, B and C chains). Each chain has a globular head region that is connected to a collagen-like tail. Binding and activation of C1q by antigen-antibody complexes occurs through the C1q head group region. Numerous non-antibody C1q activators, including proteins, lipids and nucleic acids, bind and activate C1q through a distinct site on the collagen-like stalk region. The C1qrs complex then catalyzes the activation of complement components C4 and C2, forming the C4b2a complex which functions as a C3 convertase.

The second enzymatically activated cascade, known as the alternative pathway, is a rapid, antibody-independent route for complement system activation and amplification.

The alternative pathway is a magnesium-dependent cascade which is activated by deposition and activation of C3 on certain susceptible surfaces (e.g., cell wall polysaccharides of yeast and bacteria, and certain biopolymer materials). The alternative pathway comprises several components, that include: C3, Complement Factor B (CFB), and Factor D (listed by order in the pathway). Activation of the alternative pathway occurs when C3b, a proteolytically cleaved and active form of C3, is bound to an activating surface agent such as a bacterium. CFB is then bound to C3b and cleaved by Factor D to yield the active enzyme, Bb. The resultant complement complex, C3bBb, is the alternative pathway C3 convertase. The enzyme C3b-Bb cleaves C3 to generate C3b, producing extensive deposition of C3b-Bb complexes on the activating surface.

Thus, both the classical and alternate complement pathways produce C3 convertases that split factor C3 into C3a and C3b. At this point, both C3 convertases further assemble into C5 convertases (C4b2a3b and C3b3bBb). These complexes subsequently cleave complement component C5 into two components: the C5a polypeptide (9 kDa) and the C5b polypeptide (170 kDa). The C5a polypeptide binds to a 7 transmembrane G-protein coupled receptor, which was originally associated with leukocytes and is now known to be expressed on a variety of tissues including hepatocytes and neurons. The C5a molecule is the primary chemotactic component of the human complement system and can trigger a variety of biological responses including leukocyte chemotaxis, smooth muscle contraction, activation of intracellular signal transduction pathways, neutrophil-endothelial adhesion, cytokine and lipid mediator release and oxidant formation.

The larger C5b fragment binds sequentially to later components of the complement cascade, C6, C7, C8 and C9 to form the C5b-9 membrane attack complex ("MAC"). The lipophilic C5b-9 MAC can directly lyse erythrocytes, and in greater quantities it is lytic for leukocytes and damaging to tissues such as muscle, epithelial and endothelial cells. In sublytic amounts, the C5b-9 MAC can stimulate upregulation of adhesion molecules, intracellular calcium increase and cytokine release. In addition, at sublytic concentrations the C5b-9 MAC can stimulate cells such as endothelial cells and platelets without causing cell lysis. The non-lytic effects of C5a and the C5b-9 MAC are comparable and interchangeable.

The lectin pathway is initiated when pattern-recognition molecules (MBL, CL-K1, and ficolins) bind to the so-called pathogen-associated molecular patterns (PAMPs) (D-mannose, N-acetyl-D-glucosamine, or acetyl groups), on the surface of pathogens or to apoptotic or necrotic cells (Beltrame M H, et al. The lectin pathway of complement and rheumatic heart disease. *Front Pediatr.* 2015 Jan. 21; 2:148.).

Although the complement system has an important role in the maintenance of health, it has the potential to cause or contribute to disease.

Accordingly, the isolated oligonucleotides disclosed in the present disclosure are useful in treating or preventing a disease or disorder associated with aberrant or increased expression or activity of CFB or a disease or disorder where CFB plays a role. Exemplary isolated oligonucleotides of the present disclosure are described in Table 1.

In some embodiments of the isolated oligonucleotide of the present disclosure, the sense strand comprises a sequence selected from any one of the groups of sense strand/passenger strand sequences listed in Table 1, Table 2 or Table 3. In some embodiments, the antisense strand comprises a sequence selected from any one of the groups of antisense strand/guide strand sequences listed in Table 1, Table 2 or Table 3. In some embodiments, the sense and antisense regions comprise complementary sequences selected from the group listed in Table 1, Table 2 and Table 3.

In some embodiments of the isolated oligonucleotide of the present disclosure, the antisense strand comprises a nucleotide sequence according to any one of: SEQ ID NOs: 2-35.

In some embodiments of the isolated oligonucleotide of the present disclosure, the sense strand comprises a nucleotide sequence according to any one of: SEQ ID NOs: 36-69.

In some embodiments of the isolated oligonucleotide of the present disclosure, the antisense strand comprises a nucleotide sequence according to any one of SEQ ID NOs: 2-35; and the sense strand comprises a nucleotide sequence according to any one of SEQ ID NOs: 36-69, wherein the antisense strand and the sense strand sequences have sufficient complementarity to allow formation of a double stranded region between the antisense and the sense strand.

Sequences of the Present Disclosure

The present disclosure provides an isolated oligonucleotide comprising a sense and an antisense strand, wherein the sense strand comprises a nucleotide sequence that is substantially identical to a region between any one of the nucleotide positions selected from: a) 493 to 534; b) 991 to 1054; c) 1384 to 1500; d) 1606 to 1686; e) 1821 to 1881; f) 2116 to 2307; and g) 2382 to 2468, from the 5' end of a human CFB mRNA sequence according to SEQ ID NO: 1, and the antisense strand is substantially complementary to the sense strand such that the sense strand and the antisense strand together form a double stranded region.

The present disclosure provides an isolated oligonucleotide comprising a sense and an antisense strand, wherein the sense strand comprises a nucleotide sequence that is at least 70%, at least 80%, at least 90%, at least 95%, or at least 99% identical to a region comprising 19-25 nucleotides between any one of the nucleotide positions selected from: a) 493 to 534; b) 991 to 1054; c) 1384 to 1500; d) 1606 to 1686; e) 1821 to 1881; f) 2116 to 2307; and g) 2382 to 2468, from the 5' end of a human CFB mRNA sequence according to SEQ ID NO: 1.

The present disclosure provides an isolated oligonucleotide comprising a sense and an antisense strand, wherein the sense strand comprises a nucleotide sequence that is identical to a region comprising 19-25 nucleotides between any one of the nucleotide positions selected from: a) 493 to 534; b) 991 to 1054; c) 1384 to 1500; d) 1606 to 1686; e) 1821 to 1881; f) 2116 to 2307; and g) 2382 to 2468, from the 5' end of a human CFB mRNA sequence according to SEQ ID NO: 1.

The present disclosure provides an isolated oligonucleotide comprising a sense and an antisense strand, wherein the sense strand comprises a sequence that is substantially identical to a region between any one of the nucleotide positions selected from: a) 493 to 534; b) 991 to 1054; c) 1384 to 1500; d) 1666 to 1686; e) 1821 to 1881; f) 2116 to 2136; g) 2232 to 2307; and h) 2394 to 2468, from the 5' end of a human CFB mRNA sequence according to SEQ ID NO: 1.

The present disclosure provides an isolated oligonucleotide comprising a sense and an antisense strand, wherein the sense strand comprises a sequence that is at least 70%, at least 80%, at least 90%, at least 95%, or at least 99% identical to a region between any one of the nucleotide positions selected from: a) 493 to 534; b) 991 to 1054; c) 1384 to 1500; d) 1666 to 1686; e) 1821 to 1881; f) 2116 to 2136; g) 2232 to 2307; and h) 2394 to 2468, from the 5' end of a human CFB mRNA sequence according to SEQ ID NO: 1.

The present disclosure provides an isolated oligonucleotide comprising a sense and an antisense strand, wherein the sense strand comprises a nucleotide sequence that is identical to a region between any one of the nucleotide positions selected from: a) 493 to 534; b) 991 to 1054; c) 1384 to 1500; d) 1666 to 1686; e) 1821 to 1881; f) 2116 to 2136; g) 2232 to 2307; and h) 2394 to 2468, from the 5' end of a human CFB mRNA sequence according to SEQ ID NO: 1.

In some embodiments of the isolated oligonucleotide of the present disclosure, wherein the sense strand comprises a nucleotide sequence that is identical to a region between any one of the nucleotide positions selected from: a) 493 to 534; b) 991 to 1054; c) 1384 to 1500; d) 1666 to 1686; e) 1821 to 1881; f) 2116 to 2136; g) 2232 to 2307; and h) 2394 to 2468, from the 5' end of a human CFB mRNA sequence according to SEQ ID NO: 1, the double stranded region comprises: i) an antisense strand of nucleic acid sequence according to SEQ ID NO: 2 (5' UAAAGAGAUCUCAUCACUCACA 3'), and a sense strand of nucleic acid sequence according to SEQ ID NO: 36 (5' UGAGUGAUGAGAUCUCUUUA 3'); ii) an antisense strand of nucleic acid sequence according to SEQ ID NO: 3 (5' UGGAAAGAGAUCUCAUCACUCA 3'), and a sense strand of nucleic acid sequence according to SEQ ID NO: 37 (5' AGUGAUGAGAUCUCUUUCCA 3'); iii) an antisense strand of nucleic acid sequence according to SEQ ID NO: 4 (5' UCAGUGGAAAGAGAUCUCAUCA 3'), and a sense strand of nucleic acid sequence according to SEQ ID NO: 38 (5' AUGAGAUCUCUUUCCACUGA 3'); iv) an antisense strand of nucleic acid sequence according to SEQ ID NO: 6 (5' UGUGUAACCGUCAUAGCAGUGG 3'), and a sense strand of nucleic acid sequence according to SEQ ID NO: 389 (5' ACUGCUAUGACGGUUACACA 3'); v) an antisense strand of nucleic acid sequence according to SEQ ID NO: 7 (5' UUUGACUAGACACUUUUUGGCU 3'), and a sense strand of nucleic acid sequence according to SEQ ID NO: 41 (5' CCAAAAAGUGUCUAGUCAAA 3'); vi) an antisense strand of nucleic acid sequence according to SEQ ID NO: 9 (5' UAAUUAAGUUGACUAGACACUU 3'), and a sense strand of nucleic acid sequence according to SEQ ID NO: 43 (5' GUGUCUAGUCAACUUAAUUA 3'); vii) an antisense strand of nucleic acid sequence according to SEQ ID NO: 11 (5' UAUAUCUUGGCUUCACACCAUA 3'), and a sense strand of nucleic acid sequence according to SEQ ID NO: 45 (5' UGGUGUGAAGCCAAGAUAUA 3'); viii) an antisense strand of nucleic acid sequence according to SEQ ID NO: 12 (5' UUAGACAUCCAGAUAAUCCUCC 3'), and a sense strand of nucleic acid sequence according to SEQ ID NO: 46 (5' AGGAUUAUCUGGAUGUCUAA 3'); ix) an antisense strand of nucleic acid sequence according to SEQ ID NO: 13 (5' UAAGCAUUGAUGUUCACUUGGU 3'), and a sense strand of nucleic acid sequence according to SEQ ID NO: 47 (5' CAAGUGAACAUCAAUGCUUA 3'); x) an antisense strand of nucleic acid sequence according to SEQ ID NO: 14 (5' UAAAGCAUUGAUGUUCACUUGG 3'), and a sense strand of nucleic acid sequence according to SEQ ID NO: 48 (5' AAGUGAACAUCAAUGCUUUA 3'); xi) an antisense strand of nucleic acid sequence according to SEQ ID NO: 15 (5' UAACACAUGUUGCUCAUUGUCU 3'), and a sense strand of nucleic acid sequence according to SEQ ID NO: 49 (5' ACAAUGAGCAACAUGUGUUA 3'); xii) an antisense strand of nucleic acid sequence according to SEQ ID NO: 16 (5' UUUGACUUUGAACACAUGUUGC 3'), and a sense strand of nucleic acid sequence according to SEQ ID NO: 50 (5' AACAUGUGUUCAAAGUCAAA 3'); xiii) an antisense strand of nucleic acid sequence according to SEQ ID NO: 17 (5' UAUAUCCUUGACUUUGAACACA 3'), and a sense strand of nucleic acid sequence according to SEQ ID NO: 51 (5' UGUUCAAAGUCAAGGAUAUA 3'); xiv) an antisense strand of nucleic acid sequence according to SEQ ID NO: 19 (5' UAAGUACUCAGACACCACAGCC 3'), and a sense strand of nucleic acid sequence according to SEQ ID NO: 53 (5' CUGUGGUGUCUGAGUACUUA 3'); xv) an antisense strand of nucleic acid sequence according to SEQ ID NO: 20 (5' UAUUCAGGAAUUCCUGCUUCUU 3'), and a sense strand of nucleic acid sequence according to SEQ ID NO: 54 (5' GAAGCAGGAAUUCCUGAAUA 3'); xvi) an antisense strand of nucleic acid sequence according to SEQ ID NO: 21 (5' UAAUUCAGGAAUUCCUGCUUCU 3'), and a sense strand of nucleic acid sequence according to SEQ ID NO: 55 (5' AAGCAGGAAUUCCUGAAUUA 3'); xvii) an antisense strand of nucleic acid sequence according to SEQ ID NO: 22 (5' UUAAAAUUCAGGAAUUCCUGCU 3'), and a sense strand of nucleic acid sequence according to SEQ ID NO: 56 (5' CAGGAAUUCCUGAAUUUUAA 3'); xviii) an antisense strand of nucleic acid sequence according to SEQ ID NO: 23 (5' UAUAAAAUUCAGGAAUUCCUGC 3'), and a sense strand of nucleic acid sequence according to SEQ ID NO: 57 (5' AGGAAUUCCUGAAUUUUAUA 3'); xix) an antisense strand of nucleic acid sequence according to SEQ ID NO: 24 (5' UGUCAUAAAAUUCAGGAAUUCC 3'), and a sense strand of nucleic acid sequence according to SEQ ID NO: 58 (5' AAUUCCUGAAUUUUAUGACA 3'); xx) an antisense strand of nucleic acid sequence according to SEQ ID NO: 26 (5' UUUAUUCUUGAGCUUGAUCAGG 3'), and a sense strand of nucleic acid sequence according to SEQ ID NO: 60 (5' UGAUCAAGCUCAAGAAUAAA 3'); xxi) an antisense strand of nucleic acid sequence according to SEQ ID NO: 27 (5' UUUGACUUUGUCAUAGCCUGGG 3'), and a sense strand of nucleic acid sequence according to SEQ ID NO: 61 (5' CAGGCUAUGACAAAGUCAAA 3'); xxii) an antisense strand of nucleic acid sequence according to SEQ ID NO: 29 (5' UUUCUCUUGUGAACUAUCAAGG 3'), and a sense strand of nucleic acid sequence according to SEQ ID NO: 63 (5' UUGAUAGUUCACAAGAGAAA 3'); xxiii) an antisense strand of nucleic acid sequence according to SEQ ID NO: 30 (5' UAAACGACUUCUCUUGUGAACU 3'), and a sense strand of nucleic acid sequence according to SEQ ID NO: 64 (5' UUCACAAGAGAAGUCGUUUA 3'); xxiv) an antisense strand of nucleic acid sequence according to SEQ ID NO: 31 (5' UUUUUUGCAGACAUCCACUACU 3'), and a sense strand of nucleic acid sequence according to SEQ ID NO: 65 (5' UAGUGGAUGUCUGCAAAAAA 3'); xxv) an antisense strand of nucleic acid sequence according to SEQ ID NO: 33 (5' UAACCCAAAUCCUCAUCUUGGA 3'), and a sense strand of nucleic acid sequence according to SEQ ID NO: 67 (5' CAAGAUGAGGAUUUGGGUUA 3'); xxvi) an antisense strand of nucleic acid sequence according to SEQ ID NO: 34 (5' UAAACCCAAAUCCUCAUCUUGG 3'), and a sense strand of nucleic acid sequence according to SEQ ID NO: 68 (5' AAGAUGAGGAUUUGGGUUUA 3'); or xxvii) an antisense strand of nucleic acid sequence according to SEQ ID NO: 35 (5' UCAGCUGUUUUAAUUCAAUCCC 3'), and a sense strand of nucleic acid sequence according to SEQ ID NO: 69 (5' GAUUGAAUUAAAACAGCUGA 3').

At Least 50% Knockdown of CFB at 0.1 nM

In some embodiments of the isolated oligonucleotide of the present disclosure, the sense strand comprises a sequence that is identical to a region between any one of the nucleotide positions selected from a) 493 to 534; b) 991 to 1054; c) 1384 to 1500; d) 1606 to 1686; e) 1821 to 1881; f) 2116 to 2307; and g) 2382 to 2468, from the 5' end of a human CFB mRNA sequence according to SEQ ID NO: 1, and the antisense strand is substantially complementary to the sense strand such that the sense strand and the antisense strand together form a double stranded region, wherein the isolated oligonucleotide attenuates expression of the CFB mRNA by at least 50% (e.g., 50% to 55%, 55% to 60%, 60% to 65%, 65% to 70%, 70% to 75%, 75% to 80%, 80% to 85%, 85% to 90%, 90% to 95% or 95% to 99%, 99% to 100%), at a dose of 0.1 nM.

In some embodiments of the isolated oligonucleotide of the present disclosure, the sense strand comprises a sequence that is identical to a region between any one of the nucleotide positions selected from a) 493 to 534; b) 991 to 1054; c) 1384 to 1500; d) 1606 to 1686; e) 1821 to 1881; f) 2116 to 2307; and g) 2382 to 2468, from the 5' end of a human CFB mRNA sequence according to SEQ ID NO: 1, and the antisense strand is substantially complementary to the sense strand such that the sense strand and the antisense strand together form a double stranded region, and the isolated oligonucleotide attenuates expression of the CFB mRNA by at least 50% at a dose of 0.1 nM, wherein the double stranded region comprises: i) an antisense strand of nucleic acid sequence according to SEQ ID NO: 2 (5' UAAAGAGAUCUCAUCACUCACA 3'), and a sense strand of nucleic acid sequence according to SEQ ID NO: 36 (5' UGAGUGAUGAGAUCUCUUUA 3'); ii) an antisense strand of nucleic acid sequence according to SEQ ID NO: 3 (5' UGGAAAGAGAUCUCAUCACUCA 3'), and a sense strand of nucleic acid sequence according to SEQ ID NO: 37 (5' AGUGAUGAGAUCUCUUUCCA 3'); iii) an antisense strand of nucleic acid sequence according to SEQ ID NO: 4 (5' UCAGUGGAAAGAGAUCUCAUCA 3'), and a sense strand of nucleic acid sequence according to SEQ ID NO: 38 (5' AUGAGAUCUCUUUCCACUGA 3'); iv) an antisense strand of nucleic acid sequence according to SEQ ID NO: 6 (5' UGUGUAACCGUCAUAGCAGUGG 3'), and a sense strand of nucleic acid sequence according to SEQ ID NO: 389 (5' ACUGCUAUGACGGUUACACA 3'); v) an antisense strand of nucleic acid sequence according to SEQ ID NO: 7 (5' UUUGACUAGACACUUUUUGGCU 3'), and a sense strand of nucleic acid sequence according to SEQ ID NO: 41 (5' CCAAAAAGUGUCUAGUCAAA 3'); vi) an antisense strand of nucleic acid sequence according to SEQ ID NO: 9 (5' UAAUUAAGUUGACUAGACACUU 3'), and a sense strand of nucleic acid sequence according to SEQ ID NO: 43 (5' GUGUCUAGUCAACUUAAUUA 3'); vii) an antisense strand of nucleic acid sequence according to SEQ ID NO: 11 (5' UAUAUCUUGGCUUCACACCAUA 3'), and a sense strand of nucleic acid sequence according to SEQ ID NO: 45 (5' UGGUGUGAAGCCAAGAUAUA 3'); viii) an antisense strand of nucleic acid sequence according to SEQ ID NO: 12 (5' UUAGACAUCCAGAUAAUCCUCC 3'), and a sense strand of nucleic acid sequence according to SEQ ID NO: 46 (5' AGGAUUAUCUGGAUGUCUAA 3'); ix) an antisense strand of nucleic acid sequence according to SEQ ID NO: 13 (5' UAAGCAUUGAUGUUCACUUGGU 3'), and a sense strand of nucleic acid sequence according to SEQ ID NO: 47 (5' CAAGUGAACAUCAAUGCUUA 3'); x) an antisense strand of nucleic acid sequence according to SEQ ID NO: 14 (5' UAAAGCAUUGAUGUUCACUUGG 3'), and a sense strand of nucleic acid sequence according to SEQ ID NO: 48 (5' AAGUGAACAUCAAUGCUUUA 3'); xi) an antisense strand of nucleic acid sequence according to SEQ ID NO: 15 (5' UAACACAUGUUGCUCAUUGUCU 3'), and a sense strand of nucleic acid sequence according to SEQ ID NO: 49 (5' ACAAUGAGCAACAUGUGUUA 3'); xii) an antisense strand of nucleic acid sequence according to SEQ ID NO: 16 (5' UUUGACUUUGAACACAUGUUGC 3'), and a sense strand of nucleic acid sequence according to SEQ ID NO: 50 (5' AACAUGUGUUCAAAGUCAAA 3'); xiii) an antisense strand of nucleic acid sequence according to SEQ ID NO: 17 (5' UAUAUCCUUGACUUUGAACACA 3'), and a sense strand of nucleic acid sequence according to SEQ ID NO: 51 (5' UGUUCAAAGUCAAGGAUAUA 3'); xiv) an antisense strand of nucleic acid sequence according to SEQ ID NO: 19 (5' UAAGUACUCAGACACCACAGCC 3'), and a sense strand of nucleic acid sequence according to SEQ ID NO: 53 (5' CUGUGGUGUCUGAGUACUUA 3'); xv) an antisense strand of nucleic acid sequence according to SEQ ID NO: 20 (5' UAUUCAGGAAUUCCUGCUUCUU 3'), and a sense strand of nucleic acid sequence according to SEQ ID NO: 54 (5' GAAGCAGGAAUUCCUGAAUA 3'); xvi) an antisense strand of nucleic acid sequence according to SEQ ID NO: 21 (5' UAAUUCAGGAAUUCCUGCUUCU 3'), and a sense strand of nucleic acid sequence according to SEQ ID NO: 55 (5' AAGCAGGAAUUCCUGAAUUA 3'); xvii) an antisense strand of nucleic acid sequence according to SEQ ID NO: 22 (5' UUAAAAUUCAGGAAUUCCUGCU 3'), and a sense strand of nucleic acid sequence according to SEQ ID NO: 56 (5' CAGGAAUUCCUGAAUUUUAA 3'); xviii) an antisense strand of nucleic acid sequence according to SEQ ID NO: 23 (5' UAUAAAAUUCAGGAAUUCCUGC 3'), and a sense strand of nucleic acid sequence according to SEQ ID NO: 57 (5' AGGAAUUCCUGAAUUUUAUA 3'); xix) an antisense strand of nucleic acid sequence according to SEQ ID NO: 24 (5' UGUCAUAAAAUUCAGGAAUUCC 3'), and a sense strand of nucleic acid sequence according to SEQ ID NO: 58 (5' AAUUCCUGAAUUUUAUGACA 3'); xx) an antisense strand of nucleic acid sequence according to SEQ ID NO: 26 (5' UUUAUUCUUGAGCUUGAUCAGG 3'), and a sense strand of nucleic acid sequence according to SEQ ID NO: 60 (5' UGAUCAAGCUCAAGAAUAAA 3'); xxi) an antisense strand of nucleic acid sequence according to SEQ ID NO: 27 (5' UUUGACUUUGUCAUAGCCUGGG 3'), and a sense strand of nucleic acid sequence according to SEQ ID NO: 61 (5' CAGGCUAUGACAAAGUCAAA 3'); xxii) an antisense strand of nucleic acid sequence according to SEQ ID NO: 29 (5' UUUCUCUUGUGAACUAUCAAGG 3'), and a sense strand of nucleic acid sequence according to SEQ ID NO: 63 (5' UUGAUAGUUCACAAGAGAAA 3'); xxiii) an antisense strand of nucleic acid sequence according to SEQ ID NO: 30 (5' UAAACGACUUCUCUUGUGAACU 3'), and a sense strand of nucleic acid sequence according to SEQ ID NO: 64 (5' UUCACAAGAGAAGUCGUUUA 3'); xxiv) an antisense strand of nucleic acid sequence according to SEQ ID NO: 31 (5' UUUUUUGCAGACAUCCACUACU 3'), and a sense strand of nucleic acid sequence according to SEQ ID NO: 65 (5' UAGUGGAUGUCUGCAAAAAA 3'); xxv) an antisense strand of nucleic acid sequence according to SEQ ID NO: 33 (5' UAACCCAAAUCCUCAUCUUGGA 3'), and a sense strand of nucleic acid sequence according to SEQ ID NO: 67 (5' CAAGAUGAGGAUUUGGGUUA 3'); xxvi) an antisense strand of nucleic acid sequence according to SEQ ID NO: 34 (5' UAAACCCAAAUCCUCAUCUUGG 3'), and a sense strand of nucleic acid sequence according to SEQ ID NO: 68 (5'

AAGAUGAGGAUUUGGGUUUA 3'); xxvii) an antisense strand of nucleic acid sequence according to SEQ ID NO: 35 (5' UCAGCUGUUUUAAUUCAAUCCC 3'), and a sense strand of nucleic acid sequence according to SEQ ID NO: 69 (5' GAUUGAAUUAAAACAGCUGA 3'); xxviii) an antisense strand of nucleic acid sequence according to SEQ ID NO: 8 (5' UUAAGUUGACUAGACACUUUUU 3'), and a sense strand of nucleic acid sequence according to SEQ ID NO: 42 (5' AAAGUGUCUAGUCAACUUAA 3'); xxix) an antisense strand of nucleic acid sequence according to SEQ ID NO: 10 (5' UCAAUUAAGUUGACUAGACACU 3'), and a sense strand of nucleic acid sequence according to SEQ ID NO: 44 (5' UGUCUAGUCAACUUAAUUGA 3'); xxx) an antisense strand of nucleic acid sequence according to SEQ ID NO: 18 (5' UGAGAUCUUGGCCUGCCAUGGU 3'), and a sense strand of nucleic acid sequence according to SEQ ID NO: 52 (5' CAUGGCAGGCCAAGAUCUCA 3'); xxxi) an antisense strand of nucleic acid sequence according to SEQ ID NO: 25 (5' UUAUUCUUGAGCUUGAUCAGGG 3'), and a sense strand of nucleic acid sequence according to SEQ ID NO: 59 (5' CUGAUCAAGCUCAAGAAUAA 3'); xxxii) an antisense strand of nucleic acid sequence according to SEQ ID NO: 32 (5' UCAUCUUGGAGUUUCUCCUUCA 3'), and a sense strand of nucleic acid sequence according to SEQ ID NO: 66 (5' AAGGAGAAACUCCAAGAUGA 3'); xxxiii) an antisense strand of nucleic acid sequence according to SEQ ID NO: 5 (5' UAUAGCAGUGGAAAGAGAUCUC 3'), and a sense strand of nucleic acid sequence according to SEQ ID NO: 39 (5' GAUCUCUUUCCACUGCUAUA 3'); or xxxiv) an antisense strand of nucleic acid sequence according to SEQ ID NO: 28 (5' UAAGUAUUGGGGUCAGCAUAGG 3'), and a sense strand of nucleic acid sequence according to SEQ ID NO: 62 (5' UAUGCUGACCCCAAUACUUA 3').

At Least 50% Knockdown of CFB at 0.02 nM

In some embodiments of the isolated oligonucleotide of the present disclosure, the sense strand comprises a sequence that is identical to a region between any one of the nucleotide positions selected from a) 493 to 534; b) 991 to 1054; c) 1384 to 1500; d) 1606 to 1686; e) 1821 to 1881; f) 2116 to 2307; and g) 2382 to 2468, from the 5' end of a human CFB mRNA sequence according to SEQ ID NO: 1, and the antisense strand is substantially complementary to the sense strand such that the sense strand and the antisense strand together form a double stranded region, wherein the isolated oligonucleotide attenuates expression of the CFB mRNA by at least 50% (e.g., 50% to 55%, 55% to 60%, 60% to 65%, 65% to 70%, 70% to 75%, 75% to 80%, 80% to 85%, 85% to 90%, 90% to 95% or 95% to 99%, 99% to 100%), at a dose of 0.02 nM.

In some embodiments of the isolated oligonucleotide of the present disclosure, the sense strand comprises a sequence that is identical to a region between any one of the nucleotide positions selected from a) 493 to 534; b) 991 to 1054; c) 1384 to 1500; d) 1606 to 1686; e) 1821 to 1881; f) 2116 to 2307; and g) 2382 to 2468, from the 5' end of a human CFB mRNA sequence according to SEQ ID NO: 1, and the antisense strand is substantially complementary to the sense strand such that the sense strand and the antisense strand together form a double stranded region, and the isolated oligonucleotide attenuates expression of the CFB mRNA by at least 50% at a dose of 0.02 nM, wherein the double stranded region comprises: i) an antisense strand of nucleic acid sequence according to SEQ ID NO: 2 (5' UAAAGAGAUCUCAUCACUCACA 3'), and a sense strand of nucleic acid sequence according to SEQ ID NO: 36 (5' UGAGUGAUGAGAUCUCUUUA 3'); ii) an antisense strand of nucleic acid sequence according to SEQ ID NO: 3 (5' UGGAAAGAGAUCUCAUCACUCA 3'), and a sense strand of nucleic acid sequence according to SEQ ID NO: 37 (5' AGUGAUGAGAUCUCUUUCCA 3'); iii) an antisense strand of nucleic acid sequence according to SEQ ID NO: 4 (5' UCAGUGGAAAGAGAUCUCAUCA 3'), and a sense strand of nucleic acid sequence according to SEQ ID NO: 38 (5' AUGAGAUCUCUUUCCACUGA 3'); iv) an antisense strand of nucleic acid sequence according to SEQ ID NO: 6 (5' UGUGUAACCGUCAUAGCAGUGG 3'), and a sense strand of nucleic acid sequence according to SEQ ID NO: 389 (5' ACUGCUAUGACGGUUACACA 3'); v) an antisense strand of nucleic acid sequence according to SEQ ID NO: 9 (5' UAAUUAAGUUGACUAGACACUU 3'), and a sense strand of nucleic acid sequence according to SEQ ID NO: 43 (5' GUGUCUAGUCAACUUAAUUA 3'); vi) an antisense strand of nucleic acid sequence according to SEQ ID NO: 12 (5' UUAGACAUCCAGAUAAUCCUCC 3'), and a sense strand of nucleic acid sequence according to SEQ ID NO: 46 (5' AGGAUUAUCUGGAUGUCUAA 3'); vii) an antisense strand of nucleic acid sequence according to SEQ ID NO: 13 (5' UAAGCAUUGAUGUUCACUUGGU 3'), and a sense strand of nucleic acid sequence according to SEQ ID NO: 47 (5' CAAGUGAACAUCAAUGCUUA 3'); viii) an antisense strand of nucleic acid sequence according to SEQ ID NO: 14 (5' UAAAGCAUUGAUGUUCACUUGG 3'), and a sense strand of nucleic acid sequence according to SEQ ID NO: 48 (5' AAGUGAACAUCAAUGCUUUA 3'); ix) an antisense strand of nucleic acid sequence according to SEQ ID NO: 22 (5' UUAAAAUUCAGGAAUUCCUGCU 3'), and a sense strand of nucleic acid sequence according to SEQ ID NO: 56 (5' CAGGAAUUCCUGAAUUUUAA 3'); x) an antisense strand of nucleic acid sequence according to SEQ ID NO: 23 (5' UAUAAAAUUCAGGAAUUCCUGC 3'), and a sense strand of nucleic acid sequence according to SEQ ID NO: 57 (5' AGGAAUUCCUGAAUUUUAUA 3'); xi) an antisense strand of nucleic acid sequence according to SEQ ID NO: 24 (5' UGUCAUAAAAUUCAGGAAUUCC 3'), and a sense strand of nucleic acid sequence according to SEQ ID NO: 58 (5' AAUUCCUGAAUUUUAUGACA 3'); xii) an antisense strand of nucleic acid sequence according to SEQ ID NO: 30 (5' UAAACGACUUCUCUUGUGAACU 3'), and a sense strand of nucleic acid sequence according to SEQ ID NO: 64 (5' UUCACAAGAGAAGUCGUUUA 3'); xiii) an antisense strand of nucleic acid sequence according to SEQ ID NO: 34 (5' UAAACCCAAAUCCUCAUCUUGG 3'), and a sense strand of nucleic acid sequence according to SEQ ID NO: 68 (5' AAGAUGAGGAUUUGGGUUUA 3'); xiv) an antisense strand of nucleic acid sequence according to SEQ ID NO: 35 (5' UCAGCUGUUUUAAUUCAAUCCC 3'), and a sense strand of nucleic acid sequence according to SEQ ID NO: 69 (5' GAUUGAAUUAAAACAGCUGA 3'); xv) an antisense strand of nucleic acid sequence according to SEQ ID NO: 5 (5' UAUAGCAGUGGAAAGAGAUCUC 3'), and a sense strand of nucleic acid sequence according to SEQ ID NO: 39 (5' GAUCUCUUUCCACUGCUAUA 3'); or xvi) an antisense strand of nucleic acid sequence according to SEQ ID NO: 28 (5' UAAGUAUUGGGGUCAGCAUAGG 3'), and a sense strand of nucleic acid sequence according to SEQ ID NO: 62 (5' UAUGCUGACCCCAAUACUUA 3').

20-50% Knockdown of CFB at 0.02 nM

In some embodiments of the isolated oligonucleotide of the present disclosure, the sense strand comprises a nucleotide sequence that is substantially identical to a region comprising 19-25 nucleotides between any one of the nucleotide positions selected from a) 493 to 534; b) 991 to 1054; c) 1384 to 1500; d) 1606 to 1686; e) 1821 to 1881; f) 2116 to 2307; and g) 2382 to 2468, from the 5' end of a human CFB mRNA sequence according to SEQ ID NO: 1, and the antisense strand is substantially complementary to the sense strand such that the sense strand and the antisense strand together form a double stranded region, and the isolated oligonucleotide attenuates expression of the CFB mRNA by 20% to 50% (e.g., 20% to 25%, 25% to 30%, 30% to 35%, 35% to 40%, 40% to 45% or 45% to 50%), at a dose of 0.02 nM.

In some embodiments of the isolated oligonucleotide of the present disclosure, the sense strand comprises a nucleotide sequence that is substantially identical to a region comprising 19-25 nucleotides between any one of the nucleotide positions selected from a) 493 to 534; b) 991 to 1054; c) 1384 to 1500; d) 1606 to 1686; e) 1821 to 1881; f) 2116 to 2307; and g) 2382 to 2468, from the 5' end of a human CFB mRNA sequence according to SEQ ID NO: 1, and the antisense strand is substantially complementary to the sense strand such that the sense strand and the antisense strand together form a double stranded region, and the isolated oligonucleotide attenuates expression of the CFB mRNA by 20% to 50% at a dose of 0.02 nM, wherein the double stranded region comprises: i) an antisense strand of nucleic acid sequence according to SEQ ID NO: 8 (5' UUAAGUUGACUAGACACUUUUU 3'), and a sense strand of nucleic acid sequence according to SEQ ID NO: 42 (5' AAAGUGUCUAGUCAACUUAA 3'); ii) an antisense strand of nucleic acid sequence according to SEQ ID NO: 10 (5' UCAAUUAAGUUGACUAGACACU 3'), and a sense strand of nucleic acid sequence according to SEQ ID NO: 44 (5' UGUCUAGUCAACUUAAUUGA 3'); iii) an antisense strand of nucleic acid sequence according to SEQ ID NO: 18 (5' UGAGAUCUUGGCCUGCCAUGGU 3'), and a sense strand of nucleic acid sequence according to SEQ ID NO: 52 (5' CAUGGCAGGCCAAGAUCUCA 3'); iv) an antisense strand of nucleic acid sequence according to SEQ ID NO: 25 (5' UUAUUCUUGAGCUUGAUCAGGG 3'), and a sense strand of nucleic acid sequence according to SEQ ID NO: 59 (5' CUGAUCAAGCUCAAGAAUAA 3'); v) an antisense strand of nucleic acid sequence according to SEQ ID NO: 32 (5' UCAUCUUGGAGUUUCUCCUUCA 3'), and a sense strand of nucleic acid sequence according to SEQ ID NO: 66 (5' AAGGAGAAACUCCAAGAUGA 3'); vi) an antisense strand of nucleic acid sequence according to SEQ ID NO: 31 (5' UUUUUUGCAGACAUCCACUACU 3'), and a sense strand of nucleic acid sequence according to SEQ ID NO: 65 (5' UAGUGGAUGUCUGCAAAAAA 3'); vii) an antisense strand of nucleic acid sequence according to SEQ ID NO: 33 (5' UAACCCAAAUCCUCAUCUUGGA 3'), and a sense strand of nucleic acid sequence according to SEQ ID NO: 67 (5' CAAGAUGAGGAUUUGGGUUA 3'); viii) an antisense strand of nucleic acid sequence according to SEQ ID NO: 26 (5' UUUAUUCUUGAGCUUGAUCAGG 3'), and a sense strand of nucleic acid sequence according to SEQ ID NO: 60 (5' UGAUCAAGCUCAAGAAUAAA 3'); ix) an antisense strand of nucleic acid sequence according to SEQ ID NO: 27 (5' UUUGACUUUGUCAUAGCCUGGG 3'), and a sense strand of nucleic acid sequence according to SEQ ID NO: 61 (5' CAGGCUAUGACAAAGUCAAA 3'); x) an antisense strand of nucleic acid sequence according to SEQ ID NO: 29 (5' UUUCUCUUGUGAACUAUCAAGG 3'), and a sense strand of nucleic acid sequence according to SEQ ID NO: 63 (5' UUGAUAGUUCACAAGAGAAA 3'); xi) an antisense strand of nucleic acid sequence according to SEQ ID NO: 15 (5' UAACACAUGUUGCUCAUUGUCU 3'), and a sense strand of nucleic acid sequence according to SEQ ID NO: 49 (5' ACAAUGAGCAACAUGUGUUA 3'); xii) an antisense strand of nucleic acid sequence according to SEQ ID NO: 16 (5' UUUGACUUUGAACACAUGUUGC 3'), and a sense strand of nucleic acid sequence according to SEQ ID NO: 50 (5' AACAUGUGUUCAAAGUCAAA 3'); xiii) an antisense strand of nucleic acid sequence according to SEQ ID NO: 17 (5' UAUAUCCUUGACUUUGAACACA 3'), and a sense strand of nucleic acid sequence according to SEQ ID NO: 51 (5' UGUUCAAAGUCAAGGAUAUA 3'); xiv) an antisense strand of nucleic acid sequence according to SEQ ID NO: 19 (5' UAAGUACUCAGACACCACAGCC 3'), and a sense strand of nucleic acid sequence according to SEQ ID NO: 53 (5' CUGUGGUGUCUGAGUACUUA 3'); xv) an antisense strand of nucleic acid sequence according to SEQ ID NO: 20 (5' UAUUCAGGAAUUCCUGCUUCUU 3'), and a sense strand of nucleic acid sequence according to SEQ ID NO: 54 (5' GAAGCAGGAAUUCCUGAAUA 3'); xvi) an antisense strand of nucleic acid sequence according to SEQ ID NO: 21 (5' UAAUUCAGGAAUUCCUGCUUCU 3'), and a sense strand of nucleic acid sequence according to SEQ ID NO: 55 (5' AAGCAGGAAUUCCUGAAUUA 3'); xvii) an antisense strand of nucleic acid sequence according to SEQ ID NO: 7 (5' UUUGACUAGACACUUUUUGGCU 3'), and a sense strand of nucleic acid sequence according to SEQ ID NO: 41 (5' CCAAAAAGUGUCUAGUCAAA 3'); or xviii) an antisense strand of nucleic acid sequence according to SEQ ID NO: 11 (5' UAUAUCUUGGCUUCACACCAUA 3'), and a sense strand of nucleic acid sequence according to SEQ ID NO: 45 (5' UGGUGUGAAGCCAAGAUAUA 3').

The present disclosure provides an isolated oligonucleotide comprising a sense strand and an antisense strand, wherein the sense strand comprises a nucleotide sequence that is substantially identical to a region comprising 19-25 nucleotides between any one of the nucleotide positions selected from: a) 5 to 38; b) 340 to 606; c) 776 to 828; d) 939 to 1227; e) 1305 to 1606; f) 1667 to 1746; g) 1815 to 2313; and h) 2378 to 2417, from the 5' end of a CFB mRNA sequence according to SEQ ID NO: 1, and the antisense strand is substantially complementary to the sense strand such that the sense strand and the antisense strand together form a double stranded region.

20-50% Knockdown of CFB at 0.1 nM

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 5 to 38; b) 340 to 606; c) 776 to 828; d) 939 to 1227; e) 1305 to 1606; f) 1667 to 1746; g) 1815 to 2313; and h) 2378 to 2417, from the 5' end of a CFB mRNA sequence according to SEQ ID NO: 1, and the antisense strand is substantially complementary to the sense strand such that the sense strand and the antisense strand together form a double stranded region, and the isolated oligonucleotide attenuates expression of the CFB mRNA by 20% to 50% at a dose of 0.1 nM.

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 5 to 38; b) 340 to 606; c) 776 to 828; d) 939 to 1227; e) 1305 to 1606; f) 1667 to 1746; g) 1815 to 2313; and h) 2378 to 2417, from the 5' end of a CFB mRNA sequence according to SEQ ID NO: 1, and the antisense strand is substantially complementary to the sense strand such that the sense strand and the antisense strand together form a double stranded region, and the isolated oligonucleotide attenuates expression of the CFB mRNA by 20% to 50% at a dose of 0.1 nM, wherein the double stranded region comprises: i) an antisense strand of nucleic acid sequence according to SEQ ID NO: 94 (5' UGACACUUUUUGGCUCCUGUGA 3'), and a sense strand of nucleic acid sequence according to SEQ ID NO: 204 (5' ACAGGAGCCAAAAAGUGUCA 3'); ii) an antisense strand of nucleic acid sequence according to SEQ ID NO: 124 (5' UAUGUUGCUCAUUGUCUUUCUU 3'), and a sense strand of nucleic acid sequence according to SEQ ID NO: 234 (5' GAAAGACAAUGAGCAACAUA 3'); iii) an antisense strand of nucleic acid sequence according to SEQ ID NO: 169 (5' UCUCUUGUGAACUAUCAAGGGG 3'), and a sense strand of nucleic acid sequence according to SEQ ID NO: 279 (5' CCUUGAUAGUUCACAAGAGA 3'); iv) an antisense strand of nucleic acid sequence according to SEQ ID NO: 87 (5' UGUACAUGAAGGAGUCUUGGCA 3'), and a sense strand of nucleic acid sequence according to SEQ ID NO: 197 (5' CCAAGACUCCUUCAUGUACA 3'); v) an antisense strand of nucleic acid sequence according to SEQ ID NO: 163 (5' UGUCAGCAUAGGGACUCACUCC 3'), and a sense strand of nucleic acid sequence according to SEQ ID NO: 273 (5' AGUGAGUCCCUAUGCUGACA 3'); vi) an antisense strand of nucleic acid sequence according to SEQ ID NO: 104 (5' UCUUCAACUUGUGGUCUUCAUA 3'), and a sense strand of nucleic acid sequence according to SEQ ID NO: 214 (5' UGAAGACCACAAGUUGAAGA 3'); vii) an antisense strand of nucleic acid sequence according to SEQ ID NO: 121 (5' UCUCAUUGUCUUUCUUGGAAGC 3'), and a sense strand of nucleic acid sequence according to SEQ ID NO: 231 (5' UUCCAAGAAAGACAAUGAGA 3'); viii) an antisense strand of nucleic acid sequence according to SEQ ID NO: 99 (5' UUUCUCAAUUAAGUUGACUAGA 3'), and a sense strand of nucleic acid sequence according to SEQ ID NO: 209 (5' UAGUCAACUUAAUUGAGAAA 3'); ix) an antisense strand of nucleic acid sequence according to SEQ ID NO: 155 (5' UCUCUCUCACAGCUGCCUUUCU 3'), and a sense strand of nucleic acid sequence according to SEQ ID NO: 265 (5' AAAGGCAGCUGUGAGAGAGA 3'); x) an antisense strand of nucleic acid sequence according to SEQ ID NO: 144 (5' UCUUAUUCUUGAGCUUGAUCAG 3'), and a sense strand of nucleic acid sequence according to SEQ ID NO: 254 (5' GAUCAAGCUCAAGAAUAAGA 3'); xi) an antisense strand of nucleic acid sequence according to SEQ ID NO: 136 (5' UCUGACCUUGAUUGAGUGUUCC 3'), and a sense strand of nucleic acid sequence according to SEQ ID NO: 246 (5' AACACUCAAUCAAGGUCAGA 3'); xii) an antisense strand of nucleic acid sequence according to SEQ ID NO: 76 (5' UGGAUUGCUCUGCACUCUGCCU 3'), and a sense strand of nucleic acid sequence according to SEQ ID NO: 186 (5' GCAGAGUGCAGAGCAAUCCA 3'); xiii) an antisense strand of nucleic acid sequence according to SEQ ID NO: 134 (5' UAACAAUGUGCUGCUGUCAGCA 3'), and a sense strand of nucleic acid sequence according to SEQ ID NO: 244 (5' CUGACAGCAGCACAUUGUUA 3'); xiv) an antisense strand of nucleic acid sequence according to SEQ ID NO: 158 (5' UAUUGAGCAUCUCUCUCACAGC 3'), and a sense strand of nucleic acid sequence according to SEQ ID NO: 268 (5' UGUGAGAGAGAUGCUCAAUA 3'); xv) an antisense strand of nucleic acid sequence according to SEQ ID NO: 153 (5' UCAUUCUUGAUGUAGACCUCCU 3'), and a sense strand of nucleic acid sequence according to SEQ ID NO: 263 (5' GAGGUCUACAUCAAGAAUGA 3'); xvi) an antisense strand of nucleic acid sequence according to SEQ ID NO: 73 (5' UGAAACUCCAGACCUAGACCUG 3'), and a sense strand of nucleic acid sequence according to SEQ ID NO: 183 (5' GGUCUAGGUCUGGAGUUUCA 3'); xvii) an antisense strand of nucleic acid sequence according to SEQ ID NO: 152 (5' UCUUGAUGUAGACCUCCUUCCG 3'), and a sense strand of nucleic acid sequence according to SEQ ID NO: 262 (5' GAAGGAGGUCUACAUCAAGA 3'); xviii) an antisense strand of nucleic acid sequence according to SEQ ID NO: 147 (5' UCAGAGCUUUGAUAUCCUGUGC 3'), and a sense strand of nucleic acid sequence according to SEQ ID NO: 257 (5' ACAGGAUAUCAAAGCUCUGA 3'); xix) an antisense strand of nucleic acid sequence according to SEQ ID NO: 101 (5' UCAUAACUUGCCACCUUCUCAA 3'), and a sense strand of nucleic acid sequence according to SEQ ID NO: 211 (5' GAGAAGGUGGCAAGUUAUGA 3'); xx) an antisense strand of nucleic acid sequence according to SEQ ID NO: 174 (5' UUUCUGGUUUUUGCAGACAUCC 3'), and a sense strand of nucleic acid sequence according to SEQ ID NO: 284 (5' AUGUCUGCAAAAACCAGAAA 3'); xxi) an antisense strand of nucleic acid sequence according to SEQ ID NO: 118 (5' UUUUCUUGGAAGCCAAAGCAUU 3'), and a sense strand of nucleic acid sequence according to SEQ ID NO: 228 (5' UGCUUUGGCUUCCAAGAAAA 3'); xxii) an antisense strand of nucleic acid sequence according to SEQ ID NO: 149 (5' UAAACAGAGCUUUGAUAUCCUG 3'), and a sense strand of nucleic acid sequence according to SEQ ID NO: 259 (5' GGAUAUCAAAGCUCUGUUUA 3'); xxiii) an antisense strand of nucleic acid sequence according to SEQ ID NO: 95 (5' UGACUAGACACUUUUUGGCUCC 3'), and a sense strand of nucleic acid sequence according to SEQ ID NO: 205 (5' AGCCAAAAAGUGUCUAGUCA 3'); xxiv) an antisense strand of nucleic acid sequence according to SEQ ID NO: 142 (5' UUUCUUGAGCUUGAUCAGGGCA 3'), and a sense strand of nucleic acid sequence according to SEQ ID NO: 252 (5' CCCUGAUCAAGCUCAAGAAA 3'); xxv) an antisense strand of nucleic acid sequence according to SEQ ID NO: 160 (5' UCAUAUUGAGCAUCUCUCUCAC 3'), and a sense strand of nucleic acid sequence according to SEQ ID NO: 270 (5' GAGAGAGAUGCUCAAUAUGA 3'); xxvi) an antisense strand of nucleic acid sequence according to SEQ ID NO: 164 (5' UGUAUUGGGGUCAGCAUAGGGA 3'), and a sense strand of nucleic acid sequence according to SEQ ID NO: 274 (5' CCUAUGCUGACCCCAAUACA 3'); xxvii) an antisense strand of nucleic acid sequence according to SEQ ID NO: 74 (5' UUGAAACUCCAGACCUAGACCU 3'), and a sense strand of nucleic acid sequence according to SEQ ID NO: 184 (5' GUCUAGGUCUGGAGUUUCAA 3'); xxviii) an antisense strand of nucleic acid sequence according to SEQ ID NO: 91 (5' UAUCCAUCUAGCACCAGGUAGA 3'), and a sense strand of nucleic acid sequence according to SEQ ID NO: 201 (5' UACCUGGUGCUAGAUGGAUA 3'); xxix) an antisense strand of nucleic acid sequence according to SEQ ID NO: 167 (5' UGUGAACUAUCAAGGGGCCGCC 3'), and a sense strand of nucleic acid sequence according to SEQ ID NO: 277 (5' CGGCCCCUUGAUAGUUCACA 3'); xxx) an antisense strand of nucleic acid sequence according to SEQ ID NO: 175 (5' UUUGGAGUUUCUCCUUCAGCCA 3'), and a sense strand of nucleic acid sequence according to SEQ ID NO: 285 (5' GCUGAAGGAGAAACUCCAAA 3'); xxxi) an antisense strand of nucleic acid sequence according to SEQ ID NO: 72 (5' UAAACUCCAGACCUAGACCUGG 3'), and a sense strand of nucleic acid sequence according to SEQ ID NO: 182 (5' AGGUCUAGGUCUGGAGUUUA 3'); xxxii) an antisense strand of nucleic acid sequence according to SEQ ID NO: 119 (5' UCUUUCUUG- GAAGCCAAAGCAU 3'), and a sense strand of nucleic acid sequence according to SEQ ID NO: 229 (5' GCUUUGGCUUCCAAGAAAGA 3'); xxxiii) an antisense strand of nucleic acid sequence according to SEQ ID NO: 154 (5' UCUUUCUUAUCCCCAUUCUUGA 3'), and a sense strand of nucleic acid sequence according to SEQ ID NO: 264 (5' AAGAAUGGGGAUAAGAAAGA 3'); xxxiv) an antisense strand of nucleic acid sequence according to SEQ ID NO: 70 (5' UCUAGACCUGGUCACAUUCCCU 3'), and a sense strand of nucleic acid sequence according to SEQ ID NO: 180 (5' GGAAUGUGACCAGGUCUAGA 3'); xxxv) an antisense strand of nucleic acid sequence according to SEQ ID NO: 92 (5' UCUGUCUGAUCCAUCUAGCACC 3'), and a sense strand of nucleic acid sequence according to SEQ ID NO: 202 (5' UGCUAGAUGGAUCAGACAGA 3'); xxxvi) an antisense strand of nucleic acid sequence according to SEQ ID NO: 116 (5' UCAAAGCAUUGAUGUUCACUUG 3'), and a sense strand of nucleic acid sequence according to SEQ ID NO: 226 (5' AGUGAACAUCAAUGCUUUGA 3'); xxxvii) an antisense strand of nucleic acid sequence according to SEQ ID NO: 84 (5' UGAGAGUGUAACCGUCAUAGCA 3'), and a sense strand of nucleic acid sequence according to SEQ ID NO: 194 (5' CUAUGACGGUUACACUCUCA 3'); xxxviii) an antisense strand of nucleic acid sequence according to SEQ ID NO: 89 (5' UGUCGUACAUGAAGGAGUCUUG 3'), and a sense strand of nucleic acid sequence according to SEQ ID NO: 199 (5' AGACUCCUUCAUGUACGACA 3'); xxxix) an antisense strand of nucleic acid sequence according to SEQ ID NO: 83 (5' UGAGUGUAACCGUCAUAGCAGU 3'), and a sense strand of nucleic acid sequence according to SEQ ID NO: 193 (5' UGCUAUGACGGUUACACUCA 3'); xL) an antisense strand of nucleic acid sequence according to SEQ ID NO: 107 (5' UUAAUUGGGUCCCCGCCCAUGU 3'), and a sense strand of nucleic acid sequence according to SEQ ID NO: 217 (5' AUGGGCGGGGACCCAAUUAA 3'); xLi) an antisense strand of nucleic acid sequence according to SEQ ID NO: 100 (5' UAUAACUUGCCACCUUCUCAAU 3'), and a sense strand of nucleic acid sequence according to SEQ ID NO: 210 (5' UGAGAAGGUGGCAAGUUAUA 3'); xLii) an antisense strand of nucleic acid sequence according to SEQ ID NO: 157 (5' UUUGAGCAUCUCUCUCACAGCU 3'), and a sense strand of nucleic acid sequence according to SEQ ID NO: 267 (5' CUGUGAGAGAGAUGCUCAAA 3'); xLiii) an antisense strand of nucleic acid sequence according to SEQ ID NO: 77 (5' UCUCACAUUGUAGUAGGGAGAC 3'), and a sense strand of nucleic acid sequence according to SEQ ID NO: 187 (5' CUCCCUACUACAAUGUGAGA 3'); xLiv) an antisense strand of nucleic acid sequence according to SEQ ID NO: 105 (5' UGACUUCAACUUGUGGUCUUCA 3'), and a sense strand of nucleic acid sequence according to SEQ ID NO: 215 (5' AAGACCACAAGUUGAAGUCA 3'); xLv) an antisense strand of nucleic acid sequence according to SEQ ID NO: 130 (5' UCAGGUUUUCCAUAUCCUUGAC 3'), and a sense strand of nucleic acid sequence according to SEQ ID NO: 240 (5' CAAGGAUAUGGAAAACCUGA 3'); xLvi) an antisense strand of nucleic acid sequence according to SEQ ID NO: 166 (5' UAACUAUCAAGGGGCCGCCAGA 3'), and a sense strand of nucleic acid sequence according to SEQ ID NO: 276 (5' UGGCGGCCCCUUGAUAGUUA 3'); xLvii) an antisense strand of nucleic acid sequence according to SEQ ID NO: 131 (5' UCACAGAGACUCAGAGACUGGC 3'), and a sense strand of nucleic acid sequence according to SEQ ID NO: 241 (5' CAGUCUCUGAGUCUCUGUGA 3'); xLviii) an antisense strand of nucleic acid sequence according to SEQ ID NO: 127 (5' UCUUUGAACACAUGUUGCUCAU 3'), and a sense strand of nucleic acid sequence according to SEQ ID NO: 237 (5' GAGCAACAUGUGUUCAAAGA 3'); xLix) an antisense strand of nucleic acid sequence according to SEQ ID NO: 111 (5' UAUCAAUGACAGUAAUUGGGUC 3'), and a sense strand of nucleic acid sequence according to SEQ ID NO: 221 (5' CCCAAUUACUGUCAUUGAUA 3'); L) an antisense strand of nucleic acid sequence according to SEQ ID NO: 93 (5' UCUUUUUGGCUCCUGUGAAGUU 3'), and a sense strand of nucleic acid sequence according to SEQ ID NO: 203 (5' CUUCACAGGAGCCAAAAAGA 3'); or Li) an antisense strand of nucleic acid sequence according to SEQ ID NO: 71 (5' UAACUCCAGACCUAGACCUGGU 3'), and a sense strand of nucleic acid sequence according to SEQ ID NO: 181 (5' CAGGUCUAGGUCUGGAGUUA 3').

At Least 50% Knockdown of CFB at 0.1 nM

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 5 to 38; b) 340 to 606; c) 776 to 828; d) 939 to 1227; e) 1305 to 1606; f) 1667 to 1746; g) 1815 to 2313; and h) 2378 to 2417, from the 5' end of a CFB mRNA sequence according to SEQ ID NO: 1, and the antisense strand is substantially complementary to the sense strand such that the sense strand and the antisense strand together form a double stranded region, and the isolated oligonucleotide attenuates expression of the CFB mRNA by at least 50% at a dose of 0.1 nM.

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 5 to 38; b) 340 to 606; c) 776 to 828; d) 939 to 1227; e) 1305 to 1606; f) 1667 to 1746; g) 1815 to 2313; and h) 2378 to 2417, from the 5' end of a CFB mRNA sequence according to SEQ ID NO: 1, and the antisense strand is substantially complementary to the sense strand such that the sense strand and the antisense strand together form a double stranded region, and the isolated oligonucleotide attenuates expression of the CFB mRNA by at least 50% at a dose of 0.1 nM, wherein the double stranded region comprises: i) an antisense strand of nucleic acid sequence according to SEQ ID NO: 171 (5' UAUGAAACGACUUCUCUUGUGA 3'), and a sense strand of nucleic acid sequence according to SEQ ID NO: 281 (5' ACAAGAGAAGUCGUUUCAUA 3'); ii) an antisense strand of nucleic acid sequence according to SEQ ID NO: 165 (5' UAUCACCUCUGCAAGUAUUGGG 3'), and a sense strand of nucleic acid sequence according to SEQ ID NO: 275 (5' CAAUACUUGCAGAGGUGAUA 3'); iii) an antisense strand of nucleic acid sequence according to SEQ ID NO: 129 (5' UUUUCCAUAUCCUUGACUUUGA 3'), and a sense strand of nucleic acid sequence according to SEQ ID NO: 239 (5' AAAGUCAAGGAUAUGGAAAA 3'); iv) an antisense strand of nucleic acid sequence according to SEQ ID NO: 176 (5' UAUCUUGGAGUUUCUCCUUCAG 3'), and a sense strand of nucleic acid sequence according to SEQ ID NO: 286 (5' GAAGGAGAAACUCCAAGAUA 3'); v) an antisense strand of nucleic acid sequence according to SEQ ID NO: 177 (5' UCUCAUCUUGGAGUUUCUCCUU 3'), and a sense strand of nucleic acid sequence according to SEQ ID NO: 287 (5' GGAGAAACUCCAAGAUGAGA 3'); vi) an antisense strand of nucleic acid sequence according to SEQ ID NO: 138 (5' UCAUAAAAUUCAGGAAUUCCUG 3'), and a sense strand of nucleic acid sequence according to SEQ ID NO: 248 (5' GGAAUUCCUGAAUUUUAUGA 3'); vii) an antisense strand of nucleic acid sequence according to SEQ ID NO: 140 (5' UGUCAUAGU-CAUAAAAUUCAGG 3'), and a sense strand of nucleic acid sequence according to SEQ ID NO: 250 (5' UGAAUUUUAUGACUAUGACA 3'); viii) an antisense strand of nucleic acid sequence according to SEQ ID NO: 148 (5' UAACAGAGCUUUGAUAUCCUGU 3'), and a sense strand of nucleic acid sequence according to SEQ ID NO: 258 (5' AGGAUAUCAAAGCUCUGUUA 3'); ix) an antisense strand of nucleic acid sequence according to SEQ ID NO: 150 (5' UCAAACAGAGCUUUGAUAUCCU 3'), and a sense strand of nucleic acid sequence according to SEQ ID NO: 260 (5' GAUAUCAAAGCUCUGUUUGA 3'); x) an antisense strand of nucleic acid sequence according to SEQ ID NO: 179 (5' UGAAAACCCAAAUCCUCAUCUU 3'), and a sense strand of nucleic acid sequence according to SEQ ID NO: 289 (5' GAUGAGGAUUUGGGUUUUCA 3'); xi) an antisense strand of nucleic acid sequence according to SEQ ID NO: 90 (5' UAAAGCUUCGGCCACCUCUUGA 3'), and a sense strand of nucleic acid sequence according to SEQ ID NO: 200 (5' AAGAGGUGGCCGAAGCUUUA 3'); xii) an antisense strand of nucleic acid sequence according to SEQ ID NO: 172 (5' UUUUUGCAGACAUCCACUA-CUC 3'), and a sense strand of nucleic acid sequence according to SEQ ID NO: 282 (5' GUAGUGGAUGU-CUGCAAAAA 3'); xiii) an antisense strand of nucleic acid sequence according to SEQ ID NO: 88 (5' UCGUA-CAUGAAGGAGUCUUGGC 3'), and a sense strand of nucleic acid sequence according to SEQ ID NO: 198 (5' CAAGACUCCUUCAUGUACGA 3'); xiv) an antisense strand of nucleic acid sequence according to SEQ ID NO: 168 (5' UUUGUGAACUAUCAAGGGGCCG 3'), and a sense strand of nucleic acid sequence according to SEQ ID NO: 278 (5' GCCCCUUGAUAGUUCACAAA 3'); xv) an antisense strand of nucleic acid sequence according to SEQ ID NO: 81 (5' UGUGGAAAGAGAUCUCAUCACU 3'), and a sense strand of nucleic acid sequence according to SEQ ID NO: 191 (5' UGAUGAGAUCUCUUUCCACA 3'); xvi) an antisense strand of nucleic acid sequence according to SEQ ID NO: 159 (5' UAUAUUGAGCAUCUCUCU-CACA 3'), and a sense strand of nucleic acid sequence according to SEQ ID NO: 269 (5' UGAGAGAGAUGCU-CAAUAUA 3'); xvii) an antisense strand of nucleic acid sequence according to SEQ ID NO: 82 (5' UCAUAGCAGUGGAAAGAGAUCU 3'), and a sense strand of nucleic acid sequence according to SEQ ID NO: 192 (5' AUCUCUUUCCACUGCUAUGA 3'); xviii) an antisense strand of nucleic acid sequence according to SEQ ID NO: 97 (5' UUUAAGUUGACUAGACACUUUU 3'), and a sense strand of nucleic acid sequence according to SEQ ID NO: 207 (5' AAGUGUCUAGUCAACUUAAA 3'); xix) an antisense strand of nucleic acid sequence according to SEQ ID NO: 132 (5' UUUGCUUGUGGUAAUCGGUACC 3'), and a sense strand of nucleic acid sequence according to SEQ ID NO: 242 (5' UACCGAUUACCACAAGCAAA 3'); xx) an antisense strand of nucleic acid sequence according to SEQ ID NO: 123 (5' UGUUGCUCAUUGUCUUUC-UUGG 3'), and a sense strand of nucleic acid sequence according to SEQ ID NO: 233 (5' AAGAAA-GACAAUGAGCAACA 3'); xxi) an antisense strand of nucleic acid sequence according to SEQ ID NO: 126 (5' UUUUGAACACAUGUUGCUCAUU 3'), and a sense strand of nucleic acid sequence according to SEQ ID NO: 236 (5' UGAGCAACAUGUGUUCAAAA 3'); xxii) an antisense strand of nucleic acid sequence according to SEQ ID NO: 162 (5' UGAGAUGUCCUUGACUUUGUCA 3'), and a sense strand of nucleic acid sequence according to SEQ ID NO: 272 (5' ACAAAGUCAAGGACAUCUCA 3'); xxiii) an antisense strand of nucleic acid sequence according to SEQ ID NO: 79 (5' UCAUCACUCACAUUGUAGUAGG 3'), and a sense strand of nucleic acid sequence according to SEQ ID NO: 189 (5' UACUACAAUGUGAGUGAUGA 3'); xxiv) an antisense strand of nucleic acid sequence according to SEQ ID NO: 151 (5' UCAGACACAAACAGAGC-UUUGA 3'), and a sense strand of nucleic acid sequence according to SEQ ID NO: 261 (5' AAAGCUCUGUUUGU-GUCUGA 3'); xxv) an antisense strand of nucleic acid sequence according to SEQ ID NO: 143 (5' UAUUC-UUGAGCUUGAUCAGGGC 3'), and a sense strand of nucleic acid sequence according to SEQ ID NO: 253 (5' CCUGAUCAAGCUCAAGAAUA 3'); xxvi) an antisense strand of nucleic acid sequence according to SEQ ID NO: 117 (5' UAAGCCAAAGCAUUGAUGUUCA 3'), and a sense strand of nucleic acid sequence according to SEQ ID NO: 227 (5' AACAUCAAUGCUUUGGCUUA 3'); xxvii) an antisense strand of nucleic acid sequence according to SEQ ID NO: 133 (5' UAAAGUACUCAGACACCACAGC 3'), and a sense strand of nucleic acid sequence according to SEQ ID NO: 243 (5' UGUGGUGUCUGAGUACUUUA 3'); xxviii) an antisense strand of nucleic acid sequence according to SEQ ID NO: 122 (5' UUUGCUCAUUGUCUUUC-UUGGA 3'), and a sense strand of nucleic acid sequence according to SEQ ID NO: 232 (5' CAAGAAA-GACAAUGAGCAAA 3'); xxix) an antisense strand of nucleic acid sequence according to SEQ ID NO: 110 (5' UCAAUGACAGUAAUUGGGUCCC 3'), and a sense strand of nucleic acid sequence according to SEQ ID NO: 220 (5' GACCCAAUUACUGUCAUUGA 3'); xxx) an antisense strand of nucleic acid sequence according to SEQ ID NO: 173 (5' UGUUUUUGCAGACAUCCACUAC 3'), and a sense strand of nucleic acid sequence according to SEQ ID NO: 283 (5' AGUGGAUGUCUGCAAAAACA 3'); xxxi) an antisense strand of nucleic acid sequence according to SEQ ID NO: 156 (5' UGAGCAUCUCUCUCACAGCUGC 3'), and a sense strand of nucleic acid sequence according to SEQ ID NO: 266 (5' AGCUGUGAGAGAGAUGCUCA 3'); xxxii) an antisense strand of nucleic acid sequence according to SEQ ID NO: 141 (5' UCUUGAUCAGGGCAACGU-CAUA 3'), and a sense strand of nucleic acid sequence according to SEQ ID NO: 251 (5' UGACGUUGCC-CUGAUCAAGA 3'); xxxiii) an antisense strand of nucleic acid sequence according to SEQ ID NO: 135 (5' UCUUGAUUGAGUGUUCCUUGUC 3'), and a sense strand of nucleic acid sequence according to SEQ ID NO: 245 (5' CAAGGAACACUCAAUCAAGA 3'); xxxiv) an antisense strand of nucleic acid sequence according to SEQ ID NO: 170 (5' UGACUUCUCUUGUGAACUAUCA 3'), and a sense strand of nucleic acid sequence according to SEQ ID NO: 280 (5' AUAGUUCACAAGAGAAGUCA 3'); xxxv) an antisense strand of nucleic acid sequence according to SEQ ID NO: 178 (5' UAAUCCUCAUCUUG-GAGUUUCU 3'), and a sense strand of nucleic acid sequence according to SEQ ID NO: 288 (5' AAACUC-CAAGAUGAGGAUUA 3'); xxxvi) an antisense strand of nucleic acid sequence according to SEQ ID NO: 114 (5' UAUAGACAUCCAGAUAAUCCUC 3'), and a sense strand of nucleic acid sequence according to SEQ ID NO: 224 (5' GGAUUAUCUGGAUGUCUAUA 3'); xxxvii) an antisense strand of nucleic acid sequence according to SEQ ID NO: 139 (5' UCAUAGUCAUAAAAUUCAGGAA 3'), and a sense strand of nucleic acid sequence according to SEQ ID NO: 249 (5' CCUGAAUUUUAUGACUAUGA 3');

xxxviii) an antisense strand of nucleic acid sequence according to SEQ ID NO: 125 (5' UCAUGUUGCUCAUUGUCUUUCU 3'), and a sense strand of nucleic acid sequence according to SEQ ID NO: 235 (5' AAAGACAAUGAGCAACAUGA 3'); xxxix) an antisense strand of nucleic acid sequence according to SEQ ID NO: 145 (5' UGAGACAAAUGGGCCUGAUAGU 3'), and a sense strand of nucleic acid sequence according to SEQ ID NO: 255 (5' UAUCAGGCCCAUUUGUCUCA 3'); XL) an antisense strand of nucleic acid sequence according to SEQ ID NO: 113 (5' UCUCAUCAAUGACAGUAAUUGG 3'), and a sense strand of nucleic acid sequence according to SEQ ID NO: 223 (5' AAUUACUGUCAUUGAUGAGA 3'); xLi) an antisense strand of nucleic acid sequence according to SEQ ID NO: 120 (5' UGUCUUUCUUGGAAGCCAAAGC 3'), and a sense strand of nucleic acid sequence according to SEQ ID NO: 230 (5' UUUGGCUUCCAAGAAAGACA 3'); xLii) an antisense strand of nucleic acid sequence according to SEQ ID NO: 75 (5' UGAUCUGCAGGUACGUGUCUGC 3'), and a sense strand of nucleic acid sequence according to SEQ ID NO: 185 (5' AGACACGUACCUGCAGAUCA 3'); xLiii) an antisense strand of nucleic acid sequence according to SEQ ID NO: 112 (5' UCAUCAAUGACAGUAAUUGGGU 3'), and a sense strand of nucleic acid sequence according to SEQ ID NO: 222 (5' CCAAUUACUGUCAUUGAUGA 3'); xLiV) an antisense strand of nucleic acid sequence according to SEQ ID NO: 108 (5' UAUGACAGUAAUUGGGUCCCCG 3'), and a sense strand of nucleic acid sequence according to SEQ ID NO: 218 (5' GGGACCCAAUUACUGUCAUA 3'); xLV) an antisense strand of nucleic acid sequence according to SEQ ID NO: 128 (5' UGACUUUGAACACAUGUUGCUC 3'), and a sense strand of nucleic acid sequence according to SEQ ID NO: 238 (5' GCAACAUGUGUUCAAAGUCA 3'); xLVi) an antisense strand of nucleic acid sequence according to SEQ ID NO: 161 (5' UCUUGACUUUGUCAUAGCCUGG 3'), and a sense strand of nucleic acid sequence according to SEQ ID NO: 271 (5' AGGCUAUGACAAAGUCAAGA 3'); xLVii) an antisense strand of nucleic acid sequence according to SEQ ID NO: 85 (5' UUUGUCACAGAUCGCUGUCUGC 3'), and a sense strand of nucleic acid sequence according to SEQ ID NO: 195 (5' AGACAGCGAUCUGUGACAAA 3'); xLviii) an antisense strand of nucleic acid sequence according to SEQ ID NO: 137 (5' UGAAUUCCUGCUUCUUUUUUCC 3'), and a sense strand of nucleic acid sequence according to SEQ ID NO: 247 (5' AAAAAAGAAGCAGGAAUUCA 3'); xLix) an antisense strand of nucleic acid sequence according to SEQ ID NO: 80 (5' UGAAAGAGAUCUCAUCACUCAC 3'), and a sense strand of nucleic acid sequence according to SEQ ID NO: 190 (5' GAGUGAUGAGAUCUCUUUCA 3'); L) an antisense strand of nucleic acid sequence according to SEQ ID NO: 115 (5' UCAUAGACAUCCAGAUAAUCCU 3'), and a sense strand of nucleic acid sequence according to SEQ ID NO: 225 (5' GAUUAUCUGGAUGUCUAUGA 3'); Li) an antisense strand of nucleic acid sequence according to SEQ ID NO: 96 (5' UGUUGACUAGACACUUUUUGGC 3'), and a sense strand of nucleic acid sequence according to SEQ ID NO: 206 (5' CAAAAAGUGUCUAGUCAACA 3'); Lii) an antisense strand of nucleic acid sequence according to SEQ ID NO: 146 (5' UAAGUGGUAGUUGGAGGAAGCC 3'), and a sense strand of nucleic acid sequence according to SEQ ID NO: 256 (5' CUUCCUCCAACUACCACUUA 3'); Liii) an antisense strand of nucleic acid sequence according to SEQ ID NO: 78 (5' UAUCACUCACAUUGUAGUAGGG 3'), and a sense strand of nucleic acid sequence according to SEQ ID NO: 188 (5' CUACUACAAUGUGAGUGAUA 3'); Liv) an antisense strand of nucleic acid sequence according to SEQ ID NO: 103 (5' UUUCACACCAUAACUUGCCACC 3'), and a sense strand of nucleic acid sequence according to SEQ ID NO: 213 (5' UGGCAAGUUAUGGUGUGAAA 3'); Lv) an antisense strand of nucleic acid sequence according to SEQ ID NO: 102 (5' UCACCAUAACUUGCCACCUUCU 3'), and a sense strand of nucleic acid sequence according to SEQ ID NO: 212 (5' AAGGUGGCAAGUUAUGGUGA 3'); Lvi) an antisense strand of nucleic acid sequence according to SEQ ID NO: 109 (5' UAAUGACAGUAAUUGGGUCCCC 3'), and a sense strand of nucleic acid sequence according to SEQ ID NO: 219 (5' GGACCCAAUUACUGUCAUUA 3'); Lvii) an antisense strand of nucleic acid sequence according to SEQ ID NO: 86 (5' UCAUGAAGGAGUCUUGGCAGGA 3'), and a sense strand of nucleic acid sequence according to SEQ ID NO: 196 (5' CUGCCAAGACUCCUUCAUGA 3'); Lviii) an antisense strand of nucleic acid sequence according to SEQ ID NO: 106 (5' UCUCAUCAUGCUGUACACUGCC 3'), and a sense strand of nucleic acid sequence according to SEQ ID NO: 216 (5' CAGUGUACAGCAUGAUGAGA 3'); or Lix) an antisense strand of nucleic acid sequence according to SEQ ID NO: 98 (5' UCUCAAUUAAGUUGACUAGACA 3'), and a sense strand of nucleic acid sequence according to SEQ ID NO: 208 (5' UCUAGUCAACUUAAUUGAGA 3').

20-50% Knockdown of CFB at 0.02 nM

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 5 to 38; b) 340 to 606; c) 776 to 828; d) 939 to 1227; e) 1305 to 1606; f) 1667 to 1746; g) 1815 to 2313; and h) 2378 to 2417, from the 5' end of a CFB mRNA sequence according to SEQ ID NO: 1, and the antisense strand is substantially complementary to the sense strand such that the sense strand and the antisense strand together form a double stranded region, and the isolated oligonucleotide attenuates expression of the CFB mRNA by 20% to 50% at a dose of 0.02 nM.

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 5 to 38; b) 340 to 606; c) 776 to 828; d) 939 to 1227; e) 1305 to 1606; f) 1667 to 1746; g) 1815 to 2313; and h) 2378 to 2417, from the 5' end of a CFB mRNA sequence according to SEQ ID NO: 1, and the antisense strand is substantially complementary to the sense strand such that the sense strand and the antisense strand together form a double stranded region, and the isolated oligonucleotide attenuates expression of the CFB mRNA by 20% to 50% at a dose of 0.02 nM, wherein the double stranded region comprises: i) an antisense strand of nucleic acid sequence according to SEQ ID NO: 165 (5' UAUCACCUCUGCAAGUAUUGGG 3'), and a sense strand of nucleic acid sequence according to SEQ ID NO: 275 (5' CAAUACUUGCAGAGGUGAUA 3'); ii) an antisense strand of nucleic acid sequence according to SEQ ID NO: 129 (5' UUUUCCAUAUCCUUGACUUUGA 3'), and a sense strand of nucleic acid sequence according to SEQ ID NO: 239 (5' AAAGUCAAGGAUAUGGAAAA 3'); iii) an antisense strand of nucleic acid sequence according to SEQ ID NO: 176 (5' UAUCUUGGAGUUUCUCCUUCAG 3'), and a sense strand of nucleic acid sequence according to SEQ ID NO: 286 (5' GAAGGAGAAACUCCAAGAUA 3');

iv) an antisense strand of nucleic acid sequence according to SEQ ID NO: 177 (5' UCUCAUCUUGGAGUUUCUCCUU 3'), and a sense strand of nucleic acid sequence according to SEQ ID NO: 287 (5' GGAGAAACUCCAAGAUGAGA 3'); v) an antisense strand of nucleic acid sequence according to SEQ ID NO: 138 (5' UCAUAAAAUUCAGGAAUUCCUG 3'), and a sense strand of nucleic acid sequence according to SEQ ID NO: 248 (5' GGAAUUCCUGAAUUUUAUGA 3'); vi) an antisense strand of nucleic acid sequence according to SEQ ID NO: 140 (5' UGUCAUAGUCAUAAAAUUCAGG 3'), and a sense strand of nucleic acid sequence according to SEQ ID NO: 250 (5' UGAAUUUUAUGACUAUGACA 3'); vii) an antisense strand of nucleic acid sequence according to SEQ ID NO: 148 (5' UAACAGAGCUUUGAUAUCCUGU 3'), and a sense strand of nucleic acid sequence according to SEQ ID NO: 258 (5' AGGAUAUCAAAGCUCUGUUA 3'); viii) an antisense strand of nucleic acid sequence according to SEQ ID NO: 150 (5' UCAAACAGAGCUUUGAUAUCCU 3'), and a sense strand of nucleic acid sequence according to SEQ ID NO: 260 (5' GAUAUCAAAGCUCUGUUUGA 3'); ix) an antisense strand of nucleic acid sequence according to SEQ ID NO: 179 (5' UGAAAACCCAAAUCCUCAUCUU 3'), and a sense strand of nucleic acid sequence according to SEQ ID NO: 289 (5' GAUGAGGAUUUGGGUUUUCA 3'); x) an antisense strand of nucleic acid sequence according to SEQ ID NO: 90 (5' UAAAGCUUCGGCCACCUCUUGA 3'), and a sense strand of nucleic acid sequence according to SEQ ID NO: 200 (5' AAGAGGUGGCCGAAGCUUUA 3'); xi) an antisense strand of nucleic acid sequence according to SEQ ID NO: 172 (5' UUUUUGCAGACAUCCACUACUC 3'), and a sense strand of nucleic acid sequence according to SEQ ID NO: 282 (5' GUAGUGGAUGUCUGCAAAAA 3'); xii) an antisense strand of nucleic acid sequence according to SEQ ID NO: 88 (5' UCGUACAUGAAGGAGUCUUGGC 3'), and a sense strand of nucleic acid sequence according to SEQ ID NO: 198 (5' CAAGACUCCUUCAUGUACGA 3'); xiii) an antisense strand of nucleic acid sequence according to SEQ ID NO: 168 (5' UUUGUGAACUAUCAAGGGGCCG 3'), and a sense strand of nucleic acid sequence according to SEQ ID NO: 278 (5' GCCCCUUGAUAGUUCACAAA 3'); xiv) an antisense strand of nucleic acid sequence according to SEQ ID NO: 81 (5' UGUGGAAAGAGAUCUCAUCACU 3'), and a sense strand of nucleic acid sequence according to SEQ ID NO: 191 (5' UGAUGAGAUCUCUUUCCACA 3'); xv) an antisense strand of nucleic acid sequence according to SEQ ID NO: 159 (5' UAUAUUGAGCAUCUCUCUCACA 3'), and a sense strand of nucleic acid sequence according to SEQ ID NO: 269 (5' UGAGAGAGAUGCUCAAUAUA 3'); xvi) an antisense strand of nucleic acid sequence according to SEQ ID NO: 82 (5' UCAUAGCAGUGGAAAGAGAUCU 3'), and a sense strand of nucleic acid sequence according to SEQ ID NO: 192 (5' AUCUCUUUCCACUGCUAUGA 3'); xvii) an antisense strand of nucleic acid sequence according to SEQ ID NO: 97 (5' UUUAAGUUGACUAGACACUUUU 3'), and a sense strand of nucleic acid sequence according to SEQ ID NO: 207 (5' AAGUGUCUAGUCAACUUAAA 3'); xiii) an antisense strand of nucleic acid sequence according to SEQ ID NO: 132 (5' UUUGCUUGUGGUAAUCGGUACC 3'), and a sense strand of nucleic acid sequence according to SEQ ID NO: 242 (5' UACCGAUUACCACAAGCAAA 3'); xix) an antisense strand of nucleic acid sequence according to SEQ ID NO: 123 (5' UGUUGCUCAUUGUCUUUCUUGG 3'), and a sense strand of nucleic acid sequence according to SEQ ID NO: 233 (5' AAGAAAGACAAUGAGCAACA 3'); xx) an antisense strand of nucleic acid sequence according to SEQ ID NO: 79 (5' UCAUCACUCACAUUGUAGUAGG 3'), and a sense strand of nucleic acid sequence according to SEQ ID NO: 189 (5' UACUACAAUGUGAGUGAUGA 3'); xxi) an antisense strand of nucleic acid sequence according to SEQ ID NO: 117 (5' UAAGCCAAAGCAUUGAUGUUCA 3'), and a sense strand of nucleic acid sequence according to SEQ ID NO: 227 (5' AACAUCAAUGCUUUGGCUUA 3'); xxii) an antisense strand of nucleic acid sequence according to SEQ ID NO: 122 (5' UUUGCUCAUUGUCUUUCUUGGA 3'), and a sense strand of nucleic acid sequence according to SEQ ID NO: 232 (5' CAAGAAAGACAAUGAGCAAA 3'); xxiii) an antisense strand of nucleic acid sequence according to SEQ ID NO: 110 (5' UCAAUGACAGUAAUUGGGUCCC 3'), and a sense strand of nucleic acid sequence according to SEQ ID NO: 220 (5' GACCCAAUUACUGUCAUUGA 3'); xxxiv) an antisense strand of nucleic acid sequence according to SEQ ID NO: 135 (5' UCUUGAUUGAGUGUUCCUUGUC 3'), and a sense strand of nucleic acid sequence according to SEQ ID NO: 245 (5' CAAGGAACACUCAAUCAAGA 3'); xxv) an antisense strand of nucleic acid sequence according to SEQ ID NO: 178 (5' UAAUCCUCAUCUUGGAGUUUCU 3'), and a sense strand of nucleic acid sequence according to SEQ ID NO: 288 (5' AAACUCCAAGAUGAGGAUUA 3'); xxvi) an antisense strand of nucleic acid sequence according to SEQ ID NO: 114 (5' UAUAGACAUCCAGAUAAUCCUC 3'), and a sense strand of nucleic acid sequence according to SEQ ID NO: 224 (5' GGAUUAUCUGGAUGUCUAUA 3'); xxvii) an antisense strand of nucleic acid sequence according to SEQ ID NO: 125 (5' UCAUGUUGCUCAUUGUCUUUCU 3'), and a sense strand of nucleic acid sequence according to SEQ ID NO: 235 (5' AAAGACAAUGAGCAACAUGA 3'); xxviii) an antisense strand of nucleic acid sequence according to SEQ ID NO: 113 (5' UCUCAUCAAUGACAGUAAUUGG 3'), and a sense strand of nucleic acid sequence according to SEQ ID NO: 223 (5' AAUUACUGUCAUUGAUGAGA 3'); xix) an antisense strand of nucleic acid sequence according to SEQ ID NO: 120 (5' UGUCUUUCUUGGAAGCCAAAGC 3'), and a sense strand of nucleic acid sequence according to SEQ ID NO: 230 (5' UUUGGCUUCCAAGAAAGACA 3'); xxx) an antisense strand of nucleic acid sequence according to SEQ ID NO: 75 (5' UGAUCUGCAGGUACGUGUCUGC 3'), and a sense strand of nucleic acid sequence according to SEQ ID NO: 185 (5' AGACACGUACCUGCAGAUCA 3'); xxxi) an antisense strand of nucleic acid sequence according to SEQ ID NO: 112 (5' UCAUCAAUGACAGUAAUUGGGU 3'), and a sense strand of nucleic acid sequence according to SEQ ID NO: 222 (5' CCAAUUACUGUCAUUGAUGA 3'); xxxii) an antisense strand of nucleic acid sequence according to SEQ ID NO: 108 (5' UAUGACAGUAAUUGGGUCCCCG 3'), and a sense strand of nucleic acid sequence according to SEQ ID NO: 218 (5' GGGACCCAAUUACUGUCAUA 3'); xxxiii) an antisense strand of nucleic acid sequence according to SEQ ID NO: 115 (5' UCAUAGACAUCCAGAUAAUCCU 3'), and a sense strand of nucleic acid sequence according to SEQ ID NO: 225 (5' GAUUAUCUGGAUGUCUAUGA 3'); xxxiv) an antisense strand of nucleic acid sequence according to SEQ ID NO: 102 (5' UCACCAUAACUUGCCACCUUCU 3'), and a sense strand of nucleic acid sequence according to SEQ ID NO: 212 (5' AAGGUGGCAAGUUAUGGUGA 3'); xxxv) an antisense strand of nucleic acid sequence according to SEQ ID NO: 109 (5' UAAUGACAGUAAUUGGGUCCCC 3'), and a sense strand of nucleic acid sequence according to SEQ ID NO: 219 (5' GGACCCAAUUACUGUCAUUA 3'); xxxvi) an antisense strand of nucleic acid sequence according to SEQ ID NO: 106 (5' UCUCAUCAUGCUGUACA-CUGCC 3'), and a sense strand of nucleic acid sequence according to SEQ ID NO: 216 (5' CAGUGUACAG-CAUGAUGAGA 3'); xxxvii) an antisense strand of nucleic acid sequence according to SEQ ID NO: 98 (5' UCU-CAAUUAAGUUGACUAGACA 3'), and a sense strand of nucleic acid sequence according to SEQ ID NO: 208 (5' UCUAGUCAACUUAAUUGAGA 3'); xxxviii) an antisense strand of nucleic acid sequence according to SEQ ID NO: 124 (5' UAUGUUGCUCAUUGUCUUUCUU 3'), and a sense strand of nucleic acid sequence according to SEQ ID NO: 234 (5' GAAAGACAAUGAGCAACAUA 3'); xxxix) an antisense strand of nucleic acid sequence according to SEQ ID NO: 121 (5' UCUCAUUGUCUUUCUUGGAAGC 3'), and a sense strand of nucleic acid sequence according to SEQ ID NO: 231 (5' UUCCAAGAAAGACAAUGAGA 3'); or xL) an antisense strand of nucleic acid sequence according to SEQ ID NO: 107 (5' UUAAUUGGGUCCCCGCC-CAUGU 3'), and a sense strand of nucleic acid sequence according to SEQ ID NO: 217 (5' AUGGGCGGGGACC-CAAUUAA 3').

At Least 50% Knockdown of CFB at 0.02 nM

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 5 to 38; b) 340 to 606; c) 776 to 828; d) 939 to 1227; e) 1305 to 1606; f) 1667 to 1746; g) 1815 to 2313; and h) 2378 to 2417, from the 5' end of a CFB mRNA sequence according to SEQ ID NO: 1, and the antisense strand is substantially complementary to the sense strand such that the sense strand and the antisense strand together form a double stranded region, and the isolated oligonucleotide attenuates expression of the CFB mRNA by at least 50% at a dose of 0.02 nM.

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 5 to 38; b) 340 to 606; c) 776 to 828; d) 939 to 1227; e) 1305 to 1606; f) 1667 to 1746; g) 1815 to 2313; and h) 2378 to 2417, from the 5' end of a CFB mRNA sequence according to SEQ ID NO: 1, and the antisense strand is substantially complementary to the sense strand such that the sense strand and the antisense strand together form a double stranded region, and the isolated oligonucleotide attenuates expression of the CFB mRNA by at least 50% at a dose of 0.02 nM, wherein the double stranded region comprises an antisense strand of nucleic acid sequence according to SEQ ID NO: 171 (5' UAUGAAACGACUUCUCUUGUGA 3'), and a sense strand of nucleic acid sequence according to SEQ ID NO: 281 (5' ACAAGAGAAGUCGUUUCAUA 3').

In Vivo Reduction of CFB Expression

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 493 to 534; b) 995 to 1018; c) 1034 to 1054; d) 1384 to 1404; e) 1431 to 1500; f) 1606 to 1686; g) 1822 to 1849; h) 1860 to 1881; i) 2190 to 2210; j) 2239 to 2262; k) 2287 to 2307; 1) 2382 to 2402; m) 2395 to 2415; and n) 2448 to 2468, from the 5' end of a CFB mRNA sequence according to SEQ ID NO: 1, and the antisense strand is substantially complementary to the sense strand such that the sense strand and the antisense strand together form a double stranded region, and the isolated oligonucleotide attenuates expression of CFB mRNA by at least 25% at a dose of 1 mg/kg.

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 493 to 534; b) 995 to 1018; c) 1034 to 1054; d) 1384 to 1404; e) 1431 to 1500; f) 1606 to 1686; g) 1822 to 1849; h) 1860 to 1881; i) 2190 to 2210; j) 2239 to 2262; k) 2287 to 2307; 1) 2382 to 2402; m) 2395 to 2415; and n) 2448 to 2468, from the 5' end of a CFB mRNA sequence according to SEQ ID NO: 1, and the antisense strand is substantially complementary to the sense strand such that the sense strand and the antisense strand together form a double stranded region, and the isolated oligonucleotide attenuates expression of the CFB mRNA by at least 25% at a dose of 1 mg/kg, wherein the double stranded region comprises: i) an anti-sense strand of nucleic acid sequence according to SEQ ID NO: 2 (5' UAAAGAGAUCUCAUCACUCACA 3'), and a sense strand of nucleic acid sequence according to SEQ ID NO: 36 (5' UGAGUGAUGAGAUCUCUUUA 3'); ii) an anti-sense strand of nucleic acid sequence according to SEQ ID NO: 3 (5' UGGAAAGAGAUCUCAUCACUCA 3'), and a sense strand of nucleic acid sequence according to SEQ ID NO: 37 (5' AGUGAUGAGAUCUCUUUCCA 3'); iii) an anti-sense strand of nucleic acid sequence according to SEQ ID NO: 4 (5' UCAGUGGAAAGAGAUCUCAUCA 3'), and a sense strand of nucleic acid sequence according to SEQ ID NO: 38 (5' AUGAGAUCUCUUUCCACUGA 3'); iv) an anti-sense strand of nucleic acid sequence according to SEQ ID NO: 5 (5' UAUAGCAGUGGAAAGAGAUCUC 3'), and a sense strand of nucleic acid sequence according to SEQ ID NO: 39 (5' GAUCUCUUUCCACUGCUAUA 3'); v) an anti-sense strand of nucleic acid sequence according to SEQ ID NO: 6 (5' UGUGUAACCGUCAUAGCAGUGG 3'), and a sense strand of nucleic acid sequence according to SEQ ID NO: 391 (5' ACUGCUAUGACGGUUACACA 3'); vi) an anti-sense strand of nucleic acid sequence according to SEQ ID NO: 8 (5' UUAAGUUGACUAGACACUUUUU 3'), and a sense strand of nucleic acid sequence according to SEQ ID NO: 42 (5' AAAGUGUCUAGUCAACUUAA 3'); vii) an anti-sense strand of nucleic acid sequence according to SEQ ID NO: 9 (5' UAAUUAAGUUGACUAGACACUU 3'), and a sense strand of nucleic acid sequence according to SEQ ID NO: 43 (5' GUGUCUAGUCAACUUAAUUA 3'); viii) an anti-sense strand of nucleic acid sequence according to SEQ ID NO: 11 (5' UAUAUCUUGGCUUCACACCAUA 3'), and a sense strand of nucleic acid sequence according to SEQ ID NO: 45 (5' UGGUGUGAAGCCAAGAUAUA 3'); ix) an anti-sense strand of nucleic acid sequence according to SEQ ID NO: 12 (5' UUAGACAUCCAGAUAAUC-CUCC 3'), and a sense strand of nucleic acid sequence according to SEQ ID NO: 46 (5' AGGAUUAUCUGGAU-GUCUAA 3'); x) an anti-sense strand of nucleic acid sequence according to SEQ ID NO: 13 (5' UAAGCAUUGAUGUUCACUUGGU 3'), and a sense strand of nucleic acid sequence according to SEQ ID NO: 47 (5' CAAGUGAACAUCAAUGCUUA 3'); xi) an anti-sense strand of nucleic acid sequence according to SEQ ID NO: 14 (5' UAAAGCAUUGAUGUUCACUUGG 3'), and a sense strand of nucleic acid sequence according to SEQ ID NO: 48 (5' AAGUGAACAUCAAUGCUUUA 3'); xii) an anti-sense strand of nucleic acid sequence according to SEQ ID NO: 15 (5' UAACACAUGUUGCUCAUUGUCU 3'), and a sense strand of nucleic acid sequence according to SEQ ID NO: 49 (5' ACAAUGAGCAACAUGUGUUA 3'); xiii) an anti-sense strand of nucleic acid sequence according to SEQ ID NO: 16 (5' UUUGACUUUGAACACAUGUUGC 3'), and a sense strand of nucleic acid sequence according to SEQ ID NO: 50 (5' AACAUGUGUUCAAAGUCAAA 3'); xiv) an anti-sense strand of nucleic acid sequence according to SEQ ID NO: 17 (5' UAUAUCCUUGACUUUGAACACA 3'), and a sense strand of nucleic acid sequence according to SEQ ID NO: 51 (5' UGUUCAAAGUCAAGGAUAUA 3'); xv) an anti-sense strand of nucleic acid sequence according to SEQ ID NO: 18 (5' UGAGAUCUUGGCCUGCCAUGGU 3'), and a sense strand of nucleic acid sequence according to SEQ ID NO: 52 (5' CAUGGCAGGCCAAGAUCUCA 3'); xvi) an anti-sense strand of nucleic acid sequence according to SEQ ID NO: 19 (5' UAAGUACUCAGACACCACAGCC 3'), and a sense strand of nucleic acid sequence according to SEQ ID NO: 53 (5' CUGUGGUGUCUGAGUACUUA 3'); xvii) an anti-sense strand of nucleic acid sequence according to SEQ ID NO: 21 (5' UAAUUCAGGAAUUCCUGCUUCU 3'), and a sense strand of nucleic acid sequence according to SEQ ID NO: 55 (5' AAGCAGGAAUUCCUGAAUUA 3'); xviii) an anti-sense strand of nucleic acid sequence according to SEQ ID NO: 22 (5' UUAAAAUUCAGGAAUUCCUGCU 3'), and a sense strand of nucleic acid sequence according to SEQ ID NO: 56 (5' CAGGAAUUCCUGAAUUUUAA 3'); xix) an anti-sense strand of nucleic acid sequence according to SEQ ID NO: 23 (5' UAUAAAAUUCAGGAAUUCCUGC 3'), and a sense strand of nucleic acid sequence according to SEQ ID NO: 57 (5' AGGAAUUCCUGAAUUUUAUA 3'); xx) an anti-sense strand of nucleic acid sequence according to SEQ ID NO: 24 (5' UGUCAUAAAAUUCAGGAAUUCC 3'), and a sense strand of nucleic acid sequence according to SEQ ID NO: 58 (5' AAUUCCUGAAUUUUAUGACA 3'); xxi) an anti-sense strand of nucleic acid sequence according to SEQ ID NO: 25 (5' UUAUUCUUGAGCUUGAUCAGGG 3'), and a sense strand of nucleic acid sequence according to SEQ ID NO: 59 (5' CUGAUCAAGCUCAAGAAUAA 3'); xxii) an anti-sense strand of nucleic acid sequence according to SEQ ID NO: 26 (5' UUUAUUCUUGAGCUUGAUCAGG 3'), and a sense strand of nucleic acid sequence according to SEQ ID NO: 60 (5' UGAUCAAGCUCAAGAAUAAA 3'); xxiii) an anti-sense strand of nucleic acid sequence according to SEQ ID NO: 28 (5' UAAGUAUUGGGGUCAGCAUAGG 3'), and a sense strand of nucleic acid sequence according to SEQ ID NO: 62 (5' UAUGCUGACCCCAAUACUUA 3'); xxiv) an anti-sense strand of nucleic acid sequence according to SEQ ID NO: 30 (5' UAAACGACUUCUCUUGUGAACU 3'), and a sense strand of nucleic acid sequence according to SEQ ID NO: 64 (5' UUCACAAGAGAAGUCGUUUA 3'); xxv) an anti-sense strand of nucleic acid sequence according to SEQ ID NO: 171 (5' UAUGAAACGACUUCUCUUGUGA 3'), and a sense strand of nucleic acid sequence according to SEQ ID NO: 281 (5' ACAAGAGAAGUCGUUUCAUA 3'); xxvi) an anti-sense strand of nucleic acid sequence according to SEQ ID NO: 31 (5' UUUUUUGCAGACAUCCACUACU 3'), and a sense strand of nucleic acid sequence according to SEQ ID NO: 65 (5' UAGUGGAUGUCUGCAAAAAA 3'); xxvii) an anti-sense strand of nucleic acid sequence according to SEQ ID NO: 32 (5' UCAUCUUGGAGUUUCUCCUUCA 3'), and a sense strand of nucleic acid sequence according to SEQ ID NO: 66 (5' AAGGAGAAACUCCAAGAUGA 3'); xxviii) an anti-sense strand of nucleic acid sequence according to SEQ ID NO: 34 (5' UAAACCCAAAUCCUCAUCUUGG 3'), and a sense strand of nucleic acid sequence according to SEQ ID NO: 68 (5' AAGAUGAGGAUUUGGGUUUA 3'); or xxix) an anti-sense strand of nucleic acid sequence according to SEQ ID NO: 35 (5' UCAGCUGUUUUAAUUCAAUCCC 3'), and a sense strand of nucleic acid sequence according to SEQ ID NO: 69 (5' GAUUGAAUUAAAACAGCUGA 3').

In some embodiments of the isolated oligonucleotide comprising a sense strand and an antisense strand, the sense strand comprises a nucleotide sequence that is substantially identical to a region comprising 19-25 nucleotides between any one of the nucleotide positions selected from: a) 493 to 534; b) 995 to 1018; c) 1034 to 1054; d) 1384 to 1404; e) 1431 to 1500; f) 1606 to 1686; g) 1822 to 1849; h) 1860 to 1881; i) 2190 to 2210; j) 2239 to 2262; k) 2287 to 2307; 1) 2382 to 2402; m) 2395 to 2415; and n) 2448 to 2468, from the 5' end of a CFB mRNA sequence according to SEQ ID NO: 1, and the antisense strand is substantially complementary to the sense strand such that the sense strand and the antisense strand together form a double stranded region, and the isolated oligonucleotide attenuates expression of the CFB mRNA by at least 25% at a dose of 1 mg/kg, wherein the double stranded region comprises: i) an anti-sense strand of nucleic acid sequence according to SEQ ID NO: 2 (5' UAAAGAGAUCUCAUCACUCACA 3'), and a sense strand of nucleic acid sequence according to SEQ ID NO: 36 (5' UGAGUGAUGAGAUCUCUUUA 3'); ii) an anti-sense strand of nucleic acid sequence according to SEQ ID NO: 3 (5' UGGAAAGAGAUCUCAUCACUCA 3'), and a sense strand of nucleic acid sequence according to SEQ ID NO: 37 (5' AGUGAUGAGAUCUCUUUCCA 3'); iii) an anti-sense strand of nucleic acid sequence according to SEQ ID NO: 4 (5' UCAGUGGAAAGAGAUCUCAUCA 3'), and a sense strand of nucleic acid sequence according to SEQ ID NO: 38 (5' AUGAGAUCUCUUUCCACUGA 3'); iv) an anti-sense strand of nucleic acid sequence according to SEQ ID NO: 5 (5' UAUAGCAGUGGAAAGAGAUCUC 3'), and a sense strand of nucleic acid sequence according to SEQ ID NO: 39 (5' GAUCUCUUUCCACUGCUAUA 3'); v) an anti-sense strand of nucleic acid sequence according to SEQ ID NO: 6 (5' UGUGUAACCGUCAUAGCAGUGG 3'), and a sense strand of nucleic acid sequence according to SEQ ID NO: 391 (5' ACUGCUAUGACGGUUACACA 3'); vi) an anti-sense strand of nucleic acid sequence according to SEQ ID NO: 9 (5' UAAUUAAGUUGACUAGACACUU 3'), and a sense strand of nucleic acid sequence according to SEQ ID NO: 43 (5' GUGUCUAGUCAACUUAAUUA 3'); vii) an anti-sense strand of nucleic acid sequence according to SEQ ID NO: 11 (5' UAUAUCUUGGCUUCACACCAUA 3'), and a sense strand of nucleic acid sequence according to SEQ ID NO: 45 (5' UGGUGUGAAGCCAAGAUAUA 3'); viii) an anti-sense strand of nucleic acid sequence according to SEQ ID NO: 12 (5' UUAGACAUCCAGAUAAUCCUCC 3'), and a sense strand of nucleic acid sequence according to SEQ ID NO: 46 (5' AGGAUUAUCUGGAUGUCUAA 3'); ix) an anti-sense strand of nucleic acid sequence according to SEQ ID NO: 13 (5' UAAGCAUUGAUGUUCACUUGGU 3'), and a sense strand of nucleic acid sequence according to SEQ ID NO: 47 (5' CAAGUGAACAUCAAUGCUUA 3'); x) an anti-sense strand of nucleic acid sequence according to SEQ ID NO: 14 (5' UAAAGCAUUGAUGUUCACUUGG 3'), and a sense strand of nucleic acid sequence according to SEQ ID NO: 48 (5' AAGUGAACAUCAAUGCUUUA 3'); xi) an anti-sense strand of nucleic acid sequence according to SEQ ID NO: 15 (5' UAACACAUGUUGCUCAUUGUCU 3'), and a sense strand of nucleic acid sequence according to SEQ ID NO: 49

(5' ACAAUGAGCAACAUGUGUUA 3'); xii) an anti-sense strand of nucleic acid sequence according to SEQ ID NO: 16 (5' UUUGACUUUGAACACAUGUUGC 3'), and a sense strand of nucleic acid sequence according to SEQ ID NO: 50 (5' AACAUGUGUUCAAAGUCAAA 3'); xiii) an anti-sense strand of nucleic acid sequence according to SEQ ID NO: 17 (5' UAUAUCCUUGACUUUGAACACA 3'), and a sense strand of nucleic acid sequence according to SEQ ID NO: 51 (5' UGUUCAAAGUCAAGGAUAUA 3'); xiv) an anti-sense strand of nucleic acid sequence according to SEQ ID NO: 19 (5' UAAGUACUCAGACACCACAGCC 3'), and a sense strand of nucleic acid sequence according to SEQ ID NO: 53 (5' CUGUGGUGUCUGAGUACUUA 3'); xv) an anti-sense strand of nucleic acid sequence according to SEQ ID NO: 21 (5' UAAUUCAGGAAUUCCUGC-UUCU 3'), and a sense strand of nucleic acid sequence according to SEQ ID NO: 55 (5' AAGCAGGAAUUC-CUGAAUUA 3'); xvi) an anti-sense strand of nucleic acid sequence according to SEQ ID NO: 22 (5' UUAAAAUUCAGGAAUUCCUGCU 3'), and a sense strand of nucleic acid sequence according to SEQ ID NO: 56 (5' CAGGAAUUCCUGAAUUUUAA 3'); xvii) an anti-sense strand of nucleic acid sequence according to SEQ ID NO: 23 (5' UAUAAAAUUCAGGAAUUCCUGC 3'), and a sense strand of nucleic acid sequence according to SEQ ID NO: 57 (5' AGGAAUUCCUGAAUUUUAUA 3'); xviii) an anti-sense strand of nucleic acid sequence according to SEQ ID NO: 24 (5' UGUCAUAAAAUUCAGGAAUUCC 3'), and a sense strand of nucleic acid sequence according to SEQ ID NO: 58 (5' AAUUCCUGAAUUUUAUGACA 3'); xix) an anti-sense strand of nucleic acid sequence according to SEQ ID NO: 26 (5' UUUAUUCUUGAGC-UUGAUCAGG 3'), and a sense strand of nucleic acid sequence according to SEQ ID NO: 60 (5' UGAUCAAG-CUCAAGAAUAAA 3'); xx) an anti-sense strand of nucleic acid sequence according to SEQ ID NO: 28 (5' UAAGUAUUGGGGUCAGCAUAGG 3'), and a sense strand of nucleic acid sequence according to SEQ ID NO: 62 (5' UAUGCUGACCCCAAUACUUA 3'); xxi) an anti-sense strand of nucleic acid sequence according to SEQ ID NO: 30 (5' UAAACGACUUCUCUUGUGAACU 3'), and a sense strand of nucleic acid sequence according to SEQ ID NO: 64 (5' UUCACAAGAGAAGUCGUUUA 3'); xxii) an anti-sense strand of nucleic acid sequence according to SEQ ID NO: 171 (5' UAUGAAACGACUUCUCUUGUGA 3'), and a sense strand of nucleic acid sequence according to SEQ ID NO: 281 (5' ACAAGAGAAGUCGUUUCAUA 3'); xxiii) an anti-sense strand of nucleic acid sequence according to SEQ ID NO: 31 (5' UUUUUUGCAGACAUCCACUACU 3'), and a sense strand of nucleic acid sequence according to SEQ ID NO: 65 (5' UAGUGGAUGUCUGCAAAAAA 3'); xxiv) an anti-sense strand of nucleic acid sequence according to SEQ ID NO: 34 (5' UAAACCCAAAUCCUCAUC-UUGG 3'), and a sense strand of nucleic acid sequence according to SEQ ID NO: 68 (5' AAGAUGAGGAUUUGG-GUUUA 3'); or xxv) an anti-sense strand of nucleic acid sequence according to SEQ ID NO: 35 (5' UCAGCU-GUUUUAAUUCAAUCCC 3'), and a sense strand of nucleic acid sequence according to SEQ ID NO: 69 (5' GAUUGAAUUAAAACAGCUGA 3').

In some embodiments, the isolated oligonucleotide of the present disclosure comprises at least one modified nucleotide. In some embodiments of the isolated oligonucleotide of the present disclosure, the sense strand or the antisense strand or both comprise one or more modified nucleotide(s). In some embodiments, only the sense strand comprises one or more modified nucleotide(s). In some embodiments, only the antisense strand comprises one or more modified nucleotide(s). In some embodiments, both the sense strand and antisense strand comprise one or more modified nucleotide (s). In some embodiments, the isolated oligonucleotide is partially chemically modified. In some embodiments, the isolated oligonucleotide is fully chemically modified.

In some embodiments, the isolated oligonucleotide comprises at least two modified nucleotides. In some embodiments, the isolated oligonucleotide comprises at least three modified nucleotides. In some embodiments, the isolated oligonucleotide comprises at least four modified nucleotides. In some embodiments, the isolated oligonucleotide comprises at least five modified nucleotides. In some embodiments, the isolated oligonucleotide comprises at least six modified nucleotides. In some embodiments, the isolated oligonucleotide comprises at least seven modified nucleotides. In some embodiments, the isolated oligonucleotide comprises at least eight modified nucleotides. In some embodiments, the isolated oligonucleotide comprises at least nine modified nucleotides. In some embodiments, the isolated oligonucleotide comprises at least ten modified nucleotides. In some embodiments, the isolated oligonucleotide comprises at least eleven modified nucleotides. In some embodiments, the isolated oligonucleotide comprises at least twelve modified nucleotides. In some embodiments, the isolated oligonucleotide comprises at least thirteen modified nucleotides. In some embodiments, the isolated oligonucleotide comprises at least fourteen modified nucleotides. In some embodiments, the isolated oligonucleotide comprises at least fifteen modified nucleotides. In some embodiments, the isolated oligonucleotide comprises at least sixteen modified nucleotides. In some embodiments, the isolated oligonucleotide comprises at least seventeen modified nucleotides. In some embodiments, the isolated oligonucleotide comprises at least eighteen modified nucleotides. In some embodiments, the isolated oligonucleotide comprises at least nineteen modified nucleotides. In some embodiments, the isolated oligonucleotide comprises at least twenty modified nucleotides. In some embodiments, the isolated oligonucleotide comprises more than twenty modified nucleotides. In some embodiments, the isolated oligonucleotide comprises between twenty and thirty modified nucleotides. In some embodiments, the isolated oligonucleotide comprises between thirty and forty modified nucleotides. In some embodiments, the isolated oligonucleotide comprises between forty and fifty modified nucleotides.

In some embodiments, the sense strand and/or the anti-sense strand of the isolated oligonucleotide each comprise at least one modified nucleotide. In some embodiments, the sense strand and/or the antisense strand of the isolated oligonucleotide each comprise at least two modified nucleotides. In some embodiments, the sense strand and/or the antisense strand of the isolated oligonucleotide each comprise at least three modified nucleotides. In some embodiments, the sense strand and/or the antisense strand of the isolated oligonucleotide each comprise at least four modified nucleotides. In some embodiments, the sense strand and/or the antisense strand of the isolated oligonucleotide each comprise at least five modified nucleotides. In some embodiments, the sense strand and/or the antisense strand of the isolated oligonucleotide each comprise at least six modified nucleotides. In some embodiments, the sense strand and/or the antisense strand of the isolated oligonucleotide each comprise at least seven modified nucleotides. In some embodiments, the sense strand and/or the antisense strand of the isolated oligonucleotide each comprise at least eight modified nucleotides. In some embodiments, the sense strand and/or the antisense strand of the isolated oligonucleotide each comprise at least nine modified nucleotides. In some embodiments, the sense strand and/or the antisense strand of the isolated oligonucleotide each comprise at least ten modified nucleotides. In some embodiments, the sense strand and/or the antisense strand of the isolated oligonucleotide each comprise at least eleven modified nucleotides. In some embodiments, the sense strand and/or the antisense strand of the isolated oligonucleotide each comprise at least twelve modified nucleotides. In some embodiments, the sense strand and/or the antisense strand of the isolated oligonucleotide each comprise at least thirteen modified nucleotides. In some embodiments, the sense strand and/or the antisense strand of the isolated oligonucleotide each comprise at least fourteen modified nucleotides. In some embodiments, the sense strand and/or the antisense strand of the isolated oligonucleotide each comprise at least fifteen modified nucleotides. In some embodiments, the sense strand and/or the antisense strand of the isolated oligonucleotide each comprise at least sixteen modified nucleotides. In some embodiments, the sense strand and/or the antisense strand of the isolated oligonucleotide each comprise at least seventeen modified nucleotides. In some embodiments, the sense strand and/or the antisense strand of the isolated oligonucleotide each comprise at least eighteen modified nucleotides. In some embodiments, the sense strand and/or the antisense strand of the isolated oligonucleotide each comprise at least nineteen modified nucleotides. In some embodiments, the sense strand and/or the antisense strand of the isolated oligonucleotide each comprise at least twenty modified nucleotides.

In some embodiments, wherein the isolated oligonucleotide comprises more than one modified nucleotide, at least a first nucleotide comprises a first modification and at least a second nucleotide comprises a second modification. In some embodiments, the first modification and second modification are different. In some embodiments, the at least first nucleotide and the at least second nucleotide are located on different strands of the isolated oligonucleotide. In some embodiments, the at least first nucleotide and the at least second nucleotide are located on the same strand of the isolated oligonucleotide.

In some embodiments of the isolated oligonucleotide, wherein the isolated oligonucleotide comprises more than one modified nucleotide, at least a first modified nucleotide comprises a first modification, and at least a second modified nucleotide comprises a second modification, and at least a third nucleotide comprises a third modification. In some embodiments, the isolated oligonucleotide comprises a first, a second, a third and a fourth modifications. In some embodiments, the isolated oligonucleotide comprises more than four modifications. In some embodiments, all modifications are on the sense strand. In some embodiments, all modifications are on the antisense strand. Any combination of locations of the modifications between the sense strand and antisense strand is envisaged within the isolated oligonucleotides of the present disclosure.

In some embodiments, the modified nucleotides are consecutively located on the sense strand or the antisense strand or both. In some embodiments, some but not all of the modified nucleotides are consecutively located on the sense strand or the antisense strand or both. In some embodiments, the modified nucleotides on the sense strand or the antisense strand or both are not consecutively located.

Envisaged within the present disclosure is an isolated oligonucleotide, wherein any nucleotide on the sense strand or antisense strand can be modified. In some embodiments, any nucleotide on the antisense strand can be modified. In some embodiments, any nucleotide on the antisense strand can be modified.

In some embodiments, the isolated oligonucleotide of the present disclosure comprises at least one modified nucleotide(s). In some embodiments, the one or more modified nucleotide(s) increases the stability or potency or both of the isolated oligonucleotide. In some embodiments, the one or more modified nucleotide(s) increases the stability of the RNA duplex, and siRNA.

Modifications that increase RNA stability include, but are not limited to, locked nucleic acids. As used herein, the term "locked nucleic acid" or "LNA" includes, but is not limited to, a modified RNA nucleotide in which the ribose moiety comprises a methylene bridge connecting the 2' oxygen and the 4' carbon. This methylene bridge locks the ribose in the 3'-endo confirmation, also known as the north confirmation, that is found in A-form RNA duplexes. The term inaccessible RNA can be used interchangeably with LNA. LNAs having a 2'-4' cyclic linkage, as known in the art.

In some embodiments of the isolated oligonucleotide of the present disclosure, the sense strand or the antisense strand or both comprise at least one nucleotide having a modified phosphate backbone. In some embodiments, the sense strand of the isolated oligonucleotide comprises at least one nucleotide having a modified phosphate backbone. In some embodiments, the antisense strand of the isolated oligonucleotide comprises at least one nucleotide having a modified phosphate backbone. In some embodiments, wherein the isolated oligonucleotide of the present disclosure comprises a modified phosphate backbone, the modified phosphate backbone comprises a modified phosphodiester bond. In some embodiments, the modified phosphodiester bond is modified by replacing one or more oxygen atoms with a moiety, wherein the moiety is bonded to the phosphorus atom in the phosphodiester bond with a carbon, nitrogen, or sulfur atom in the moiety, or by forming a 2'-5' linkage. In some embodiments, the modified phosphodiester bond comprises phosphorothioate, phosphorodithioate, methylphosphonate, phosphoramidate diester, mesyl phosphoramidate, or phosphonoacetate.

In some embodiments, the isolated oligonucleotide of the present disclosure comprises one or more non-natural base-containing nucleotide, a locked nucleotide, or an abasic nucleotide. In some embodiments, the one or more modified nucleotide comprises a phosphorothioate derivative or an acridine substituted nucleotide. In some embodiments, the isolated oligonucleotides of the present disclosure comprise a phosphate mimic at the 5'-terminus of antisense strand, including but not limited to vinylphosphonate or other phosphate analogues. In some embodiments, the 5'-phosphate mimic is ethylphosphonate, vinylphosphonate or an analog thereof.

In some embodiments, the modified nucleotide comprises 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methyl-aminomethyluracil, 5-methoxyaminomethyl-2-thiouracil, beta-D-mannosylqueosine, 5'-methoxycarboxymethyluracil, 5-methoxyuracil, 2-methylthio-N-isopenten-yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, or 2, 6-diaminopurine.

Modification of the Nucleotides

Provided herein is an isolated oligonucleotide, comprising: (a) a sense strand comprising X1 nucleotides, wherein at least one nucleotide is modified with a first modification, each of the remaining nucleotides is independently modified with a second modification, and X1 is an integer selected from 13-36, wherein the first modification and the second modification are different; and (b) an antisense strand comprising X2 nucleotides, wherein at least one nucleotide is modified with a third modification, each of the remaining nucleotides is independently modified with a fourth modification, and X2 is an integer selected from 18-31, wherein the third modification and the fourth modification are different.

In some embodiments, the X1 nucleotides of the sense strand of the isolated oligonucleotide of the present disclosure, is 18-21 and the X2 nucleotides of the antisense strand of the isolated oligonucleotide of the present disclosure is 20-23. In some embodiments, the X1 nucleotides of the sense strand of the isolated oligonucleotide of the present disclosure, is 20 or 21 and the X2 nucleotides of the antisense strand of the isolated oligonucleotide of the present disclosure is 22 or 23. In some embodiments, the X2 nucleotides of the antisense strand of the isolated oligonucleotide of the present disclosure equals the X1 nucleotides of the sense strand of the isolated oligonucleotide of the present disclosure plus 2. In some embodiments, the X1 nucleotides of the sense strand of the isolated oligonucleotide of the present disclosure is 21 and the X2 nucleotides of the antisense strand of the isolated oligonucleotide of the present disclosure is 23. In some embodiments, the X1 nucleotides of the sense strand of the isolated oligonucleotide of the present disclosure is 20 and the X2 nucleotides of the antisense strand of the isolated oligonucleotide of the present disclosure is 22.

In some embodiments of the isolated oligonucleotide of the present disclosure, the isolated oligonucleotide comprises: (a) a sense strand comprising 20 nucleotides, wherein at least one nucleotide is modified with a first modification, each of the remaining nucleotides is independently modified with a second modification, wherein the first modification and the second modification are the same or different; and (b) an antisense strand comprising 22 nucleotides, wherein at least one nucleotide is modified with a third modification, each of the remaining nucleotides is independently modified with a fourth modification, wherein the third modification and the fourth modification are the same or different.

In some embodiments, the first modification is modification of the sugar moiety of the at least one nucleotide at the 2'-position selected from 2'-F modification, 2'-CN modification, 2'-$N_3$ modification, 2'-deoxy modification, and an equivalent thereof, and a combination thereof. In some embodiments, the first modification is 2'-F modification, 2'-CN modification, 2'-$N_3$ modification, or 2'-deoxy modification, or a stereoisomer thereof. In some embodiments, the first modification is 2'-F modification, 2'-CN modification, or 2'-$N_3$ modification, or a stereoisomer thereof. In some embodiments, the first modification is 2'-F modification or a stereoisomer thereof.

In some embodiments, the second modification is modification of the sugar moiety of one or more of the remaining nucleotides at the 2'-position selected from 2'-$C_1$-$C_6$ alkyl, 2'-OR modification wherein R is $C_1$-$C_6$ alkyl optionally substituted with $C_1$-$C_6$ alkoxy, acetamide, phenyl, or heteroaryl comprising a 5- or 6-membered ring and 1 or 2 heteroatoms selected from N, O, and S, 2'-amino, and morpholino replacement, and an equivalent thereof, and a combination thereof. In some embodiments, the second modification is 2'-OR modification, or morpholino replacement, or a combination thereof. In some embodiments, the second modification is 2'-OR modification. In some embodiments, the second modification is 2'-O-methyl modification or 2'-methoxyethoxy modification. In some embodiments, the second modification is 2'-O-methyl modification. In some embodiments, the second modification is morpholino replacement.

In some embodiments, the first modification is 2'-F modification or a stereoisomer thereof, and the second modification is 2'-O-methyl modification or 2'-methoxyethoxy modification. In some embodiments, the first modification is 2'-F modification or a stereoisomer thereof, and the second modification is 2'-O-methyl modification.

In some embodiments, the third modification is modification of the sugar moiety of the at least one nucleotide at the 2'-position selected from 2'-F modification, 2'-CN modification, 2'-$N_3$ modification, 2'-deoxy modification, and an equivalent thereof, and a combination thereof. In some embodiments, the third modification is 2'-F modification, 2'-CN modification, 2'-$N_3$ modification, or 2'-deoxy modification, or a stereoisomer thereof. In some embodiments, the third modification is 2'-F modification, 2'-CN modification, or 2'-$N_3$ modification, or a stereoisomer thereof. In some embodiments, the third modification is 2'-F modification or a stereoisomer thereof.

In some embodiments, the fourth modification is modification of the sugar moiety of one or more of the remaining nucleotides at the 2'-position selected from 2'-$C_1$-$C_6$ alkyl, 2'-OR modification wherein R is $C_1$-$C_6$ alkyl optionally substituted with $C_1$-$C_6$ alkoxy, acetamide, phenyl, or heteroaryl comprising a 5- or 6-membered ring and 1 or 2 heteroatoms selected from N, O, and S, 2'-amino, and morpholino replacement, and an equivalent thereof, and a combination thereof. In some embodiments, the fourth modification is 2'-OR modification, or morpholino replacement, or a combination thereof. In some embodiments, the fourth modification is 2'-OR modification. In some embodiments, the fourth modification is 2'-O-methyl modification or 2'-methoxyethoxy modification. In some embodiments, the fourth modification is 2'-O-methyl modification. In some embodiments, the fourth modification is morpholino replacement.

In some embodiments, the third modification is 2'-F modification or a stereoisomer thereof, and the fourth modification is 2'-O-methyl modification or 2'-methoxyethoxy modification. In some embodiments, the third modification is 2'-F modification or a stereoisomer thereof, and the fourth modification is 2'-O-methyl modification.

Sense Strand

In some embodiments of the isolated oligonucleotide of the present disclosure comprising a sense and an antisense strand, in the sense strand of the isolated oligonucleotide of the present disclosure, at least three nucleotides are modified with the first modification. In some embodiments, in the sense strand of the isolated oligonucleotide of the present disclosure, at least two of the at least three nucleotides modified with the first modification are consecutively located. In some embodiments, in the sense strand of the isolated oligonucleotide of the present disclosure, at least three of the at least three nucleotides modified with the first modification are consecutively located.

In some embodiments, in the sense strand of the isolated oligonucleotide of the present disclosure, at least four nucleotides are modified with the first modification. In some embodiments, in the sense strand of the isolated oligonucleotide of the present disclosure, at least three of the at least four nucleotides modified with the first modification are consecutively located. In some embodiments, in the sense strand of the isolated oligonucleotide of the present disclosure, at least four of the at least four nucleotides modified with the first modification are consecutively located.

In some embodiments, in the sense strand of the isolated oligonucleotide of the present disclosure, at least five nucleotides are modified with the first modification. In some embodiments, in the sense strand of the isolated oligonucleotide of the present disclosure, at least three of the at least five nucleotides modified with the first modification are consecutively located. In some embodiments, in the sense strand of the isolated oligonucleotide of the present disclosure, at least four of the at least five nucleotides modified with the first modification are consecutively located.

In some embodiments, in the sense strand of the isolated oligonucleotide of the present disclosure, the at least three nucleotides, the at least four nucleotides, or the at least five nucleotides modified with the first modification are located from position 10 to position 15 from the nucleotide complementary to the first nucleotide at the 5'-terminus of the antisense strand.

In some embodiments, in the sense strand of the isolated oligonucleotide of the present disclosure, two of the at least three nucleotides modified with the first modification are located at positions selected from position 10, 11, 12, and 13 from the nucleotide complementary to the first nucleotide at the 5'-terminus of the antisense strand. In some embodiments, in the sense strand of the isolated oligonucleotide of the present disclosure, three of the at least three nucleotides modified with the first modification are located at positions selected from position 10, 11, 12, and 13 from the nucleotide complementary to the first nucleotide at the 5'-terminus of the antisense strand. In some embodiments, in the sense strand of the isolated oligonucleotide of the present disclosure, one of the at least three nucleotides modified with the first modification is located at position 11 from the nucleotide complementary to the first nucleotide at the 5'-terminus of the antisense strand.

In some embodiments, in the sense strand of the isolated oligonucleotide of the present disclosure, three of the at least three nucleotides modified with the first modification are located at positions 11, 12 and 13 from the nucleotide complementary to the first nucleotide at the 5'-terminus of the antisense strand. In some embodiments, in the sense strand of the isolated oligonucleotide of the present disclosure, three of the at least three nucleotides modified with the first modification are located at positions 12, 13 and 14 from the nucleotide complementary to the first nucleotide at the 5'-terminus of the antisense strand. In some embodiments, in the sense strand of the isolated oligonucleotide of the present disclosure, three of the at least three nucleotides modified with the first modification are located at positions 10, 11 and 12 from the nucleotide complementary to the first nucleotide at the 5'-terminus of the antisense strand.

In some embodiments, in the sense strand of the isolated oligonucleotide of the present disclosure, one of the at least four nucleotides modified with the first modification is located at position 10 from the nucleotide complementary to the first nucleotide at the 5'-terminus of the antisense strand. In some embodiments, in the sense strand of the isolated oligonucleotide of the present disclosure, one of the at least four nucleotides modified with the first modification is located at position 11 from the nucleotide complementary to the first nucleotide at the 5'-terminus of the antisense strand. In some embodiments, in the sense strand of the isolated oligonucleotide of the present disclosure, one of the at least four nucleotides modified with the first modification is located at position 12 from the nucleotide complementary to the first nucleotide at the 5'-terminus of the antisense strand. In some embodiments, in the sense strand of the isolated oligonucleotide of the present disclosure, one of the at least four nucleotides modified with the first modification is located at position 13 from the nucleotide complementary to the first nucleotide at the 5'-terminus of the antisense strand. In some embodiments, in the sense strand of the isolated oligonucleotide of the present disclosure, one of the at least four nucleotides modified with the first modification is located at position 14 from the nucleotide complementary to the first nucleotide at the 5'-terminus of the antisense strand. In some embodiments, in the sense strand of the isolated oligonucleotide of the present disclosure, one of the at least four nucleotides modified with the first modification is located at position 15 from the nucleotide complementary to the first nucleotide at the 5'-terminus of the antisense strand.

In some embodiments, in the sense strand of the isolated oligonucleotide of the present disclosure, the at least four nucleotides modified with the first modification are located at positions 10, 11, 12 and 13 from the nucleotide complementary to the first nucleotide at the 5'-terminus of the antisense strand.

In some embodiments, in the sense strand of the isolated oligonucleotide of the present disclosure, the at least five nucleotides modified with the first modification are located at positions 10, 11, 12, 13 and 15 from the nucleotide complementary to the first nucleotide at the 5'-terminus of the antisense strand.

In some embodiments of the isolated oligonucleotide of the present disclosure, the sense strand comprises five nucleotides modified with the first modification, wherein the five nucleotides modified with the first modification are located at positions 10, 11, 12, 13 and 15 from the nucleotide complementary to the first nucleotide at the 5'-terminus of the antisense strand.

In some embodiments, in the sense strand of the isolated oligonucleotide of the present disclosure, not all of the at least three nucleotides, the at least four nucleotides, or the at least five nucleotides modified with the first modification are consecutively located. In some embodiments, in the sense strand of the isolated oligonucleotide of the present disclosure, the at least three nucleotides, the at least four nucleotides, or the at least five nucleotides are modified with 2'-F modification.

In some embodiments of the isolated oligonucleotide of the present disclosure, the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_d(M)_c(F)_b(M)_a$ 3', wherein M is 2'-O-methyl modified nucleotide, F is 2'-F modified nucleotide, and a, b, c, d, e, f and g are each independently any one of 0-16, and wherein the sense strand is 5'$(M)_0(F)_0(M)_5(F)_1(M)_1(F)_4(M)_9$ 3'.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_d(M)_c(F)_b(M)_a$ 3', wherein M is 2'-O- methyl modified nucleotide, F is 2'-F modified nucleotide, and a, b, c, d, e, f and g are each independently any one of 0-16, and wherein the sense strand is $5'(M)_0(F)_0(M)_5(F)_1(M)_1(F)_4(M)_9$ 3', the sense strand comprises a nucleotide sequence according to any one of SEQ ID NOs: 37, 39, 49, 55, 56, 58 or 389.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_d(M)_c(F)_b(M)_a$ 3', wherein M is 2'-O-methyl modified nucleotide, F is 2'-F modified nucleotide, and a, b, c, d, e, f and g are each independently any one of 0-16, and wherein the sense strand is $5'(M)_0(F)_0(M)_5(F)_1(M)_1(F)_4(M)_9$ 3', the sense strand comprises a nucleotide sequence according to SEQ ID NO: 58.

In some embodiments of the isolated oligonucleotide of the present disclosure, wherein the sense strand of the isolated oligonucleotide comprises nucleotides modified with 2'-F modification ("F"), and nucleotides modified with 2'-O-methyl modification ("M"), according to the formula: 5' $(M)_g(F)_f(M)_e(F)_d(M)_c(F)_b(M)_a$ 3', wherein M is 2'-O-methyl modified nucleotide, F is 2'-F modified nucleotide, and a, b, c, d, e, f and g are each independently any one of 0-16, and wherein the sense strand is $5'(M)_0(F)_0(M)_5(F)_1(M)_1(F)_4(M)_9$ 3', the sense strand comprises a nucleotide sequence according to SEQ ID NO: 58, and the antisense strand comprises a nucleotide sequence according to SEQ ID NO: 24.

In some embodiments of the isolated oligonucleotide of the present disclosure, wherein the sense strand comprises a nucleotide sequence that is identical to a region between the nucleotide positions 1829 to 1849, from the 5' end of a CFB mRNA sequence according to SEQ ID NO: 1, the double stranded region comprises an antisense strand of nucleic acid sequence according to SEQ ID NO: 24 (5' UGUCAUAAAAUUCAGGAAUUCC 3'), and a sense strand of nucleic acid sequence according to SEQ ID NO: 58 (5' AAUUCCUGAAUUUUAUGACA 3').

In some embodiments of the isolated oligonucleotide of the present disclosure, wherein the sense strand comprises a nucleotide sequence that is identical to a region between the nucleotide positions 1825 to 1845, from the 5' end of a CFB mRNA sequence according to SEQ ID NO: 1, the double stranded region comprises an antisense strand of nucleic acid sequence according to SEQ ID NO: 22 (5' UUAAAAUUCAGGAAUUCCUGCU 3'), and a sense strand of nucleic acid sequence according to SEQ ID NO: 56 (5' CAGGAAUUCCUGAAUUUUAA 3').

In some embodiments of the isolated oligonucleotide of the present disclosure, wherein the sense strand comprises a nucleotide sequence that is identical to a region between the nucleotide positions 1822 to 1842, from the 5' end of a CFB mRNA sequence according to SEQ ID NO: 1, the double stranded region comprises an antisense strand of nucleic acid sequence according to SEQ ID NO: 21 (5' UAAUUCAGGAAUUCCUGCUUCU 3'), and a sense strand of nucleic acid sequence according to SEQ ID NO: 55 (5' AAGCAGGAAUUCCUGAAUUA 3').

In some embodiments of the isolated oligonucleotide of the present disclosure, wherein the sense strand comprises a nucleotide sequence that is identical to a region between the nucleotide positions 1829 to 1849, from the 5' end of a CFB mRNA sequence according to SEQ ID NO: 1, the double stranded region comprises an antisense strand of nucleic acid sequence according to SEQ ID NO: 24 (5' UGUCAUAAAAUUCAGGAAUUCC 3'), and a sense strand of nucleic acid sequence according to SEQ ID NO: 58 (5' AAUUCCUGAAUUUUAUGACA 3').

Antisense Strand

In some embodiments, in the antisense strand of the isolated oligonucleotide of the present disclosure, at most seven nucleotides are modified with the third modification.

In some embodiments, in the antisense strand of the isolated oligonucleotide of the present disclosure, at most four of the at most seven nucleotides modified with the third modification are located from position 2 to position 8 from the first nucleotide at the 5'-terminus of the antisense strand. In some embodiments, in the antisense strand of the isolated oligonucleotide of the present disclosure, at least one of the at most seven nucleotides are modified with the third modification is located at position 2 from the first nucleotide at the 5'-terminus of the antisense strand.

In some embodiments, in the antisense strand of the isolated oligonucleotide of the present disclosure, at most two of the at most seven nucleotides modified with the third modification are consecutively located. In some embodiments, in the antisense strand of the isolated oligonucleotide of the present disclosure, the at most two consecutively located of the at most seven nucleotides modified with the third modification are located at positions 2 and 3 from the first nucleotide at the 5'-terminus of the antisense strand.

In some embodiments, in the antisense strand of the isolated oligonucleotide of the present disclosure, at least one of the at most seven nucleotides modified with the third modification is located at position 14 from the first nucleotide at the 5'-terminus of the antisense strand. In some embodiments, in the antisense strand of the isolated oligonucleotide of the present disclosure, two or three of the at most seven nucleotides modified with the third modification are located at positions selected from position 2, 3, 5, and 6 from the first nucleotide at the 5'-terminus of the antisense strand. In some embodiments, in the antisense strand of the isolated oligonucleotide of the present disclosure, three of the at most seven nucleotides modified with the third modification are located at positions selected from position 2, 3, 5, and 6 from the first nucleotide at the 5'-terminus of the antisense strand. In some embodiments, in the antisense strand of the isolated oligonucleotide of the present disclosure, two of the at most seven nucleotides modified with the third modification are located at positions 2 and 5 from the first nucleotide at the 5'-terminus of the antisense strand. In some embodiments, in the antisense strand of the isolated oligonucleotide of the present disclosure, two of the at most seven nucleotides modified with the third modification are located at positions 2 and 3 from the first nucleotide at the 5'-terminus of the antisense strand.

In some embodiments, in the antisense strand of the isolated oligonucleotide of the present disclosure, three of the at most seven nucleotides modified with the third modification are located at positions 2, 3 and 5 from the first nucleotide at the 5'-terminus of the antisense strand.

In some embodiments, in the antisense strand of the isolated oligonucleotide of the present disclosure, one or two of the at most seven nucleotides modified with the third modification are located at positions selected from position 14 and 16 from the first nucleotide at the 5'-terminus of the antisense strand. In some embodiments, in the antisense strand of the isolated oligonucleotide of the present disclosure, two of the at most seven nucleotides modified with the third modification are located at positions 14 and 16 from the first nucleotide at the 5'-terminus of the antisense strand. In some embodiments, in the antisense strand of the isolated oligonucleotide of the present disclosure, the at most seven nucleotides are modified with 2'-F modification. In some embodiments, in the antisense strand of the isolated oligonucleotide of the present disclosure, one of the at most seven nucleotides modified with the third modification is located at position 14 from the first nucleotide at the 5'-terminus of the antisense strand. In some embodiments, in the antisense strand of the isolated oligonucleotide of the present disclosure, two of the at most seven nucleotides modified with the third modification is located at positions 14 and 16 from the first nucleotide at the 5'-terminus of the antisense strand.

In some embodiments of the isolated oligonucleotides of the present disclosure, wherein the antisense strand comprises at most seven nucleotides modified with the third modification, the at most seven nucleotides are modified with 2'-F modification. In some embodiments, in the antisense strand of the isolated oligonucleotide of the present disclosure, one of the at most seven nucleotides modified with the third modification is located at position 2 from the first nucleotide at the 5'-terminus of the antisense strand. In some embodiments, in the antisense strand of the isolated oligonucleotide of the present disclosure, one of the at most seven nucleotides modified with the third modification is located at position 3 from the first nucleotide at the 5'-terminus of the antisense strand. In some embodiments, in the antisense strand of the isolated oligonucleotide of the present disclosure, one of the at most seven nucleotides modified with the third modification is located at position 5 from the first nucleotide at the 5'-terminus of the antisense strand. In some embodiments, in the antisense strand of the isolated oligonucleotide of the present disclosure, one of the at most seven nucleotides modified with the third modification is located at position 7 from the first nucleotide at the 5'-terminus of the antisense strand. In some embodiments, in the antisense strand of the isolated oligonucleotide of the present disclosure, one of the at most seven nucleotides modified with the third modification is located at position 10 from the first nucleotide at the 5'-terminus of the antisense strand. In some embodiments, in the antisense strand of the isolated oligonucleotide of the present disclosure, one of the at most seven nucleotides modified with the third modification is located at position 14 from the first nucleotide at the 5'-terminus of the antisense strand. In some embodiments, in the antisense strand of the isolated oligonucleotide of the present disclosure, one of the at most seven nucleotides modified with the third modification is located at position 16 from the first nucleotide at the 5'-terminus of the antisense strand. In some embodiments, in the antisense strand of the isolated oligonucleotide of the present disclosure, the at most seven nucleotides modified with the third modification are located at positions 2, 3, 5, 7, 10, 14 and 16 from the first nucleotide at the 5'-terminus of the antisense strand.

In some embodiments, in the antisense strand of the isolated oligonucleotide of the present disclosure, the antisense strand comprises nucleotides modified with 2'-F modification ("F"), and nucleotides modified with 2'-O-methyl modification ("M"), according to the formula: 3' $(M)_a(F)_b(M)_c(F)_a(M)_e(F)_f(M)_g(F)_h(M)_i(F)_j(M)_k(F)_l(M)_m(F)_n(M)_o$ 5', wherein M is 2'-O-methyl modified nucleotide, F is 2'-F modified nucleotide, and a, b, c, d, e, f, g, h, i, j, k, l, m, n and o are each independently any one of 0-16, wherein the antisense strand is any one of: 3'$(M)_0(F)_0(M)_6(F)_1(M)_1(F)_1(M)_3(F)_1(M)_2(F)_1(M)_1(F)_1(M)_1(F)_2(M)_1$ 5'.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: 3' $(M)_a(F)_b(M)_c(F)_a(M)_e(F)_f(M)_g(F)_h(M)_i(F)_j(M)_k(F)_l(M)_m(F)_n(M)_o$ 5', wherein M is 2'-O-methyl modified nucleotide, F is 2'-F modified nucleotide, and a, b, c, d, e, f, g, h, i, j, k, l, m, n and o are each independently any one of 0-16, wherein the antisense strand is any one of: 3'$(M)_0(F)_0(M)_6(F)_1(M)_1(F)_1(M)_3(F)_1(M)_2(F)_1(M)_1(F)_1(M)_1(F)_2(M)_1$ 5', the antisense strand comprises a nucleotide sequence according to any one of SEQ ID NOs: 3, 5, 6, 15, 21, 22 or 24.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: 3' $(M)_a(F)_b(M)_c(F)_a(M)_e(F)_f(M)_g(F)_h(M)_i(F)_j(M)_k(F)_l(M)_m(F)_n(M)_o$ 5', wherein M is 2'-O-methyl modified nucleotide, F is 2'-F modified nucleotide, and a, b, c, d, e, f, g, h, i, j, k, l, m, n and o are each independently any one of 0-16, wherein the antisense strand is any one of: 3'$(M)_0(F)_0(M)_6(F)_1(M)_1(F)_1(M)_3(F)_1(M)_2(F)_1(M)_1(F)_1(M)_1(F)_2(M)_1$ 5', and the antisense strand comprises a nucleotide sequence according to SEQ ID NO: 24.

In some embodiments of the isolated oligonucleotide of the present disclosure, wherein the antisense strand of the isolated oligonucleotide comprises nucleotides modified with 2'-F modification ("F"), and nucleotides modified with 2'-O-methyl modification ("M"), according to the formula: 3' $(M)_a(F)_b(M)_c(F)_a(M)_e(F)_f(M)_g(F)_h(M)_i(F)_j(M)_k(F)_l(M)_m(F)_n(M)_o$ 5', wherein M is 2'-O-methyl modified nucleotide, F is 2'-F modified nucleotide, and a, b, c, d, e, f, g, h, i, j, k, l, m, n and o are each independently any one of 0-16, wherein the antisense strand is any one of: 3'$(M)_0(F)_0(M)_6(F)_1(M)_1(F)_1(M)_3(F)_1(M)_2(F)_1(M)_1(F)_1(M)_1(F)_2(M)_1$ 5', and the antisense strand comprises a nucleotide sequence according to SEQ ID NO: 24, and the sense strand comprises a nucleotide sequence according to SEQ ID NO: 58.

Targeting Ligand

In some embodiments of the isolated oligonucleotide of the present disclosure, the sense strand or the antisense strand or both comprise a terminal or internal nucleotide linked to one or more targeting ligands. In some embodiments, the terminal or internal nucleotide is linked to the one or more targeting ligands directly.

In some embodiments, in the sense strand or the antisense strand or both of the isolated oligonucleotide of the present disclosure, a terminal or internal nucleotide is linked to a targeting ligand. In some embodiments, the targeting ligand is attached to one or more nucleotides at the 5' end of the sense strand of the isolated oligonucleotide of the present disclosure. In some embodiments, the targeting ligand is attached to one or more nucleotides at the 3' end of the sense strand of the isolated oligonucleotide of the present disclosure. In some embodiments, the targeting ligand is attached to one or more nucleotides at the 5' end of the antisense strand of the isolated oligonucleotide of the present disclosure. In some embodiments, the targeting ligand is attached to one or more nucleotides at the 3' end of the antisense strand of the isolated oligonucleotide of the present disclosure. In some embodiments, the targeting ligand is attached to one or more nucleotides of the at least two single-stranded nucleotides at the 3'-terminus of the antisense strand of the isolated oligonucleotide of the present disclosure.

In some embodiments, the targeting ligand is selected from one or more of a carbohydrate, a peptide, a lipid, an antibody or a fragment thereof, an aptamer, an albumin, a fibrinogen, and a folate. In some embodiments, the targeting ligand binds to a surface protein on a cell expressing a target mRNA of the isolated oligonucleotide of the present disclosure. In some embodiments, the targeting ligand mediates entry of the isolated oligonucleotide of the present disclosure, into a cell expressing a target mRNA of the isolated oligonucleotide of the present disclosure.

In some embodiments, the targeting ligand is a therapeutic ligand. In some embodiments, the targeting ligand is a therapeutic antibody.

In some embodiments, the targeting ligand is attached to the isolated oligonucleotide of the present disclosure indirectly by a linker. In some embodiments, the linker is any one or a protein, a DNA, an RNA or a chemical compound.

In some embodiments, the one or more targeting ligands linked directly or indirectly to the terminal or internal nucleotide can further comprise a PK modulator. In some embodiments, the PK modulator is a competitive modulator, a positive allosteric modulator, a negative allosteric modulator or a neutral allosteric modulator.

In some embodiments, the isolated oligonucleotide, the linker and the targeting ligand, of the present disclosure form a scaffold. As used herein, the term "scaffold" refers to a compound or complex that comprises a linker of the present disclosure, wherein the linker is covalently attached to either a ligand or an isolated oligonucleotide or both.

In some embodiments, the isolated oligonucleotide, the linker and the targeting ligand, of the present disclosure form a conjugate. As used herein, the term "conjugate" refers to a compound or complex that comprises an isolated oligonucleotide being covalently attached to a ligand via a linker of the present disclosure.

As used herein, the term "targeting ligand" or "ligand" refers to a moiety that, when being covalently attached to an oligonucleotide either directly or indirectly, is capable of mediating its entry into, or facilitating or allowing its delivery to, a target site (e.g., a target cell or tissue). In some embodiments, the targeting ligand comprises a sugar ligand moiety (e.g., N-acetylgalactosamine (GalNAc)) which may direct uptake of an oligonucleotide into the liver.

In some embodiments, the targeting ligand binds to the asialoglycoprotein receptor (ASGPR). In some embodiments, the targeting ligand binds to (e.g., through ASGPR) the liver, such as the parenchymal cells of the liver.

Suitable targeting ligands are known in the art.

In some embodiments, the targeting ligand comprises a carbohydrate moiety.

As used herein, "carbohydrate moiety" refers to a moiety which comprises one or more monosaccharide units each having at least six carbon atoms (which may be linear, branched or cyclic), with an oxygen, nitrogen or sulfur atom bonded to each carbon atom. In some embodiments, the carbohydrate moiety comprises a monosaccharide, a disaccharide, a trisaccharide, or a tetrasaccharide. In some embodiments, the carbohydrate moiety comprises an oligosaccharide containing from about 4-9 monosaccharide units. In some embodiments, the carbohydrate moiety comprises a polysaccharide (e.g., a starch, a glycogen, a cellulose, or a polysaccharide gum).

In some embodiments, the carbohydrate moiety comprises a monosaccharide, a disaccharide, a trisaccharide, or a tetrasaccharide. In some embodiments, the carbohydrate moiety comprises an oligosaccharide (e.g., containing from about four to about nine monosaccharide units). In some embodiments, the carbohydrate moiety comprises a polysaccharide (e.g., a starch, a glycogen, a cellulose, or a polysaccharide gum).

In some embodiments, the ligand is capable of binding to a human asialoglycoprotein receptor (ASGPR), e.g., human asialoglycoprotein receptor 2 (ASGPR2).

In some embodiments, the carbohydrate moiety comprises a sugar (e.g., one, two, or three sugar). In some embodiments, the carbohydrate moiety comprises galactose or a derivative thereof (e.g., one, two, or three galactose or the derivative thereof). In some embodiments, the carbohydrate moiety comprises N-acetylgalactosamine or a derivative thereof (e.g., one, two, or three N-acetylgalactosamine or the derivative thereof). In some embodiments, the carbohydrate moiety comprises N-acetyl-D-galactosylamine or a derivative thereof (e.g., one, two, or three N-acetyl-D-galactosylamine or the derivative thereof).

In some embodiments, the carbohydrate moiety comprises N-acetylgalactosamine (e.g., one, two, or three N-acetylgalactosamine). In some embodiments, the carbohydrate moiety comprises N-acetyl-D-galactosylamine (e.g., one, two, or three N-acetyl-D-galactosylamine).

In some embodiments, the carbohydrate moiety comprises mannose or a derivative thereof (e.g., mannose-6-phosphate). In some embodiments, the carbohydrate moiety further comprises a linking moiety that connects the one or more sugar (e.g., N-acetyl-D-galactosylamine) with a linker.

In some embodiments the linker comprises thioether (e.g., thiosuccinimide, or the hydrolysis analogue thereof), disulfide, triazole, phosphorothioate, phosphodiester, ester, amide, or any combination thereof. In some embodiments, the linker is a triantennary linking moiety.

In some embodiments, the targeting ligand comprises a lipid or a lipid moiety (e.g., one, two, or three lipid moiety). In some embodiments the lipid moiety comprises (e.g., one, two, of three of) $C_8$-$C_{24}$ fatty acid, cholesterol, vitamin, sterol, phospholipid, or any combination thereof.

In some embodiments, the targeting ligand comprises a peptide or a peptide moiety (e.g., one, two, or three peptide moiety). In some embodiments, the peptide moiety comprises (e.g., one, two, or three of) integrin, insulin, glucagon-like peptide, or any combination thereof. In some embodiments, the targeting ligand comprises an antibody or an antibody moiety (e.g., transferrin). In some embodiments, the targeting ligand comprises one, two, or three antibody moieties (e.g., transferrin).

In some embodiments, the targeting ligand comprises an oligonucleotide (e.g., aptamer or CpG). In some embodiments, the targeting ligand comprises one, two, or three oligonucleotides (e.g., aptamer or CpG).

In some embodiments, the ligand comprises one, two, or three sugar (e.g., N-acetyl-D-galactosylamine); one, two, or three lipid moieties; one, two, or three peptide moieties; one, two, or three antibody moieties; one, two, or three oligonucleotides; or any combination thereof.

In some embodiments, the linker is attached to the isolated oligonucleotide of the present disclosure, via a phosphate group, or an analog of a phosphate group, in the isolated oligonucleotide.

In some embodiments, the ligand comprises a sugar ligand moiety (e.g., N-acetylgalactosamiine (GalNAc)) which may direct uptake of an oligonucleotide into the liver.

In some embodiments, the ligand comprises GalNAc, or a derivative thereof.

In some embodiments, the ligand comprises a GalNAc G1b structure shown below, and as disclosed in PCT patent application WO2023/014938, the content of which is incorporated herein by reference:

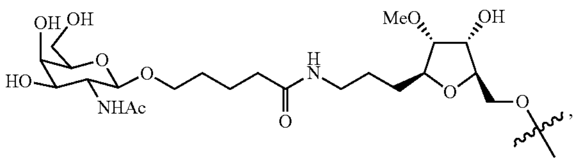

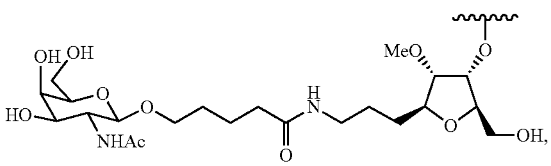

or

-continued

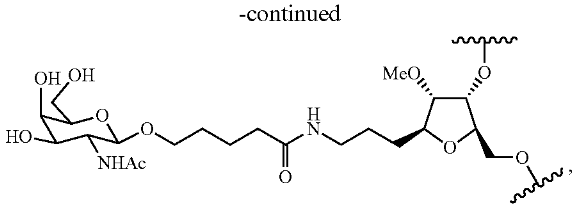

wherein each

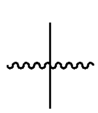

independently indicates the point of attachment to the oligonucleotide compound or another GalNAc G1b moiety In some embodiments, the ligand comprises three GalNAc moieties, or three derivatives thereof. In some embodiments, the ligand comprises three GalNAc G1 b moieties. In some embodiments, wherein the ligand comprises three GalNAc G b moieties, the GalNAc G1b moieties are consecutively located. In some embodiments, the consecutively located GalNAc G1b moieties are located on the 3' end of the sense strand. In some embodiments, wherein the ligand comprises three GalNAc G1b ("G1b") moieties that are consecutively located, the first G1b moiety is linked to the second G1b moiety and the second G1b is linked to the third G1b moiety. In some embodiments, the first GalNAc G1b moiety is linked to the sense strand of the isolated oligonucleotide of the present disclosure.

In some embodiments, the ligand comprises a [GalNAc G1b][GalNAc G1b][GalNAc G1b] moiety, with structure shown below:

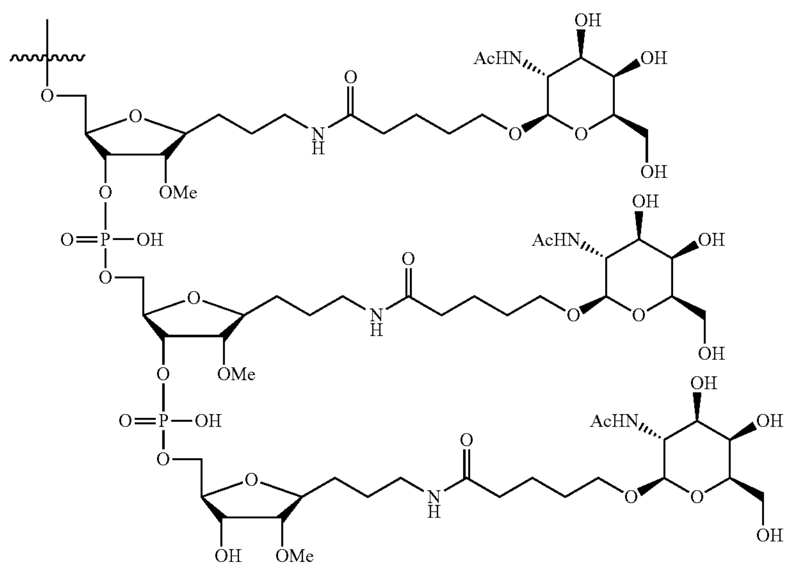

([GalNAc G1b][GalNAc G1b][GalNAc G1b])

In some embodiments of the isolated oligonucleotide of the present disclosure, wherein the ligand comprises three GalNAc G1b ("G1b") moieties, wherein the first GalNAc G1b moiety is linked to the sense strand of the isolated oligonucleotide, the first GalNAc G1b moiety is also linked to the second GalNAc G1b moiety, and the second G1b is linked to the third G b moiety. In some embodiments, wherein the ligand comprises three GalNAc G1b moieties, the three GalNAc G1 b moieties are consecutively located on the 3' end of the sense strand.

In some embodiments of the isolated oligonucleotide of the present disclosure, the isolated oligonucleotide is linked to the ligand (e.g., GalNAc G1b, or three GalNAc G1b moieties). In some embodiments, the isolated oligonucleotide is linked to the ligand via an internal or terminal nucleotide of the isolated oligonucleotide. In some embodiments, the isolated oligonucleotide is linked to the ligand via a ligand linker.

In some embodiments of the isolated oligonucleotide of the present disclosure, wherein the isolated oligonucleotide comprises a sense and an antisense strand, and wherein the ligand comprises three GalNAc G1b moieties, and the three GalNAc G1b moieties are consecutively located on the 3' end of the sense strand, the ligand is linked to a terminal nucleotide on the sense strand of the isolated oligonucleotide. In some embodiments, the ligand is linked to a terminal nucleotide on the sense strand via a ligand linker. In some embodiments, the ligand linker is a monovalent linker. In some embodiments, the ligand linker is a bivalent linker. In some embodiments, the ligand linker is a trivalent linker.

In some embodiments of the isolated oligonucleotide of the present disclosure wherein the sense strand comprises a nucleotide sequence that is identical to a region between the nucleotide positions from 1822 to 1849 from the 5' end of a CFB mRNA sequence according to SEQ ID NO: 1, and the antisense strand is substantially complementary to the sense strand such that the sense strand and the antisense strand together form a double stranded region, a targeting ligand is attached to the 3' end of the sense strand. In some embodiments, the targeting ligand comprises three GalNAc G1b moieties.

In some embodiments of the isolated oligonucleotide of the present disclosure wherein the sense strand comprises a nucleotide sequence that is identical to a region between the nucleotide positions from 1822 to 1849 from the 5' end of a CFB mRNA sequence according to SEQ ID NO: 1, and the antisense strand is substantially complementary to the sense strand such that the sense strand and the antisense strand together form a double stranded region, wherein the targeting ligand comprises three GalNAc G1b moieties attached to the 3' end of the sense strand, the sense strand comprises a nucleic acid sequence according to SEQ ID NO: 55 (5' AAGCAGGAAUUCCUGAAUUA 3'); SEQ ID NO: 56 (5' CAGGAAUUCCUGAAUUUUAA 3') or SEQ ID NO: 58 (5' AAUUCCUGAAUUUUAUGACA 3').

The linkage at the 3' end of the isolated oligonucleotide of the present disclosure may be directly via 5', 3' or 2' hydroxyl groups, or indirectly, via a non-nucleotide linker or a nucleoside, utilizing either the 2' or 3' hydroxyl positions of the nucleoside. Linkages may also utilize a functionalized sugar or nucleobase of a 3' terminal nucleotide. In some embodiments, the ligand described herein can be attached to the isolated oligonucleotide of the present disclosure with various ligand linkers that can be cleavable or non-cleavable.

Modification of the Phosphate Groups

Modified Terminal Phosphate Groups

The present disclosure further provides oligonucleotides and conjugates containing modified phosphate groups (also referred to as phosphate mimics or phosphate derivatives) for nucleic acid delivery. The present disclosure also relates to uses of oligonucleotides and conjugates containing modified phosphate groups, e.g., in delivering nucleic acid and/or treating or preventing diseases.

In some embodiments, the present disclosure provides phosphate mimics of 5'-terminal nucleotides. Without wishing to be bound by theory, it is understood that, when being incorporated into oligonucleotides (e.g., at the 5'-terminus of the antisense strand), the phosphate mimics could improve the Ago2 binding/loading and enhance the metabolic stability of the oligonucleotides, thus enhancing the potency and duration of the isolated oligonucleotides (e.g., dsRNA or siRNA).

In some embodiments of the isolated oligonucleotides of the present disclosure, the oligonucleotides comprise 5'-terminal nucleotide modifications. In some embodiments, the 5'-terminal modifications provide the functional effect of a phosphate group, but are more stable in the environmental conditions that the oligonucleotide will be exposed to when administered to a subject. In some embodiments, the isolated oligonucleotide comprises phosphate mimics that are more resistant to phosphatases and other enzymes while minimizing negative impact on the oligonucleotide's function (e.g., minimizing any reduction in gene target knockdown when used as an RNAi inhibitor molecule).

In some embodiments, the 5'-terminal modification is a chemical modification. In some embodiments, the chemical modification enhances stability against nucleases or other enzymes that degrade or interfere with the structure or activity of the isolated oligonucleotide.

In some embodiments, the sense or antisense strand of the isolated oligonucleotides of the present disclosure comprise a 5'-terminal phosphate group. In some embodiments, the 5'-terminal phosphate group comprises an unmodified phosphate having the formula: —O—P(═O)(OH)OH. In some embodiments, the 5'-terminal phosphate group comprises a modified phosphate. In some embodiments, the 5'-terminal phosphate group comprises a modified phosphate having the formula $—CH_2—P(═X)(OR^1)OR^2$, wherein X is O or S, $R^1$ is H or $C_1$-$C_6$ alkyl, and $R^2$ is H or $C_1$-$C_6$ alkyl. In some embodiments, the modified phosphate is referred to as a "phosphate mimic".

The term, "halo" or "halogen", as used herein, refers to fluoro, chloro, bromo and iodo.

The term, "aryl", as used herein, includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like.

The term, "alkyl" or "$C_1$-$C_6$ alkyl", as used herein, is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms. In some embodiments, the straight chain alkyl has one carbon atom. In some embodiments, the straight chain alkyl has two carbon atoms.

In some embodiments, the phosphate mimic is linked to the 5'-terminus of the isolated oligonucleotides (e.g., siRNAs) as shown in the following formula:

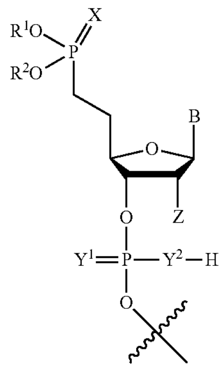

wherein:

B is H or a nucleobase moiety;

X is O or S;

$R^1$ is H or $C_1$-$C_6$ alkyl;

$R^2$ is H or $C_1$-$C_6$ alkyl;

$Y^1$ is O or S;

$Y^2$ is O or S;

Z is H, halogen, or —$OR^Z$;

$R^Z$ is H, $C_1$-$C_6$ alkyl, or —($C_1$-$C_6$ alkyl)-($C_6$-$C_{10}$ aryl), wherein the $C_1$-$C_6$ alkyl or —($C_1$-$C_6$ alkyl)-($C_6$-$C_{10}$ aryl) is optionally substituted with one or more $R^{Za}$;

each $R^{Za}$ independently is halogen, $C_1$-$C_6$ alkyl, or —O—($C_1$-$C_6$ alkyl), wherein the $C_1$-$C_6$ alkyl or —O—($C_1$-$C_6$ alkyl) is optionally substituted with one or more halogen; and

indicates an attachment to a nucleotide of the isolated oligonucleotide (e.g., siRNA).

In some embodiments, the phosphate mimic is linked to the 5'-terminus of the isolated oligonucleotides (e.g., siRNAs) as shown in the following formula:

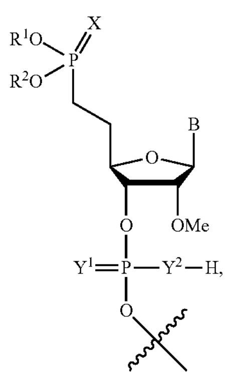

wherein:

B is H or a nucleobase moiety;

X is O or S;

$R^1$ is H or $C_1$-$C_6$ alkyl;

$R^2$ is H or $C_1$-$C_6$ alkyl;

$Y^1$ is O or S;

$Y^2$ is O or S; and

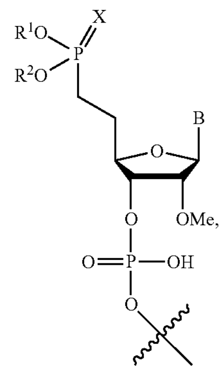

In some embodiments, the phosphate mimic is linked to the 5'-terminus of the isolated oligonucleotides (e.g., siRNAs) as shown in the following formula:

wherein:

B is H or a nucleobase moiety;

X is O or S;

$R^1$ is H or $C_1$-$C_6$ alkyl;

$R^2$ is H or $C_1$-$C_6$ alkyl; and

indicates an attachment to a nucleotide of the isolated oligonucleotide (e.g., siRNA).

In some embodiments, X is O.

In some embodiments, X is S.

In some embodiments, $R^1$ is H.

In some embodiments, $R^1$ is $C_1$-$C_6$ alkyl (e.g., methyl, ethyl, n-propyl, i-propyl, n-butyl, i-butyl, s-butyl, t-butyl, pentyl, or hexyl).

In some embodiments, $R^1$ is methyl.

In some embodiments, $R^2$ is H.

In some embodiments, $R^2$ is $C_1$-$C_6$ alkyl (e.g., methyl, ethyl, n-propyl, i-propyl, n-butyl, i-butyl, s-butyl, t-butyl, pentyl, or hexyl).

In some embodiments, $R^2$ is methyl.

In some embodiments, $Y^1$ is O.

In some embodiments, $Y^1$ is S.

In some embodiments, $Y^2$ is O.

In some embodiments, $Y^2$ is S.

In some embodiments, Z is H.

In some embodiments, Z is not H.

In some embodiments, Z is halogen (e.g., F, Cl, Br, or I).

In some embodiments, Z is F or Cl.

In some embodiments, Z is F

In some embodiments, Z is —$OR^Z$.

In some embodiments, Z is —OH.

In some embodiments, Z is not —OH.

In some embodiments, Z is —O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl).

In some embodiments, Z is —$OCH_3$.

In some embodiments, Z is —O—($C_1$-$C_6$ alkyl)-O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl).

In some embodiments, Z is —$OCH_2CH_2OCH_3$.

In some embodiments, Z is —O—($C_1$-$C_6$ alkyl)-($C_6$-$C_{10}$ aryl) optionally substituted with one or more $R^{Za}$.

In some embodiments, Z is —O—($C_1$-$C_6$ alkyl)-($C_6$-$C_{10}$ aryl).

In some embodiments, Z is

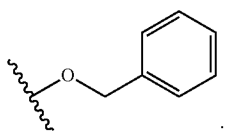 [SMILES: *OCc1ccccc1]

In some embodiments, Z is

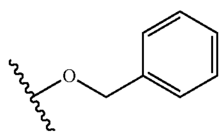 [SMILES: *OCc1ccccc1]

optionally substituted with one or more $R^{Za}$.

In some embodiments, Z is

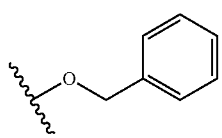 [SMILES: *OCc1ccccc1]

optionally substituted with one or more halogen.

In some embodiments, Z is

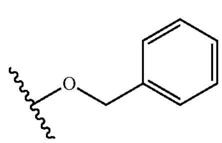 [SMILES: *OCc1ccccc1]

optionally substituted with one or more $C_1$-$C_6$ alkyl or —O—($C_1$-$C_6$ alkyl), wherein the $C_1$-$C_6$ alkyl or —O—($C_1$-$C_6$ alkyl) is optionally substituted with one or more halogen.

In some embodiments, $R^Z$ is H.

In some embodiments, $R^Z$ is not H.

In some embodiments, $R^Z$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more $R^{Za}$.

In some embodiments, $R^Z$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I) or —O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl) optionally substituted with one or more halogen.

In some embodiments, $R^Z$ is $C_1$-$C_6$ alkyl (e.g., methyl, ethyl, n-propyl, i-propyl, n-butyl, i-butyl, s-butyl, t-butyl, pentyl, or hexyl).

In some embodiments, $R^Z$ is methyl, ethyl, or propyl.

In some embodiments, $R^Z$ is methyl.

In some embodiments, $R^Z$ is $C_1$-$C_6$ alkyl (e.g., methyl, ethyl, n-propyl, i-propyl, n-butyl, i-butyl, s-butyl, t-butyl, pentyl, or hexyl) substituted with one or more halogen (e.g., F, Cl, Br, or I).

In some embodiments, $R^Z$ is $C_1$-$C_6$ alkyl (e.g., methyl, ethyl, n-propyl, i-propyl, n-butyl, i-butyl, s-butyl, t-butyl, pentyl, or hexyl) substituted with one or more —O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl), wherein the —O—($C_1$-$C_6$ alkyl) is optionally substituted with one or more halogen.

In some embodiments, $R^Z$ is —($C_1$-$C_6$ alkyl)-($C_6$-$C_{10}$ aryl) optionally substituted with one or more $R^{Za}$.

In some embodiments, $R^Z$ is —($C_1$-$C_6$ alkyl)-($C_6$-$C_{10}$ aryl) optionally substituted with one or more halogen (e.g., F, Cl, Br, or I), $C_1$-$C_6$ alkyl (e.g., methyl, ethyl, n-propyl, i-propyl, n-butyl, i-butyl, s-butyl, t-butyl, pentyl, or hexyl), or —O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl), wherein the $C_1$-$C_6$ alkyl or —O—($C_1$-$C_6$ alkyl) is optionally substituted with one or more halogen.

In some embodiments, $R^Z$ is —($C_1$-$C_6$ alkyl)-($C_6$-$C_{10}$ aryl).

In some embodiments, at least one $R^{Za}$ is halogen (e.g., F, Cl, Br, or I).

In some embodiments, at least one $R^{Za}$ is F or Cl.

In some embodiments, at least one $R^{Za}$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I).

In some embodiments, at least one $R^{Za}$ is $C_1$-$C_6$ alkyl (e.g., methyl, ethyl, n-propyl, i-propyl, n-butyl, i-butyl, s-butyl, t-butyl, pentyl, or hexyl).

In some embodiments, at least one $R^{Za}$ is $C_1$-$C_6$ alkyl (e.g., methyl, ethyl, n-propyl, i-propyl, n-butyl, i-butyl, s-butyl, t-butyl, pentyl, or hexyl) substituted with one or more halogen (e.g., F, Cl, Br, or I).

In some embodiments, at least one $R^{Za}$ is —O—($C_1$-$C_6$ alkyl) optionally substituted with one or more halogen (e.g., F, Cl, Br, or I).

In some embodiments, at least one $R^{Za}$ is —O—($C_1$-$C_6$ alkyl).

In some embodiments, at least one $R^{Za}$ is —O—($C_1$-$C_6$ alkyl) substituted with one or more halogen (e.g., F, Cl, Br, or I).

In some embodiments, B is H.

In some embodiments, B is a nucleobase moiety.

The term "nucleobase moiety", as used herein, refers to a nucleobase that is attached to the rest of the isolated oligonucleotides (e.g., dsRNA or siRNA) of the present disclosure, e.g., via an atom of the nucleobase or a functional group thereof.

In some embodiments, the nucleobase moiety is adenine (A), cytosine (C), guanine (G), thymine (T), or uracil (U).

In some embodiments, the nucleobase moiety is uracil (U).

In some embodiments, the phosphate mimic is linked to the 5'-terminus of the isolated oligonucleotides as shown in the following formula:

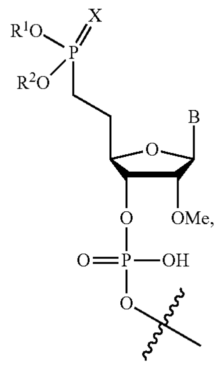

wherein:

B is a nucleobase moiety, wherein the nucleobase moiety is uracil (U), wherein the uracil is at position 1 from the 5'-terminus of the sense strand or at position 1 from the 5'-terminus of the antisense strand;

X is O;

$R^1$ is $C_1$ alkyl;

$R^2$ is H; and

indicates an attachment to a nucleotide of the isolated oligonucleotide (e.g., siRNA).

In some embodiments of the isolated oligonucleotides of the present disclosure, the phosphate mimic is attached to the 5'-terminus of the antisense strand of the isolated oligonucleotide.

In some embodiments, the phosphate mimic is attached to a 5'-terminal uridine of the antisense strand of the isolated oligonucleotide, having the following structure (5'-MeEPmU).

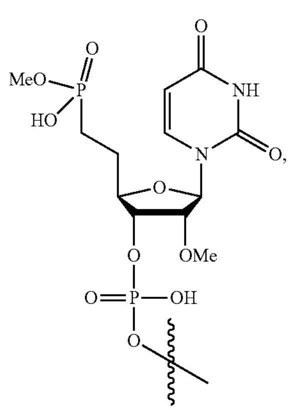

5'-MeEPmU wherein "mU" is a 2'-O-methyl modified uridine nucleotide and "MeEP" is a mono methyl protected phosphate mimic.

In some embodiments, the phosphate mimic is attached to a 5'-terminal uridine of the antisense strand of the isolated oligonucleotide, having the following structure (5'-MeEP-mUs).

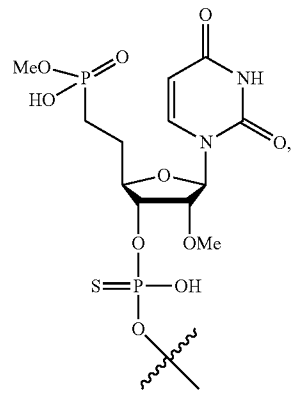

5'-MeEPmUs wherein "mU" is a 2'-O-methyl modified uridine nucleotide, "MeEP" is a mono methyl protected phosphate mimic, and "s" is a phosphorothioate internucleotide linkage.

In some embodiments, the phosphate mimic is attached to a 5'-terminal uridine of the antisense strand of the isolated oligonucleotide, having the following structure (5'-EPmUs).

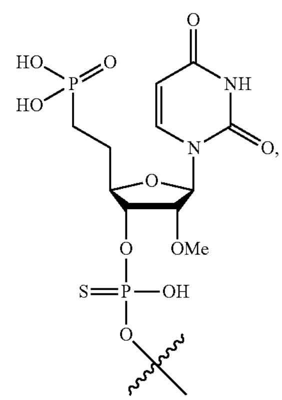

5'-EPmUs wherein "mU" is a 2'-O-methyl modified uridine nucleotide, "EP" is a phosphate mimic, and "s" is a phosphorothioate internucleotide linkage.

The terms "5'-MeEP", "5'-MeEP", and "5' MeEP" are used interchangeably herein.

In some embodiments of the isolated oligonucleotide of the present disclosure wherein the sense strand comprises a nucleotide sequence that is identical to a region between the nucleotide positions from 1822 to 1849 from the 5' end of a CFB mRNA sequence according to SEQ ID NO: 1, and the antisense strand is substantially complementary to the sense strand such that the sense strand and the antisense strand together form a double stranded region, the antisense strand comprises a mono methyl protected phosphate mimic (MeEP). In some embodiments, the MeEP is linked to the 5' end of the antisense strand (5'-MeEP).

In some embodiments, wherein the MeEP is linked to the 5' end of the antisense strand, the phosphate mimic is attached to a 5'-terminal uridine of the antisense strand.

In some embodiments, the 5'-terminal uridine is a 2'-O-methyl modified nucleotide.

In some embodiments of the isolated oligonucleotide of the present disclosure wherein the sense strand comprises a nucleotide sequence that is identical to a region between the nucleotide positions from 1822 to 1849 from the 5' end of a CFB mRNA sequence according to SEQ ID NO: 1, and the antisense strand is substantially complementary to the sense strand such that the sense strand and the antisense strand together form a double stranded region, wherein the antisense strand comprises a 5'-MeEP linked to the 5' end of the antisense strand, the antisense strand comprises a nucleic acid sequence according to SEQ ID NO: 21 (5' UAAUUCAGGAAUUCCUGCUUCU 3'); SEQ ID NO: 22 (5' UUAAAAUUCAGGAAUUCCUGCU 3'); or SEQ ID NO: 24 (5' UGUCAUAAAAUUCAGGAAUUCC 3').

In some embodiments of the isolated oligonucleotide of the present disclosure wherein the sense strand comprises a nucleotide sequence that is identical to a region between the nucleotide positions from 1822 to 1849 from the 5' end of a CFB mRNA sequence according to SEQ ID NO: 1, and the antisense strand is substantially complementary to the sense strand such that the sense strand and the antisense strand together form a double stranded region, wherein the antisense strand comprises a 5'-MeEP linked to the 5' end of the antisense strand, the sense strand comprises a targeting ligand comprising three GalNAc G1b moieties attached to the 3' end of the sense strand.

Modified Backbone Phosphate/Phosphodiester Bond

In some embodiments of the isolated oligonucleotide of the present disclosure, the sense strand or the antisense strand or both comprise at least one nucleotide having a modified phosphate backbone. In some embodiments, the sense strand of the isolated oligonucleotide comprises at least one nucleotide having a modified phosphate backbone. In some embodiments, the antisense strand of the isolated oligonucleotide comprises at least one nucleotide having a modified phosphate backbone. In some embodiments, wherein the isolated oligonucleotide of the present disclosure comprises a modified phosphate backbone, the modified phosphate backbone comprises a modified phosphodiester bond. A phosphodiester bond comprises a linkage having the formula:

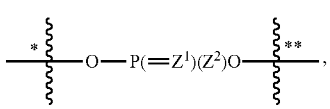

wherein

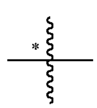

denotes attachment to a 3' carbon of a first nucleotide in the isolated oligonucleotide of the present disclosure; and

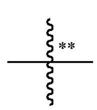

denotes attachment to a 5' carbon of a second nucleotide in the isolated oligonucleotide of the present disclosure. In some embodiments, the phosphodiester bond is unmodified, wherein $Z^1$ is O and $Z^2$ is OH or $O^-$. In some embodiments, the phosphodiester bond is modified, wherein $Z^1$ is O, S, NH, or N($C_1$-$C_6$ alkyl) and $Z^2$ is OH, SH, $NH_2$, NH($C_1$-$C_6$ alkyl), $O^-$, $S^-$, $HN^-$, or ($C_1$-$C_6$ alkyl)$N^-$, and wherein when $Z^1$ is O, $Z^2$ is not OH or $O^-$.

In some embodiments, $Z_1$ is O.

In some embodiments, $Z_1$ is S.

In some embodiments, $Z_1$ is NH.

In some embodiments, $Z_1$ is N($C_1$-$C_6$ alkyl).

In some embodiments, $Z_2$ is OH.

In some embodiments, $Z_2$ is SH.

In some embodiments, $Z_2$ is $NH_2$.

In some embodiments, $Z_2$ is NH($C_1$-$C_6$ alkyl).

In some embodiments, $Z_2$ is SH, $NH_2$, or NH($C_1$-$C_6$ alkyl).

In some embodiments, $Z_2$ is $O^-$.

In some embodiments, $Z_2$ is $S^-$.

In some embodiments, $Z_2$ is $HN^-$.

In some embodiments, $Z_2$ is ($C_1$-$C_6$ alkyl)$N^-$.

In some embodiments, $Z_2$ is $S^-$, $HN^-$, or ($C_1$-$C_6$ alkyl)$N^-$.

In some embodiments, $Z_1$ is O and $Z_2$ is SH.

In some embodiments, $Z_1$ is O and $Z_2$ is $NH_2$.

In some embodiments, $Z_1$ is O and $Z_2$ is NH($C_1$-$C_6$ alkyl).

In some embodiments, $Z_1$ is S and $Z_2$ is OH.

In some embodiments, $Z_1$ is S and $Z_2$ is SH.

In some embodiments, $Z_1$ is S and $Z_2$ is $NH_2$.

In some embodiments, $Z_1$ is S and $Z_2$ is NH($C_1$-$C_6$ alkyl).

In some embodiments, $Z_1$ is NH and $Z_2$ is OH.

In some embodiments, $Z_1$ is NH and $Z_2$ is SH.

In some embodiments, $Z_1$ is NH and $Z_2$ is $NH_2$.

In some embodiments, $Z_1$ is NH and $Z_2$ is NH($C_1$-$C_6$ alkyl).

In some embodiments, $Z_1$ is N($C_1$-$C_6$ alkyl) and $Z_2$ is OH.

In some embodiments, $Z_1$ is N($C_1$-$C_6$ alkyl) and $Z_2$ is SH.

In some embodiments, $Z_1$ is N($C_1$-$C_6$ alkyl) and $Z_2$ is $NH_2$.

In some embodiments, $Z_1$ is N($C_1$-$C_6$ alkyl) and $Z_2$ is NH($C_1$-$C_6$ alkyl).

In some embodiments, $Z_1$ is O and $Z_2$ is $S^-$.

In some embodiments, $Z_1$ is O and $Z_2$ is $HN^-$.

In some embodiments, $Z_1$ is O and $Z_2$ is ($C_1$-$C_6$ alkyl)$N^-$.

In some embodiments, $Z_1$ is S and $Z_2$ is $O^-$.

In some embodiments, $Z_1$ is S and $Z_2$ is $S^-$.

In some embodiments, $Z_1$ is S and $Z_2$ is $HN^-$.

In some embodiments, $Z_1$ is S and $Z_2$ is ($C_1$-$C_6$ alkyl)$N^-$.

In some embodiments, $Z_1$ is NH and $Z_2$ is $O^-$.

In some embodiments, $Z_1$ is NH and $Z_2$ is $S^-$.

In some embodiments, $Z_1$ is NH and $Z_2$ is $HN^-$.

In some embodiments, $Z_1$ is NH and $Z_2$ is ($C_1$-$C_6$ alkyl)$N^-$.

In some embodiments, $Z_1$ is N($C_1$-$C_6$ alkyl) and $Z_2$ is $O^-$.

In some embodiments, $Z_1$ is N($C_1$-$C_6$ alkyl) and $Z_2$ is $S^-$.

In some embodiments, $Z_1$ is N($C_1$-$C_6$ alkyl) and $Z_2$ is $HN^-$.

In some embodiments, $Z_1$ is N($C_1$-$C_6$ alkyl) and $Z_2$ is ($C_1$-$C_6$ alkyl)$N^-$.

In some embodiments, the modified phosphodiester bond comprises a phosphorothioate internucleotide linkage.

In some embodiments, the modified phosphodiester bond comprises

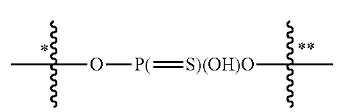

or

-continued

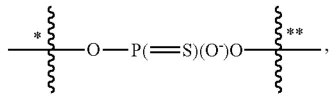

wherein

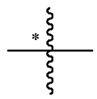

denotes attachment to a 3' carbon of a first nucleotide in the isolated oligonucleotide of the present disclosure; and

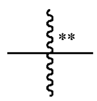

denotes attachment to a 5' carbon of a second nucleotide in the isolated oligonucleotide of the present disclosure.

In some embodiments, the modified phosphodiester bond comprises

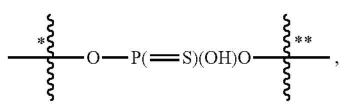

wherein

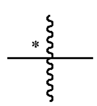

denotes attachment to a 3' carbon of a first nucleotide in the isolated oligonucleotide of the present disclosure; and

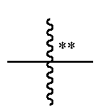

denotes attachment to a 5' carbon of a second nucleotide in the isolated oligonucleotide of the present disclosure.

In some embodiments, the modified phosphodiester bond comprises

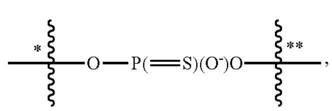

wherein

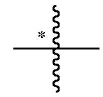

denotes attachment to a 3' carbon of a first nucleotide in the isolated oligonucleotide of the present disclosure; and

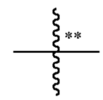

denotes attachment to a 5' carbon of a second nucleotide in the isolated oligonucleotide of the present disclosure.

In some embodiments, the isolated oligonucleotide of the present disclosure comprises at least one modified phosphodiester bond(s). In some embodiments of the isolated oligonucleotide of the present disclosure, the sense strand or the antisense strand or both comprise one or more modified phosphodiester bonds. In some embodiments, only the sense strand comprises one or more modified phosphodiester bonds. In some embodiments, only the antisense strand comprises one or more modified phosphodiester bonds. In some embodiments, both the sense strand and antisense strand comprise one or more modified phosphodiester bonds.

In some embodiments, the isolated oligonucleotide comprises at least two modified phosphodiester bonds. In some embodiments, the isolated oligonucleotide comprises at least three modified phosphodiester bonds. In some embodiments, the isolated oligonucleotide comprises at least four modified phosphodiester bonds. In some embodiments, the isolated oligonucleotide comprises at least five modified phosphodiester bonds. In some embodiments, the isolated oligonucleotide comprises at least six modified phosphodiester bonds. In some embodiments, the isolated oligonucleotide comprises at least seven modified phosphodiester bonds. In some embodiments, the isolated oligonucleotide comprises at least eight modified phosphodiester bonds. In some embodiments, the isolated oligonucleotide comprises at least nine modified phosphodiester bonds. In some embodiments, the isolated oligonucleotide comprises at least ten modified phosphodiester bonds. In some embodiments, the isolated oligonucleotide comprises at least eleven modified phosphodiester bonds. In some embodiments, the isolated oligonucleotide comprises at least twelve modified phosphodiester bonds. In some embodiments, the isolated oligonucleotide comprises at least thirteen modified phosphodiester bonds. In some embodiments, the isolated oligonucleotide comprises at least fourteen modified phosphodiester bonds. In some embodiments, the isolated oligonucleotide comprises at least fifteen modified phosphodiester bonds. In some embodiments, the isolated oligonucleotide comprises at least sixteen modified phosphodiester bonds. In some embodiments, the isolated oligonucleotide comprises at least seventeen modified phosphodiester bonds. In some embodiments, the isolated oligonucleotide comprises at least eighteen modified phosphodiester bonds. In some embodiments, the isolated oligonucleotide comprises at least nineteen modified phosphodiester bonds. In some embodiments, the isolated oligonucleotide comprises at least twenty modified phosphodiester bonds. In some embodiments, the isolated oligonucleotide comprises more than twenty modified phosphodiester bonds. In some embodiments, the isolated oligonucleotide comprises between twenty and thirty modified phosphodiester bonds. In some embodiments, the isolated oligonucleotide comprises between thirty and forty modified phosphodiester bonds. In some embodiments, the isolated oligonucleotide comprises between forty and fifty modified phosphodiester bonds.

In some embodiments, the isolated oligonucleotide comprises at least two phosphorothioate internucleotide linkages. In some embodiments, the isolated oligonucleotide comprises at least three phosphorothioate internucleotide linkages. In some embodiments, the isolated oligonucleotide comprises at least four phosphorothioate internucleotide linkages. In some embodiments, the isolated oligonucleotide comprises at least five phosphorothioate internucleotide linkages. In some embodiments, the isolated oligonucleotide comprises at least six phosphorothioate internucleotide linkages. In some embodiments, the isolated oligonucleotide comprises at least seven phosphorothioate internucleotide linkages. In some embodiments, the isolated oligonucleotide comprises at least eight phosphorothioate internucleotide linkages. In some embodiments, the isolated oligonucleotide comprises at least nine phosphorothioate internucleotide linkages. In some embodiments, the isolated oligonucleotide comprises at least ten phosphorothioate internucleotide linkages. In some embodiments, the isolated oligonucleotide comprises at least eleven phosphorothioate internucleotide linkages. In some embodiments, the isolated oligonucleotide comprises at least twelve phosphorothioate internucleotide linkages. In some embodiments, the isolated oligonucleotide comprises at least thirteen phosphorothioate internucleotide linkages. In some embodiments, the isolated oligonucleotide comprises at least fourteen phosphorothioate internucleotide linkages. In some embodiments, the isolated oligonucleotide comprises at least fifteen phosphorothioate internucleotide linkages. In some embodiments, the isolated oligonucleotide comprises at least sixteen phosphorothioate internucleotide linkages. In some embodiments, the isolated oligonucleotide comprises at least seventeen phosphorothioate internucleotide linkages. In some embodiments, the isolated oligonucleotide comprises at least eighteen phosphorothioate internucleotide linkages. In some embodiments, the isolated oligonucleotide comprises at least nineteen phosphorothioate internucleotide linkages. In some embodiments, the isolated oligonucleotide comprises at least twenty phosphorothioate internucleotide linkages. In some embodiments, the isolated oligonucleotide comprises more than twenty phosphorothioate internucleotide linkages. In some embodiments, the isolated oligonucleotide comprises between twenty and thirty phosphorothioate internucleotide linkages. In some embodiments, the isolated oligonucleotide comprises between thirty and forty phosphorothioate internucleotide linkages. In some embodiments, the isolated oligonucleotide comprises between forty and fifty phosphorothioate internucleotide linkages.

In some embodiments, the sense strand and/or the antisense strand of the isolated oligonucleotide each comprise at least one modified phosphodiester bond(s). In some embodiments, the sense strand and/or the antisense strand of the isolated oligonucleotide each comprise at least two modified phosphodiester bonds. In some embodiments, the sense strand and/or the antisense strand of the isolated oligonucleotide each comprise at least three modified phosphodiester bonds. In some embodiments, the sense strand and/or the antisense strand of the isolated oligonucleotide each comprise at least four modified phosphodiester bonds. In some embodiments, the sense strand and/or the antisense strand of the isolated oligonucleotide each comprise at least five modified phosphodiester bonds. In some embodiments, the sense strand and/or the antisense strand of the isolated oligonucleotide each comprise at least six modified phosphodiester bonds. In some embodiments, the sense strand and/or the antisense strand of the isolated oligonucleotide each comprise at least seven modified phosphodiester bonds. In some embodiments, the sense strand and/or the antisense strand of the isolated oligonucleotide each comprise at least eight modified phosphodiester bonds. In some embodiments, the sense strand and/or the antisense strand of the isolated oligonucleotide each comprise at least nine modified phosphodiester bonds. In some embodiments, the sense strand and/or the antisense strand of the isolated oligonucleotide each comprise at least ten modified phosphodiester bonds. In some embodiments, the sense strand and/or the antisense strand of the isolated oligonucleotide each comprise at least eleven modified phosphodiester bonds. In some embodiments, the sense strand and/or the antisense strand of the isolated oligonucleotide each comprise at least twelve modified phosphodiester bonds. In some embodiments, the sense strand and/or the antisense strand of the isolated oligonucleotide each comprise at least thirteen modified phosphodiester bonds. In some embodiments, the sense strand and/or the antisense strand of the isolated oligonucleotide each comprise at least fourteen modified phosphodiester bonds. In some embodiments, the sense strand and/or the antisense strand of the isolated oligonucleotide each comprise at least fifteen modified phosphodiester bonds. In some embodiments, the sense strand and/or the antisense strand of the isolated oligonucleotide each comprise at least sixteen modified phosphodiester bonds. In some embodiments, the sense strand and/or the antisense strand of the isolated oligonucleotide each comprise at least seventeen modified phosphodiester bonds. In some embodiments, the sense strand and/or the antisense strand of the isolated oligonucleotide each comprise at least eighteen modified phosphodiester bonds. In some embodiments, the sense strand and/or the antisense strand of the isolated oligonucleotide each comprise at least nineteen modified phosphodiester bonds. In some embodiments, the sense strand and/or the antisense strand of the isolated oligonucleotide each comprise at least twenty modified phosphodiester bonds.

In some embodiments, the sense strand and/or the antisense strand of the isolated oligonucleotide each comprise at least one phosphorothioate internucleotide linkage(s). In some embodiments, the sense strand and/or the antisense strand of the isolated oligonucleotide each comprise at least two phosphorothioate internucleotide linkages. In some embodiments, the sense strand and/or the antisense strand of the isolated oligonucleotide each comprise at least three phosphorothioate internucleotide linkages. In some embodiments, the sense strand and/or the antisense strand of the isolated oligonucleotide each comprise at least four phosphorothioate internucleotide linkages. In some embodiments, the sense strand and/or the antisense strand of the isolated oligonucleotide each comprise at least five phosphorothioate internucleotide linkages. In some embodiments, the sense strand and/or the antisense strand of the isolated oligonucleotide each comprise at least six phosphorothioate internucleotide linkages. In some embodiments, the sense strand and/or the antisense strand of the isolated oligonucleotide each comprise at least seven phosphorothioate internucleotide linkages. In some embodiments, the sense strand and/or the antisense strand of the isolated oligonucleotide each comprise at least eight phosphorothioate internucleotide linkages. In some embodiments, the sense strand and/or the antisense strand of the isolated oligonucleotide each comprise at least nine phosphorothioate internucleotide linkages. In some embodiments, the sense strand and/or the antisense strand of the isolated oligonucleotide each comprise at least ten phosphorothioate internucleotide linkages. In some embodiments, the sense strand and/or the antisense strand of the isolated oligonucleotide each comprise at least eleven phosphorothioate internucleotide linkages. In some embodiments, the sense strand and/or the antisense strand of the isolated oligonucleotide each comprise at least twelve phosphorothioate internucleotide linkages. In some embodiments, the sense strand and/or the antisense strand of the isolated oligonucleotide each comprise at least thirteen phosphorothioate internucleotide linkages. In some embodiments, the sense strand and/or the antisense strand of the isolated oligonucleotide each comprise at least fourteen phosphorothioate internucleotide linkages. In some embodiments, the sense strand and/or the antisense strand of the isolated oligonucleotide each comprise at least fifteen phosphorothioate internucleotide linkages. In some embodiments, the sense strand and/or the antisense strand of the isolated oligonucleotide each comprise at least sixteen phosphorothioate internucleotide linkages. In some embodiments, the sense strand and/or the antisense strand of the isolated oligonucleotide each comprise at least seventeen phosphorothioate internucleotide linkages. In some embodiments, the sense strand and/or the antisense strand of the isolated oligonucleotide each comprise at least eighteen phosphorothioate internucleotide linkages. In some embodiments, the sense strand and/or the antisense strand of the isolated oligonucleotide each comprise at least nineteen phosphorothioate internucleotide linkages. In some embodiments, the sense strand and/or the antisense strand of the isolated oligonucleotide each comprise at least twenty phosphorothioate internucleotide linkages.

In some embodiments, the modified phosphodiester bonds are consecutively located on the sense strand or the antisense strand or both. In some embodiments, some but not all of the modified phosphodiester bonds are consecutively located on the sense strand or the antisense strand or both. In some embodiments, the modified phosphodiester bonds on the sense strand or the antisense strand or both are not consecutively located.

Envisaged within the present disclosure is an isolated oligonucleotide, wherein any phosphodiester bond on the sense strand or antisense strand can be modified. In some embodiments, any phosphodiester bond on the antisense strand can be modified. In some embodiments, any phosphodiester bond on the antisense strand can be modified.

In some embodiments of the isolated oligonucleotide of the present disclosure, the antisense strand comprises between one and twenty, between one and fifteen, between one and ten, between one and five, or less than five modified phosphodiester bonds. In some embodiments, the between one and twenty, between one and fifteen, between one and ten, between one and five, or less than five modified phosphodiester bonds comprise phosphorothioate internucleotide linkages. In some embodiments, the antisense strand comprises less than five modified phosphodiester bonds. In some embodiments, the antisense strand comprises one, two, three, or four modified phosphodiester bonds. In some embodiments, wherein the antisense strand comprises one, two, three, or four modified phosphodiester bonds, the one, two, three, or four modified phosphodiester bonds comprise phosphorothioate internucleotide linkages. In some embodiments, the antisense strand comprises four modified phosphodiester bonds. In some embodiments, wherein the antisense strand comprises four modified phosphodiester bonds, the modified phosphodiester bonds comprise phosphorothioate.

In some embodiments, wherein the antisense strand comprises at least one, at least two, at least three, or at least four phosphorothioate internucleotide linkages, the phosphorothioate internucleotide linkages connect the nucleotides at position 1 and position 2 from the first nucleotide at the 5'-terminus of the antisense strand. In some embodiments, wherein the antisense strand comprises at least one, at least two, at least three, or at least four phosphorothioate internucleotide bonds, the phosphorothioate internucleotide linkages connect the nucleotides at position 2 and position 3 from the first nucleotide at the 5'-terminus of the antisense strand. In some embodiments, wherein the antisense strand comprises at least one, at least two, at least three, or at least four phosphorothioate internucleotide bonds, the phosphorothioate internucleotide linkages connect the nucleotides at position 20 and position 21 from the first nucleotide at the 5'-terminus of the antisense strand. In some embodiments, wherein the antisense strand comprises at least one, at least two, at least three, or at least four phosphorothioate internucleotide bonds, the phosphorothioate internucleotide linkages connect the nucleotides at position 21 and position 22 from the first nucleotide at the 5'-terminus of the antisense strand. In some embodiments, wherein the antisense strand comprises at least one, at least two, at least three, or at least four modified phosphodiester bonds, wherein the modified phosphodiester bonds comprise phosphorothioate internucleotide linkages, the phosphorothioate internucleotide linkages are located between nucleotides at position 1 and 2, position 2 and 3, position 20 and 21, and position 21 and 22 from the first nucleotide at the 5'-terminus of the antisense strand.

In some embodiments of the isolated oligonucleotide of the present disclosure, wherein the antisense strand comprises at least one, at least two, at least three, or at least four phosphorothioate internucleotide linkages, the phosphorothioate internucleotide linkages are located between nucleotides at position 1 to 3 and nucleotides at position 20 to 22 from the first nucleotide at the 5'-terminus of the antisense strand.

In some embodiments of the isolated oligonucleotide of the present disclosure, wherein the antisense strand comprises at least four phosphorothioate internucleotide linkages, the phosphorothioate internucleotide linkages are located between nucleotides at position 1 to 3 and nucleotides at position 20 to 22 from the first nucleotide at the 5'-terminus of the antisense strand.

In some embodiments of the isolated oligonucleotide of the present disclosure, the antisense strand comprises four phosphorothioate internucleotide linkages. In some embodiments, wherein the antisense strand comprises four phosphorothioate internucleotide linkages, the phosphorothioate internucleotide linkages are located between nucleotides at position 1 to 3 and nucleotides at position 20 to 22 from the first nucleotide at the 5'-terminus of the antisense strand.

In some embodiments of the isolated oligonucleotide of the present disclosure, the sense strand comprises between one and twenty, between one and fifteen, between one and ten, between one and five, or less than five modified phosphodiester bonds. In some embodiments, the between one and twenty, between one and fifteen, between one and ten, between one and five, or less than five modified phosphodiester bonds comprise phosphorothioate internucleotide linkages. In some embodiments, the sense strand comprises less than five modified phosphodiester bonds. In some embodiments, wherein the sense strand comprises less than five modified phosphodiester bonds, the sense strand comprises one, two, three, or four modified phosphodiester bonds. In some embodiments, wherein the sense strand comprises one, two, three, or four modified phosphodiester bonds, the one, two, three, or four modified phosphodiester bonds comprise phosphorothioate internucleotide linkages. In some embodiments, the sense strand comprises four modified phosphodiester bonds. In some embodiments, wherein the sense strand comprises four modified phosphodiester bonds, the modified phosphodiester bonds comprise phosphorothioate internucleotide linkages.

In some embodiments, wherein the sense strand comprises at least one, at least two, at least three, or at least four modified phosphodiester bonds, the phosphodiester bonds comprise phosphorothioate internucleotide linkages. In some embodiments, wherein the sense strand comprises at least one, at least two, at least three, or at least four phosphorothioate internucleotide linkages, the phosphorothioate internucleotide linkages connect the nucleotides at position 1 and position 2 from the first nucleotide at the 5'-terminus of the sense strand. In some embodiments, wherein the sense strand comprises at least one, at least two, at least three, or at least four phosphorothioate internucleotide linkages, the phosphorothioate internucleotide linkages connect the nucleotides at position 2 and position 3 from the first nucleotide at the 5'-terminus of the sense strand. In some embodiments, wherein the sense strand comprises at least one, at least two, at least three, or at least four phosphorothioate internucleotide linkages, the phosphorothioate internucleotide linkages connect the nucleotides at position 18 and position 19 from the first nucleotide at the 5'-terminus of the sense strand. In some embodiments, wherein the sense strand comprises at least one, at least two, at least three, or at least four phosphorothioate internucleotide linkages, the phosphorothioate internucleotide linkages connect the nucleotides at position 19 and position 20 from the first nucleotide at the 5'-terminus of the sense strand. In some embodiments, wherein the sense strand comprises at least one, at least two, at least three, or at least four modified phosphodiester bonds, wherein the modified phosphodiester bonds comprise phosphorothioate internucleotide linkages, the phosphorothioate internucleotide linkages are located between nucleotides at position 1 and 2, position 2 and 3, position 18 and 19, and position 19 and 20 from the first nucleotide at the 5'-terminus of the sense strand. In some embodiments, wherein the sense strand comprises at least one, at least two, at least three, or at least four phosphorothioate internucleotide linkages, the phosphorothioate internucleotide linkages connect the nucleotides at position 1 and position 2 and position 2 and position 3 (i.e. nucleotides 1 to 3) from the first nucleotide at the 5'-terminus of the sense strand.

In some embodiments of the isolated oligonucleotide of the present disclosure, wherein the sense strand comprises at least one, at least two, at least three, or at least four phosphorothioate internucleotide linkages, the phosphorothioate internucleotide linkages are located between nucleotides at position 1 to 3 and nucleotides at position 18 to 20 from the first nucleotide at the 5'-terminus of the sense strand.

In some embodiments of the isolated oligonucleotide of the present disclosure, wherein the sense strand comprises at least four phosphorothioate internucleotide linkages, the at least four phosphorothioate internucleotide linkages are located between nucleotides at position 1 to 3 and nucleotides at position 18 to 20 from the first nucleotide at the 5'-terminus of the sense strand.

In some embodiments of the isolated oligonucleotide of the present disclosure, the sense strand comprises four phosphorothioate internucleotide linkages. In some embodiments, wherein the sense strand comprises four phosphorothioate internucleotide linkages, the phosphorothioate internucleotide linkages are located between nucleotides at position 1 to 3 and nucleotides at position 18 to 20 from the first nucleotide at the 5'-terminus of the sense strand.

In some embodiments of the isolated oligonucleotide of the present disclosure, wherein the antisense strand and the sense strand comprise four phosphorothioate internucleotide linkages, the antisense strand comprises phosphorothioate internucleotide linkages located between nucleotides at position 1 to 3 and nucleotides at position 20 to 22 from the first nucleotide at the 5'-terminus of the antisense strand, and the sense strand comprises phosphorothioate internucleotide linkages located between nucleotides at position 1 to 3 and nucleotides at position 18 to 20 from the first nucleotide at the 5'-terminus of the sense strand.

In some embodiments of the isolated oligonucleotide of the present disclosure, the antisense strand comprises any one of: i) an antisense strand of nucleic acid sequence according to SEQ ID NO: 370 (5' [MeEPmUs][fGs][fU][mC][fA][mU][fA][mA][mA][fA][mU][mU][mC][fA][mG][fG][mA][mA][mU][mUs][mCs][mC]3');

ii) an antisense strand of nucleic acid sequence according to SEQ ID NO: 371 (5' [MeEPmUs][fUs][fA][mA][fA][mA][fU][mU][mC][fA][mG][mG][mA][fA][mU][fU][mC][mC][mU][mGs][mCs][mU]3');

iii) an antisense strand of nucleic acid sequence according to SEQ ID NO: 372 (5' [MeEPmUs][fGs][fG][mA][fA][mA][fG][mA][mG][fA][mU][mC][mU][fC][mA][fU][mC][mA][mC][mUs][mCs][mA]3');

iv) an antisense strand of nucleic acid sequence according to SEQ ID NO: 373 (5' [MeEPmUs][fAs][fA][mU][fU][mC][fA][mG][mG][fA][mA][mU][mU][fC][mC][fU][mG][mC][mU][mUs][mCs][mU]3');

v) an antisense strand of nucleic acid sequence according to SEQ ID NO: 374 (5' [MeEPmUs][fAs][fA][mC][fA][mC][fA][mU][mG][fU][mU][mG][mC][fU][mC][fA][mU][mU][mG][mUs][mCs][mU]3');

vi) an antisense strand of nucleic acid sequence according to SEQ ID NO: 375 (5' [MeEPmUs][fGs][fU][mG][fU][mA][fA][mC][mC][fG][mU][mC][mA][fU][mA][fG][mC][mA][mG][mUs][mGs][mG]3');

vii) an antisense strand of nucleic acid sequence according to SEQ ID NO: 376 (5' [MeEPmUs][fAs][fU][mA][fG][mC][fA][mG][mU][fG][mG][mA][mA][fA][mG][fA][mG][mA][mU][mCs][mUs][mC]3');

viii) an antisense strand of nucleic acid sequence according to SEQ ID NO: 377 (5' [mUs][fGs][fU][mC][fA][mU][fA][mA][mA][fA][mU][mU][mC][fA][mG][fG][mA][mA][mU][mUs][mCs][mC]3');

ix) an antisense strand of nucleic acid sequence according to SEQ ID NO: 378 (5' [mUs][fUs][fA][mA][fA][mA][fU][mU][mC][fA][mG][mG][mA][fA][mU][fU][mC][mC][mU][mGs][mCs][mU]3'); or x) an antisense strand of nucleic acid sequence according to SEQ ID NO: 379 (5' [mUs][fGs][fG][mA][fA][mA][fG][mA][mG][fA][mU][mC][mU][fC][mA][fU][mC][mA][mC][mUs][mCs][mA]3'), wherein "m" is a 2'-O-methyl modified nucleotide, "f" is a 2'-F modified nucleotide, "s" is a phosphorothioate internucleotide linkage, "MeEP" is a mono methyl protected phosphate mimic.

In some embodiments of the isolated oligonucleotide of the present disclosure, wherein the sense strand comprises any one of:

i) a sense strand of nucleic acid sequence according to SEQ ID NO: 381 (5' [mAs][mAs][mU][mU][mC][fC][mU][fG][fA][fA][fU][mU][mU][mU][mA][mU][mG][mAs][m Cs][mA][G1b][G1b][G1b]3');

ii) a sense strand of nucleic acid sequence according to SEQ ID NO: 382 (5' [mCs][mAs][mG][mG][mA][fA][mU][fU][fC][fC][fU][mG][mA][mA][mU][mU][mU][mUs][m As][mA][G1b][G1b][G1b]3');

iii) a sense strand of nucleic acid sequence according to SEQ ID NO: 383 (5' [mAs][mGs][mU][mG][mA][fU][mG][fA][fG][fA][fU][mC][mU][mC][mU][mU][mU][mCs][m Cs][mA][G1b][G1b][G1b]3');

iv) a sense strand of nucleic acid sequence according to SEQ ID NO: 384 (5' [mAs][mAs][mG][mC][mA][fG][mG][fA][fA][fU][fU][mC][mC][mU][mG][mA][mA][mUs][m Us][mA][G1b][G1b][G1b]3');

v) a sense strand of nucleic acid sequence according to SEQ ID NO: 385 (5' [mAs][mCs][mA][mA][mU][fG][mA][fG][fC][fA][fA][mC][mA][mU][mG][mU][mG][mUs][m Us][mA][G1b][G1b][G1b]3');

vi) a sense strand of nucleic acid sequence according to SEQ ID NO: 386 (5' [mAs][mCs][mU][mG][mC][fU][mA][fU][fG][fA][fC][mG][mG][mU][mU][mA][mC][mAs][m Cs][mA][G1b][G1b][G1b]3');

vii) a sense strand of nucleic acid sequence according to SEQ ID NO: 387 (5' [mGs][mAs][mU][mC][mU][fC][mU][fU][fU][fC][fC][mA][mC][mU][mG][mC][mU][mAs][m Us][mA][G1b][G1b][G1b]3'); or viii) a sense strand of nucleic acid sequence according to SEQ ID NO: 388 (5' [mAs][mAs][mU][mU][mC][fC][mU][fG][fA][fA][fU][mU][mU][mU][mA][mU][mG][mA][m C][mA][G1b][G1b][G1b]3'), wherein "m" is a 2'-O-methyl modified nucleotide, "f" is a 2'-F modified nucleotide, "s" is a phosphorothioate internucleotide linkage, and "G1b" is a GalNAc G1b moiety.

In some embodiments of the isolated oligonucleotide of the present disclosure is selected from:

i) an antisense strand of nucleic acid sequence according to SEQ ID NO: 370 (5' [MeEPmUs][fGs][fU][mC][fA][mU][fA][mA][mA][fA][mU][mU][mC][fA][mG][fG][mA][mA][mU][mUs][mCs][mC]3'), and a sense strand of nucleic acid sequence according to SEQ ID NO: 381 (5' [mAs][mAs][mU][mU][mC][fC][mU][fG][fA][fA][fU][mU][mU][mU][mA][mU][mG][mAs][m Cs][mA][G1b][G1b][G1b]3');

ii) an antisense strand of nucleic acid sequence according to SEQ ID NO: 371 (5' [MeEPmUs][fUs][fA][mA][fA][mA][fU][mU][mC][fA][mG][mG][mA][fA][mU][fU][mC][mC][mU][mGs][mCs][mU]3'), and a sense strand of nucleic acid sequence according to SEQ ID NO: 382 (5' [mCs][mAs][mG][mG][mA][fA][mU][fU][fC][fC][fU][mG][mA][mA][mU][mU][mU][mUs][m As][mA][G1b][G1b][G1b]3');

iii) an antisense strand of nucleic acid sequence according to SEQ ID NO: 372 (5' [MeEPmUs][fGs][fG][mA][fA][mA][fG][mA][mG][fA][mU][mC][mU][fC][mA][fU][mC][mA][mC][mUs][mCs][mA]3'), and a sense strand of nucleic acid sequence according to SEQ ID NO: 383 (5' [mAs][mGs][mU][mG][mA][fU][mG][fA][fG][fA][fU][mC][mU][mC][mU][mU][mU][mCs][m Cs][mA][G1b][G1b][G1b]3');

iv) an antisense strand of nucleic acid sequence according to SEQ ID NO: 373 (5' [MeEPmUs][fAs][fA][mU][fU][mC][fA][mG][mG][fA][mA][mU][mU][fC][mC][fU][mG][mC][mU][mUs][mCs][mU]3'), and a sense strand of nucleic acid sequence according to SEQ ID NO: 384 (5' [mAs][mAs][mG][mC][mA][fG][mG][fA][fA][fU][fU][mC][mC][mU][mG][mA][mA][mUs][m Us][mA][G1b][G1b][G1b]3');

v) an antisense strand of nucleic acid sequence according to SEQ ID NO: 374 (5' [MeEPmUs][fAs][fA][mC][fA][mC][fA][mU][mG][fU][mU][mG][mC][fU][mC][fA][mU][mU][mG][mUs][mCs][mU]3'), and a sense strand of nucleic acid sequence according to SEQ ID NO: 385 (5' [mAs][mCs][mA][mA][mU][fG][mA][fG][fC][fA][fA][mC][mA][mU][mG][mU][mG][mUs][m Us][mA][G1b][G1b][G1b]3');

vi) an antisense strand of nucleic acid sequence according to SEQ ID NO: 375 (5' [MeEPmUs][fGs][fU][mG][fU][mA][fA][mC][mC][fG][mU][mC][mA][fU][mA][fG][mC][mA][mG][mUs][mGs][mG]3'), and a sense strand of nucleic acid sequence according to SEQ ID NO: 386 (5' [mAs][mCs][mU][mG][mC][fU][mA][fU][fG][fA][fC][mG][mG][mU][mU][mA][mC][mAs][m Cs][mA][G1b][G1b][G1b]3');

vii) an antisense strand of nucleic acid sequence according to SEQ ID NO: 376 (5' [MeEPmUs][fAs][fU][mA][fG][mC][fA][mG][mU][fG][mG][mA][mA][fA][mG][fA][mG][mA][mU][mCs][mUs][mC]3'), and a sense strand of nucleic acid sequence according to SEQ ID NO: 387 (5' [mGs][mAs][mU][mC][mU][fC][mU][fU][fU][fC][fC][mA][mC][mU][mG][mC][mU][mAs][m Us][mA][G1b][G1b][G1b]3');

viii) an antisense strand of nucleic acid sequence according to SEQ ID NO: 377 (5' [mUs][fGs][fU][mC][fA][mU][fA][mA][mA][fA][mU][mU][mC][fA][mG][fG][mA][mA][mU][mUs][mCs][mC]3'), and a sense strand of nucleic acid sequence according to SEQ ID NO: 381 (5' [mAs][mAs][mU][mU][mC][fC][mU][fG][fA][fA][fU][mU][mU][mU][mA][mU][mG][mAs][m Cs][mA][G1b][G1b][G1b]3');

ix) an antisense strand of nucleic acid sequence according to SEQ ID NO: 378 (5' [mUs][fUs][fA][mA][fA][mA][fU][mU][mC][fA][mG][mG][mA][fA][mU][fU][mC][mC][mU][mGs][mCs][mU]3'), and a sense strand of nucleic acid sequence according to SEQ ID NO: 382 (5' [mCs][mAs][mG][mG][mA][fA][mU][fU][fC][fC][fU][mG][mA][mA][mU][mU][mU][mUs][m As][mA][G1b][G1b][G1b]3');

x) an antisense strand of nucleic acid sequence according to SEQ ID NO: 379 (5' [mUs][fGs][fG][mA][fA][mA][fG][mA][mG][fA][mU][mC][mU][fC][mA][fU][mC][mA][mC][mUs][mCs][mA]3'), and a sense strand of nucleic acid sequence according to SEQ ID NO: 383 (5' [mAs][mGs][mU][mG][mA][fU][mG][fA][fG][fA][fU][mC][mU][mC][mU][mU][mU][mCs][m Cs][mA][G1b][G1b][G1b]3');

xi) an antisense strand of nucleic acid sequence according to SEQ ID NO: 370 (5' [MeEPmUs][fGs][fU][mC][fA][mU][fA][mA][mA][fA][mU][mU][mC][fA][mG][fG][mA][mA][mU][mUs][mCs][mC]3'), and a sense strand of nucleic acid sequence according to SEQ ID NO: 388 (5' [mAs][mAs][mU][mU][mC][fC][mU][fG][fA][fA][fU][mU][mU][mU][mA][mU][mG][mA][m C][mA][G1b][G1b][G1b]3'); or xii) an antisense strand of nucleic acid sequence according to SEQ ID NO: 377 (5' [mUs][fGs][fU][mC][fA][mU][fA][mA][mA][fA][mU][mU][mC][fA][mG][fG][mA][mA][mU][mUs][mCs][mC]3'), and a sense strand of nucleic acid sequence according to SEQ ID NO: 388 (5' [mAs][mAs][mU][mU][mC][fC][mU][fG][fA][fA][fU][mU][mU][mU][mA][mU][mG][mA][mC][mA][G1b][G1b][G1b]3'), wherein "m" is a 2'-O-methyl modified nucleotide, "f" is a 2'-F modified nucleotide, "s" is a phosphorothioate internucleotide linkage, "MeEP" is a mono methyl protected phosphate mimic, and "G1b" is a GalNAc G1b moiety.

Nucleic Acids and Vectors

The present disclosure also provides a vector encoding at least one isolated oligonucleotide disclosed herein. In some embodiments, the vector is any one of a plasmid, a cosmid or a viral vector. In some embodiments, the vector is an adenoviral vector. In some embodiments, the vector is a lentiviral vector. In some embodiments, the plasmid is an expression plasmid. In some embodiments, the vector encodes one isolated oligonucleotide disclosed herein. In some embodiments, the vector encodes more than one isolated oligonucleotide disclosed herein. In some embodiments, the vector encodes, two, three, four, or five isolated oligonucleotides disclosed herein. In some embodiments, the vector encodes more than five isolated oligonucleotides disclosed herein.

The disclosure provides nucleic acids comprising the sequences encoding the isolated oligonucleotides (e.g., dsRNAs or siRNAs) targeting CFB described herein.

In some embodiments, the nucleic acids are ribonucleic acids (RNAs). In some embodiments, the nucleic acids are deoxyribonucleic acids (DNAs). The DNAs may be a vector or a plasmid, e.g., an expression vector.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

By the term "express" or "expression" of a polynucleotide coding sequence, it is meant that the sequence is transcribed, and optionally, translated. Typically, according to the present disclosure, expression of a coding sequence of the disclosure will result in production of the polypeptide of the disclosure. The entire expressed polypeptide or fragment can also function in intact cells without purification.

In some embodiments, the vector is an expression vector for manufacturing siRNAs of the disclosure. Exemplary expression vectors may comprise a sequence encoding the sense and/or antisense strand of the isolated oligonucleotide of the present disclosure, under the control of a suitable promoter for transcription. Interfering RNAs may be expressed from a variety of eukaryotic promoters known to those of ordinary skill in the art, including pol III promoters, such as the U6 or H1 promoters, or pol II promoters, such as the cytomegalovirus promoter. Those of skill in the art will recognize that these promoters can also be adapted to allow inducible expression of the interfering RNA.

The isolated oligonucleotide of the present disclosure (e.g., dsRNAs and siRNAs) can be expressed endogenously from plasmid or viral expression vectors, or from minimal expression cassettes, for example, PCR generated fragments comprising one or more promoters and an appropriate template or templates for transcribing the siRNA. Examples of commercially available plasmid-based expression vectors for shRNA include members of the pSilencer™ series (Ambion®) and pCpG-siRNA (InvivoGen®). Examples of kits for production of PCR-generated shRNA expression cassettes include Silencer™ Express (Ambion®) and siXpress® (Mirus®)

Viral vectors for the in vivo expression of the isolated oligonucleotides (e.g., siRNAs and dsRNAs) in eukaryotic cells are also contemplated as within the scope of the instant disclosure. Viral vectors may be derived from a variety of viruses including adenovirus, adeno-associated virus, lentivirus (e.g., HIV, FIV, and EIAV), and herpes virus. Examples of commercially available viral vectors for shRNA expression include pSilencer™ adeno (Ambion®) and pLenti6/BLOCK-iT-DEST™ (Invitrogen®). Selection of viral vectors, methods for expressing the siRNA from the vector and methods of delivering the viral vector, for example incorporated within a nanoparticle, are within the ordinary skill of one in the art.

It will be apparent to those skilled in the art that any suitable vector, optionally incorporated into a nanoparticle, can be used to deliver the isolated oligonucleotides of the present discloser (e.g., dsRNAs or siRNAs) described herein to a cell or subject. The vector can be delivered to cells in vivo. In other embodiments, the vector can be delivered to cells ex vivo, and then cells containing the vector are delivered to the subject. The choice of delivery vector can be made based on a number of factors known in the art, including age and species of the target host, in vitro versus in vivo delivery, level and persistence of expression desired, intended purpose (e.g., for therapy or screening), the target cell or organ, route of delivery, size of the isolated polynucleotide, safety concerns, and the like.

Delivery Systems

The present disclosure also provides a delivery system comprising at least one isolated oligonucleotide disclosed herein or vector of the present disclosure encoding at least one isolated oligonucleotide disclosed herein. In some embodiments, the delivery system is any one of a liposome, a nanoparticle, a polymer-based delivery system or a ligand-conjugate delivery system. In some embodiments, the ligand-conjugate delivery system comprises one or more of an antibody, a peptide, a sugar moiety or a combination thereof.

In some embodiments, the delivery system of the present disclosure comprises nanoparticles comprising the isolated oligonucleotides of the present disclosure (e.g., siRNA or dsRNAs) targeting a CFB mRNA for degradation. In some embodiments, the nanoparticle comprises a polymer-based nanoparticle, a lipid-polymer based nanoparticle, a metal-based nanoparticle, a carbon-nanotube based nanoparticle, a nanocrystal or a polymeric micelle. In some embodiments, the polymer-based nanoparticle comprises a multiblock copolymer, a diblock copolymer, a polymeric micelle or a hyperbranched macromolecule. In some embodiments, the polymer-based nanoparticle comprises a multiblock copolymer a diblock copolymer. In some embodiments, the polymer-based nanoparticle is pH responsive. In some embodiments, the polymer-based nanoparticle further comprises a buffering component.

In some embodiments, the delivery system comprises a liposome. Liposomes are spherical vesicles having at least one lipid bilayer, and in some embodiments, an aqueous core. In some embodiments, the lipid bilayer of the liposome may comprise phospholipids. Exemplary liposomes suitable for delivering the oligonucleotides of the present disclosure will be apparent to those skilled in the art.

In some embodiments, the liposome or the nanoparticle of the present disclosure comprises a micelle. A micelle is an aggregate of surfactant molecules. An exemplary micelle comprises an aggregate of amphiphilic macromolecules, polymers or copolymers in aqueous solution, wherein the hydrophilic head portions contact the surrounding solvent, while the hydrophobic tail regions are sequestered in the center of the micelle.

In some embodiments, the nanoparticle comprises a nanocrystal. Exemplary nanocrystals are crystalline particles with at least one dimension of less than 1000 nanometers, preferably of less than 100 nanometers.

In some embodiments, the nanoparticle comprises a polymer-based nanoparticle. In some embodiments, the polymer comprises a multiblock copolymer, a diblock copolymer, a polymeric micelle or a hyperbranched macromolecule. In some embodiments, the particle comprises one or more cationic polymers. In some embodiments, the cationic polymer is chitosan, protamine, polylysine, polyhistidine, polyarginine or poly(ethylene)imine. In other embodiments, the one or more polymers contain the buffering component, degradable component, hydrophilic component, cleavable bond component or some combination thereof.

In some embodiments, the nanoparticles or some portion thereof are degradable. In other embodiments, the lipids and/or polymers of the nanoparticles are degradable.

In some embodiments, any of these delivery systems of the present disclosure can comprise a buffering component. In other embodiments, any of the of the present disclosure can comprise a buffering component and a degradable component. In still other embodiments, any of the of the present disclosure can comprise a buffering component and a hydrophilic component. In yet other embodiments, any of the of the present disclosure can comprise a buffering component and a cleavable bond component. In yet other embodiments, any of the of the present disclosure can comprise a buffering component, a degradable component and a hydrophilic component. In still other embodiments, any of the of the present disclosure can comprise a buffering component, a degradable component and a cleavable bond component. In further embodiments, any of the of the present disclosure can comprise a buffering component, a hydrophilic component and a cleavable bond component. In yet another embodiment, any of the of the present disclosure can comprise a buffering component, a degradable component, a hydrophilic component and a cleavable bond component. In some embodiments, the particle is composed of one or more polymers that contain any of the aforementioned combinations of components.

In some embodiments of the isolated oligonucleotides of the present disclosure, the delivery system comprises a ligand-conjugate delivery system. In some embodiments, the ligand-conjugate delivery system comprises one or more of an antibody, a peptide, a sugar moiety, lipid or a combination thereof In further embodiments, the isolated oligonucleotide of the present disclosure targeting a CFB mRNA (e.g., siRNA or dsRNA) is conjugated to, complexed to, or encapsulated by the one or more lipids or polymers of the delivery system. In further embodiments, the isolated oligonucleotide of the present disclosure targeting a CFB mRNA (e.g., siRNA or dsRNA) can be encapsulated in the hollow core of a nanoparticle. Alternatively, or in addition, the isolated oligonucleotide of the present disclosure targeting a CFB mRNA (e.g., siRNA or dsRNA) can be incorporated into the lipid or polymer-based shell of the delivery system, for example via intercalation. Alternatively, or in addition, the isolated oligonucleotide of the present disclosure targeting a CFB mRNA (e.g., siRNA or dsRNA) can be attached to the surface of the delivery system. In some embodiments, the isolated oligonucleotide of the present disclosure targeting a CFB mRNA (e.g., siRNA or dsRNA) is conjugated to one or more lipids or polymers of the delivery system, e.g. via covalent attachment.

In some embodiments, the ligand conjugate delivery system further comprises a targeting agent. In some embodiments, the targeting agent comprises a peptide ligand, a nucleotide ligand, a polysaccharide ligand, a fatty acid ligand, a lipid ligand, a small molecule ligand, an antibody, an antibody fragment, an antibody mimetic or an antibody mimetic fragment.

In some embodiments, the isolated oligonucleotide disclosed herein may further comprise a ligand that facilitates delivery or uptake of the isolated oligonucleotide to a particular tissue or cell, such as a liver cell. In certain embodiments, the ligand targets delivery of the RNAi construct to hepatocytes. In these and other embodiments, the ligand may comprise galactose, galactosamine or N-acetyl-galactosamine (GalNAc). In certain embodiments, the ligand comprises a multivalent galactose or multivalent GalNAc moiety, such as a trivalent or tetravalent galactose or GalNAc moiety. The ligand can be covalently attached to the 5' or 3' end of the sense strand of the RNAi construct, optionally via a linker.

In some embodiments, the targeting agent comprises a binding partner for a cell surface protein that is upregulated or overexpressed or normally expressed in a target cell encoding CFB mRNA and expressing CFB protein. In some embodiments, the binding partner can be a transmembrane peptidoglycan expressed on the surface of many types of such cells. Targeting of cell surface protein by the delivery system of the present disclosure thus provides superior delivery and specificity of the compositions of the disclosure to target cells. In some embodiments, the target cell can be any one of an intestinal cell, an arterial cell, a cell of the cardiovascular system, a hepatocyte, a pancreatic cell or a combination thereof.

In some embodiments, the delivery system of the present disclosure comprises a polymer based delivery system. In some embodiments, polymer based delivery system comprises a blending polymer. In some embodiments, the blending polymer is a copolymer comprising a degradable component and hydrophilic component. In some embodiments, the degradable component of the blending polymer is a polyester, poly(ortho ester), poly(ethylene imine), poly(caprolactone), polyanhydride, poly(acrylic acid), polyglycolide or poly(urethane). In some embodiments, the degradable component of the blending polymer is poly(lactic acid) (PLA) or poly(lactic-co-glycolic acid) (PLGA). In some embodiments, the hydrophilic component of the blending polymer is a polyalkylene glycol or a polyalkylene oxide. In some embodiments, the polyalkylene glycol is polyethylene glycol (PEG). In other embodiments, the polyalkylene oxide is polyethylene oxide (PEO).

In some embodiments, the delivery system of the present disclosure is a polymer-based nanoparticle. Polymer based nanoparticles comprise one or more polymers. In some embodiments, the one or more polymers comprise a polyester, poly(ortho ester), poly(ethylene imine), poly(caprolactone), polyanhydride, poly(acrylic acid), polyglycolide or poly(urethane). In still other embodiments, the one or more polymers comprise poly(lactic acid) (PLA) or poly(lactic-co-glycolic acid) (PLGA). In some embodiments, the one or more polymers comprise poly(lactic-co-glycolic acid) (PLGA). In some embodiments, the one or more polymers comprise poly(lactic acid) (PLA). In some embodiments, the one or more polymers comprise polyalkylene glycol or a polyalkylene oxide. In some embodiments, the polyalkylene glycol is polyethylene glycol (PEG) or the polyalkylene oxide is polyethylene oxide (PEO).

In some embodiments, the polymer-based nanoparticle comprises poly(lactic-co-glycolic acid) PLGA polymers. In some embodiments, the PLGA nanoparticle further comprises a targeting agent, as described herein.

Pharmaceutical Compositions

The present disclosure also provides a pharmaceutical composition comprising at least one oligonucleotide disclosed herein, a vector of the present disclosure encoding at least one isolated oligonucleotide disclosed herein, or a delivery system of the present disclosure, and a pharmaceutically acceptable carrier, diluent, or excipient.

Pharmaceutical compositions of the present disclosure can contain any of the reagents discussed above, and one or more of a pharmaceutically acceptable carrier, a diluent or an excipient.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

As used herein, "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids.

Methods of Making Isolated Oligonucleotides

Provided herein are methods of making the one or more oligonucleotides of (e.g., dsRNAs or siRNAs) targeting CFB of the present disclosure and delivery systems comprising same.

The one or more oligonucleotides of (e.g., dsRNAs or siRNAs) targeting CFB of the present disclosure, may be generated exogenously by chemical synthesis, by in vitro transcription, or by cleavage of longer double-stranded RNA with Dicer or another appropriate nuclease with similar activity. Chemically synthesized siRNAs, produced from protected ribonucleoside phosphoramidites using a conventional DNA/RNA synthesizer, may be obtained from commercial suppliers. The siRNAs can be purified by extraction with a solvent or resin, precipitation, electrophoresis, chromatography, or a combination thereof, for example. Alternatively, siRNAs may be used with little if any purification to avoid losses due to sample processing.

In some embodiments, the one or more oligonucleotides of (e.g., dsRNAs or siRNAs) targeting CFB of the present disclosure can be produced using an expression vector into which a nucleic acid encoding the double stranded RNA has been cloned, for example under control of a suitable promoter.

In some embodiments, the one or more oligonucleotides of (e.g., dsRNAs or siRNAs) targeting CFB of the present disclosure can be incorporated in a delivery system of the present disclosure.

Delivery systems comprising dsRNAs or siRNAs of the disclosure can be prepared by any suitable means known in the art. For example, polymeric nanoparticles can be prepared using various methods including, but not limited to, solvent evaporation, spontaneous emulsification, solvent diffusion, desolation, dialysis, ionic gelation, nanoprecipitation, salting out, spray drying and supercritical fluid methods. The dispersion of preformed polymers and the polymerization of monomers are two additional strategies for preparation of polymeric nanoparticles. However, the choice of an appropriate method depends upon various factors, which will be known to the person of ordinary skill in the art.

Methods of Use

The present disclosure also provides a method of inhibiting or downregulating the expression or level of complement CFB in a subject in need thereof, wherein the method comprises administering to the subject an effective amount at least one isolated oligonucleotide disclosed herein, at least one vector disclosed herein, at least one delivery system disclosed herein, or at least one pharmaceutical composition disclosed herein.

The present disclosure also provides a method of treating or preventing a disease or disorder associated with aberrant or increased expression or activity of complement CFB or a disease or disorder where complement CFB plays a role in a subject in need thereof, wherein the method comprises administering to the subject an effective amount of at least one isolated oligonucleotide disclosed herein, at least one vector disclosed herein, at least one delivery system disclosed herein, or at least one pharmaceutical composition disclosed herein.

The present disclosure also provides at least one isolated oligonucleotide disclosed herein, a vector of the of the present disclosure encoding at least one isolated oligonucleotide disclosed herein, a delivery system of the present disclosure, or a pharmaceutical composition of the present disclosure, for use in treatment or prevention of a disease or disorder associated with aberrant or increased expression or activity of CFB or a disease or disorder where CFB plays a role, in a subject in need thereof.

The present disclosure also provides use of at least one isolated oligonucleotide disclosed herein, a vector of the of the present disclosure encoding at least one isolated oligonucleotide disclosed herein, a delivery system of the present disclosure, or a pharmaceutical composition of the present disclosure, in the manufacture of a medicament for treatment or prevention of a disease or disorder associated with aberrant or increased expression or activity of CFB or a disease or disorder where CFB plays a role in a subject in need thereof.

Provided herein are methods of inhibiting or downregulating CFB expression or activity in a cell, comprising contacting the cell with the one or more oligonucleotides (e.g., dsRNA or siRNA) targeting CFB as described herein. The one or more oligonucleotides (e.g., dsRNA or siRNA) targeting CFB as described herein can reduce or inhibit CFB activity through the RNAi pathway. The cell can be in vitro, in vivo or ex vivo. For example, the cell can be from a cell line, or in vivo in a subject in need thereof.

In some embodiments, the one or more oligonucleotides (e.g., dsRNA or siRNA) targeting CFB as described herein are capable of inducing RNAi-mediated degradation of an CFB mRNA in a cell of a subject.

As used herein, the terms "contacting," "introducing" and "administering" are used interchangeably and refer to a process by which dsRNA or siRNA of the present disclosure or a nucleic acid molecule encoding a dsRNA or siRNA of this disclosure is delivered to a cell in order to inhibit or alter or modify expression of a target gene. The dsRNA may be administered in a number of ways including, but not limited to, direct introduction into a cell (i.e., intracellularly) and/or extracellular introduction into a cavity, interstitial space, or into the circulation of the organism.

"Introducing" in the context of a cell or organism means presenting the nucleic acid molecule to the organism and/or cell in such a manner that the nucleic acid molecule gains access to the interior of a cell. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into cells in a single transformation event or in separate transformation events. Thus, the term "transformation" as used herein refers to the introduction of a heterologous nucleic acid into a cell. Transformation of a cell may be stable or transient.

The term "inhibit" or "reduce" or grammatical variations thereof, as used herein, refer to a decrease or diminishment in the specified level or activity of at least about 5%, about 10%, about 15%, about 25%, about 35%, about 40%, about 50%, about 60%, about 75%, about 80%, about 90%, about 95% or more. In some embodiments, the inhibition or reduction results in little or essentially no detectible activity (at most, an insignificant amount, e.g., less than about 10% or even 5%).

In contrast, the term "increase" or grammatical variations thereof as used herein refers to an increase or elevation in the specified level or activity of at least about 5%, about 10%, about 15%, about 25%, about 35%, about 40%, about 50%, about 60%, about 75%, about 80%, about 90%, about 95% or more. Increases in activity can be described in terms of fold change. For example, activity can be increased 1.2×, 1.5×, 2×, 3×, 5×, 6×, 7×, 8×, 9×, 10× or more compared to a baseline level of activity.

As used herein, the term "IC50" or "$IC_{50}$ value" refers to the concentration of an agent where cell viability is reduced by half. The $IC_{50}$ is thus a measure of the effectiveness of an agent in inhibiting a biological process. In an exemplary model, cell lines are cultured using standard techniques, treated with any of the one or more oligonucleotides (e.g., dsRNA or siRNA) targeting CFB as described herein, and the $IC_{50}$ value of the oligonucleotides (e.g., dsRNA or siRNA) targeting CFB is calculated after 24, 48 and/or 72 hours to determine its effectiveness in downregulating or inhibiting the level of CFB mRNA or protein to 50%, as compared to the level of CFB mRNA or protein in an untreated cell or in the same cell before initiation of treatment with the isolated oligonucleotide.

Methods of monitoring of CFB mRNA and/or protein expression can be used to characterize gene silencing, and to determine the effectiveness of the compositions described herein. Expression of CFB may be evaluated by any technique known in the art. Examples thereof include immunoprecipitations methods, utilizing CFB antibodies in assays such as ELISAs, western blotting, or immunohistochemistry to visualize CFB protein expression in cells, or flow cytometry. Additional methods include various hybridization methods utilizing a nucleic acid that specifically hybridizes with a nucleic acid encoding CFB or a unique fragment thereof, or a transcription product (e.g., mRNA) or splicing product of said nucleic acid, northern blotting methods, Southern blotting methods, and various PCR-based methods such as RT-PCR, qPCR or digital droplet PCR. CFB mRNA expression may additionally be assessed using high throughput sequencing techniques.

Methods of assaying the effect of individual isolated oligonucleotides (e.g., dsRNA or siRNA) targeting CFB include transfecting representative cell lines with isolated oligonucleotides and measuring viability. For example, cells from representative cell lines can be transfected using methods known in the art, such as the RNAiMAX Lipofectamine™ kit (Invitrogen®) and cultured using any suitable technique known in the art. Following a suitable incubation period, such as 24-96 hours, cell viability can be measured using methods such as Cell Titer Glo 2.0@ (Promega®) to determine cell viability, and/or CFB mRNA and protein levels can be assessed using the methods described herein.

In some embodiments of the methods of inhibiting or downregulating CFB expression or activity in a cell of the present disclosure, the subject is a human. In some embodiments of the methods of inhibiting or downregulating CFB expression or activity in a cell of the present disclosure, the subject experiences symptoms of or suffers from Paroxysmal Nocturnal Hemoglobinuria (PNH), rheumatoid arthritis, ischemia-reperfusion injuries, Multiple Sclerosis (MS), Guillain-Barre syndrome, Systemic lupus erythmatosis, C3 Glomerulonephritis, atypical Hemolytic Uremic Syndrome (aHUS), Myasthenia Gravis (MG), Neuromyelistis Optic nerve and Spinal Cord (NMOSD), Dense Deposit Disease (DDD), Age-related Macular Degeneration (AMD), IgA nephropathy, Multifocal Motor Neuropathy (MMN), organ transplantation and neurodegenerative diseases.

In some embodiments of the methods of inhibiting or downregulating CFB expression or activity in a cell of the present disclosure, the subject is a human. In some embodiments of the methods of inhibiting or downregulating CFB expression or activity in a cell of the present disclosure, the subject experiences symptoms of or suffers from Paroxysmal Nocturnal Hemoglobinuria (PNH), rheumatoid arthritis, ischemia-reperfusion injuries, Multiple Sclerosis (MS), Guillain-Barre syndrome, Systemic lupus erythmatosis, C3 Glomerulonephritis, atypical Hemolytic Uremic Syndrome (aHUS), Myasthenia Gravis (MG), Neuromyelistis Optic nerve and Spinal Cord (NMOSD), Dense Deposit Disease (DDD), Age-related Macular Degeneration (AMD), IgA nephropathy, Multifocal Motor Neuropathy (MMN), organ transplantation and neurodegenerative diseases, or a related disorder or symptom associated with an overreactive inflammatory response.

In some embodiments of the method of treating or preventing a disease or disorder associated with aberrant or increased expression or activity of CFB or a disease or disorder where CFB plays a role of the present disclosure, the subject is a human. In some embodiments of the method of treating or preventing a disease or disorder associated with aberrant or increased expression or activity of CFB or a disease or disorder where CFB plays a role of the present disclosure, the disease or disorder is or is associated with Paroxysmal Nocturnal Hemoglobinuria (PNH), rheumatoid arthritis, ischemia-reperfusion injuries, Multiple Sclerosis (MS), Guillain-Barre syndrome, Systemic lupus erythmatosis, C3 Glomerulonephritis, atypical Hemolytic Uremic Syndrome (aHUS), Myasthenia Gravis (MG), Neuromyelistis Optic nerve and Spinal Cord (NMOSD), Dense Deposit Disease (DDD), Age-related Macular Degeneration (AMD), IgA nephropathy, Multifocal Motor Neuropathy (MMN), organ transplantation, a neurodegenerative diseases, or a related disorder or symptom associated with an overreactive inflammatory response.

In some embodiments of the use for treating or preventing a disease or disorder associated with aberrant or increased expression or activity of CFB or a disease or disorder where CFB plays a role of the present disclosure, the subject is a human. In some embodiments of the use for treating or preventing a disease or disorder associated with aberrant or increased expression or activity of CFB or a disease or disorder where CFB plays a role of the present disclosure, the disease or disorder is or is associated with Paroxysmal Nocturnal Hemoglobinuria (PNH), rheumatoid arthritis, ischemia-reperfusion injuries, Multiple Sclerosis (MS), Guillain-Barre syndrome, Systemic lupus erythmatosis, C3 Glomerulonephritis, atypical Hemolytic Uremic Syndrome (aHUS), Myasthenia Gravis (MG), Neuromyelistis Optic nerve and Spinal Cord (NMOSD), Dense Deposit Disease (DDD), Age-related Macular Degeneration (AMD), IgA nephropathy, Multifocal Motor Neuropathy (MMN), organ transplantation, neurodegenerative diseases, or a related disorder or symptom associated with an overreactive inflammatory response.

In some embodiments of the use in the manufacture of a medicament for treatment or prevention of a disease or disorder associated with aberrant or increased expression or activity of CFB of the present disclosure, the subject is a human. In some embodiments, the subject is not a human. In some embodiments, the disease or disorder is or is associated with Paroxysmal Nocturnal Hemoglobinuria (PNH), rheumatoid arthritis, ischemia-reperfusion injuries, Multiple Sclerosis (MS), Guillain-Barre syndrome, Systemic lupus erythmatosis, C3 Glomerulonephritis, atypical Hemolytic Uremic Syndrome (aHUS), Myasthenia Gravis (MG), Neuromyelistis Optic nerve and Spinal Cord (NMOSD), Dense Deposit Disease (DDD), Age-related Macular Degeneration (AMD), IgA nephropathy, Multifocal Motor Neuropathy (MMN), organ transplantation, neurodegenerative diseases, or a related disorder or symptom associated with an overreactive inflammatory response.

The term "effective amount" or "therapeutically effective amount", as used interchangeably herein, refers to an amount of a pharmaceutical agent to treat, ameliorate, inhibit, downregulate or control the expression of CFB or symptoms associated with aberrant or abnormal expression of CFB in a subject, or to exhibit a detectable therapeutic or inhibitory effect in a subject. The effect can be detected by any assay method known in the art. The precise effective amount for a subject will depend upon the subject's body weight, size, and health; the nature and extent of the condition; and the therapeutic or combination of therapeutics selected for administration.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed invention. Based on the present disclosure the skilled artisan can identify and employ other components and methodology useful for practicing the present disclosure.

Sequences of the Disclosure

TABLE 1

Exemplary Sequences of the Present Application

| SEQ ID NO: | Antisense strand (guide) sequence | start pos. | end pos. | SEQ ID NO: | Sense strand (passenger) sequence | start pos. | end pos. |
|---|---|---|---|---|---|---|---|
| 2 | UAAAGAGAUCUCAUCACUCACA | 493 | 513 | 36 | UGAGUGAUGAGAUCUCUUUA | 495 | 513 |
| 3 | UGGAAAGAGAUCUCAUCACUCA | 495 | 515 | 37 | AGUGAUGAGAUCUCUUUCCA | 497 | 515 |
| 4 | UCAGUGGAAAGAGAUCUCAUCA | 499 | 519 | 38 | AUGAGAUCUCUUUCCACUGA | 501 | 519 |
| 5 | UAUAGCAGUGGAAAGAGAUCUC | 503 | 523 | 39 | GAUCUCUUUCCACUGCUAUA | 505 | 523 |
| 6 | UGUGUAACCGUCAUAGCAGUGG | 514 | 534 | 40 | AUCUCUUUCCACUGCUAUGA | 516 | 534 |
| 7 | UUUGACUAGACACUUUUUGGCU | 991 | 1011 | 41 | CCAAAAAGUGUCUAGUCAAA | 993 | 1011 |
| 8 | UUAAGUUGACUAGACACUUUUU | 995 | 1015 | 42 | AAAGUGUCUAGUCAACUUAA | 997 | 1015 |
| 9 | UAAUUAAGUUGACUAGACACUU | 998 | 1018 | 43 | GUGUCUAGUCAACUUAAUUA | 1000 | 1018 |
| 10 | UCAAUUAAGUUGACUAGACACU | 999 | 1019 | 44 | UGUCUAGUCAACUUAAUUGA | 1001 | 1019 |

TABLE 1-continued

| Exemplary Sequences of the Present Application | | | | | | | |
|---|---|---|---|---|---|---|---|
| SEQ | Antisense strand (guide) | | | SEQ | Sense strand (passenger) | | |
| ID NO: | sequence | start pos. | end pos. | ID NO: | sequence | start pos. | end pos. |
| 11 | UAUAUCUUGGCUUCACACCAUA | 1034 | 1054 | 45 | UGGUGUGAAGCCAAGAUAUA | 1036 | 1054 |
| 12 | UUAGACAUCCAGAUAAUCCUCC | 1384 | 1404 | 46 | AGGAUUAUCUGGAUGUCUAA | 1386 | 1404 |
| 13 | UAAGCAUUGAUGUUCACUUGGU | 1431 | 1451 | 47 | CAAGUGAACAUCAAUGCUUA | 1433 | 1451 |
| 14 | UAAAGCAUUGAUGUUCACUUGG | 1432 | 1452 | 48 | AAGUGAACAUCAAUGCUUUA | 1434 | 1452 |
| 15 | UAACACAUGUUGCUCAUUGUCU | 1465 | 1485 | 49 | ACAAUGAGCAACAUGUGUUA | 1467 | 1485 |
| 16 | UUUGACUUUGAACACAUGUUGC | 1474 | 1494 | 50 | AACAUGUGUUCAAAGUCAAA | 1476 | 1494 |
| 17 | UAUAUCCUUGACUUUGAACACA | 1480 | 1500 | 51 | UGUUCAAAGUCAAGGAUAUA | 1482 | 1500 |
| 18 | UGAGAUCUUGGCCUGCCAUGGU | 1606 | 1626 | 52 | CAUGGCAGGCCAAGAUCUCA | 1608 | 1626 |
| 19 | UAAGUACUCAGACACCACAGCC | 1666 | 1686 | 53 | CUGUGGUGUCUGAGUACUUA | 1668 | 1686 |
| 20 | UAUUCAGGAAUUCCUGCUUCUU | 1821 | 1841 | 54 | GAAGCAGGAAUUCCUGAAUA | 1823 | 1841 |
| 21 | UAAUUCAGGAAUUCCUGCUUCU | 1822 | 1842 | 55 | AAGCAGGAAUUCCUGAAUUA | 1824 | 1842 |
| 22 | UUAAAAUUCAGGAAUUCCUGCU | 1825 | 1845 | 56 | CAGGAAUUCCUGAAUUUUAA | 1827 | 1845 |
| 23 | UAUAAAAUUCAGGAAUUCCUGC | 1826 | 1846 | 57 | AGGAAUUCCUGAAUUUUAUA | 1828 | 1846 |
| 24 | UGUCAUAAAAUUCAGGAAUUCC | 1829 | 1849 | 58 | AAUUCCUGAAUUUUAUGACA | 1831 | 1849 |
| 25 | UUAUUCUUGAGCUUGAUCAGGG | 1860 | 1880 | 59 | CUGAUCAAGCUCAAGAAUAA | 1862 | 1880 |
| 26 | UUUAUUCUUGAGCUUGAUCAGG | 1861 | 1881 | 60 | UGAUCAAGCUCAAGAAUAAA | 1863 | 1881 |
| 27 | UUUGACUUUGUCAUAGCCUGGG | 2116 | 2136 | 61 | CAGGCUAUGACAAAGUCAAA | 2118 | 2136 |
| 28 | UAAGUAUUGGGGUCAGCAUAGG | 2190 | 2210 | 62 | UAUGCUGACCCCAAUACUUA | 2192 | 2210 |
| 29 | UUUCUCUUGUGAACUAUCAAGG | 2232 | 2252 | 63 | UUGAUAGUUCACAAGAGAAA | 2234 | 2252 |
| 30 | UAAACGACUUCUCUUGUGAACU | 2239 | 2259 | 64 | UUCACAAGAGAAGUCGUUUA | 2241 | 2259 |
| 31 | UUUUUUGCAGACAUCCACUACU | 2287 | 2307 | 65 | UAGUGGAUGUCUGCAAAAAA | 2289 | 2307 |
| 32 | UCAUCUUGGAGUUUCUCCUUCA | 2382 | 2402 | 66 | AAGGAGAAACUCCAAGAUGA | 2384 | 2402 |
| 33 | UAACCCAAAUCCUCAUCUUGGA | 2394 | 2414 | 67 | CAAGAUGAGGAUUUGGGUUA | 2396 | 2414 |
| 34 | UAAACCCAAAUCCUCAUCUUGG | 2395 | 2415 | 68 | AAGAUGAGGAUUUGGGUUUA | 2397 | 2415 |
| 35 | UCAGCUGUUUUAAUUCAAUCCC | 2448 | 2468 | 69 | GAUUGAAUUAAAACAGCUGA | 2450 | 2468 |

TABLE 2

| Exemplary Sequences of the Present Application and Their Potency | | | | | | | | | | | |
|---|---|---|---|---|---|---|---|---|---|---|---|
| Guide Strand 3' | | | Guide strand sequence | SEQ | Passenger strand sequence | SEQ | | % of gene remaining at 0.02 nM | | % of gene remaining at 0.1 nM | |
| end | Start | End | (5'-3') | ID | (5'-3') | ID | | Mean | SEM | Mean | SEM |
| 514 | 493 | 513 | **UAAAGAGAUCU CAUCACUCACA** | 2 | **UGAGUGAUGAG AUCUCUUUA** | 36 | * | 43.43 | 4.73 | 24.37 | 3.42 |
| 516 | 495 | 515 | **UGGAAAGAGAU CUCAUCACUCA** | 3 | **AGUGAUGAGAU CUCUUUCCA** | 37 | *^ | 40.97 | 2.39 | 28.17 | 0.34 |
| 520 | 499 | 519 | **UCAGUGGAAAG AGAUCUCAUCA** | 4 | **AUGAGAUCUCU UUCCACUGA** | 38 | * | 44.83 | 2.22 | 23.37 | 1.51 |

TABLE 2-continued

| Exemplary Sequences of the Present Application and Their Potency | | | | | | | | | | | |
|---|---|---|---|---|---|---|---|---|---|---|---|
| Guide Strand 3' | | | Guide strand sequence | SEQ | Passenger strand sequence | SEQ | | % of gene remaining at 0.02 nM | | % of gene remaining at 0.1 nM | |
| end | Start | End | (5'-3') | ID | (5'-3') | ID | | Mean | SEM | Mean | SEM |
| 524 | 503 | 523 | **UAUAGCAGUGGAAAGAGAUCUC** | 5 | **GAUCUCUUUCCACUGCUAUA** | 39 | *^ | 50.03 | 1.14 | 30.43 | 1.36 |
| 535 | 514 | 534 | **UGUGUAACCGUCAUAGCAGUGG** | 6 | **ACUGCUAUGACGGUUACACA** | 389 | *^ | 39.33 | 1.84 | 23.90 | 1.31 |
| 1012 | 991 | 1011 | **UUUGACUAGACACUUUUUGGCU** | 7 | **CCAAAAAGUGUCUAGUCAAA** | 41 | | 52.13 | 2.17 | 34.10 | 0.40 |
| 1016 | 995 | 1015 | **UUAAGUUGACUAGACACUUUUU** | 8 | **AAAGUGUCUAGUCAACUUAA** | 42 | * | 51.37 | 4.56 | 33.03 | 1.42 |
| 1019 | 998 | 1018 | **UAAUUAAGUUGACUAGACACUU** | 9 | **GUGUCUAGUCAACUUAAUUA** | 43 | *^ | 40.30 | 2.32 | 26.87 | 0.64 |
| 1020 | 999 | 1019 | **UCAAUUAAGUUGACUAGACACU** | 10 | **UGUCUAGUCAACUUAAUUGA** | 44 | | 55.20 | 0.46 | 33.03 | 1.07 |
| 1055 | 1034 | 1054 | **UAUAUCUUGGCUUCACACCAUA** | 11 | **UGGUGUGAAGCCAAGAUAUA** | 45 | * | 56.97 | 4.32 | 29.03 | 3.70 |
| 1405 | 1384 | 1404 | **UUAGACAUCCAGAUAAUCCUCC** | 12 | **AGGAUUAUCUGGAUGUCUAA** | 46 | * | 43.30 | 1.97 | 33.90 | 7.10 |
| 1452 | 1431 | 1451 | **UAAGCAUUGAUGUUCACUUGGU** | 13 | **CAAGUGAACAUCAAUGCUUA** | 47 | *^ | 44.70 | 1.02 | 26.90 | 0.95 |
| 1453 | 1432 | 1452 | **UAAAGCAUUGAUGUUCACUUGG** | 14 | **AAGUGAACAUCAAUGCUUUA** | 48 | * | 46.33 | 0.64 | 25.60 | 2.80 |
| 1486 | 1465 | 1485 | **UAACACAUGUUGCUCAUUGUCU** | 15 | **ACAAUGAGCAACAUGUGUUA** | 49 | *^ | 54.57 | 1.47 | 19.50 | 0.40 |
| 1495 | 1474 | 1494 | **UUUGACUUUGAACACAUGUUGC** | 16 | **AACAUGUGUUCAAAGUCAAA** | 50 | * | 50.83 | 3.94 | 19.47 | 1.71 |
| 1501 | 1480 | 1500 | **UAUAUCCUUGACUUUGAACACA** | 17 | **UGUUCAAAGUCAAGGAUAUA** | 51 | *^ | 63.20 | 3.68 | 20.03 | 1.87 |
| 1627 | 1606 | 1626 | **UGAGAUCUUGGCCUGCCAUGGU** | 18 | **CAUGGCAGGCCAAGAUCUCA** | 52 | * | 57.23 | 3.58 | 23.57 | 1.53 |
| 1687 | 1666 | 1686 | **UAAGUACUCAGACACCACAGCC** | 19 | **CUGUGGUGUCUGAGUACUUA** | 53 | *^ | 59.27 | 1.15 | 25.77 | 1.68 |
| 1842 | 1821 | 1841 | **UAUUCAGGAAUUCCUGCUUCUU** | 20 | **GAAGCAGGAAUUCCUGAAUA** | 54 | | 64.80 | 5.31 | 26.83 | 3.54 |
| 1843 | 1822 | 1842 | **UAAUUCAGGAAUUCCUGCUUCU** | 21 | **AAGCAGGAAUUCCUGAAUUA** | 55 | *^ | 55.90 | 3.38 | 23.27 | 1.64 |
| 1846 | 1825 | 1845 | **UUAAAAUUCAGGAAUUCCUGCU** | 22 | **CAGGAAUUCCUGAAUUUUAA** | 56 | *^ | 40.50 | 2.80 | 19.67 | 0.63 |
| 1847 | 1826 | 1846 | **UAUAAAAUUCAGGAAUUCCUGC** | 23 | **AGGAAUUCCUGAAUUUUAUA** | 57 | * | 41.40 | 1.37 | 19.63 | 0.19 |
| 1850 | 1829 | 1849 | **UGUCAUAAAAUUCAGGAAUUCC** | 24 | **AAUUCCUGAAUUUUAUGACA** | 58 | *^ | 42.47 | 2.41 | 20.90 | 1.27 |
| 1881 | 1860 | 1880 | **UUAUUCUUGAGCUUGAUCAGGG** | 25 | **CUGAUCAAGCUCAAGAAUAA** | 59 | *^ | 55.80 | 1.15 | 25.87 | 2.51 |
| 1882 | 1861 | 1881 | **UUUAUUCUUGAGCUUGAUCAGG** | 26 | **UGAUCAAGCUCAAGAAUAAA** | 60 | *^ | 53.17 | 0.72 | 23.67 | 0.84 |
| 2137 | 2116 | 2136 | **UUUGACUUUGUCAUAGCCUGGG** | 27 | **CAGGCUAUGACAAAGUCAAA** | 61 | | 60.13 | 1.28 | 28.33 | 1.73 |
| 2211 | 2190 | 2210 | **UAAGUAUUGGGGUCAGCAUAGG** | 28 | **UAUGCUGACCCCAAUACUUA** | 62 | *^ | 45.90 | 0.66 | 22.03 | 0.55 |

TABLE 2-continued

Exemplary Sequences of the Present Application and Their Potency

| Guide Strand 3' end | Start | End | Guide strand sequence (5'-3') | SEQ ID | Passenger strand sequence (5'-3') | SEQ ID | | % of gene remaining at 0.02 nM Mean | % of gene remaining at 0.02 nM SEM | % of gene remaining at 0.1 nM Mean | % of gene remaining at 0.1 nM SEM |
|---|---|---|---|---|---|---|---|---|---|---|---|
| 2253 | 2232 | 2252 | **UUUCUCUUGUG AACUAUCAAGG** | 29 | **UUGAUAGUUCA CAAGAGAAA** | 63 | | 65.70 | 6.05 | 27.37 | 1.87 |
| 2260 | 2239 | 2259 | **UAAACGACUUC UCUUGUGAACU** | 30 | **UUCACAAGAGA AGUCGUUUA** | 64 | *^ | 35.63 | 1.77 | 17.40 | 0.25 |
| 2308 | 2287 | 2307 | **UUUUUUGCAGA CAUCCACUACU** | 31 | **UAGUGGAUGUC UGCAAAAAA** | 65 | *^ | 55.07 | 1.11 | 26.80 | 1.00 |
| 2403 | 2382 | 2402 | **UCAUCUUGGAG UUUCUCCUUCA** | 32 | **AAGGAGAAACU CCAAGAUGA** | 66 | *^ | 55.00 | 6.03 | 22.67 | 1.08 |
| 2415 | 2394 | 2414 | **UAACCCAAAUC CUCAUCUUGGA** | 33 | **CAAGAUGAGGA UUUGGGUUA** | 67 | | 62.33 | 4.60 | 30.17 | 2.59 |
| 2416 | 2395 | 2415 | **UAAACCCAAAU CCUCAUCUUGG** | 34 | **AAGAUGAGGAU UUGGGUUUA** | 68 | *^ | 43.23 | 2.84 | 23.47 | 1.18 |
| 2469 | 2448 | 2468 | **UCAGCUGUUUU AAUUCAAUCCC** | 35 | **GAUUGAAUUAA AACAGCUGA** | 69 | * | 46.93 | 1.82 | 26.27 | 0.58 |
| 26 | 5 | 25 | UCUAGACCUGG UCACAUUCCCU | 70 | GGAAUGUGACC AGGUCUAGA | 180 | | 100.03 | 3.94 | 67.63 | 7.63 |
| 36 | 15 | 35 | UAACUCCAGAC CUAGACCUGGU | 71 | CAGGUCUAGGU CUGGAGUUA | 181 | | 108.53 | 4.32 | 78.45 | 3.15 |
| 37 | 16 | 36 | UAAACUCCAGA CCUAGACCUGG | 72 | AGGUCUAGGUC UGGAGUUUA | 182 | | 98.97 | 2.02 | 64.50 | 4.10 |
| 38 | 17 | 37 | UGAAACUCCAG ACCUAGACCUG | 73 | GGUCUAGGUCU GGAGUUUCA | 183 | | 93.00 | 2.25 | 57.85 | 4.35 |
| 39 | 18 | 38 | UUGAAACUCCA GACCUAGACCU | 74 | GUCUAGGUCUG GAGUUUCAA | 184 | | 104.73 | 3.46 | 62.15 | 2.75 |
| 361 | 340 | 360 | **UGAUCUGCAGG UACGUGUCUGC** | 75 | **AGACACGUACC UGCAGAUCA** | 185 | | 77.90 | 2.10 | 42.35 | 0.35 |
| 432 | 411 | 431 | UGGAUUGCUCU GCACUCUGCCU | 76 | GCAGAGUGCAG AGCAAUCCA | 186 | | 85.77 | 3.30 | 56.10 | 2.58 |
| 499 | 478 | 498 | UCUCACAUUGU AGUAGGGAGAC | 77 | CUCCCUACUAC AAUGUGAGA | 187 | | 97.10 | 6.87 | 73.23 | 1.84 |
| 503 | 482 | 502 | UAUCACUCACA UUGUAGUAGGG | 78 | CUACUACAAUG UGAGUGAUA | 188 | | 82.03 | 4.17 | 47.53 | 0.52 |
| 504 | 483 | 503 | **UCAUCACUCAC AUUGUAGUAGG** | 79 | **UACUACAAUGU GAGUGAUGA** | 189 | | 67.43 | 4.90 | 36.47 | 0.65 |
| 515 | 494 | 514 | UGAAAGAGAUC UCAUCACUCAC | 80 | GAGUGAUGAGA UCUCUUUCA | 190 | | 81.27 | 1.79 | 44.30 | 2.51 |
| 518 | 497 | 517 | **UGUGGAAAGAG AUCUCAUCACU** | 81 | **UGAUGAGAUCU CUUUCCACA** | 191 | | 72.37 | 5.56 | 35.30 | 2.81 |
| 525 | 504 | 524 | **UCAUAGCAGUG GAAAGAGAUCU** | 82 | **AUCUCUUUCCA CUGCUAUGA** | 192 | | 65.07 | 4.10 | 35.40 | 0.84 |
| 537 | 516 | 536 | UGAGUGUAACC GUCAUAGCAGU | 83 | UGCUAUGACGG UUACACUCA | 193 | | 103.20 | 2.51 | 70.37 | 1.43 |
| 539 | 518 | 538 | UGAGAGUGUAA CCGUCAUAGCA | 84 | CUAUGACGGUU ACACUCUCA | 194 | | 109.37 | 5.79 | 70.03 | 2.07 |
| 607 | 586 | 606 | UUUGUCACAGA UCGCUGUCUGC | 85 | AGACAGCGAUC UGUGACAAA | 195 | | 96.17 | 3.42 | 44.00 | 1.21 |
| 797 | 776 | 796 | UCAUGAAGGAG UCUUGGCAGGA | 86 | CUGCCAAGACU CCUUCAUGA | 196 | | 85.97 | 6.60 | 49.30 | 2.57 |

TABLE 2-continued

Exemplary Sequences of the Present Application and Their Potency

| Guide Strand 3' end | Start | End | Guide strand sequence (5'-3') | SEQ ID | Passenger strand sequence (5'-3') | SEQ ID | % of gene remaining at 0.02 nM Mean | SEM | % of gene remaining at 0.1 nM Mean | SEM |
|---|---|---|---|---|---|---|---|---|---|---|
| 800 | 779 | 799 | UGUACAUGAAGGAGUCUUGGCA | 87 | CCAAGACUCCUUCAUGUACA | 197 | 88.77 | 1.81 | 52.10 | 1.55 |
| 801 | 780 | 800 | **UCGUACAUGAAGGAGUCUUGGC** | 88 | **CAAGACUCCUUCAUGUACGA** | 198 | 66.07 | 1.73 | 34.07 | 0.58 |
| 803 | 782 | 802 | UGUCGUACAUGAAGGAGUCUUG | 89 | AGACUCCUUCAUGUACGACA | 199 | 93.53 | 0.84 | 70.07 | 1.95 |
| 829 | 808 | 828 | **UAAAGCUUCGGCCACCUCUUGA** | 90 | **AAGAGGUGGCCGAAGCUUUA** | 200 | 78.67 | 29.34 | 31.83 | 1.53 |
| 960 | 939 | 959 | UAUCCAUCUAGCACCAGGUAGA | 91 | UACCUGGUGCUAGAUGGAUA | 201 | 91.50 | 1.18 | 63.07 | 3.87 |
| 967 | 946 | 966 | UCUGUCUGAUCCAUCUAGCACC | 92 | UGCUAGAUGGAUCAGACAGA | 202 | 98.17 | 1.33 | 68.70 | 3.66 |
| 1001 | 980 | 1000 | UCUUUUUGGCUCCUGUGAAGUU | 93 | CUUCACAGGAGCCAAAAAGA | 203 | 109.17 | 2.98 | 78.10 | 3.41 |
| 1005 | 984 | 1004 | UGACACUUUUUGGCUCCUGUGA | 94 | ACAGGAGCCAAAAAGUGUCA | 204 | 86.37 | 2.29 | 50.30 | 3.93 |
| 1010 | 989 | 1009 | UGACUAGACACUUUUUGGCUCC | 95 | AGCCAAAAAGUGUCUAGUCA | 205 | 92.17 | 2.23 | 59.93 | 1.49 |
| 1013 | 992 | 1012 | UGUUGACUAGACACUUUUUGGC | 96 | CAAAAAGUGUCUAGUCAACA | 206 | 82.50 | 3.56 | 47.10 | 0.87 |
| 1017 | 996 | 1016 | **UUUAAGUUGACUAGACACUUUU** | 97 | **AAGUGUCUAGUCAACUUAAA** | 207 | 53.50 | 0.20 | 35.40 | 0.78 |
| 1022 | 1001 | 1021 | **UCUCAAUUAAGUUGACUAGACA** | 98 | **UCUAGUCAACUUAAUUGAGA** | 208 | 73.60 | 3.65 | 49.90 | 4.61 |
| 1024 | 1003 | 1023 | UUUCUCAAUUAAGUUGACUAGA | 99 | UAGUCAACUUAAUUGAGAAA | 209 | 88.37 | 2.39 | 54.10 | 4.71 |
| 1037 | 1016 | 1036 | UAUAACUUGCCACCUUCUCAAU | 100 | UGAGAAGGUGGCAAGUUAUA | 210 | 89.93 | 3.15 | 71.40 | 1.91 |
| 1038 | 1017 | 1037 | UCAUAACUUGCCACCUUCUCAA | 101 | GAGAAGGUGGCAAGUUAUGA | 211 | 89.57 | 6.29 | 58.70 | 4.31 |
| 1041 | 1020 | 1040 | **UCACCAUAACUUGCCACCUUCU** | 102 | **AAGGUGGCAAGUUAUGGUGA** | 212 | 78.73 | 4.21 | 48.87 | 1.43 |
| 1045 | 1024 | 1044 | UUUCACACCAUAACUUGCCACC | 103 | UGGCAAGUUAUGGUGUGAAA | 213 | 85.37 | 3.25 | 48.60 | 2.84 |
| 1178 | 1157 | 1177 | UCUUCAACUUGUGGUCUUCAUA | 104 | UGAAGACCACAAGUUGAAGA | 214 | 86.87 | 2.84 | 53.00 | 2.23 |
| 1180 | 1159 | 1179 | UGACUUCAACUUGUGGUCUUCA | 105 | AAGACCACAAGUUGAAGUCA | 215 | 86.97 | 4.64 | 73.60 | 8.92 |
| 1228 | 1207 | 1227 | **UCUCAUCAUGCUGUACACUGCC** | 106 | **CAGUGUACAGCAUGAUGAGA** | 216 | 73.07 | 3.92 | 49.53 | 1.16 |
| 1326 | 1305 | 1325 | **UUAAUUGGGUCCCCGCCCAUGU** | 107 | **AUGGGCGGGGACCCAAUUAA** | 217 | 74.17 | 2.55 | 70.60 | 1.90 |
| 1333 | 1312 | 1332 | **UAUGACAGUAAUUGGGUCCCCG** | 108 | **GGGACCCAAUUACUGUCAUA** | 218 | 75.57 | 0.93 | 43.20 | 3.30 |
| 1334 | 1313 | 1333 | **UAAUGACAGUAAUUGGGUCCCC** | 109 | **GGACCCAAUUACUGUCAUUA** | 219 | 78.07 | 1.61 | 49.10 | 1.50 |
| 1335 | 1314 | 1334 | **UCAAUGACAGUAAUUGGGUCCC** | 110 | **GACCCAAUUACUGUCAUUGA** | 220 | 67.87 | 3.27 | 39.03 | 1.98 |

TABLE 2-continued

Exemplary Sequences of the Present Application and Their Potency

| Guide Strand 3' end | Start | End | Guide strand sequence (5'-3') | SEQ ID | Passenger strand sequence (5'-3') | SEQ ID | % of gene remaining at 0.02 nM Mean | % of gene remaining at 0.02 nM SEM | % of gene remaining at 0.1 nM Mean | % of gene remaining at 0.1 nM SEM |
|---|---|---|---|---|---|---|---|---|---|---|
| 1337 | 1316 | 1336 | UAUCAAUGACAGUAAUUGGGUC | 111 | CCCAAUUACUGUCAUUGAUA | 221 | 96.20 | 2.17 | 77.10 | 2.16 |
| 1338 | 1317 | 1337 | **UCAUCAAUGACAGUAAUUGGGU** | 112 | **CCAAUUACUGUCAUUGAUGA** | 222 | 60.00 | 2.71 | 43.00 | 6.99 |
| 1340 | 1319 | 1339 | **UCUCAUCAAUGACAGUAAUUGG** | 113 | **AAUUACUGUCAUUGAUGAGA** | 223 | 73.97 | 1.59 | 42.07 | 1.77 |
| 1406 | 1385 | 1405 | **UAUAGACAUCCAGAUAAUCCUC** | 114 | **GGAUUAUCUGGAUGUCUAUA** | 224 | 69.53 | 2.30 | 41.03 | 0.12 |
| 1407 | 1386 | 1406 | **UCAUAGACAUCCAGAUAAUCCU** | 115 | **GAUUAUCUGGAUGUCUAUGA** | 225 | 76.00 | 1.30 | 44.83 | 4.68 |
| 1454 | 1433 | 1453 | UCAAAGCAUUGAUGUUCACUUG | 116 | AGUGAACAUCAAUGCUUUGA | 226 | 92.70 | 4.40 | 69.80 | 2.41 |
| 1458 | 1437 | 1457 | **UAAGCCAAAGCAUUGAUGUUCA** | 117 | **AACAUCAAUGCUUUGGCUUA** | 227 | 64.30 | 4.36 | 37.23 | 1.52 |
| 1466 | 1445 | 1465 | UUUUCUUGGAAGCCAAAGCAUU | 118 | UGCUUUGGCUUCCAAGAAAA | 228 | 85.47 | 1.85 | 59.80 | 0.95 |
| 1467 | 1446 | 1466 | UCUUUCUUGGAAGCCAAAGCAU | 119 | GCUUUGGCUUCCAAGAAAGA | 229 | 88.23 | 4.54 | 65.93 | 2.16 |
| 1469 | 1448 | 1468 | **UGUCUUUCUUGGAAGCCAAAGC** | 120 | **UUUGGCUUCCAAGAAAGACA** | 230 | 71.17 | 1.75 | 42.10 | 1.44 |
| 1475 | 1454 | 1474 | **UCUCAUUGUCUUUCUUGGAAGC** | 121 | **UUCCAAGAAAGACAAUGAGA** | 231 | 73.60 | 2.15 | 53.47 | 3.22 |
| 1478 | 1457 | 1477 | **UUUGCUCAUUGUCUUUCUUGGA** | 122 | **CAAGAAAGACAAUGAGCAAA** | 232 | 69.57 | 4.68 | 38.90 | 2.16 |
| 1479 | 1458 | 1478 | **UGUUGCUCAUUGUCUUUCUUGG** | 123 | **AAGAAAGACAAUGAGCAACA** | 233 | 61.23 | 2.82 | 36.33 | 3.02 |
| 1481 | 1460 | 1480 | **UAUGUUGCUCAUUGUCUUUCUU** | 124 | **GAAAGACAAUGAGCAACAUA** | 234 | 62.70 | 1.70 | 50.73 | 6.51 |
| 1482 | 1461 | 1481 | **UCAUGUUGCUCAUUGUCUUUCU** | 125 | **AAAGACAAUGAGCAACAUGA** | 235 | 78.77 | 6.54 | 41.27 | 1.64 |
| 1490 | 1469 | 1489 | UUUUGAACACAUGUUGCUCAUU | 126 | UGAGCAACAUGUGUUCAAAA | 236 | 92.00 | 0.71 | 36.37 | 3.64 |
| 1491 | 1470 | 1490 | UCUUUGAACACAUGUUGCUCAU | 127 | GAGCAACAUGUGUUCAAAGA | 237 | 111.67 | 1.64 | 75.03 | 4.55 |
| 1493 | 1472 | 1492 | UGACUUUGAACACAUGUUGCUC | 128 | GCAACAUGUGUUCAAAGUCA | 238 | 100.37 | 1.19 | 43.60 | 3.69 |
| 1506 | 1485 | 1505 | **UUUUCCAUAUCCUUGACUUUGA** | 129 | **AAAGUCAAGGAUAUGGAAAA** | 239 | 71.53 | 3.49 | 26.70 | 1.76 |
| 1511 | 1490 | 1510 | UCAGGUUUUCCAUAUCCUUGAC | 130 | CAAGGAUAUGGAAAACCUGA | 240 | 98.37 | 2.03 | 73.90 | 2.69 |
| 1563 | 1542 | 1562 | UCACAGAGACUCAGAGACUGGC | 131 | CAGUCUCUGAGUCUCUGUGA | 241 | 99.33 | 4.91 | 74.73 | 5.32 |
| 1607 | 1586 | 1606 | **UUUGCUUGUGGUAAUCGGUACC** | 132 | **UACCGAUUACCACAAGCAAA** | 242 | 76.37 | 3.24 | 35.80 | 1.56 |
| 1688 | 1667 | 1687 | UAAAGUACUCAGACACCACAGC | 133 | UGUGGUGUCUGAGUACUUUA | 243 | 81.20 | 2.55 | 38.33 | 4.78 |
| 1710 | 1689 | 1709 | UAACAAUGUGCUGCUGUCAGCA | 134 | CUGACAGCAGCACAUUGUUA | 244 | 92.07 | 6.25 | 56.87 | 11.06 |

TABLE 2-continued

Exemplary Sequences of the Present Application and Their Potency

| Guide Strand 3' end | Start | End | Guide strand sequence (5'-3') | SEQ ID | Passenger strand sequence (5'-3') | SEQ ID | % of gene remaining at 0.02 nM Mean | % of gene remaining at 0.02 nM SEM | % of gene remaining at 0.1 nM Mean | % of gene remaining at 0.1 nM SEM |
|---|---|---|---|---|---|---|---|---|---|---|
| 1742 | 1721 | 1741 | **UCUUGAUUGAG UGUUCCUUGUC** | 135 | **CAAGGAACACU CAAUCAAGA** | 245 | 78.00 | 2.25 | 40.33 | 4.77 |
| 1747 | 1726 | 1746 | UCUGACCUUGA UUGAGUGUUCC | 136 | AACACUCAAUC AAGGUCAGA | 246 | 96.17 | 5.47 | 55.57 | 6.20 |
| 1836 | 1815 | 1835 | UGAAUUCCUGC UUCUUUUUUCC | 137 | AAAAAAGAAGC AGGAAUUCA | 247 | 84.13 | 1.22 | 44.07 | 5.74 |
| 1848 | 1827 | 1847 | **UCAUAAAAUUC AGGAAUUCCUG** | 138 | **GGAAUUCCUGA AUUUUAUGA** | 248 | 68.40 | 2.10 | 29.40 | 2.10 |
| 1854 | 1833 | 1853 | UCAUAGUCAUA AAAUUCAGGAA | 139 | CCUGAAUUUUA UGACUAUGA | 249 | 86.67 | 3.20 | 41.07 | 0.79 |
| 1856 | 1835 | 1855 | **UGUCAUAGUCA UAAAAUUCAGG** | 140 | **UGAAUUUUAUG ACUAUGACA** | 250 | 70.17 | 4.04 | 30.03 | 3.42 |
| 1871 | 1850 | 1870 | UCUUGAUCAGG GCAACGUCAUA | 141 | UGACGUUGCCC UGAUCAAGA | 251 | 90.70 | 2.77 | 39.70 | 4.51 |
| 1879 | 1858 | 1878 | UUUCUUGAGCU UGAUCAGGGCA | 142 | CCCUGAUCAAG CUCAAGAAA | 252 | 99.63 | 2.39 | 60.50 | 4.31 |
| 1880 | 1859 | 1879 | UAUUCUUGAGC UUGAUCAGGGC | 143 | CCUGAUCAAGC UCAAGAAUA | 253 | 82.77 | 2.34 | 36.93 | 1.48 |
| 1883 | 1862 | 1882 | UCUUAUUCUUG AGCUUGAUCAG | 144 | GAUCAAGCUCA AGAAUAAGA | 254 | 88.63 | 4.09 | 55.10 | 3.84 |
| 1919 | 1898 | 1918 | UGAGACAAAUG GGCCUGAUAGU | 145 | UAUCAGGCCCA UUUGUCUCA | 255 | 83.83 | 2.23 | 41.43 | 1.23 |
| 1971 | 1950 | 1970 | UAAGUGGUAGU UGGAGGAAGCC | 146 | CUUCCUCCAAC UACCACUUA | 256 | 85.97 | 0.99 | 47.40 | 3.92 |
| 2021 | 2000 | 2020 | UCAGAGCUUUG AUAUCCUGUGC | 147 | ACAGGAUAUCA AAGCUCUGA | 257 | 91.37 | 3.18 | 58.10 | 2.70 |
| 2023 | 2002 | 2022 | **UAACAGAGCUU UGAUAUCCUGU** | 148 | **AGGAUAUCAAA GCUCUGUUA** | 258 | 66.20 | 1.68 | 30.37 | 2.63 |
| 2024 | 2003 | 2023 | UAAACAGAGCU UUGAUAUCCUG | 149 | GGAUAUCAAAG CUCUGUUUA | 259 | 92.77 | 1.10 | 59.83 | 3.00 |
| 2025 | 2004 | 2024 | **UCAAACAGAGC UUUGAUAUCCU** | 150 | **GAUAUCAAAGC UCUGUUUGA** | 260 | 74.77 | 2.16 | 31.10 | 3.00 |
| 2031 | 2010 | 2030 | UCAGACACAAA CAGAGCUUUGA | 151 | AAAGCUCUGUU UGUGUCUGA | 261 | 89.27 | 7.05 | 36.90 | 3.43 |
| 2072 | 2051 | 2071 | UCUUGAUGUAG ACCUCCUUCCG | 152 | GAAGGAGGUCU ACAUCAAGA | 262 | 93.67 | 2.58 | 57.90 | 4.35 |
| 2076 | 2055 | 2075 | UCAUUCUUGAU GUAGACCUCCU | 153 | GAGGUCUACAU CAAGAAUGA | 263 | 92.13 | 0.26 | 57.50 | 5.41 |
| 2088 | 2067 | 2087 | UCUUUCUUAUC CCCAUUCUUGA | 154 | AAGAAUGGGGA UAAGAAAGA | 264 | 149.93 | 24.82 | 67.17 | 3.57 |
| 2103 | 2082 | 2102 | UCUCUCUCACA GCUGCCUUUCU | 155 | AAAGGCAGCUG UGAGAGAGA | 265 | 94.53 | 4.90 | 54.93 | 0.84 |
| 2109 | 2088 | 2108 | UGAGCAUCUCU CUCACAGCUGC | 156 | AGCUGUGAGAG AGAUGCUCA | 266 | 82.23 | 2.93 | 39.60 | 2.90 |
| 2111 | 2090 | 2110 | UUUGAGCAUCU CUCUCACAGCU | 157 | CUGUGAGAGAG AUGCUCAAA | 267 | 107.80 | 3.18 | 72.93 | 0.78 |
| 2112 | 2091 | 2111 | UAUUGAGCAUC UCUCUCACAGC | 158 | UGUGAGAGAGA UGCUCAAUA | 268 | 96.43 | 3.88 | 56.97 | 2.84 |

TABLE 2-continued

Exemplary Sequences of the Present Application and Their Potency

| Guide Strand 3' end | Start | End | Guide strand sequence (5'-3') | SEQ ID | Passenger strand sequence (5'-3') | SEQ ID | | % of gene remaining at 0.02 nM Mean | SEM | % of gene remaining at 0.1 nM Mean | SEM |
|---|---|---|---|---|---|---|---|---|---|---|---|
| 2114 | 2093 | 2113 | **UAUAUUGAGCA UCUCUCUCACA** | 159 | **UGAGAGAGAUG CUCAAUAUA** | 269 | | 75.13 | 0.37 | 35.33 | 0.41 |
| 2115 | 2094 | 2114 | UCAUAUUGAGC AUCUCUCUCAC | 160 | GAGAGAGAUGC UCAAUAUGA | 270 | | 108.77 | 2.29 | 61.07 | 1.71 |
| 2138 | 2117 | 2137 | UCUUGACUUUG UCAUAGCCUGG | 161 | AGGCUAUGACA AAGUCAAGA | 271 | | 83.90 | 1.97 | 43.90 | 1.96 |
| 2146 | 2125 | 2145 | UGAGAUGUCCU UGACUUUGUCA | 162 | ACAAAGUCAAG GACAUCUCA | 272 | | 82.03 | 5.27 | 36.37 | 1.85 |
| 2201 | 2180 | 2200 | UGUCAGCAUAG GGACUCACUCC | 163 | AGUGAGUCCCU AUGCUGACA | 273 | | 89.60 | 3.33 | 52.43 | 4.78 |
| 2209 | 2188 | 2208 | UGUAUUGGGGU CAGCAUAGGGA | 164 | CCUAUGCUGAC CCCAAUACA | 274 | | 107.57 | 6.53 | 61.70 | 3.85 |
| 2222 | 2201 | 2221 | **UAUCACCUCUG CAAGUAUUGGG** | 165 | **CAAUACUUGCA GAGGUGAUA** | 275 | | 74.30 | 8.75 | 25.57 | 3.38 |
| 2243 | 2222 | 2242 | UAACUAUCAAG GGGCCGCCAGA | 166 | UGGCGGCCCCU UGAUAGUUA | 276 | | 91.70 | 0.99 | 74.00 | 3.85 |
| 2246 | 2225 | 2245 | UGUGAACUAUC AAGGGGCCGCC | 167 | CGGCCCCUUGA UAGUUCACA | 277 | | 91.93 | 3.69 | 63.67 | 5.62 |
| 2248 | 2227 | 2247 | **UUUGUGAACUA UCAAGGGGCCG** | 168 | **GCCCCUUGAUA GUUCACAAA** | 278 | | 75.07 | 1.39 | 34.10 | 0.42 |
| 2251 | 2230 | 2250 | UCUCUUGUGAA CUAUCAAGGGG | 169 | CCUUGAUAGUU CACAAGAGA | 279 | | 92.43 | 2.42 | 51.23 | 4.15 |
| 2256 | 2235 | 2255 | UGACUUCUCUU GUGAACUAUCA | 170 | AUAGUUCACAA GAGAAGUCA | 280 | | 81.60 | 4.46 | 40.70 | 5.31 |
| 2263 | 2242 | 2262 | **UAUGAAACGAC UUCUCUUGUGA** | 171 | **ACAAGAGAAGU CGUUUCAUA** | 281 | * | 25.67 | 1.21 | 15.67 | 1.05 |
| 2307 | 2286 | 2306 | **UUUUUGCAGAC AUCCACUACUC** | 172 | **GUAGUGGAUGU CUGCAAAAA** | 282 | | 73.33 | 2.54 | 33.47 | 1.39 |
| 2309 | 2288 | 2308 | UGUUUUUGCAG ACAUCCACUAC | 173 | AGUGGAUGUCU GCAAAAACA | 283 | | 90.23 | 1.30 | 39.10 | 1.81 |
| 2314 | 2293 | 2313 | UUUCUGGUUUU UGCAGACAUCC | 174 | AUGUCUGCAAA AACCAGAAA | 284 | | 105.50 | 1.12 | 58.97 | 0.86 |
| 2399 | 2378 | 2398 | UUUGGAGUUUC UCCUUCAGCCA | 175 | GCUGAAGGAGA AACUCCAAA | 285 | | 93.83 | 0.44 | 63.83 | 0.75 |
| 2402 | 2381 | 2401 | **UAUCUUGGAGU UUCUCCUUCAG** | 176 | **GAAGGAGAAAC UCCAAGAUA** | 286 | | 75.43 | 3.16 | 28.63 | 1.52 |
| 2405 | 2384 | 2404 | **UCUCAUCUUGG AGUUUCUCCUU** | 177 | **GGAGAAACUCC AAGAUGAGA** | 287 | | 73.90 | 4.95 | 29.13 | 1.56 |
| 2409 | 2388 | 2408 | **UAAUCCUCAUC UUGGAGUUUCU** | 178 | **AAACUCCAAGA UGAGGAUUA** | 288 | | 75.87 | 1.47 | 40.83 | 0.98 |
| 2418 | 2397 | 2417 | **UGAAAACCCAA AUCCUCAUCUU** | 179 | **GAUGAGGAUUU GGGUUUUCA** | 289 | | 69.60 | 2.10 | 31.33 | 0.87 |
| 40 | 19 | 39 | UCUGAAACUCC AGACCUAGACC | 290 | UCUAGGUCUGG AGUUUCAGA | 330 | | 101.87 | 1.80 | 80.17 | 6.81 |
| 53 | 32 | 52 | UCUCAGUGUCC AAGCUGAAACU | 291 | UUUCAGCUUGG ACACUGAGA | 331 | | 112.07 | 3.92 | 143.13 | 36.85 |
| 260 | 239 | 259 | UGAUCUCUACC CCCUCCAGAGA | 292 | UCUGGAGGGGG UAGAGAUCA | 332 | | 116.10 | 9.49 | 119.00 | 16.30 |

TABLE 2-continued

Exemplary Sequences of the Present Application and Their Potency

| Guide Strand 3' end | Start | End | Guide strand sequence (5'-3') | SEQ ID | Passenger strand sequence (5'-3') | SEQ ID | % of gene remaining at 0.02 nM Mean | SEM | % of gene remaining at 0.1 nM Mean | SEM |
|---|---|---|---|---|---|---|---|---|---|---|
| 287 | 266 | 286 | UUUGGAGAAGU CGGAAGGAGCC | 293 | CUCCUUCCGAC UUCUCCAAA | 333 | 144.60 | 43.86 | 109.80 | 20.04 |
| 290 | 269 | 289 | UCUCUUGGAGA AGUCGGAAGGA | 294 | CUUCCGACUUC UCCAAGAGA | 334 | 107.80 | 4.53 | 80.40 | 4.60 |
| 341 | 320 | 340 | UCACAGGGUAC GGGUAGAAGCC | 295 | CUUCUACCCGU ACCCUGUGA | 335 | 113.43 | 13.79 | 112.25 | 3.05 |
| 569 | 548 | 568 | UCACUUGGCAG GUGCGAUUGGC | 296 | CAAUCGCACCU GCCAAGUGA | 336 | 125.73 | 1.47 | 117.47 | 3.80 |
| 571 | 550 | 570 | UUUCACUUGGC AGGUGCGAUUG | 297 | AUCGCACCUGC CAAGUGAAA | 337 | 130.47 | 4.37 | 130.53 | 5.79 |
| 763 | 742 | 762 | UCUCCAAGAGC CACCUUCCUGA | 298 | AGGAAGGUGGC UCUUGGAGA | 338 | 106.90 | 6.02 | 89.33 | 0.82 |
| 790 | 769 | 789 | UGAGUCUUGGC AGGAAGGCUCC | 299 | AGCCUUCCUGC CAAGACUCA | 339 | 104.97 | 8.54 | 110.57 | 0.99 |
| 805 | 784 | 804 | UGUGUCGUACA UGAAGGAGUCU | 300 | ACUCCUUCAUG UACGACACA | 340 | 106.17 | 1.59 | 95.70 | 2.21 |
| 839 | 818 | 838 | UGGAAGACAGG AAAGCUUCGGC | 301 | CGAAGCUUUCC UGUCUUCCA | 341 | 101.45 | 10.35 | 102.47 | 7.63 |
| 844 | 823 | 843 | UGUCAGGGAAG ACAGGAAAGCU | 302 | CUUUCCUGUCU UCCCUGACA | 342 | 159.80 | 39.70 | 82.20 | 2.85 |
| 867 | 846 | 866 | UCAUCGACUCC UUCUAUGGUCU | 303 | ACCAUAGAAGG AGUCGAUGA | 343 | 108.70 | 9.41 | 93.63 | 3.23 |
| 938 | 917 | 937 | UGUUCAUGGAG CCUGAAGGGUC | 304 | CCCUUCAGGCU CCAUGAACA | 344 | 161.93 | 45.43 | 106.77 | 4.94 |
| 939 | 918 | 938 | UUGUUCAUGGA GCCUGAAGGGU | 305 | CCUUCAGGCUC CAUGAACAA | 345 | 127.33 | 7.65 | 100.87 | 4.07 |
| 940 | 919 | 939 | UAUGUUCAUGG AGCCUGAAGGG | 306 | CUUCAGGCUCC AUGAACAUA | 346 | 103.23 | 10.15 | 83.83 | 1.24 |
| 947 | 926 | 946 | UCAGGUAGAUG UUCAUGGAGCC | 307 | CUCCAUGAACA UCUACCUGA | 347 | 115.17 | 7.69 | 92.57 | 5.27 |
| 950 | 929 | 949 | UCACCAGGUAG AUGUUCAUGGA | 308 | CAUGAACAUCU ACCUGGUGA | 348 | 104.07 | 2.74 | 83.27 | 1.64 |
| 956 | 935 | 955 | UAUCUAGCACC AGGUAGAUGUU | 309 | CAUCUACCUGG UGCUAGAUA | 349 | 106.43 | 0.54 | 107.10 | 10.08 |
| 957 | 936 | 956 | UCAUCUAGCAC CAGGUAGAUGU | 310 | AUCUACCUGGU GCUAGAUGA | 350 | 100.70 | 5.93 | 105.60 | 11.23 |
| 1192 | 1171 | 1191 | UGUGUUAGUCC CUGACUUCAAC | 311 | UGAAGUCAGGG ACUAACACA | 351 | 91.97 | 2.11 | 80.83 | 2.71 |
| 1289 | 1268 | 1288 | UCAUGAGGAUG AUGACAUGGCG | 312 | CCAUGUCAUCA UCCUCAUGA | 352 | 98.53 | 2.86 | 91.97 | 2.07 |
| 1291 | 1270 | 1290 | UGUCAUGAGGA UGAUGACAUGG | 313 | AUGUCAUCAUC CUCAUGACA | 353 | 91.70 | 5.82 | 82.33 | 1.39 |
| 1327 | 1306 | 1326 | UGUAAUUGGGU CCCCGCCCAUG | 314 | UGGGCGGGGAC CCAAUUACA | 354 | 120.30 | 1.84 | 102.47 | 4.76 |
| 1329 | 1308 | 1328 | UCAGUAAUUGG GUCCCCGCCCA | 315 | GGCGGGGACCC AAUUACUGA | 355 | 126.17 | 10.02 | 113.37 | 12.38 |
| 1331 | 1310 | 1330 | UGACAGUAAUU GGGUCCCCGCC | 316 | CGGGGACCCAA UUACUGUCA | 356 | 118.13 | 1.67 | 103.50 | 4.35 |

TABLE 2-continued

Exemplary Sequences of the Present Application and Their Potency

| Guide Strand 3' end | Start | End | Guide strand sequence (5'-3') | SEQ ID | Passenger strand sequence (5'-3') | SEQ ID | % of gene remaining at 0.02 nM Mean | SEM | % of gene remaining at 0.1 nM Mean | SEM |
|---|---|---|---|---|---|---|---|---|---|---|
| 1332 | 1311 | 1331 | UUGACAGUAAU UGGGUCCCCGC | 317 | GGGGACCCAAU UACUGUCAA | 357 | 108.43 | 2.72 | 96.57 | 3.34 |
| 1505 | 1484 | 1504 | UUUCCAUAUCC UUGACUUUGAA | 318 | CAAAGUCAAGG AUAUGGAAA | 358 | 107.93 | 3.46 | 93.23 | 0.95 |
| 1508 | 1487 | 1507 | UGUUUUCCAUA UCCUUGACUUU | 319 | AGUCAAGGAUA UGGAAAACA | 359 | 102.67 | 2.46 | 88.57 | 3.01 |
| 1951 | 1930 | 1950 | UCUCAAAGCUC GAGUUGUUCCC | 320 | GAACAACUCGA GCUUUGAGA | 360 | 99.80 | 2.96 | 94.70 | 4.51 |
| 2033 | 2012 | 2032 | UCUCAGACACA AACAGAGCUUU | 321 | AGCUCUGUUUG UGUCUGAGA | 361 | 100.67 | 2.18 | 87.47 | 4.79 |
| 2069 | 2048 | 2068 | UGAUGUAGACC UCCUUCCGAGU | 322 | UCGGAAGGAGG UCUACAUCA | 362 | 101.30 | 3.64 | 92.60 | 7.44 |
| 2087 | 2066 | 2086 | UUUUCUUAUCC CCAUUCUUGAU | 323 | CAAGAAUGGGG AUAAGAAAA | 363 | 103.07 | 1.24 | 83.03 | 4.30 |
| 2141 | 2120 | 2140 | UGUCCUUGACU UUGUCAUAGCC | 324 | CUAUGACAAAG UCAAGGACA | 364 | 102.63 | 4.02 | 82.33 | 5.04 |
| 2245 | 2224 | 2244 | UUGAACUAUCA AGGGGCCGCCA | 325 | GCGGCCCCUUG AUAGUUCAA | 365 | 103.47 | 8.19 | 83.60 | 9.88 |
| 2249 | 2228 | 2248 | UCUUGUGAACU AUCAAGGGGCC | 326 | CCCCUUGAUAG UUCACAAGA | 366 | 97.70 | 2.51 | 93.40 | 4.48 |
| 2324 | 2303 | 2323 | UCUUUUGCCGC UUCUGGUUUUU | 327 | AAACCAGAAGC GGCAAAAGA | 367 | 122.60 | 1.11 | 97.73 | 4.12 |
| 2336 | 2315 | 2335 | UAGCAGGUACC UGCUUUUGCCG | 328 | GCAAAAGCAGG UACCUGCUA | 368 | 100.27 | 2.46 | 89.90 | 1.43 |
| 2400 | 2379 | 2399 | UCUUGGAGUUU CUCCUUCAGCC | 329 | CUGAAGGAGAA ACUCCAAGA | 369 | 106.20 | 1.87 | 92.43 | 2.38 |

Figure 2:
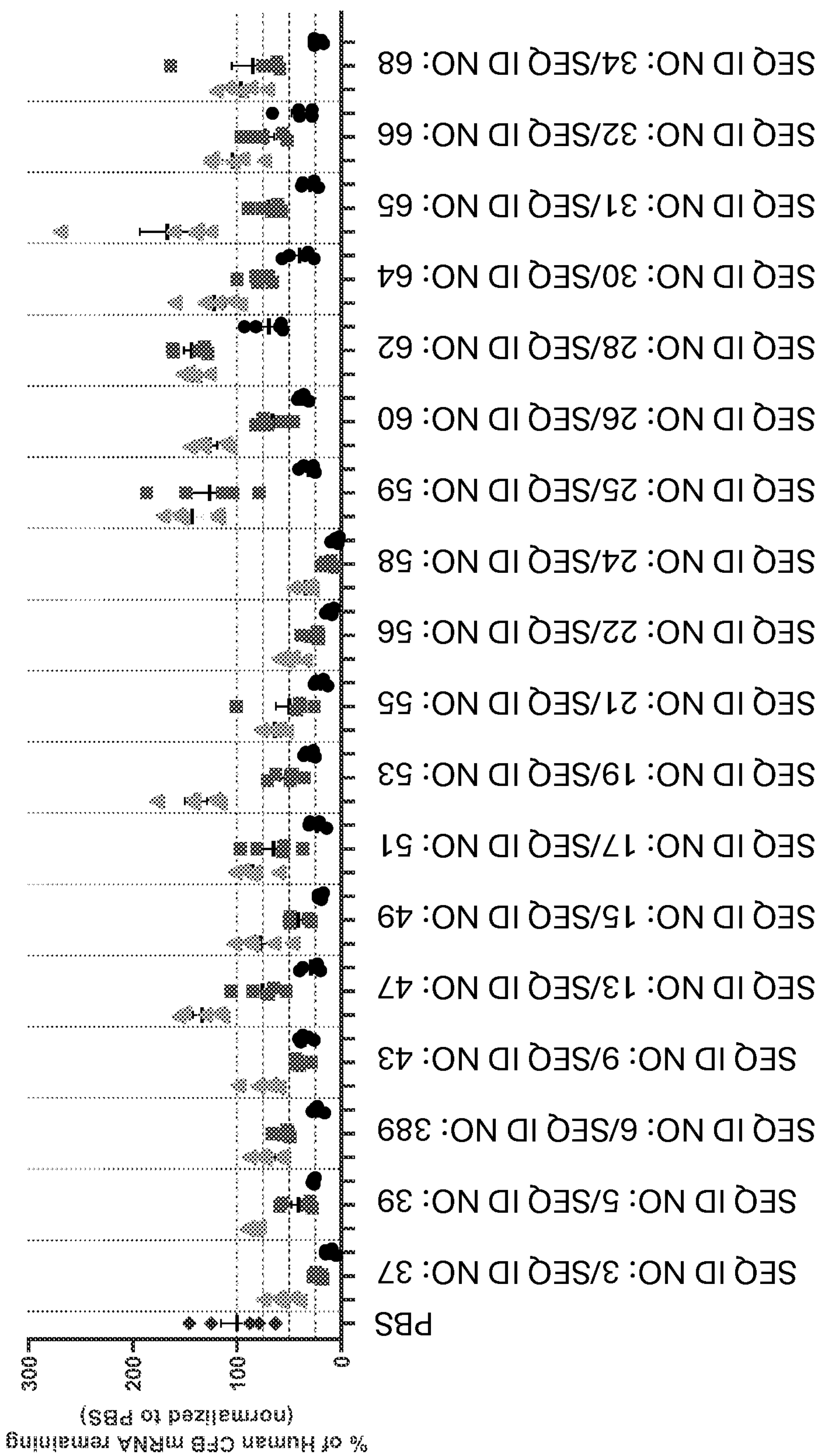
FIG. 2 is a graph showing the in vivo dose response of a subset of compounds listed in Table 2 in mouse HDI liver at 0.25, 0.5, or 1 mg/kg at day 4 post-dosing. Data is presented as % of human CFB mRNA remaining relative to PBS when normalized to NeoR mRNA levels (Mean, +/−SEM).

*Exemplary results of in vivo CFB dose response in HDI mouse liver are shown in FIG. 1
^Exemplary results of in vivo CFB dose response in HDI mouse liver are shown in FIG. 2

TABLE 3

Exemplary Modified Sequences of the Disclosure

| | Sequence | SEQ ID NO: |
|---|---|---|
| G (5'-3') | [MeEPmUs][fGs][fU][mC][fA][mU][fA][mA][mA][fA][mU][mU][mC][fA][mG][fG] [mA][mA][mU][mUs][mCs][mC] | SEQ ID NO: 370 |
| P (5'-3') | [mAs][mAs][mU][mU][mC][fC][mU][fG][fA][fA][fU][mU][mU][mU][mA][mU][mG] [mAs][mCs][mA][Glb][Glb][Glb] | SEQ ID NO: 381 |
| G (5'-3') | [MeEPmUs][fUs][fA][mA][fA][mA][fU][mU][mC][fA][mG][mG][mA][fA][mU][fU] [mC][mC][mU][mGs][mCs][mU] | SEQ ID NO: 371 |
| P (5'-3') | [mCs][mAs][mG][mG][mA][fA][mU][fU][fC][fC][fU][mG][mA][mA][mU][mU][mU] [mUs][mAs][mA][Glb][Glb][Glb] | SEQ ID NO: 382 |
| G (5'-3') | [MeEPmUs][fGs][fG][mA][fA][mA][fG][mA][mG][fA][mU][mC][mU][fC][mA][fU] [mC][mA][mC][mUs][mCs][mA] | SEQ ID NO: 372 |
| P (5'-3') | [mAs][mGs][mU][mG][mA][fU][mG][fA][fG][fA][fU][mC][mU][mC][mU][mU][mU] [mCs][mCs][mA][Glb][Glb][Glb] | SEQ ID NO: 383 |
| G (5'-3') | [MeEPmUs][fAs][fA][mU][fU][mC][fA][mG][mG][fA][mA][mU][mU][fC][mC][fU] [mG][mC][mU][mUs][mCs][mU] | SEQ ID NO: 373 |
| P (5'-3') | [mAs][mAs][mG][mC][mA][fG][mG][fA][fA][fU][fU][mC][mC][mU][mG][mA][mA] [mUs][mUs][mA][Glb][Glb][Glb] | SEQ ID NO: 384 |

TABLE 3-continued

| Exemplary Modified Sequences of the Disclosure | | |
|---|---|---|
| | Sequence | SEQ ID NO: |
| G (5'-3') | [MeEPmUs][fAs][fA][mC][fA][mC][fA][mU][mG][fU][mU][mG][mC][fU][mC][fA] [mU][mU][mG][mUs][mCs][mU] | SEQ ID NO: 374 |
| P (5'-3') | [mAs][mCs][mA][mA][mU][fG][mA][fG][fC][fA][fA][mC][mA][mU][mG][mU][mG] [mUs][mUs][mA][Glb][Glb][Glb] | SEQ ID NO: 385 |
| G (5'-3') | [MeEPmUs][fGs][fU][mG][fU][mA][fA][mC][mC][fG][mU][mC][mA][fU][mA][fG] [mC][mA][mG][mUs][mGs][mG] | SEQ ID NO: 375 |
| P (5'-3') | [mAs][mCs][mU][mG][mC][fU][mA][fU][fG][fA][fC][mG][mG][mU][mU][mA][mC] [mAs][mCs][mA][Glb][Glb][Glb] | SEQ ID NO: 386 |
| G (5'-3') | [MeEPmUs][fAs][fU][mA][fG][mC][fA][mG][mU][fG][mG][mA][mA][fA][mG][fA] [mG][mA][mU][mCs][mUs][mC] | SEQ ID NO: 376 |
| P (5'-3') | [mGs][mAs][mU][mC][mU][fC][mU][fU][fU][fC][fC][mA][mC][mU][mG][mC][mU] [mAs][mUs][mA][Glb][Glb][Glb] | SEQ ID NO: 387 |
| G (5'-3') | [mUs][fGs][fU][mC][fA][mU][fA][mA][mA][fA][mU][mU][mC][fA][mG][fG][mA] [mA][mU][mUs][mCs][mC] | SEQ ID NO: 377 |
| P (5'-3') | [mAs][mAs][mU][mU][mC][fC][mU][fG][fA][fA][fU][mU][mU][mU][mA][mU][mG] [mAs][mCs][mA][Glb][Glb][Glb] | SEQ ID NO: 381 |
| G (5'-3') | [mUs][fUs][fA][mA][fA][mA][fU][mU][mC][fA][mG][mG][mA][fA][mU][fU][mC] [mC][mU][mGs] [mCs][mU] | SEQ ID NO: 378 |
| P (5'-3') | [mCs][mAs][mG][mG][mA][fA][mU][fU][fC][fC][fU][mG][mA][mA][mU][mU][mU] [mUs][mAs][mA][Glb][Glb][Glb] | SEQ ID NO: 382 |
| G (5'-3') | [mUs][fGs][fG][mA][fA][mA][fG][mA][mG][fA][mU][mC][mU][fC][mA][fU][mC] [mA][mC][mUs][mCs][mA] | SEQ ID NO: 379 |
| P (5'-3') | [mAs][mGs][mU][mG][mA][fU][mG][fA][fG][fA][fU][mC][mU][mC][mU][mU][mU] [mCs][mCs][mA][Glb][Glb][Glb] | SEQ ID NO: 383 |
| G (5'-3') | [MeEPmUs][fGs][fU][mC][fA][mU][fA][mA][mA][fA][mU][mU][mC][fA][mG][fG] [mA][mA][mU][mUs][mCs][mC] | SEQ ID NO: 370 |
| P (5'-3') | [mAs][mAs][mU][mU][mC][fC][mU][fG][fA][fA][fU][mU][mU][mU][mA][mU][mG] [mA][mC][mA][Glb][Glb][Glb] | SEQ ID NO: 388 |
| G (5'-3') | [mUs][fGs][fU][mC][fA][mU][fA][mA][mA][fA][mU][mU][mC][fA][mG][fG][mA] [mA][mU][mUs][mCs][mC] | SEQ ID NO: 377 |
| P (5'-3') | [mAs][mAs][mU][mU][mC][fC][mU][fG][fA][fA][fU][mU][mU][mU][mA][mU][mG] [mA][mC][mA][Glb][Glb][Glb] | SEQ ID NO: 388 |

G: guide strand,

P: passenger strand

"m" indicates 2'-O-methyl modification,

"f" indicates a 2'-F modification,

"MeEPmU" is a mono methyl protected phosphate mimic linked to a 5'-terminal uracil (shown below), "s" is a phosphorothioate internucleotide linkage, and "[G1b][[G1b][G1b]" is a [GalNAc G1b][GaINAc G1b][GalNAc G1b] moiety (shown below).

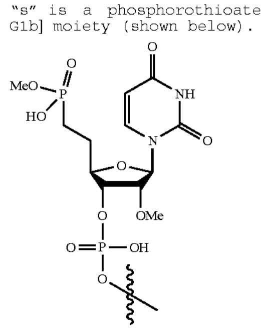

(5'-MeEPmU)

TABLE 3-continued

| Exemplary Modified Sequences of the Disclosure | |
|---|---|
| Sequence | SEQ ID NO: |
| 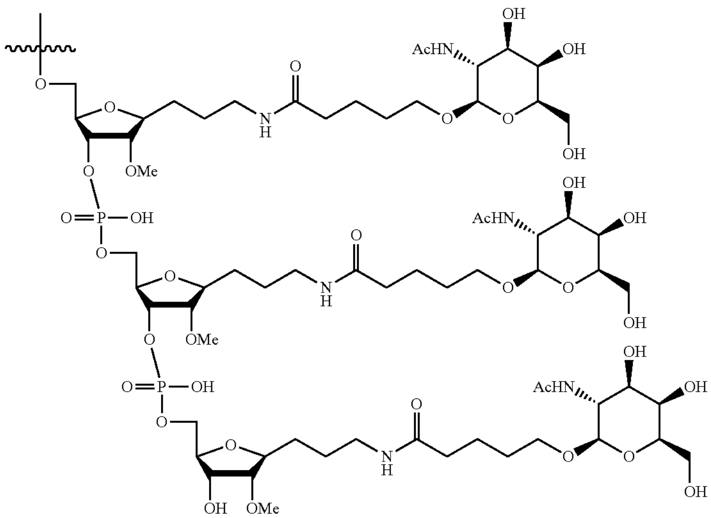 | |
| ([GalNAc G1b][GalNAc G1b][GalNAc G1b]) | |

EXAMPLES

Example 1: Design and Efficacy of siRNA Compounds Against Human Complement Factor B (CFB) mRNA Compound Design A set of 184 siRNAs compounds against human CFB transcript (Accession No: NM_001710.6) were designed (see Table 2).

Oligonucleotide Synthesis

Oligonucleotides were prepared by solid-phase synthesis according to standard protocols. Briefly, oligonucleotide synthesis was conducted on a solid support to incorporate each nucleoside phosphoramidites from 3'-end to 5'-end to prepare oligo single strands. ETT or BTT was used as an activator for the coupling reaction. Iodine in water/pyridine/THF was used to oxidize phosphite-triester (P(III)) to afford phosphate backbones and DDTT was used for the preparation of phosphorothioate linkages. Aqueous ammonium was used to cleave oligos from solid support and to remove protecting groups globally. The oligonucleotide crude was then concentrated by Genevac and purified by AEX-HPLC. The pure fractions were combined and concentrated, and their purity was analyzed by LC-MS. The oligonucleotides were then dialyzed against water using MidiTrap G-25 column, concentrated, and their OD amounts were measured.

To prepare siRNA duplexes, the sense and antisense strands were annealed at 95° C. for 10 min, based on equal molar amounts, and cooled down to room temperature. The duplex purity was determined by AEX-HPLC, and the solutions were lyophilized to afford the desired siRNA duplex powder.

In Vitro Screening

The compounds were diluted into the desired concentration with PBS. The diluted compounds were then transfected into the cultured Huh-7 cells with Lipofectamine™ RNAiMAX (Invitrogen®-13778-150) reagents on Day 0. Each compound was tested at concentrations of 0.02 nM and 0.1 nM. At 24 hours post transfection on Day 1, mRNA was extracted from the transfected cells using RNeasy® 96 kit (Qiagen®-74182).

The percentage of human CFB mRNA remaining in cells relative to mock transfection when normalized to Gapdh mRNA levels, was determined for each compound at a concentration of either 0.02 nM and 0.1 nM. The results identified several compounds that were able to reduce the level of human CFB mRNA in transfected cells by 20% to 50% or more than 50% at the defined concentrations as described in Table 2. Also, several compounds shown in bold in Table 2 were able to reduce the level of human CFB mRNA in transfected cells by between 20% to 50% or at least 50% at 0.02 nM and 0.1 nM. In summary, the present disclosure identifies numerous siRNA compounds that reduce the level of CFB mRNA in target cells when administered at a dosage of 0.02 nM or 0.1 nM, or at both concentrations.

In Vivo HDI Screening

A subset of compounds with GalNAc conjugations from Table 2 were formulated in 1×PBS dosed on day 1 through subcutaneous dosing to BALB/c female animals (6-8 weeks old). Animals then received 10 μg of pcDNA3.1-hsCFB plasmids on day 4. Liver biopsies were taken on day 5 for mRNA remaining analysis through RT-qPCR.

For dose response study, 6-8 weeks old female BALB/c mice were dosed subcutaneously at 0.25 mg/kg (grey triangles), 0.5 mg/kg (grey squares) or 1 mg/kg (black circles) (FIG. 2). The control animals were dosed with PBS. Animals were sacrificed 4 days post-dose and liver samples were collected for RNA extraction and human CFB mRNA expression analysis by RT-qPCR. The results of the experiments are shown in FIG. 1 and FIG. 2. The tested compounds were able to reduce the level of human CFB mRNA.

In Vivo Potency and Duration Evaluation in *Macaca fascicularis*

To determine CFB knockdown in non-human primates, a nonterminal study was conducted in cynomolgus macaques. A subset of the compounds with GalNAc conjugations (Table 3) were tested. A liver biopsy was taken from cyno monkeys in the study to determine the baseline mRNA expression level one week before dosing (Day −7). Animals were dosed with a single dose of 3 mg/kg subcutaneously a week after a biopsy (Day 1). A biopsy of the liver was taken at 15, 29, 57, 85 and 113 days post dosing. Serum samples were collected 7, 14, 21, 28, 42, 56, 70 and 84 days post dosing. Liver samples were used for mRNA remaining analysis by RT-qPCR and blood samples were used for serum CFB protein analysis by ELISA.

RT-qPCR

Liver mRNA samples were prepared with RNeasy® Plus mini kit (Qiagen®, 74104). mRNAs were reverse transcribed into cDNAs using High-Capacity cDNA Reverse transcription kits with RNase Inhibitors (Thermo Fisher Scientific®, 4374967). TaqMan® multiplex qPCR assays (Thermo Fisher Scientific®, 4444557) were performed to determine the relative CFB mRNA levels over time.

ELISA

Figure 3A:
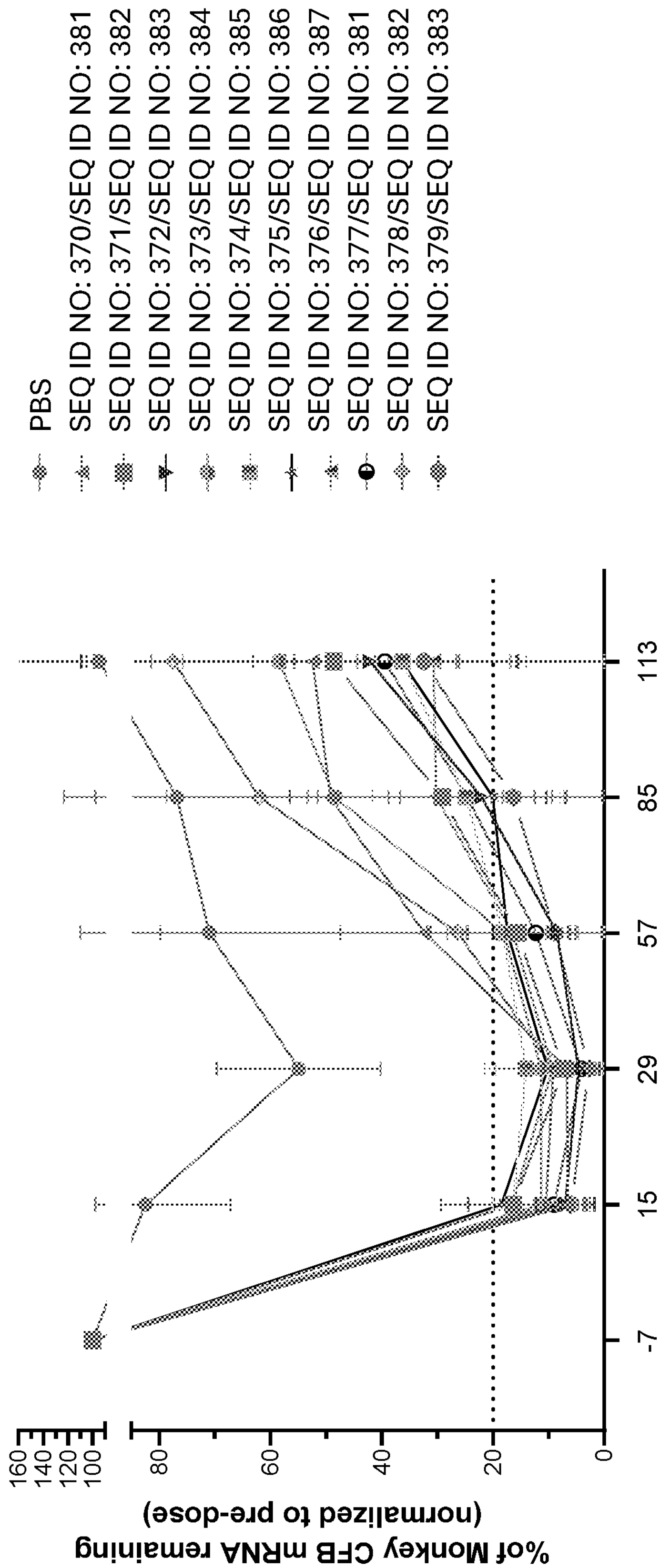
FIGS. 3A-3B are graphs showing in vivo potency evaluations of compounds listed in Table 3 in Macacafascicularis after a 3 mg/kg single s.c. dosing. Cyno CFB mRNA remaining in liver (FIG. 3A) and serum CFB protein remaining (FIG. 3B) were measured over time. Data was normalized to pre-dose mRNA or protein levels of each animal.
Figure 3B:
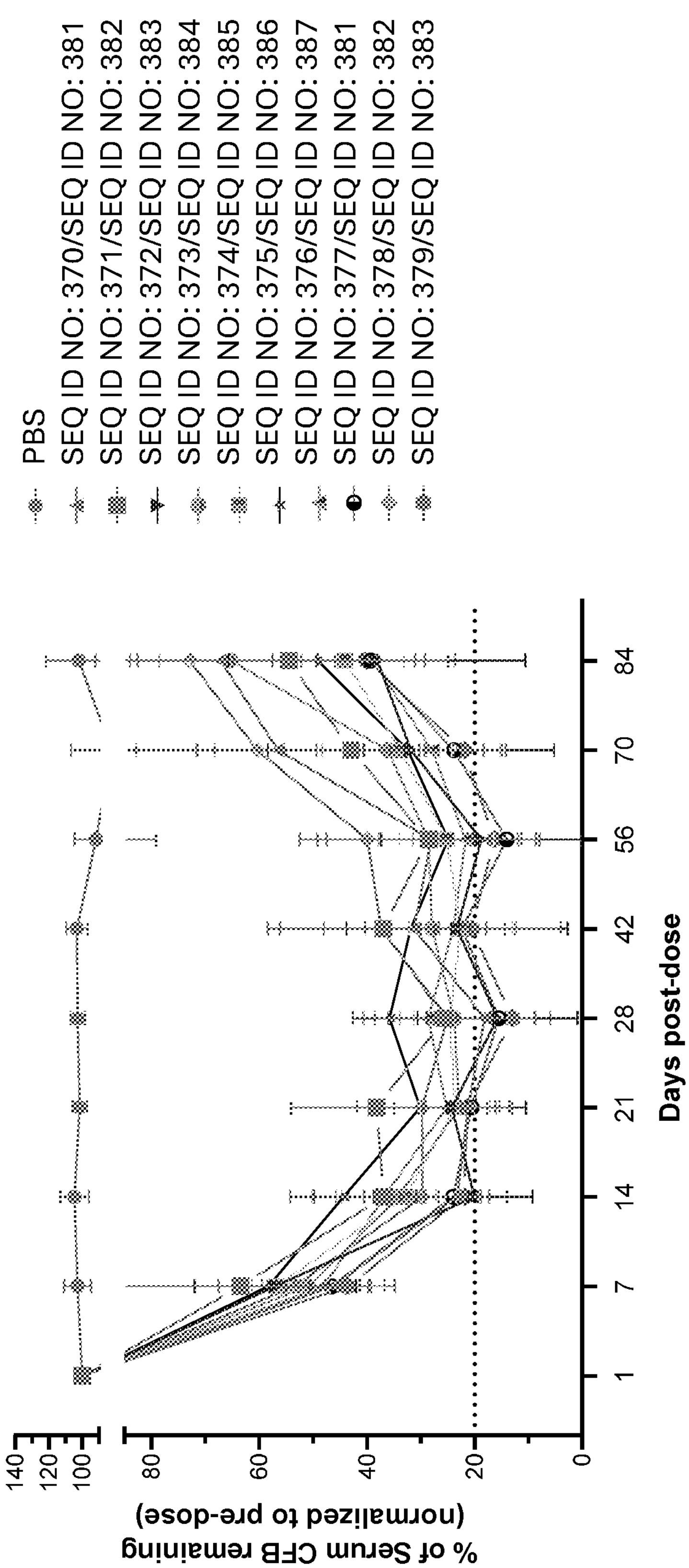

CFB Human ELISA kit (Abcam, ab137973) was validated for cross reactivity to Cynomolgus monkey. Serum samples were diluted 1:3,000 and ELISA were performed. CFB protein level (μg/ml) was calculated based on standard curve and normalized to pre-dose. The results of the experiment are shown in FIGS. 3A and 3B. As shown in FIG. 3A by Day 15, all compounds had reduced liver CFB mRNA by at least 80% relative to pre-dosing levels (Day −7). The maximum reduction in CFB mRNA for all compounds was seen at Day 15 post-dosing, as shown in FIG. 3A. As shown in FIG. 3B by Days, 14, 21, 28, 42 and 56 all compounds had reduced serum CFB protein by at least 60% relative to pre-dosing levels (Day −7). The maximum reduction in serum CFB protein for all compounds was seen at Day 28 post-dosing, as shown in FIG. 3B.

Example 2: Additional Screening of siRNA of Interest

In Vitro Potency in Huh7 and PHH Cells

An isolated oligonucleotide comprising an antisense strand of nucleic acid sequence according to SEQ ID NO: 24 (5' UGUCAUAAAAUUCAGGAAUUCC 3'), and a sense strand of nucleic acid sequence according to SEQ ID NO: 58 (5' AAUUCCUGAAUUUUAUGACA 3') was further investigated for in vitro potency in Huh7 and Primary Human Hepatocyte (PHH) cells.

Huh7 cells: The experiment included PBS control group and groups of the siRNA of interest. The siRNA groups included eight concentrations: 10 nM, 1 nM, 0.1 nM, 0.01 nM, 0.001 nM, 0.0001 nM, 0.00001 nM, and 0.000001 nM. After 24 hours of incubation of the siRNA of interest with Huh7 cells, RNA was extracted, and CFB mRNA levels were analyzed by reverse transcription quantitative PCR (RT-qPCR). The inhibitory activity of the siRNA of interest on CFB mRNA was evaluated by comparing the CFB mRNA levels to the PBS control. IC50 (half maximal inhibitory concentration) values were calculated from the dose-response curve.

Figure 4A:
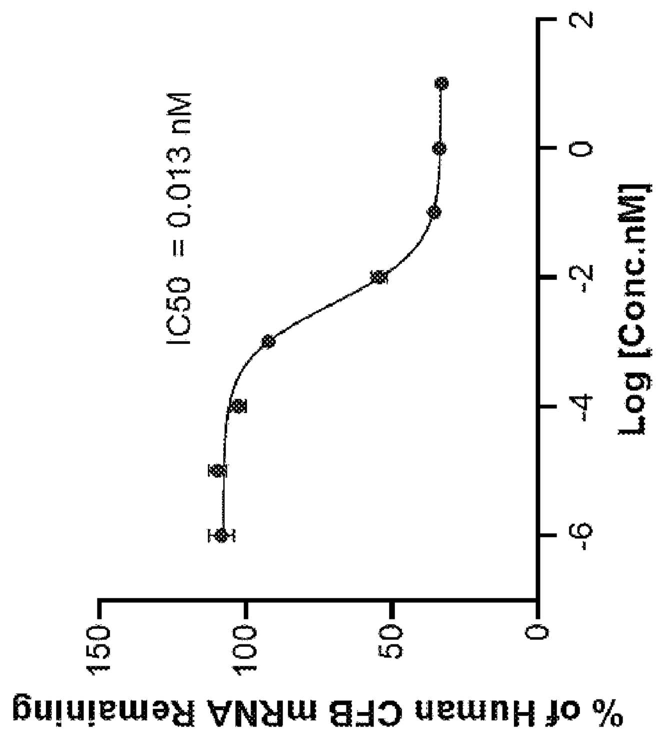
FIGS. 4A and 4B are graphs showing in vitro potency of an siRNA of interest in Huh7 and PHH cells, respectively.

As seen in FIG. 4A, the results showed that the siRNA of interest exhibited high activity in Huh7 cells, with IC50 values of 0.013 nM.

PHH cells: Experimental groups included a solvent control (PBS) and groups administered with the siRNA of interest at four concentrations (1 nM, 10 nM, 100 nM, and 1000 nM). Following a 48-hour incubation with PBS or the siRNA of interest, total RNA was extracted from PHH cells, and CFB mRNA levels were quantified using reverse transcription quantitative PCR (RT-qPCR). The inhibitory activity of the siRNA of interest on CFB mRNA expression was assessed by comparing levels across treatment concentrations relative to PBS control.

Figure 4B:
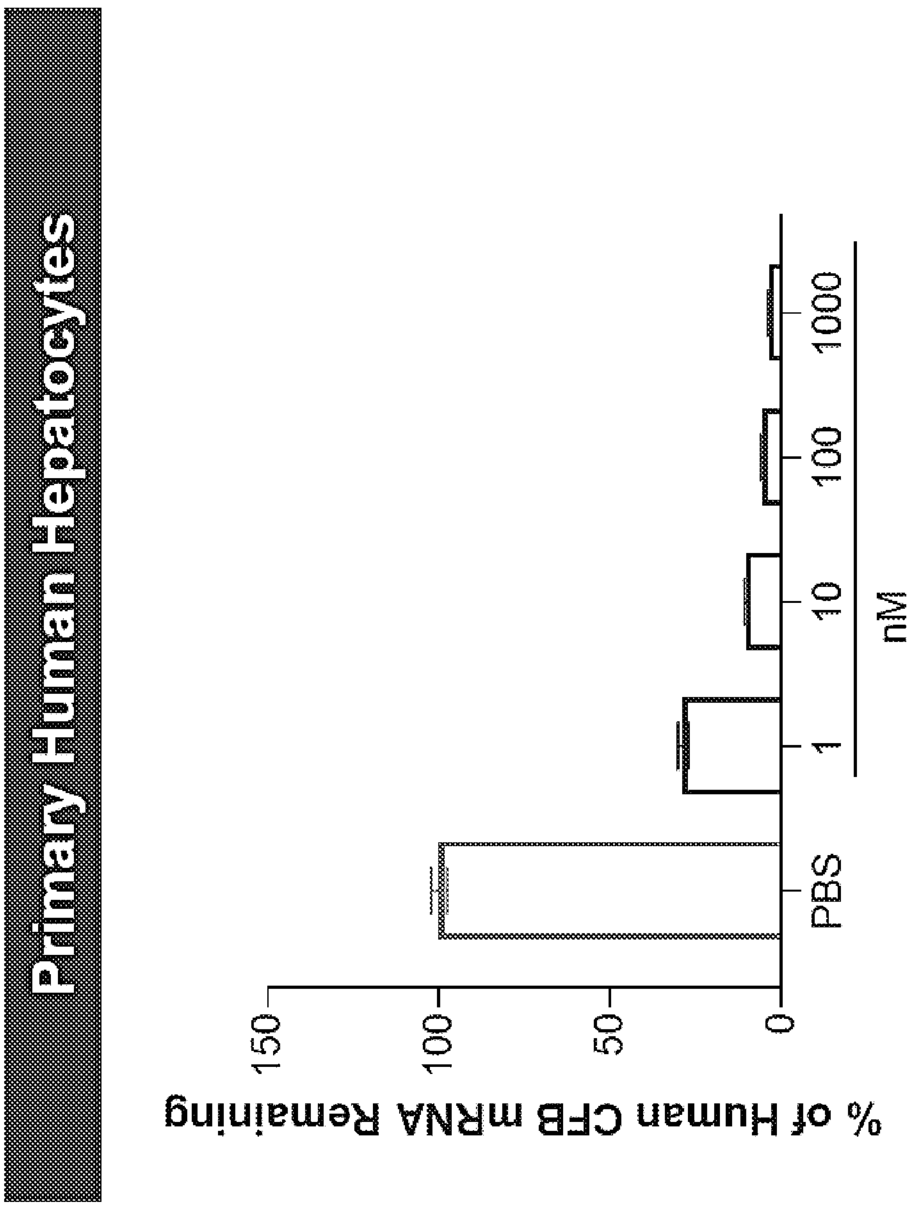

As seen in FIG. 4B, the siRNA of interested showed high potency (estimated IC50<1 nM) and exhibited a clear dose-dependent inhibitory effect on CFB mRNA in PHH, at 71.1%, 89.5%, 94.3%, 96.3% at 1 nM, 10 nM, 100 nM, and 1,000 nM, respectively.

In Vivo Studies in Human CFB Transgenic Mice

An isolated oligonucleotide comprising an antisense strand of nucleic acid sequence according to SEQ ID NO: 377 (5' [mUs][fGs][fU][mC][fA][mU][fA][mA][mA][fA][mU][mU][mC][fA][mG][fG][mA][mA][mU][mUs][mCs][mC]3'), and a sense strand of nucleic acid sequence according to SEQ ID NO: 388 (5' [mAs][mAs][mU][mU][mC][fC][mU][fG][fA][fA][fU][mU][mU][mU][mA][mU][mG][mA][m C][mA][G1b][G1b][G1b]3') was further investigated in vivo in human CFB transgenic mice.

The experiment consisted of four groups: vehicle control, and the siRNA of interest at doses of 0.1 mg/kg (0.1 MPK), 1 mg/kg (1 MPK), and 10 mg/kg (10 MPK). Blood samples were collected four days prior to dosing (D-4), on the day of dosing before administration (DO), and at multiple points post-dosing (D7, D14, D28, D42, D56) to measure serum human CFB protein levels. Liver samples were collected at the end of the study for analysis of human CFB mRNA expression in the liver.

Figure 5:
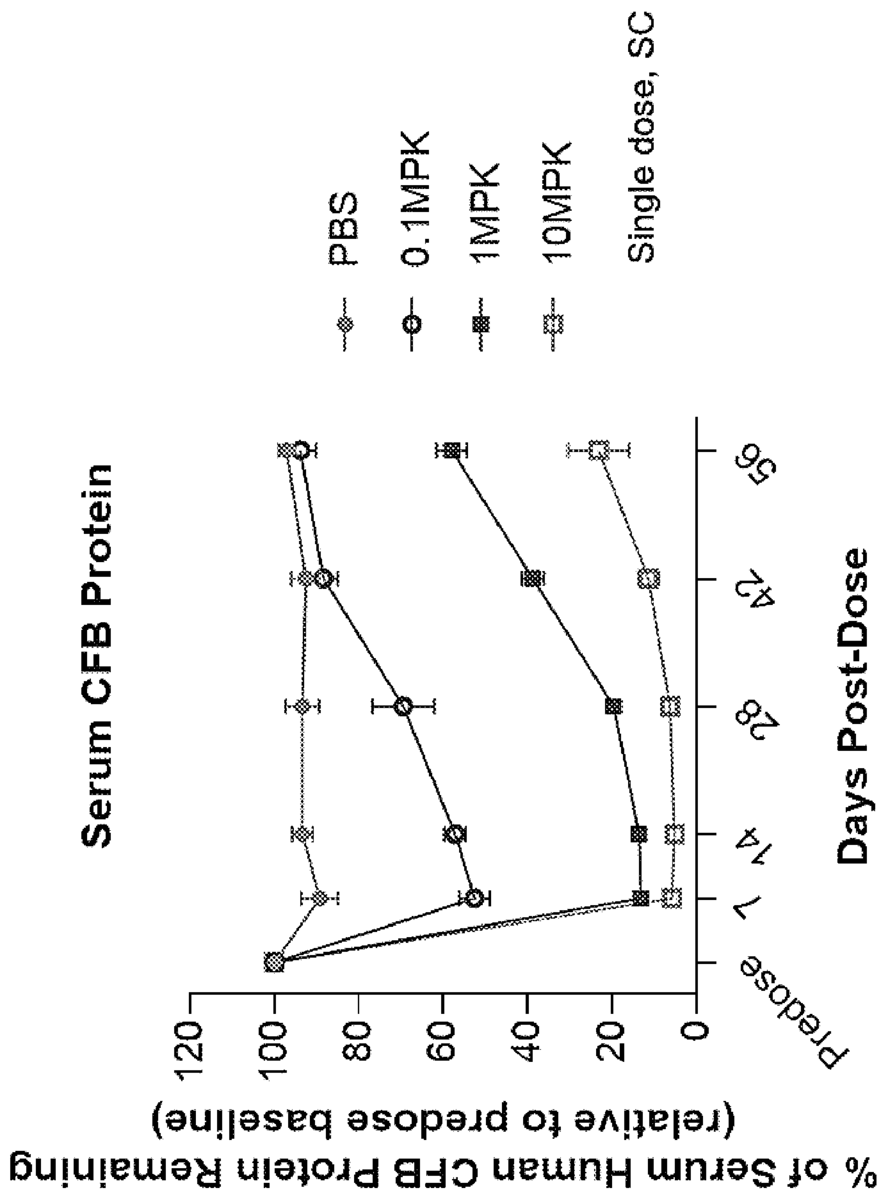
FIG. 5 is a graph showing the in vivo dose response of an siRNA of interest in human CFB transgenic mice

Serum CFB protein analysis showed a strong dose-dependent decrease in human CFB protein following subcutaneous administration of the siRNA of interest, with maximal suppression observed on day 7 (FIG. 5). Relative to pre-dose levels, serum human CFB protein decreased by 47.3%, 86.8%, and 94.2% at 0.1 mg/kg (low-dose), 1 mg/kg (mid-dose), and 10 mg/kg (high-dose) doses, respectively. By day 56 post-dose, the low-, mid-, and high-dose groups recovered to 93.9%, 58%, and 23.2% of pre-dose levels, respectively, with the mid- and high-dose groups maintaining substantial knockdown. Similarly, endpoint liver analysis (D56) of human CFB mRNA expression confirmed a clear dose-response relationship. Administering the siRNA of interest at low, mid, and high doses achieved reductions of 15%, 61%, and 85% in liver CFB mRNA, respectively, in humanized mice at 56 days after dose.

In Vivo Potency Evaluation in Cynomolgus Monkey

The isolated oligonucleotide comprising an antisense strand of nucleic acid sequence according to SEQ ID NO: 377 (5' [mUs][fGs][fU][mC][fA][mU][fA][mA][mA][fA][mU][mU][mC][fA][mG][fG][mA][mA][mU][mUs][mCs][mC]3'), and a sense strand of nucleic acid sequence according to SEQ ID NO: 388 (5' [mAs][mAs][mU][mU][mC][fC][mU][fG][fA][fA][fU][mU][mU][mU][mA][mU][mG][mA][m C][mA][G1b][G1b][G1b]3') was investigated in Cynomolgus monkey. Twenty-four (12 per sex) non-naïve cynomolgus monkeys were divided into four groups with 3 animals/sex/group. Animals in Group 1 were administered with the siRNA of interest by single intravenous infusion at 3 mg/kg (data not shown). Animals in Groups 2, 3 and 4 were administered with the siRNA of interest by single subcutaneous (SC) injection at 1 mg/kg (1 MPK), 3 mg/kg (3 MPK), and 10 mg/kg (10 MPK), respectively. Serum samples were collected at pre-dose (Day −1), pre-dose (0), Days 7, 14, 21, 28, 42, 56, 70 and 84 post-dose. Serum CFB protein, hemolytic activity, and complement activation activity in the serum samples were tested to evaluate the pharmacodynamic effects of the siRNA of interest in healthy cynomolgus monkeys. Serum CFB protein was analyzed by Western Blot. The WIESLAB@Complement System Alternative Pathway ELISA Kit was used to analyze the formation of $C_5b$-9 (MAC) in serum, i.e., CAP activity. Rabbit erythrocytes were used in the alternative pathway hemolysis assay to measure the alternative pathway hemolytic activity. Measurement parameters of each animal were statistically evaluated as percentage (%) change relative to pre-dose values. The percentage (%) change after dosing was calculated using the baseline value from pre-dose (0), i.e., dosing day before dosing.

Figure 6A:
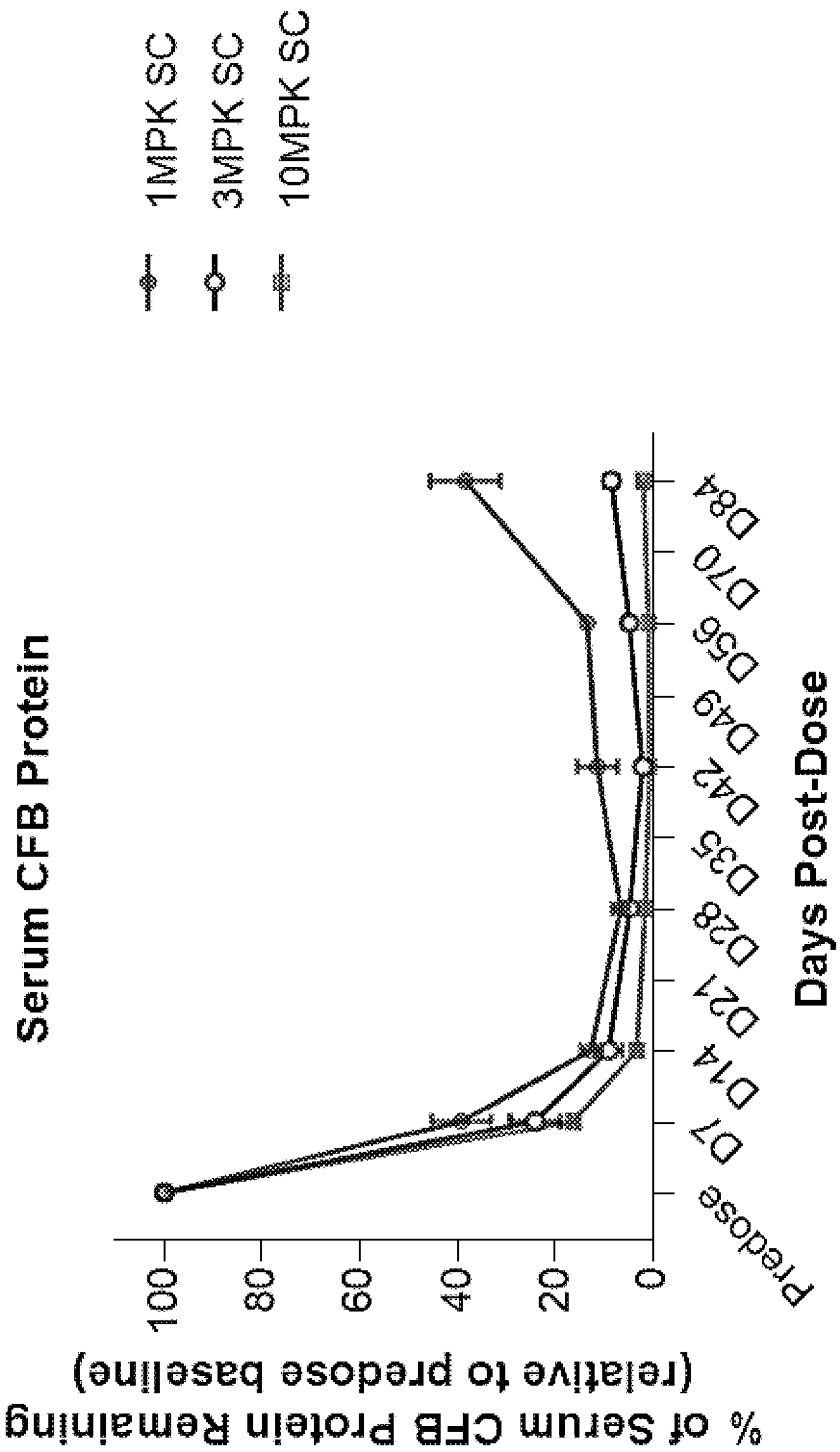
FIGS. 6A-6C are graphs showing in vivo potency evaluations of an siRNA of interest in Cynomolgus Monkey.

As shown in FIG. 6A, serum CFB protein was significantly decreased after injections of the siRNA of interest compared with pre-dose baseline. Serum CFB protein levels decreased rapidly in the first three weeks after administration, and the rate of decline was proportional to the dose level. The maximum reduction was observed on day 28, with reductions of 93%, 95%, 98 for the 1 MPK SC, 3 MPK SC, and 10 MPK SC groups, respectively. The inhibitory effect gradually recovered, but by the end of the study (day 84 post-dose), significant inhibitory effects remained, with reductions of 61%, 91%, and 98%, respectively.

Figure 6B:
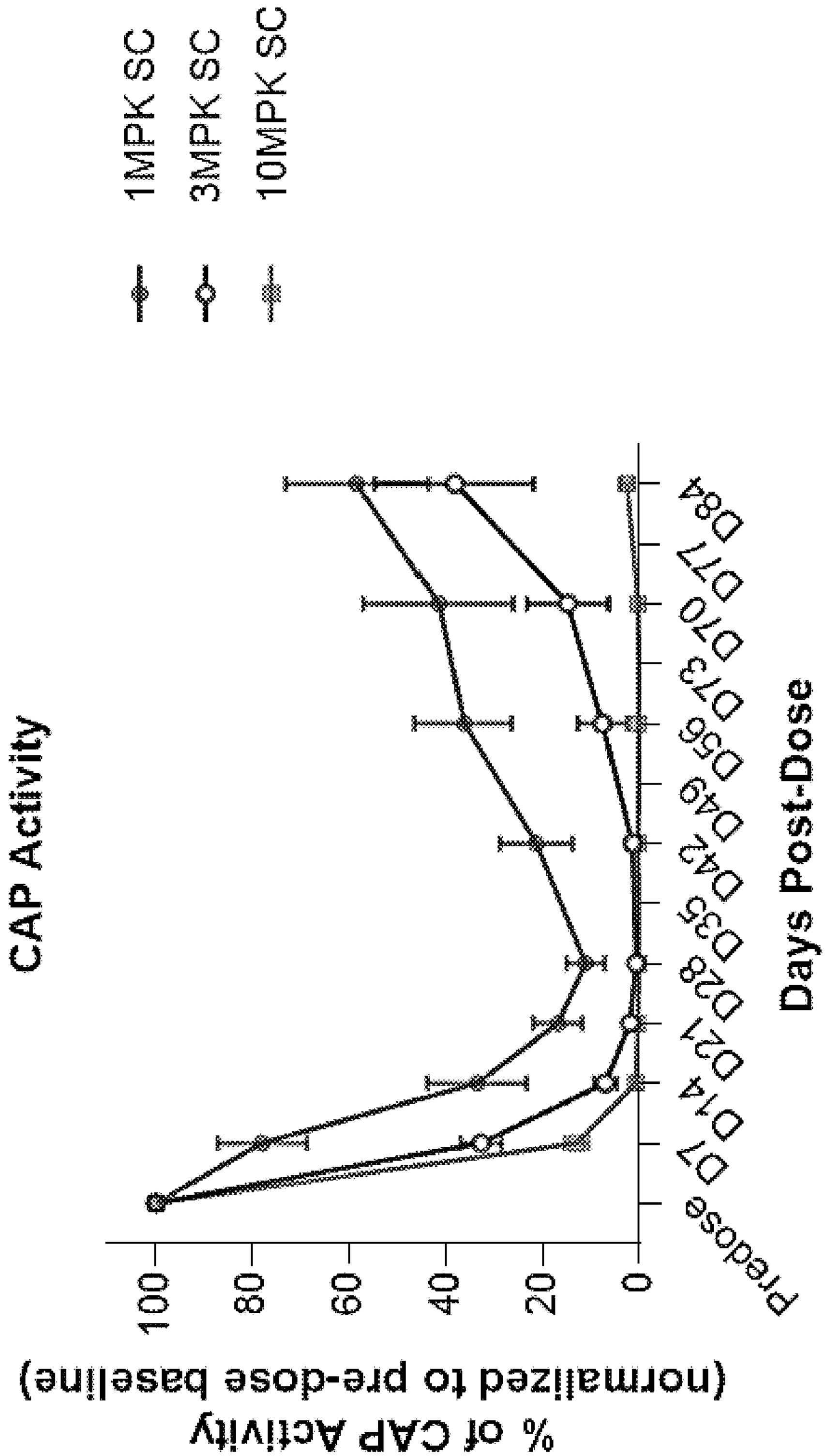

As shown in FIG. 6B, CAP activity was significantly decreased after injections of the siRNA of interest compared with pre-dose baseline. CAP activity levels decreased rapidly in the first three weeks after administration, and the rate of decline was proportional to the dose level. The maximum reduction was observed on day 28, with reductions of 88.9%, 99.2%, and 99.8% for the 1 MPK SC, 3 MPK SC, and 10 MPK SC groups, respectively. The inhibitory effect gradually recovered, but by the end of the study (day 84 post-dose), significant inhibitory effects remained, with reductions of 42%, 62%, and 97%, respectively.

Figure 6C:
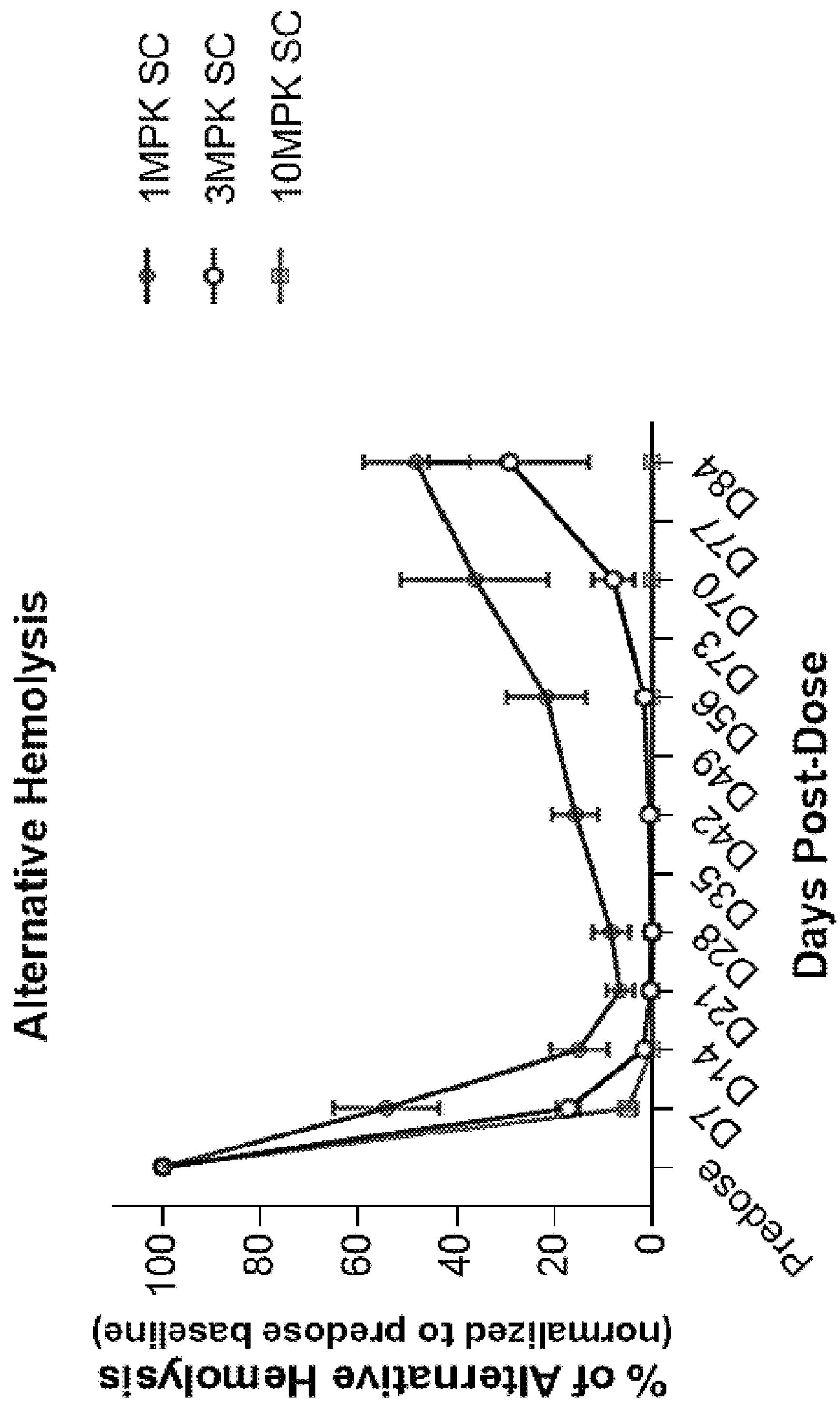

As shown in FIG. 6C, alternative hemolysis was significantly decreased after injections of the siRNA of interest compared with pre-dose baseline. Alternative hemolytic activity levels decreased rapidly in the first two weeks after administration, and the rate of decline was proportional to the dose level. The maximum reduction was observed on day 21, with reductions of 93.7%, 99.3%, and 100% for the 1 MPK SC, 3 MPK SC, and 10 MPK SC groups, respectively. The inhibitory effect gradually recovered, but by the end of the study (day 84 post-dose), significant inhibitory effects remained in three subcutaneous injected groups, with reductions of 52%, 61%, and 100% for 1 MPK SC, 3 MPK SC, and 10 MPK SC groups, respectively.

Additional embodiments of the disclosure include the following:

Embodiment 1. An isolated oligonucleotide comprising a sense strand and an antisense strand, wherein the sense strand comprises a nucleotide sequence that is substantially identical to a region comprising 19-25 nucleotides between any one of the nucleotide positions from 1821 to 1881 from the 5' end of a human CFB mRNA sequence according to SEQ ID NO: 1, and the antisense strand is substantially complementary to the sense strand such that the sense strand and the antisense strand together form a double stranded region.

Embodiment 2. The isolated oligonucleotide of embodiment 1, wherein the sense strand comprises a nucleotide sequence that is at least 70%, at least 80%, at least 90%, at least 95%, or at least 99% identical to a region comprising 19-25 nucleotides between any one of the nucleotide positions from 1821 to 1881 from the 5' end of a human CFB mRNA sequence according to SEQ ID NO: 1.

Embodiment 3. The isolated oligonucleotide of embodiment 1, wherein the sense strand comprises a nucleotide sequence that is identical to a region comprising 19-25 nucleotides between any one of the nucleotide positions from 1821 to 1881 from the 5' end of a human CFB mRNA sequence according to SEQ ID NO: 1.

Embodiment 4. The isolated oligonucleotide of any one of embodiments 1-3, wherein the sense strand comprises a nucleotide sequence that is substantially identical to a region between any one of the nucleotide positions from 1829 to 1850 from the 5' end of a human CFB mRNA sequence according to SEQ ID NO: 1.

Embodiment 5. The isolated oligonucleotide of embodiment 4, wherein the sense strand comprises a nucleotide sequence that is at least 70%, at least 80%, at least 90%, at least 95%, or at least 99% identical to a region between any one of the nucleotide positions from 1829 to 1850 from the 5' end of a human CFB mRNA sequence according to SEQ ID NO: 1.

Embodiment 6. The isolated oligonucleotide of embodiment 4, wherein the sense strand comprises a nucleotide sequence that is identical to a region between any one of the nucleotide positions from 1829 to 1850 from the 5' end of a human CFB mRNA sequence according to SEQ ID NO: 1.

Embodiment 7. The isolated oligonucleotide of any one of embodiments 1-3, wherein the sense strand comprises a nucleotide sequence that is substantially identical to a region between any one of the nucleotide positions from 1821 to 1881 from the 5' end of a human CFB mRNA sequence according to SEQ ID NO: 1.

Embodiment 8. The isolated oligonucleotide of embodiment 7, wherein the sense strand comprises a nucleotide sequence that is at least 70%, at least 80%, at least 90%, at least 95%, or at least 99% identical to a region between any one of the nucleotide positions from 1821 to 1881 from the 5' end of a human CFB mRNA sequence according to SEQ ID NO: 1.

Embodiment 9. The isolated oligonucleotide of embodiment 7, wherein the sense strand comprises a nucleotide sequence that is identical to a region between any one of the nucleotide positions from 1821 to 1881 from the 5' end of a human CFB mRNA sequence according to SEQ ID NO: 1.

Embodiment 10. The isolated oligonucleotide of any one of embodiments 1-3, wherein the sense strand comprises a nucleotide sequence that is substantially identical to a region between any one of the nucleotide positions from 1860 to 1880 from the 5' end of a human CFB mRNA sequence according to SEQ ID NO: 1.

Embodiment 11. The isolated oligonucleotide of embodiment 10, wherein the sense strand comprises a nucleotide sequence that is at least 70%, at least 80%, at least 90%, at least 95%, or at least 99% identical to a region between any one of the nucleotide positions from 1860 to 1880 from the 5' end of a human CFB mRNA sequence according to SEQ ID NO: 1.

Embodiment 12. The isolated oligonucleotide of embodiment 10, wherein the sense strand comprises a nucleotide sequence that is identical to a region between any one of the nucleotide positions from 1860 to 1880 from the 5' end of a human CFB mRNA sequence according to SEQ ID NO: 1.

Embodiment 13. The isolated oligonucleotide of any one of embodiments 1-12, wherein the isolated oligonucleotide is capable of inducing degradation of the CFB mRNA.

Embodiment 14. The isolated oligonucleotide of any one of embodiments 1-13, wherein either the sense strand or antisense strand is a single stranded RNA molecule.

Embodiment 15. The isolated oligonucleotide of any one of embodiments 1-13, wherein both the sense strand and the antisense strand are single stranded RNA molecules.

Embodiment 16. The isolated oligonucleotide of any one of embodiments 1-15, wherein the antisense strand comprises a 3' overhang.

Embodiment 17. The isolated oligonucleotide of embodiment 16, wherein the 3' overhang comprises at least one nucleotide.

Embodiment 18. The isolated oligonucleotide of any one of embodiments 1-17, wherein the sense strand comprises an RNA sequence of at least 20 nucleotides in length.

Embodiment 19. The isolated oligonucleotide of any one of embodiments 1-18, wherein the antisense strand comprises an RNA sequence of at least 22 nucleotides in length.

Embodiment 20. The isolated oligonucleotide of any one of embodiments 1-19, wherein the double stranded region is between 19 and 21 nucleotides in length.

Embodiment 21. The isolated oligonucleotide of any one of embodiments 1-20, wherein the antisense strand comprises a nucleotide sequence according to any one of: SEQ ID NOs: 20-26.

Embodiment 22. The isolated oligonucleotide of any one of embodiments 1-21, wherein the sense strand comprises a nucleotide sequence according to any one of: SEQ ID NOs: 54-60.

Embodiment 23. The isolated oligonucleotide of embodiment 9, wherein the double stranded region comprises:

i) an antisense strand of nucleic acid sequence according to SEQ ID NO: 20 (5' UAUUCAGGAAUUCCUGCUUCUU 3'), and a sense strand of nucleic acid sequence according to SEQ ID NO: 54 (5' GAAGCAGGAAUUCCUGAAUA 3');

ii) an antisense strand of nucleic acid sequence according to SEQ ID NO: 21 (5' UAAUUCAGGAAUUCCUGCUUCU 3'), and a sense strand of nucleic acid sequence according to SEQ ID NO: 55 (5' AAGCAGGAAUUCCUGAAUUA 3');

iii) an antisense strand of nucleic acid sequence according to SEQ ID NO: 22 (5' UUAAAAUUCAGGAAUUCCUGCU 3'), and a sense strand of nucleic acid sequence according to SEQ ID NO: 56 (5' CAGGAAUUCCUGAAUUUUAA 3');

iv) an antisense strand of nucleic acid sequence according to SEQ ID NO: 23 (5' UAUAAAAUUCAGGAAUUCCUGC 3'), and a sense strand of nucleic acid sequence according to SEQ ID NO: 57 (5' AGGAAUUCCUGAAUUUUAUA 3');

v) an antisense strand of nucleic acid sequence according to SEQ ID NO: 24 (5' UGUCAUAAAAUUCAGGAAUUCC 3'), and a sense strand of nucleic acid sequence according to SEQ ID NO: 58 (5' AAUUCCUGAAUUUUAUGACA 3');

vi) an antisense strand of nucleic acid sequence according to SEQ ID NO: 25 (5' UUAUUCUUGAGCUUGAUCAGGG 3'), and a sense strand of nucleic acid sequence according to SEQ ID NO: 59 (5' CUGAUCAAGCUCAAGAAUAA 3'); or vii) an antisense strand of nucleic acid sequence according to SEQ ID NO: 26 (5' UUUAUUCUUGAGCUUGAUCAGG 3'), and a sense strand of nucleic acid sequence according to SEQ ID NO: 60 (5' UGAUCAAGCUCAAGAAUAAA 3').

Embodiment 24. The isolated oligonucleotide of embodiment 12, wherein the double stranded region comprises an antisense strand of nucleic acid sequence according to SEQ ID NO: 25 (5' UUAUUCUUGAGCUUGAUCAGGG 3'), and a sense strand of nucleic acid sequence according to SEQ ID NO: 59 (5' CUGAUCAAGCUCAAGAAUAA 3').

Embodiment 25. The isolated oligonucleotide of any one of embodiments 1-24, wherein the isolated oligonucleotide attenuates expression of the CFB mRNA by at least 50% at a dose of 0.1 nM.

Embodiment 26. The isolated oligonucleotide of embodiment 25, wherein the double stranded region comprises:

i) an antisense strand of nucleic acid sequence according to SEQ ID NO: 20 (5' UAUUCAGGAAUUCCUGCUUCUU 3'), and a sense strand of nucleic acid sequence according to SEQ ID NO: 54 (5' GAAGCAGGAAUUCCUGAAUA 3');

ii) an antisense strand of nucleic acid sequence according to SEQ ID NO: 21 (5' UAAUUCAGGAAUUCCUGCUUCU 3'), and a sense strand of nucleic acid sequence according to SEQ ID NO: 55 (5' AAGCAGGAAUUCCUGAAUUA 3');

iii) an antisense strand of nucleic acid sequence according to SEQ ID NO: 22 (5' UUAAAAUUCAGGAAUUCCUGCU 3'), and a sense strand of nucleic acid sequence according to SEQ ID NO: 56 (5' CAGGAAUUCCUGAAUUUUAA 3');

iv) an antisense strand of nucleic acid sequence according to SEQ ID NO: 23 (5' UAUAAAAUUCAGGAAUUCCUGC 3'), and a sense strand of nucleic acid sequence according to SEQ ID NO: 57 (5' AGGAAUUCCUGAAUUUUAUA 3');

v) an antisense strand of nucleic acid sequence according to SEQ ID NO: 24 (5' UGUCAUAAAAUUCAGGAAUUCC 3'), and a sense strand of nucleic acid sequence according to SEQ ID NO: 58 (5' AAUUCCUGAAUUUUAUGACA 3');

vi) an antisense strand of nucleic acid sequence according to SEQ ID NO: 26 (5' UUUAUUCUUGAGCUUGAUCAGG 3'), and a sense strand of nucleic acid sequence according to SEQ ID NO: 60 (5' UGAUCAAGCUCAAGAAUAAA 3'); or vii) an antisense strand of nucleic acid sequence according to SEQ ID NO: 25 (5' UUAUUCUUGAGCUUGAUCAGGG 3'), and a sense strand of nucleic acid sequence according to SEQ ID NO: 59 (5' CUGAUCAAGCUCAAGAAUAA 3').

Embodiment 27. The isolated oligonucleotide of any one of embodiments 1-24, wherein the isolated oligonucleotide attenuates expression of the CFB mRNA by at least 50% at a dose of 0.02 nM.

Embodiment 28. The isolated oligonucleotide of embodiment 27, wherein the double stranded region comprises:

i) an antisense strand of nucleic acid sequence according to SEQ ID NO: 22 (5' UUAAAAUUCAGGAAUUCCUGCU 3'), and a sense strand of nucleic acid sequence according to SEQ ID NO: 56 (5' CAGGAAUUCCUGAAUUUUAA 3');

ii) an antisense strand of nucleic acid sequence according to SEQ ID NO: 23 (5' UAUAAAAUUCAGGAAUUCCUGC 3'), and a sense strand of nucleic acid sequence according to SEQ ID NO: 57 (5' AGGAAUUCCUGAAUUUUAUA 3'); or iii) an antisense strand of nucleic acid sequence according to SEQ ID NO: 24 (5' UGUCAUAAAAUUCAGGAAUUCC 3'), and a sense strand of nucleic acid sequence according to SEQ ID NO: 58 (5' AAUUCCUGAAUUUUAUGACA 3').

Embodiment 29. The isolated oligonucleotide of embodiment 24, wherein the isolated oligonucleotide attenuates expression of the CFB mRNA by 20% to 50% at a dose of 0.02 nM.

Embodiment 30. The isolated oligonucleotide of embodiment 29, wherein the double stranded region comprises:

i) an antisense strand of nucleic acid sequence according to SEQ ID NO: 25 (5' UUAUUCUUGAGCUUGAUCAGGG 3'), and a sense strand of nucleic acid sequence according to SEQ ID NO: 59 (5' CUGAUCAAGCUCAAGAAUAA 3');

ii) an antisense strand of nucleic acid sequence according to SEQ ID NO: 26 (5' UUUAUUCUUGAGCUUGAUCAGG 3'), and a sense strand of nucleic acid sequence according to SEQ ID NO: 60 (5' UGAUCAAGCUCAAGAAUAAA 3');

iii) an antisense strand of nucleic acid sequence according to SEQ ID NO: 20 (5' UAUUCAGGAAUUCCUGCUUCUU 3'), and a sense strand of nucleic acid sequence according to SEQ ID NO: 54 (5' GAAGCAGGAAUUCCUGAAUA 3'); or iv) an antisense strand of nucleic acid sequence according to SEQ ID NO: 21 (5' UAAUUCAGGAAUUCCUGCUUCU 3'), and a sense strand of nucleic acid sequence according to SEQ ID NO: 55 (5' AAGCAGGAAUUCCUGAAUUA 3').

Embodiment 31. An isolated oligonucleotide comprising a sense strand and an antisense strand, wherein the sense strand comprises a nucleotide sequence that is substantially identical to a region comprising 19-25 nucleotides between any one of the nucleotide positions from 1815 to 2313 from the 5' end of a CFB mRNA sequence according to SEQ ID NO: 1, and the antisense strand is substantially complementary to the sense strand such that the sense strand and the antisense strand together form a double stranded region.

Embodiment 32. The isolated oligonucleotide of embodiment 31, wherein the isolated oligonucleotide attenuates expression of the CFB mRNA by 20% to 50% at a dose of 0.1 nM.

Embodiment 33. The isolated oligonucleotide of embodiment 32, wherein the double stranded region comprises:

i) an antisense strand of nucleic acid sequence according to SEQ ID NO: 144 (5' UCUUAUUCUUGAGCUUGAUCAG 3'), and a sense strand of nucleic acid sequence according to SEQ ID NO: 254 (5' GAUCAAGCUCAAGAAUAAGA 3'); or ii) an antisense strand of nucleic acid sequence according to SEQ ID NO: 142 (5' UUUCUUGAGCUUGAUCAGGGCA 3'), and a sense strand of nucleic acid sequence according to SEQ ID NO: 252 (5' CCCUGAUCAAGCUCAAGAAA 3'); xxv).

Embodiment 34. The isolated nucleotide of embodiment 31, wherein the isolated oligonucleotide attenuates expression of the CFB mRNA by at least 50% at a dose of 0.1 nM.

Embodiment 35. The isolated oligonucleotide of embodiment 34, wherein the double stranded region comprises:

i) an antisense strand of nucleic acid sequence according to SEQ ID NO: 138 (5' UCAUAAAAUUCAGGAAUUCCUG 3'), and a sense strand of nucleic acid sequence according to SEQ ID NO: 248 (5' GGAAUUCCUGAAUUUUAUGA 3');

ii) an antisense strand of nucleic acid sequence according to SEQ ID NO: 143 (5' UAUUCUUGAGCUUGAUCAGGGC 3'), and a sense strand of nucleic acid sequence according to SEQ ID NO: 253 (5' CCUGAUCAAGCUCAAGAAUA 3');

iii) an antisense strand of nucleic acid sequence according to SEQ ID NO: 141 (5' UCUUGAUCAGGGCAACGUCAUA 3'), and a sense strand of nucleic acid sequence according to SEQ ID NO: 251 (5' UGACGUUGCCCUGAUCAAGA 3');

iv) an antisense strand of nucleic acid sequence according to SEQ ID NO: 139 (5' UCAUAGUCAUAAAAUUCAGGAA 3'), and a sense strand of nucleic acid sequence according to SEQ ID NO: 249 (5' CCUGAAUUUUAUGACUAUGA 3'); or v) an antisense strand of nucleic acid sequence according to SEQ ID NO: 137 (5' UGAAUUCCUGCUUCUUUUUUCC 3'), and a sense strand of nucleic acid sequence according to SEQ ID NO: 247 (5' AAAAAAGAAGCAGGAAUUCA 3').

Embodiment 36. The isolated oligonucleotide of embodiment 31, wherein the isolated oligonucleotide attenuates expression of the CFB mRNA by 20% to 50% at a dose of 0.02 nM.

Embodiment 37. The isolated oligonucleotide of embodiment 36, wherein the double stranded region comprises:

i) an antisense strand of nucleic acid sequence according to SEQ ID NO: 138 (5' UCAUAAAAUUCAGGAAUUCCUG 3'), and a sense strand of nucleic acid sequence according to SEQ ID NO: 248 (5' GGAAUUCCUGAAUUUUAUGA 3'); or ii) an antisense strand of nucleic acid sequence according to SEQ ID NO: 140 (5' UGUCAUAGUCAUAAAAUUCAGG 3'), and a sense strand of nucleic acid sequence according to SEQ ID NO: 250 (5' UGAAUUUUAUGACUAUGACA 3').

Embodiment 38. The isolated oligonucleotide of embodiment 31, wherein the isolated oligonucleotide attenuates expression of the CFB mRNA by at least 50% at a dose of 0.02 nM.

Embodiment 39. The isolated oligonucleotide of any one of embodiments 1-38, wherein the sense strand or the antisense strand or both comprise one or more modified nucleotide(s).

Embodiment 40. The isolated oligonucleotide of any one of embodiments 1-39, wherein in the sense strand or the antisense strand or both, a terminal or internal nucleotide is linked to a targeting ligand.

Embodiment 41. The isolated oligonucleotide of embodiment 40, wherein the targeting ligand comprises at least one GalNAc G1b moiety.

Embodiment 42. The isolated oligonucleotide of embodiment 41, wherein the antisense strand comprises a nucleic acid sequence according to SEQ ID NO: 377 (5'

[mUs][fGs][fU][mC][fA][mU][fA][mA][mA][fA][mU][mU][mC][fA][mG][fG][mA][mA][mU][mUs][mCs][mC]3'), wherein "m" is a 2'-O-methyl modified nucleotide, "f" is a 2'-F modified nucleotide, and "s" is a phosphorothioate internucleotide linkage.

Embodiment 43. The isolated oligonucleotide of embodiment 42, wherein the sense strand comprises a nucleic acid sequence according to SEQ ID NO: 388 (5' [mAs][mAs][mU][mU][mC][fC][mU][fG][fA][fA][fU][mU][mU][mU][mA][mU][mG][mA][m C][mA][G1b][G1b][G1b]3'), wherein "m" is a 2'-O-methyl modified nucleotide, "f" is a 2'-F modified nucleotide, "s" is a phosphorothioate internucleotide linkage, and "G1b" is a GalNAc G1b moiety.

Embodiment 44. The isolated oligonucleotide of embodiment 41, wherein the double stranded region comprising of an antisense strand of nucleic acid sequence according to SEQ ID NO: 370 (5' [MeEPmUs][fGs][fU][mC][fA][mU][fA][mA][mA][fA][mU][mU][mC][fA][mG][fG][mA][mA][mU][mUs][mCs][mC]3'), and a sense strand of nucleic acid sequence according to SEQ ID NO: 388 (5' [mAs][mAs][mU][mU][mC][fC][mU][fG][fA][fA][fU][mU][mU][mU][mA][mU][mG][mA][m C][mA][G1b][G1b][G1b]3').

Embodiment 45. An isolated oligonucleotide comprising a sense strand and an antisense strand, wherein the sense strand and the antisense strand together form a double stranded region, wherein the double stranded region comprises (i) an antisense strand of nucleic acid sequence according to SEQ ID NO: 370 (5' [MeEPmUs][fGs][fU][mC][fA][mU][fA][mA][mA][fA][mU][mU][mC][fA][mG][fG][mA][mA][mU][mUs][mCs][mC]3'), and a sense strand of nucleic acid sequence according to SEQ ID NO: 388 (5' [mAs][mAs][mU][mU][mC][fC][mU][fG][fA][fA][fU][mU][mU][mU][mA][mU][mG][mA][m C][mA][G1b][G1b][G1b]3'); or (ii) an antisense strand of nucleic acid sequence according to SEQ ID NO: 377 (5' [mUs][fGs][fU][mC][fA][mU][fA][mA][mA][fA][mU][mU][mC][fA][mG][fG][mA][mA][mU][mUs][mCs][mC]3'), and a sense strand of nucleic acid sequence according to SEQ ID NO: 388 (5' [mAs][mAs][mU][mU][mC][fC][mU][fG][fA][fA][fU][mU][mU][mU][mA][mU][mG][mA][m C][mA][G1b][G1b][G1b]3').

Embodiment 46. The isolated oligonucleotide of embodiment 45, wherein the double stranded region comprising of an antisense strand of nucleic acid sequence according to SEQ ID NO: 377 (5' [mUs][fGs][fU][mC][fA][mU][fA][mA][mA][fA][mU][mU][mC][fA][mG][fG][mA][mA][mU][mUs][mCs][mC]3'), and a sense strand of nucleic acid sequence according to SEQ ID NO: 388 (5' [mAs][mAs][mU][mU][mC][fC][mU][fG][fA][fA][fU][mU][mU][mU][mA][mU][mG][mA][m C][mA][G1b][G1b][G1b]3').

Embodiment 47. A vector encoding the isolated oligonucleotide of any one of embodiments 1-46.

Embodiment 48. A delivery system comprising the isolated oligonucleotide of any one of embodiments 1-46 or the vector of embodiment 47.

Embodiment 49. A pharmaceutical composition comprising at least one isolated oligonucleotide of any one of embodiments 1-46, the vector of embodiment 47, or the delivery system of embodiment 48, and a pharmaceutically acceptable carrier, diluent or excipient.

Embodiment 50. A kit comprising at least one isolated oligonucleotide of any one of embodiments 1-46, the vector of embodiment 47, the delivery system of embodiment 48, or the pharmaceutical composition of embodiment 49.

Embodiment 51. A method of inhibiting or downregulating the expression or level of CFB in a subject in need thereof, wherein the method comprises administering to the subject an effective amount of at least one isolated oligonucleotide of any one of embodiments 1-46, the vector of embodiment 47, the delivery system of embodiment 48, or the pharmaceutical composition of embodiment 49.

Embodiment 52. A method of treating or preventing a disease or disorder associated with aberrant or increased expression or activity of CFB or a disease or disorder where CFB plays a role in a subject in need thereof, wherein the method comprises administering to the subject an effective amount of at least one isolated oligonucleotide of any one of embodiments 1-46, the vector of embodiment 47, the delivery system of embodiment 48, or the pharmaceutical composition of embodiment 49.

Embodiment 53. The isolated oligonucleotide of embodiment 1, wherein the isolated oligonucleotide attenuates expression of the CFB mRNA by at least 25% at a dose of 1 mg/kg.

Embodiment 54. The isolated oligonucleotide of embodiment 53, wherein the double stranded region comprises:

i) an anti-sense strand of nucleic acid sequence according to SEQ ID NO: 21 (5' UAAUUCAGGAAUUCCUGCUUCU 3'), and a sense strand of nucleic acid sequence according to SEQ ID NO: 55 (5' AAGCAGGAAUUCCUGAAUUA 3');

ii) an anti-sense strand of nucleic acid sequence according to SEQ ID NO: 22 (5' UUAAAAUUCAGGAAUUCCUGCU 3'), and a sense strand of nucleic acid sequence according to SEQ ID NO: 56 (5' CAGGAAUUCCUGAAUUUUAA 3');

iii) an anti-sense strand of nucleic acid sequence according to SEQ ID NO: 23 (5' UAUAAAAUUCAGGAAUUCCUGC 3'), and a sense strand of nucleic acid sequence according to SEQ ID NO: 57 (5' AGGAAUUCCUGAAUUUUAUA 3');

iv) an anti-sense strand of nucleic acid sequence according to SEQ ID NO: 24 (5' UGUCAUAAAAUUCAGGAAUUCC 3'), and a sense strand of nucleic acid sequence according to SEQ ID NO: 58 (5' AAUUCCUGAAUUUUAUGACA 3');

v) an anti-sense strand of nucleic acid sequence according to SEQ ID NO: 25 (5' UUAUUCUUGAGCUUGAUCAGGG 3'), and a sense strand of nucleic acid sequence according to SEQ ID NO: 59 (5' CUGAUCAAGCUCAAGAAUAA 3');

vi) an anti-sense strand of nucleic acid sequence according to SEQ ID NO: 26 (5' UUUAUUCUUGAGCUUGAUCAGG 3'), and a sense strand of nucleic acid sequence according to SEQ ID NO: 60 (5' UGAUCAAGCUCAAGAAUAAA 3').

Embodiment 55. The isolated oligonucleotide of embodiment 53, wherein the double stranded region comprises:

i) an anti-sense strand of nucleic acid sequence according to SEQ ID NO: 21 (5' UAAUUCAGGAAUUCCUGC- UUCU 3'), and a sense strand of nucleic acid sequence according to SEQ ID NO: 55 (5' AAGCAGGAAUUCCUGAAUUA 3');

ii) an anti-sense strand of nucleic acid sequence according to SEQ ID NO: 22 (5' UUAAAAUUCAGGAAUUCCUGCU 3'), and a sense strand of nucleic acid sequence according to SEQ ID NO: 56 (5' CAGGAAUUCCUGAAUUUUAA 3');

iii) an anti-sense strand of nucleic acid sequence according to SEQ ID NO: 23 (5' UAUAAAAUUCAGGAAUUCCUGC 3'), and a sense strand of nucleic acid sequence according to SEQ ID NO: 57 (5' AGGAAUUCCUGAAUUUUAUA 3');

iv) an anti-sense strand of nucleic acid sequence according to SEQ ID NO: 24 (5' UGUCAUAAAAUUCAGGAAUUCC 3'), and a sense strand of nucleic acid sequence according to SEQ ID NO: 58 (5' AAUUCCUGAAUUUUAUGACA 3');

v) an anti-sense strand of nucleic acid sequence according to SEQ ID NO: 26 (5' UUUAUUCUUGAGCUUGAUCAGG 3'), and a sense strand of nucleic acid sequence according to SEQ ID NO: 60 (5' UGAUCAAGCUCAAGAAUAAA 3').

What is claimed is:

1. A small interfering RNA (siRNA) comprising:

an antisense strand consisting of a sequence according to SEQ ID NO: 377 (5' [mUs][fGs][fU][mC][fA][mU][fA][mA][mA][fA][mU][mU][mC][fA][mG][fG][mA][mA][mU][mUs][mCs][mC]3'), and a sense strand consisting of a sequence according to SEQ ID NO: 388 (5' [mAs][mAs][mU][mU][mC][fC][mU][fG][fA][fA][fU][mU][mU][mU][mA][mU][mG][mA][m C][mA][G1b][G1b][G1b]3');

wherein:

m is a 2'-O-methyl modification, f is a 2'-F modification, s is a phosphorothioate linkage, and

[G1b][G1b][G1b] has the structure:

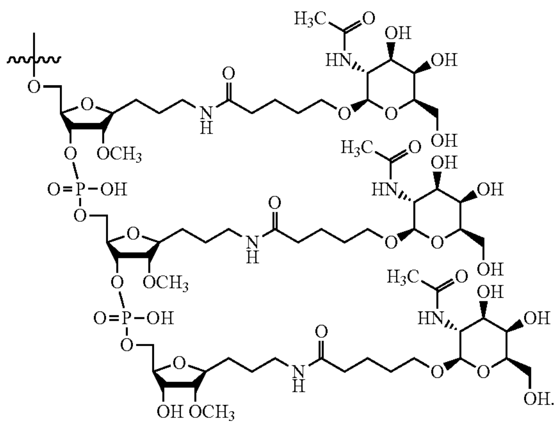

2. A pharmaceutical composition comprising the siRNA of claim 1, and a pharmaceutically acceptable carrier, diluent, or excipient.

3. A method of treating a disease or disorder associated with increased expression or activity of complement factor B (CFB) in a subject in need thereof, wherein the method comprises administering to the subject an effective amount of the pharmaceutical composition of claim 2.

4. The method of claim 3, wherein the disease or disorder associated with increased expression of CFB is selected from the group consisting of Paroxysmal Nocturnal Hemoglobinuria (PNH), rheumatoid arthritis, ischemia-reperfusion injuries, Multiple Sclerosis (MS), Guillain-Barre syndrome, Systemic lupus erythmatosis, $C_3$ Glomerulonephritis, atypical Hemolytic Uremic Syndrome (aHUS), Myasthenia Gravis (MG), Neuromyelistis Optic nerve and Spinal Cord (NMOSD), Dense Deposit Disease (DDD), Age-related Macular Degeneration (AMD), IgA nephropathy, Multifocal Motor Neuropathy (MMN), organ transplantation, and neurodegenerative diseases.

5. The method of claim 3, wherein the subject is a human.

6. A method of downregulating the expression or level of complement factor B (CFB) in a subject in need thereof, wherein the method comprises administering to the subject an effective amount of the pharmaceutical composition of claim 2.

7. The method of claim 6, wherein the subject is a human.

8. A method of treating a disease or disorder associated with increased expression or activity of complement factor B (CFB) in a subject in need thereof, wherein the method comprises administering to the subject an effective amount of the siRNA of claim 1.

9. The method of claim 8, wherein the disease or disorder associated with increased expression of CFB is selected from the group consisting of Paroxysmal Nocturnal Hemoglobinuria (PNH), rheumatoid arthritis, ischemia-reperfusion injuries, Multiple Sclerosis (MS), Guillain-Barre syndrome, Systemic lupus erythmatosis, $C_3$ Glomerulonephritis, atypical Hemolytic Uremic Syndrome (aHUS), Myasthenia Gravis (MG), Neuromyelistis Optic nerve and Spinal Cord (NMOSD), Dense Deposit Disease (DDD), Age-related Macular Degeneration (AMD), IgA nephropathy, Multifocal Motor Neuropathy (MMN), organ transplantation, and neurodegenerative diseases.

10. The method of claim 8, wherein the subject is a human.

11. A method of downregulating the expression or level of complement factor B (CFB) in a subject in need thereof, wherein the method comprises administering to the subject an effective amount of the siRNA of claim 1.

12. The method of claim 11, wherein the subject is a human.

* * * * *

SEQUENCE LISTING

```
Sequence total quantity: 391
SEQ ID NO: 1            moltype = RNA  length = 2476
FEATURE                 Location/Qualifiers
source                  1..2476
                        mol_type = mRNA
                        organism = Homo sapiens
SEQUENCE: 1
gggaagggaa tgtgaccagg tctaggtctg gagtttcagc ttggacactg agccaagcag  60
acaagcaaag caagccagga cacaccatcc tgccccaggc ccagcttctc tcctgccttc  120
caacgccatg gggagcaatc tcagccccca actctgcctg atgcccttta tcttgggcct  180
cttgtctgga ggtgtgacca ccactccatg gtctttggcc cggccccagg gatcctgctc  240
tctggagggg gtagagatca aaggcggctc cttccgactt ctccaagagg gccaggcact  300
ggagtacgtg tgtccttctg gcttctaccc gtaccctgtg cagacacgta cctgcagatc  360
tacggggtcc tggagcaccc tgaagactca agaccaaaag actgtcagga aggcagagtg  420
cagagcaatc cactgtccaa gaccacacga cttcgagaac ggggaatact ggccccggtc  480
tccctactac aatgtgagtg atgagatctc tttccactgc tatgacggtt acactctccg  540
gggctctgcc aatcgcacct gccaagtgaa tggccgatgg agtgggcaga cagcgatctg  600
tgacaacgga gcggggtact gctccaaccc gggcatcccc attggcacaa ggaaggtggg  660
cagccagtac cgccttgaag acagcgtcac ctaccactgc agccgggggc ttaccctgcg  720
tggctcccag cggcgaacgt gtcaggaagg tggctcttgg agcgggacgg agccttcctg  780
ccaagactcc ttcatgtacg acacccctca agaggtggcc gaagctttcc tgtcttccct  840
gacagagacc atagaaggag tcgatgctga ggatgggcac ggcccagggg aacaacagaa  900
gcggaagatc gtcctggacc cttcaggctc catgaacatc tacctggtgc tagatggatc  960
agacagcatt ggggccagca acttcacagg agccaaaaag tgtctagtca acttaattga  1020
gaaggtggca agttatggtg tgaagccaag atatggtcta gtgacatatg ccacataccc  1080
caaaatttgg gtcaaagtgt ctgaagcaga cagcagtaat gcagactggg tcacgaagca  1140
gctcaatgaa atcaattatg aagaccacaa gttgaagtca gggactaaca ccaagaaggc  1200
cctccaggca gtgtacagca tgatgagctg gccagatgac gtccctcctg aaggctggaa  1260
ccgcacccgc catgtcatca tcctcatgac tgatggattg cacaacatgg gcggggaccc  1320
aattactgtc attgatgaga tccgggactt gctatacatt ggcaaggatc gcaaaaaccc  1380
aagggaggat tatctggatg tctatgtgtt tggggtcggg cctttggtga accaagtgaa  1440
catcaatgct ttggcttcca agaaagacaa tgagcaacat gtgttcaaag tcaaggatat  1500
ggaaaacctg gaagatgttt tctaccaaat gatcgatgaa agccagtctc tgagtctctg  1560
tggcatggtt tgggaacaca ggaagggtac cgattaccac aagcaaccat ggcaggccaa  1620
gatctcagtc attcgccctt caaagggaca cgagagctgt atgggggctg tggtgtctga  1680
gtactttgtg ctgacagcag cacattgttt cactgtggat gacaaggaac actcaatcaa  1740
ggtcagcgta ggaggggaga agcgggacct ggagatagaa gtagtcctat ttcaccccaa  1800
ctacaacatt aatgggaaaa aagaagcagg aattcctgaa ttttatgact atgacgttgc  1860
cctgatcaag ctcaagaata agctgaaata tggccagact atcaggccca tttgtctccc  1920
ctgcaccgag ggaacaactc gagctttgag gcttcctcca actaccactt gccagcaaca  1980
aaaggaagag ctgctccctg cacaggatat caaagctctg tttgtgtctg aggaggagaa  2040
aaagctgact cggaaggagg tctacatcaa gaatggggat aagaaaggca gctgtgagag  2100
agatgctcaa tatgccccag gctatgacaa agtcaaggac atctcagagg tggtcacccc  2160
tcggttcctt tgtactggag gagtgagtcc ctatgctgac cccaatactt gcagaggtga  2220
ttctggcggc cccttgatag ttcacaagag aagtcgtttc attcaagttg gtgtaatcag  2280
ctggggagta gtggatgtct gcaaaaacca gaagcggcaa aagcaggtac ctgctcacgc  2340
ccgagacttt cacatcaacc tctttcaagt gctgccctgg ctgaaggaga aactccaaga  2400
tgaggatttg ggttttctat aaggggtttc ctgctggaca ggggcgtggg attgaattaa  2460
aacagctgcg acaaca                                                  2476

SEQ ID NO: 2            moltype = RNA  length = 22
FEATURE                 Location/Qualifiers
source                  1..22
                        mol_type = other RNA
                        organism = synthetic construct
SEQUENCE: 2
taaagagatc tcatcactca ca                                           22
```

-continued

```
SEQ ID NO: 3            moltype = RNA  length = 22
FEATURE                 Location/Qualifiers
source                  1..22
                        mol_type = other RNA
                        organism = synthetic construct
SEQUENCE: 3
tggaaagaga tctcatcact ca                                            22

SEQ ID NO: 4            moltype = RNA  length = 22
FEATURE                 Location/Qualifiers
source                  1..22
                        mol_type = other RNA
                        organism = synthetic construct
SEQUENCE: 4
tcagtggaaa gagatctcat ca                                            22

SEQ ID NO: 5            moltype = RNA  length = 22
FEATURE                 Location/Qualifiers
source                  1..22
                        mol_type = other RNA
                        organism = synthetic construct
SEQUENCE: 5
tatagcagtg gaaagagatc tc                                            22

SEQ ID NO: 6            moltype = RNA  length = 22
FEATURE                 Location/Qualifiers
source                  1..22
                        mol_type = other RNA
                        organism = synthetic construct
SEQUENCE: 6
tgtgtaaccg tcatagcagt gg                                            22

SEQ ID NO: 7            moltype = RNA  length = 22
FEATURE                 Location/Qualifiers
source                  1..22
                        mol_type = other RNA
                        organism = synthetic construct
SEQUENCE: 7
tttgactaga cactttttgg ct                                            22

SEQ ID NO: 8            moltype = RNA  length = 22
FEATURE                 Location/Qualifiers
source                  1..22
                        mol_type = other RNA
                        organism = synthetic construct
SEQUENCE: 8
ttaagttgac tagacacttt tt                                            22

SEQ ID NO: 9            moltype = RNA  length = 22
FEATURE                 Location/Qualifiers
source                  1..22
                        mol_type = other RNA
                        organism = synthetic construct
SEQUENCE: 9
taattaagtt gactagacac tt                                            22

SEQ ID NO: 10           moltype = RNA  length = 22
FEATURE                 Location/Qualifiers
source                  1..22
                        mol_type = other RNA
                        organism = synthetic construct
SEQUENCE: 10
tcaattaagt tgactagaca ct                                            22

SEQ ID NO: 11           moltype = RNA  length = 22
FEATURE                 Location/Qualifiers
source                  1..22
                        mol_type = other RNA
                        organism = synthetic construct
SEQUENCE: 11
tatatcttgg cttcacacca ta                                            22

SEQ ID NO: 12           moltype = RNA  length = 22
FEATURE                 Location/Qualifiers
source                  1..22
                        mol_type = other RNA
                        organism = synthetic construct
```

-continued

```
SEQUENCE: 12
ttagacatcc agataatcct cc                                            22

SEQ ID NO: 13          moltype = RNA  length = 22
FEATURE                Location/Qualifiers
source                 1..22
                       mol_type = other RNA
                       organism = synthetic construct
SEQUENCE: 13
taagcattga tgttcacttg gt                                            22

SEQ ID NO: 14          moltype = RNA  length = 22
FEATURE                Location/Qualifiers
source                 1..22
                       mol_type = other RNA
                       organism = synthetic construct
SEQUENCE: 14
taaagcattg atgttcactt gg                                            22

SEQ ID NO: 15          moltype = RNA  length = 22
FEATURE                Location/Qualifiers
source                 1..22
                       mol_type = other RNA
                       organism = synthetic construct
SEQUENCE: 15
taacacatgt tgctcattgt ct                                            22

SEQ ID NO: 16          moltype = RNA  length = 22
FEATURE                Location/Qualifiers
source                 1..22
                       mol_type = other RNA
                       organism = synthetic construct
SEQUENCE: 16
tttgactttg aacacatgtt gc                                            22

SEQ ID NO: 17          moltype = RNA  length = 22
FEATURE                Location/Qualifiers
source                 1..22
                       mol_type = other RNA
                       organism = synthetic construct
SEQUENCE: 17
tatatccttg actttgaaca ca                                            22

SEQ ID NO: 18          moltype = RNA  length = 22
FEATURE                Location/Qualifiers
source                 1..22
                       mol_type = other RNA
                       organism = synthetic construct
SEQUENCE: 18
tgagatcttg gcctgccatg gt                                            22

SEQ ID NO: 19          moltype = RNA  length = 22
FEATURE                Location/Qualifiers
source                 1..22
                       mol_type = other RNA
                       organism = synthetic construct
SEQUENCE: 19
taagtactca gacaccacag cc                                            22

SEQ ID NO: 20          moltype = RNA  length = 22
FEATURE                Location/Qualifiers
source                 1..22
                       mol_type = other RNA
                       organism = synthetic construct
SEQUENCE: 20
tattcaggaa ttcctgcttc tt                                            22

SEQ ID NO: 21          moltype = RNA  length = 22
FEATURE                Location/Qualifiers
source                 1..22
                       mol_type = other RNA
                       organism = synthetic construct
SEQUENCE: 21
taattcagga attcctgctt ct                                            22
```

```
SEQ ID NO: 22           moltype = RNA  length = 22
FEATURE                 Location/Qualifiers
source                  1..22
                        mol_type = other RNA
                        organism = synthetic construct
SEQUENCE: 22
ttaaaattca ggaattcctg ct                                           22

SEQ ID NO: 23           moltype = RNA  length = 22
FEATURE                 Location/Qualifiers
source                  1..22
                        mol_type = other RNA
                        organism = synthetic construct
SEQUENCE: 23
tataaaattc aggaattcct gc                                           22

SEQ ID NO: 24           moltype = RNA  length = 22
FEATURE                 Location/Qualifiers
source                  1..22
                        mol_type = other RNA
                        organism = synthetic construct
SEQUENCE: 24
tgtcataaaa ttcaggaatt cc                                           22

SEQ ID NO: 25           moltype = RNA  length = 22
FEATURE                 Location/Qualifiers
source                  1..22
                        mol_type = other RNA
                        organism = synthetic construct
SEQUENCE: 25
ttattcttga gcttgatcag gg                                           22

SEQ ID NO: 26           moltype = RNA  length = 22
FEATURE                 Location/Qualifiers
source                  1..22
                        mol_type = other RNA
                        organism = synthetic construct
SEQUENCE: 26
tttattcttg agcttgatca gg                                           22

SEQ ID NO: 27           moltype = RNA  length = 22
FEATURE                 Location/Qualifiers
source                  1..22
                        mol_type = other RNA
                        organism = synthetic construct
SEQUENCE: 27
tttgactttg tcatagcctg gg                                           22

SEQ ID NO: 28           moltype = RNA  length = 22
FEATURE                 Location/Qualifiers
source                  1..22
                        mol_type = other RNA
                        organism = synthetic construct
SEQUENCE: 28
taagtattgg ggtcagcata gg                                           22

SEQ ID NO: 29           moltype = RNA  length = 22
FEATURE                 Location/Qualifiers
source                  1..22
                        mol_type = other RNA
                        organism = synthetic construct
SEQUENCE: 29
tttctcttgt gaactatcaa gg                                           22

SEQ ID NO: 30           moltype = RNA  length = 22
FEATURE                 Location/Qualifiers
source                  1..22
                        mol_type = other RNA
                        organism = synthetic construct
SEQUENCE: 30
taaacgactt ctcttgtgaa ct                                           22

SEQ ID NO: 31           moltype = RNA  length = 22
FEATURE                 Location/Qualifiers
source                  1..22
                        mol_type = other RNA
                        organism = synthetic construct
```

-continued

```
SEQUENCE: 31
tttttgcag acatccacta ct                                        22

SEQ ID NO: 32          moltype = RNA  length = 22
FEATURE                Location/Qualifiers
source                 1..22
                       mol_type = other RNA
                       organism = synthetic construct
SEQUENCE: 32
tcatcttgga gtttctcctt ca                                       22

SEQ ID NO: 33          moltype = RNA  length = 22
FEATURE                Location/Qualifiers
source                 1..22
                       mol_type = other RNA
                       organism = synthetic construct
SEQUENCE: 33
taacccaaat cctcatcttg ga                                       22

SEQ ID NO: 34          moltype = RNA  length = 22
FEATURE                Location/Qualifiers
source                 1..22
                       mol_type = other RNA
                       organism = synthetic construct
SEQUENCE: 34
taaacccaaa tcctcatctt gg                                       22

SEQ ID NO: 35          moltype = RNA  length = 22
FEATURE                Location/Qualifiers
source                 1..22
                       mol_type = other RNA
                       organism = synthetic construct
SEQUENCE: 35
tcagctgttt taattcaatc cc                                       22

SEQ ID NO: 36          moltype = RNA  length = 20
FEATURE                Location/Qualifiers
source                 1..20
                       mol_type = other RNA
                       organism = synthetic construct
SEQUENCE: 36
tgagtgatga gatctcttta                                          20

SEQ ID NO: 37          moltype = RNA  length = 20
FEATURE                Location/Qualifiers
source                 1..20
                       mol_type = other RNA
                       organism = synthetic construct
SEQUENCE: 37
agtgatgaga tctctttcca                                          20

SEQ ID NO: 38          moltype = RNA  length = 20
FEATURE                Location/Qualifiers
source                 1..20
                       mol_type = other RNA
                       organism = synthetic construct
SEQUENCE: 38
atgagatctc tttccactga                                          20

SEQ ID NO: 39          moltype = RNA  length = 20
FEATURE                Location/Qualifiers
source                 1..20
                       mol_type = other RNA
                       organism = synthetic construct
SEQUENCE: 39
gatctctttc cactgctata                                          20

SEQ ID NO: 40          moltype = RNA  length = 20
FEATURE                Location/Qualifiers
source                 1..20
                       mol_type = other RNA
                       organism = synthetic construct
SEQUENCE: 40
atctctttcc actgctatga                                          20
```

```
SEQ ID NO: 41           moltype = RNA  length = 20
FEATURE                 Location/Qualifiers
source                  1..20
                        mol_type = other RNA
                        organism = synthetic construct
SEQUENCE: 41
ccaaaaagtg tctagtcaaa                                              20

SEQ ID NO: 42           moltype = RNA  length = 20
FEATURE                 Location/Qualifiers
source                  1..20
                        mol_type = other RNA
                        organism = synthetic construct
SEQUENCE: 42
aaagtgtcta gtcaacttaa                                              20

SEQ ID NO: 43           moltype = RNA  length = 20
FEATURE                 Location/Qualifiers
source                  1..20
                        mol_type = other RNA
                        organism = synthetic construct
SEQUENCE: 43
gtgtctagtc aacttaatta                                              20

SEQ ID NO: 44           moltype = RNA  length = 20
FEATURE                 Location/Qualifiers
source                  1..20
                        mol_type = other RNA
                        organism = synthetic construct
SEQUENCE: 44
tgtctagtca acttaattga                                              20

SEQ ID NO: 45           moltype = RNA  length = 20
FEATURE                 Location/Qualifiers
source                  1..20
                        mol_type = other RNA
                        organism = synthetic construct
SEQUENCE: 45
tggtgtgaag ccaagatata                                              20

SEQ ID NO: 46           moltype = RNA  length = 20
FEATURE                 Location/Qualifiers
source                  1..20
                        mol_type = other RNA
                        organism = synthetic construct
SEQUENCE: 46
aggattatct ggatgtctaa                                              20

SEQ ID NO: 47           moltype = RNA  length = 20
FEATURE                 Location/Qualifiers
source                  1..20
                        mol_type = other RNA
                        organism = synthetic construct
SEQUENCE: 47
caagtgaaca tcaatgctta                                              20

SEQ ID NO: 48           moltype = RNA  length = 20
FEATURE                 Location/Qualifiers
source                  1..20
                        mol_type = other RNA
                        organism = synthetic construct
SEQUENCE: 48
aagtgaacat caatgcttta                                              20

SEQ ID NO: 49           moltype = RNA  length = 20
FEATURE                 Location/Qualifiers
source                  1..20
                        mol_type = other RNA
                        organism = synthetic construct
SEQUENCE: 49
acaatgagca acatgtgtta                                              20

SEQ ID NO: 50           moltype = RNA  length = 20
FEATURE                 Location/Qualifiers
source                  1..20
                        mol_type = other RNA
                        organism = synthetic construct
```

```
SEQUENCE: 50
aacatgtgtt caaagtcaaa                                      20

SEQ ID NO: 51          moltype = RNA  length = 20
FEATURE                Location/Qualifiers
source                 1..20
                       mol_type = other RNA
                       organism = synthetic construct
SEQUENCE: 51
tgttcaaagt caaggatata                                      20

SEQ ID NO: 52          moltype = RNA  length = 20
FEATURE                Location/Qualifiers
source                 1..20
                       mol_type = other RNA
                       organism = synthetic construct
SEQUENCE: 52
catggcaggc caagatctca                                      20

SEQ ID NO: 53          moltype = RNA  length = 20
FEATURE                Location/Qualifiers
source                 1..20
                       mol_type = other RNA
                       organism = synthetic construct
SEQUENCE: 53
ctgtggtgtc tgagtactta                                      20

SEQ ID NO: 54          moltype = RNA  length = 20
FEATURE                Location/Qualifiers
source                 1..20
                       mol_type = other RNA
                       organism = synthetic construct
SEQUENCE: 54
gaagcaggaa ttcctgaata                                      20

SEQ ID NO: 55          moltype = RNA  length = 20
FEATURE                Location/Qualifiers
source                 1..20
                       mol_type = other RNA
                       organism = synthetic construct
SEQUENCE: 55
aagcaggaat tcctgaatta                                      20

SEQ ID NO: 56          moltype = RNA  length = 20
FEATURE                Location/Qualifiers
source                 1..20
                       mol_type = other RNA
                       organism = synthetic construct
SEQUENCE: 56
caggaattcc tgaattttaa                                      20

SEQ ID NO: 57          moltype = RNA  length = 20
FEATURE                Location/Qualifiers
source                 1..20
                       mol_type = other RNA
                       organism = synthetic construct
SEQUENCE: 57
aggaattcct gaattttata                                      20

SEQ ID NO: 58          moltype = RNA  length = 20
FEATURE                Location/Qualifiers
source                 1..20
                       mol_type = other RNA
                       organism = synthetic construct
SEQUENCE: 58
aattcctgaa ttttatgaca                                      20

SEQ ID NO: 59          moltype = RNA  length = 20
FEATURE                Location/Qualifiers
source                 1..20
                       mol_type = other RNA
                       organism = synthetic construct
SEQUENCE: 59
ctgatcaagc tcaagaataa                                      20

SEQ ID NO: 60          moltype = RNA  length = 20
FEATURE                Location/Qualifiers
```

```
source                  1..20
                        mol_type = other RNA
                        organism = synthetic construct
SEQUENCE: 60
tgatcaagct caagaataaa                                                20

SEQ ID NO: 61           moltype = RNA  length = 20
FEATURE                 Location/Qualifiers
source                  1..20
                        mol_type = other RNA
                        organism = synthetic construct
SEQUENCE: 61
caggctatga caaagtcaaa                                                20

SEQ ID NO: 62           moltype = RNA  length = 20
FEATURE                 Location/Qualifiers
source                  1..20
                        mol_type = other RNA
                        organism = synthetic construct
SEQUENCE: 62
tatgctgacc ccaatactta                                                20

SEQ ID NO: 63           moltype = RNA  length = 20
FEATURE                 Location/Qualifiers
source                  1..20
                        mol_type = other RNA
                        organism = synthetic construct
SEQUENCE: 63
ttgatagttc acaagagaaa                                                20

SEQ ID NO: 64           moltype = RNA  length = 20
FEATURE                 Location/Qualifiers
source                  1..20
                        mol_type = other RNA
                        organism = synthetic construct
SEQUENCE: 64
ttcacaagag aagtcgttta                                                20

SEQ ID NO: 65           moltype = RNA  length = 20
FEATURE                 Location/Qualifiers
source                  1..20
                        mol_type = other RNA
                        organism = synthetic construct
SEQUENCE: 65
tagtggatgt ctgcaaaaaa                                                20

SEQ ID NO: 66           moltype = RNA  length = 20
FEATURE                 Location/Qualifiers
source                  1..20
                        mol_type = other RNA
                        organism = synthetic construct
SEQUENCE: 66
aaggagaaac tccaagatga                                                20

SEQ ID NO: 67           moltype = RNA  length = 20
FEATURE                 Location/Qualifiers
source                  1..20
                        mol_type = other RNA
                        organism = synthetic construct
SEQUENCE: 67
caagatgagg atttgggtta                                                20

SEQ ID NO: 68           moltype = RNA  length = 20
FEATURE                 Location/Qualifiers
source                  1..20
                        mol_type = other RNA
                        organism = synthetic construct
SEQUENCE: 68
aagatgagga tttgggttta                                                20

SEQ ID NO: 69           moltype = RNA  length = 20
FEATURE                 Location/Qualifiers
source                  1..20
                        mol_type = other RNA
                        organism = synthetic construct
SEQUENCE: 69
gattgaatta aaacagctga                                                20

SEQ ID NO: 70           moltype = RNA  length = 22
```

```
FEATURE                Location/Qualifiers
source                 1..22
                       mol_type = other RNA
                       organism = synthetic construct
SEQUENCE: 70
tctagacctg gtcacattcc ct                                          22

SEQ ID NO: 71          moltype = RNA  length = 22
FEATURE                Location/Qualifiers
source                 1..22
                       mol_type = other RNA
                       organism = synthetic construct
SEQUENCE: 71
taactccaga cctagacctg gt                                          22

SEQ ID NO: 72          moltype = RNA  length = 22
FEATURE                Location/Qualifiers
source                 1..22
                       mol_type = other RNA
                       organism = synthetic construct
SEQUENCE: 72
taaactccag acctagacct gg                                          22

SEQ ID NO: 73          moltype = RNA  length = 22
FEATURE                Location/Qualifiers
source                 1..22
                       mol_type = other RNA
                       organism = synthetic construct
SEQUENCE: 73
tgaaactcca gacctagacc tg                                          22

SEQ ID NO: 74          moltype = RNA  length = 22
FEATURE                Location/Qualifiers
source                 1..22
                       mol_type = other RNA
                       organism = synthetic construct
SEQUENCE: 74
ttgaaactcc agacctagac ct                                          22

SEQ ID NO: 75          moltype = RNA  length = 22
FEATURE                Location/Qualifiers
source                 1..22
                       mol_type = other RNA
                       organism = synthetic construct
SEQUENCE: 75
tgatctgcag gtacgtgtct gc                                          22

SEQ ID NO: 76          moltype = RNA  length = 22
FEATURE                Location/Qualifiers
source                 1..22
                       mol_type = other RNA
                       organism = synthetic construct
SEQUENCE: 76
tggattgctc tgcactctgc ct                                          22

SEQ ID NO: 77          moltype = RNA  length = 22
FEATURE                Location/Qualifiers
source                 1..22
                       mol_type = other RNA
                       organism = synthetic construct
SEQUENCE: 77
tctcacattg tagtagggag ac                                          22

SEQ ID NO: 78          moltype = RNA  length = 22
FEATURE                Location/Qualifiers
source                 1..22
                       mol_type = other RNA
                       organism = synthetic construct
SEQUENCE: 78
tatcactcac attgtagtag gg                                          22

SEQ ID NO: 79          moltype = RNA  length = 22
FEATURE                Location/Qualifiers
source                 1..22
                       mol_type = other RNA
                       organism = synthetic construct
SEQUENCE: 79
tcatcactca cattgtagta gg                                          22
```

-continued

```
SEQ ID NO: 80          moltype = RNA  length = 22
FEATURE                Location/Qualifiers
source                 1..22
                       mol_type = other RNA
                       organism = synthetic construct
SEQUENCE: 80
tgaaagagat ctcatcactc ac                                          22

SEQ ID NO: 81          moltype = RNA  length = 22
FEATURE                Location/Qualifiers
source                 1..22
                       mol_type = other RNA
                       organism = synthetic construct
SEQUENCE: 81
tgtggaaaga gatctcatca ct                                          22

SEQ ID NO: 82          moltype = RNA  length = 22
FEATURE                Location/Qualifiers
source                 1..22
                       mol_type = other RNA
                       organism = synthetic construct
SEQUENCE: 82
tcatagcagt ggaaagagat ct                                          22

SEQ ID NO: 83          moltype = RNA  length = 22
FEATURE                Location/Qualifiers
source                 1..22
                       mol_type = other RNA
                       organism = synthetic construct
SEQUENCE: 83
tgagtgtaac cgtcatagca gt                                          22

SEQ ID NO: 84          moltype = RNA  length = 22
FEATURE                Location/Qualifiers
source                 1..22
                       mol_type = other RNA
                       organism = synthetic construct
SEQUENCE: 84
tgagagtgta accgtcatag ca                                          22

SEQ ID NO: 85          moltype = RNA  length = 22
FEATURE                Location/Qualifiers
source                 1..22
                       mol_type = other RNA
                       organism = synthetic construct
SEQUENCE: 85
tttgtcacag atcgctgtct gc                                          22

SEQ ID NO: 86          moltype = RNA  length = 22
FEATURE                Location/Qualifiers
source                 1..22
                       mol_type = other RNA
                       organism = synthetic construct
SEQUENCE: 86
tcatgaagga gtcttggcag ga                                          22

SEQ ID NO: 87          moltype = RNA  length = 22
FEATURE                Location/Qualifiers
source                 1..22
                       mol_type = other RNA
                       organism = synthetic construct
SEQUENCE: 87
tgtacatgaa ggagtcttgg ca                                          22

SEQ ID NO: 88          moltype = RNA  length = 22
FEATURE                Location/Qualifiers
source                 1..22
                       mol_type = other RNA
                       organism = synthetic construct
SEQUENCE: 88
tcgtacatga aggagtcttg gc                                          22

SEQ ID NO: 89          moltype = RNA  length = 22
FEATURE                Location/Qualifiers
source                 1..22
                       mol_type = other RNA
                       organism = synthetic construct
SEQUENCE: 89
tgtcgtacat gaaggagtct tg                                          22
```

-continued

```
SEQ ID NO: 90          moltype = RNA  length = 22
FEATURE                Location/Qualifiers
source                 1..22
                       mol_type = other RNA
                       organism = synthetic construct
SEQUENCE: 90
taaagcttcg gccacctctt ga                                              22

SEQ ID NO: 91          moltype = RNA  length = 22
FEATURE                Location/Qualifiers
source                 1..22
                       mol_type = other RNA
                       organism = synthetic construct
SEQUENCE: 91
tatccatcta gcaccaggta ga                                              22

SEQ ID NO: 92          moltype = RNA  length = 22
FEATURE                Location/Qualifiers
source                 1..22
                       mol_type = other RNA
                       organism = synthetic construct
SEQUENCE: 92
tctgtctgat ccatctagca cc                                              22

SEQ ID NO: 93          moltype = RNA  length = 22
FEATURE                Location/Qualifiers
source                 1..22
                       mol_type = other RNA
                       organism = synthetic construct
SEQUENCE: 93
tctttttggc tcctgtgaag tt                                              22

SEQ ID NO: 94          moltype = RNA  length = 22
FEATURE                Location/Qualifiers
source                 1..22
                       mol_type = other RNA
                       organism = synthetic construct
SEQUENCE: 94
tgacactttt tggctcctgt ga                                              22

SEQ ID NO: 95          moltype = RNA  length = 22
FEATURE                Location/Qualifiers
source                 1..22
                       mol_type = other RNA
                       organism = synthetic construct
SEQUENCE: 95
tgactagaca ctttttggct cc                                              22

SEQ ID NO: 96          moltype = RNA  length = 22
FEATURE                Location/Qualifiers
source                 1..22
                       mol_type = other RNA
                       organism = synthetic construct
SEQUENCE: 96
tgttgactag acactttttg gc                                              22

SEQ ID NO: 97          moltype = RNA  length = 22
FEATURE                Location/Qualifiers
source                 1..22
                       mol_type = other RNA
                       organism = synthetic construct
SEQUENCE: 97
tttaagttga ctagacactt tt                                              22

SEQ ID NO: 98          moltype = RNA  length = 22
FEATURE                Location/Qualifiers
source                 1..22
                       mol_type = other RNA
                       organism = synthetic construct
SEQUENCE: 98
tctcaattaa gttgactaga ca                                              22

SEQ ID NO: 99          moltype = RNA  length = 22
FEATURE                Location/Qualifiers
source                 1..22
                       mol_type = other RNA
                       organism = synthetic construct
```

```
SEQUENCE: 99
tttctcaatt aagttgacta ga                                          22

SEQ ID NO: 100         moltype = RNA  length = 22
FEATURE                Location/Qualifiers
source                 1..22
                       mol_type = other RNA
                       organism = synthetic construct
SEQUENCE: 100
tataacttgc caccttctca at                                          22

SEQ ID NO: 101         moltype = RNA  length = 22
FEATURE                Location/Qualifiers
source                 1..22
                       mol_type = other RNA
                       organism = synthetic construct
SEQUENCE: 101
tcataacttg ccaccttctc aa                                          22

SEQ ID NO: 102         moltype = RNA  length = 22
FEATURE                Location/Qualifiers
source                 1..22
                       mol_type = other RNA
                       organism = synthetic construct
SEQUENCE: 102
tcaccataac ttgccacctt ct                                          22

SEQ ID NO: 103         moltype = RNA  length = 22
FEATURE                Location/Qualifiers
source                 1..22
                       mol_type = other RNA
                       organism = synthetic construct
SEQUENCE: 103
tttcacacca taacttgcca cc                                          22

SEQ ID NO: 104         moltype = RNA  length = 22
FEATURE                Location/Qualifiers
source                 1..22
                       mol_type = other RNA
                       organism = synthetic construct
SEQUENCE: 104
tcttcaactt gtggtcttca ta                                          22

SEQ ID NO: 105         moltype = RNA  length = 22
FEATURE                Location/Qualifiers
source                 1..22
                       mol_type = other RNA
                       organism = synthetic construct
SEQUENCE: 105
tgacttcaac ttgtggtctt ca                                          22

SEQ ID NO: 106         moltype = RNA  length = 22
FEATURE                Location/Qualifiers
source                 1..22
                       mol_type = other RNA
                       organism = synthetic construct
SEQUENCE: 106
tctcatcatg ctgtacactg cc                                          22

SEQ ID NO: 107         moltype = RNA  length = 22
FEATURE                Location/Qualifiers
source                 1..22
                       mol_type = other RNA
                       organism = synthetic construct
SEQUENCE: 107
ttaattgggt ccccgcccat gt                                          22

SEQ ID NO: 108         moltype = RNA  length = 22
FEATURE                Location/Qualifiers
source                 1..22
                       mol_type = other RNA
                       organism = synthetic construct
SEQUENCE: 108
tatgacagta attgggtccc cg                                          22

SEQ ID NO: 109         moltype = RNA  length = 22
FEATURE                Location/Qualifiers
```

```
source                  1..22
                        mol_type = other RNA
                        organism = synthetic construct
SEQUENCE: 109
taatgacagt aattgggtcc cc                                                22

SEQ ID NO: 110          moltype = RNA  length = 22
FEATURE                 Location/Qualifiers
source                  1..22
                        mol_type = other RNA
                        organism = synthetic construct
SEQUENCE: 110
tcaatgacag taattgggtc cc                                                22

SEQ ID NO: 111          moltype = RNA  length = 22
FEATURE                 Location/Qualifiers
source                  1..22
                        mol_type = other RNA
                        organism = synthetic construct
SEQUENCE: 111
tatcaatgac agtaattggg tc                                                22

SEQ ID NO: 112          moltype = RNA  length = 22
FEATURE                 Location/Qualifiers
source                  1..22
                        mol_type = other RNA
                        organism = synthetic construct
SEQUENCE: 112
tcatcaatga cagtaattgg gt                                                22

SEQ ID NO: 113          moltype = RNA  length = 22
FEATURE                 Location/Qualifiers
source                  1..22
                        mol_type = other RNA
                        organism = synthetic construct
SEQUENCE: 113
tctcatcaat gacagtaatt gg                                                22

SEQ ID NO: 114          moltype = RNA  length = 22
FEATURE                 Location/Qualifiers
source                  1..22
                        mol_type = other RNA
                        organism = synthetic construct
SEQUENCE: 114
tatagacatc cagataatcc tc                                                22

SEQ ID NO: 115          moltype = RNA  length = 22
FEATURE                 Location/Qualifiers
source                  1..22
                        mol_type = other RNA
                        organism = synthetic construct
SEQUENCE: 115
tcatagacat ccagataatc ct                                                22

SEQ ID NO: 116          moltype = RNA  length = 22
FEATURE                 Location/Qualifiers
source                  1..22
                        mol_type = other RNA
                        organism = synthetic construct
SEQUENCE: 116
tcaaagcatt gatgttcact tg                                                22

SEQ ID NO: 117          moltype = RNA  length = 22
FEATURE                 Location/Qualifiers
source                  1..22
                        mol_type = other RNA
                        organism = synthetic construct
SEQUENCE: 117
taagccaaag cattgatgtt ca                                                22

SEQ ID NO: 118          moltype = RNA  length = 22
FEATURE                 Location/Qualifiers
source                  1..22
                        mol_type = other RNA
                        organism = synthetic construct
SEQUENCE: 118
ttttcttgga agccaaagca tt                                                22

SEQ ID NO: 119          moltype = RNA  length = 22
```

```
FEATURE                Location/Qualifiers
source                 1..22
                       mol_type = other RNA
                       organism = synthetic construct
SEQUENCE: 119
tctttcttgg aagccaaagc at                                            22

SEQ ID NO: 120         moltype = RNA  length = 22
FEATURE                Location/Qualifiers
source                 1..22
                       mol_type = other RNA
                       organism = synthetic construct
SEQUENCE: 120
tgtctttctt ggaagccaaa gc                                            22

SEQ ID NO: 121         moltype = RNA  length = 22
FEATURE                Location/Qualifiers
source                 1..22
                       mol_type = other RNA
                       organism = synthetic construct
SEQUENCE: 121
tctcattgtc tttcttggaa gc                                            22

SEQ ID NO: 122         moltype = RNA  length = 22
FEATURE                Location/Qualifiers
source                 1..22
                       mol_type = other RNA
                       organism = synthetic construct
SEQUENCE: 122
tttgctcatt gtctttcttg ga                                            22

SEQ ID NO: 123         moltype = RNA  length = 22
FEATURE                Location/Qualifiers
source                 1..22
                       mol_type = other RNA
                       organism = synthetic construct
SEQUENCE: 123
tgttgctcat tgtctttctt gg                                            22

SEQ ID NO: 124         moltype = RNA  length = 22
FEATURE                Location/Qualifiers
source                 1..22
                       mol_type = other RNA
                       organism = synthetic construct
SEQUENCE: 124
tatgttgctc attgtctttc tt                                            22

SEQ ID NO: 125         moltype = RNA  length = 22
FEATURE                Location/Qualifiers
source                 1..22
                       mol_type = other RNA
                       organism = synthetic construct
SEQUENCE: 125
tcatgttgct cattgtcttt ct                                            22

SEQ ID NO: 126         moltype = RNA  length = 22
FEATURE                Location/Qualifiers
source                 1..22
                       mol_type = other RNA
                       organism = synthetic construct
SEQUENCE: 126
ttttgaacac atgttgctca tt                                            22

SEQ ID NO: 127         moltype = RNA  length = 22
FEATURE                Location/Qualifiers
source                 1..22
                       mol_type = other RNA
                       organism = synthetic construct
SEQUENCE: 127
tctttgaaca catgttgctc at                                            22

SEQ ID NO: 128         moltype = RNA  length = 22
FEATURE                Location/Qualifiers
source                 1..22
                       mol_type = other RNA
                       organism = synthetic construct
SEQUENCE: 128
tgactttgaa cacatgttgc tc                                            22
```

```
SEQ ID NO: 129         moltype = RNA  length = 22
FEATURE                Location/Qualifiers
source                 1..22
                       mol_type = other RNA
                       organism = synthetic construct
SEQUENCE: 129
ttttccatat ccttgacttt ga                                            22

SEQ ID NO: 130         moltype = RNA  length = 22
FEATURE                Location/Qualifiers
source                 1..22
                       mol_type = other RNA
                       organism = synthetic construct
SEQUENCE: 130
tcaggttttc catatccttg ac                                            22

SEQ ID NO: 131         moltype = RNA  length = 22
FEATURE                Location/Qualifiers
source                 1..22
                       mol_type = other RNA
                       organism = synthetic construct
SEQUENCE: 131
tcacagagac tcagagactg gc                                            22

SEQ ID NO: 132         moltype = RNA  length = 22
FEATURE                Location/Qualifiers
source                 1..22
                       mol_type = other RNA
                       organism = synthetic construct
SEQUENCE: 132
tttgcttgtg gtaatcggta cc                                            22

SEQ ID NO: 133         moltype = RNA  length = 22
FEATURE                Location/Qualifiers
source                 1..22
                       mol_type = other RNA
                       organism = synthetic construct
SEQUENCE: 133
taaagtactc agacaccaca gc                                            22

SEQ ID NO: 134         moltype = RNA  length = 22
FEATURE                Location/Qualifiers
source                 1..22
                       mol_type = other RNA
                       organism = synthetic construct
SEQUENCE: 134
taacaatgtg ctgctgtcag ca                                            22

SEQ ID NO: 135         moltype = RNA  length = 22
FEATURE                Location/Qualifiers
source                 1..22
                       mol_type = other RNA
                       organism = synthetic construct
SEQUENCE: 135
tcttgattga gtgttccttg tc                                            22

SEQ ID NO: 136         moltype = RNA  length = 22
FEATURE                Location/Qualifiers
source                 1..22
                       mol_type = other RNA
                       organism = synthetic construct
SEQUENCE: 136
tctgaccttg attgagtgtt cc                                            22

SEQ ID NO: 137         moltype = RNA  length = 22
FEATURE                Location/Qualifiers
source                 1..22
                       mol_type = other RNA
                       organism = synthetic construct
SEQUENCE: 137
tgaattcctg cttctttttt cc                                            22

SEQ ID NO: 138         moltype = RNA  length = 22
FEATURE                Location/Qualifiers
source                 1..22
                       mol_type = other RNA
                       organism = synthetic construct
SEQUENCE: 138
tcataaaatt caggaattcc tg                                            22
```

```
SEQ ID NO: 139          moltype = RNA  length = 22
FEATURE                 Location/Qualifiers
source                  1..22
                        mol_type = other RNA
                        organism = synthetic construct
SEQUENCE: 139
tcatagtcat aaaattcagg aa                                            22

SEQ ID NO: 140          moltype = RNA  length = 22
FEATURE                 Location/Qualifiers
source                  1..22
                        mol_type = other RNA
                        organism = synthetic construct
SEQUENCE: 140
tgtcatagtc ataaaattca gg                                            22

SEQ ID NO: 141          moltype = RNA  length = 22
FEATURE                 Location/Qualifiers
source                  1..22
                        mol_type = other RNA
                        organism = synthetic construct
SEQUENCE: 141
tcttgatcag ggcaacgtca ta                                            22

SEQ ID NO: 142          moltype = RNA  length = 22
FEATURE                 Location/Qualifiers
source                  1..22
                        mol_type = other RNA
                        organism = synthetic construct
SEQUENCE: 142
tttcttgagc ttgatcaggg ca                                            22

SEQ ID NO: 143          moltype = RNA  length = 22
FEATURE                 Location/Qualifiers
source                  1..22
                        mol_type = other RNA
                        organism = synthetic construct
SEQUENCE: 143
tattcttgag cttgatcagg gc                                            22

SEQ ID NO: 144          moltype = RNA  length = 22
FEATURE                 Location/Qualifiers
source                  1..22
                        mol_type = other RNA
                        organism = synthetic construct
SEQUENCE: 144
tcttattctt gagcttgatc ag                                            22

SEQ ID NO: 145          moltype = RNA  length = 22
FEATURE                 Location/Qualifiers
source                  1..22
                        mol_type = other RNA
                        organism = synthetic construct
SEQUENCE: 145
tgagacaaat gggcctgata gt                                            22

SEQ ID NO: 146          moltype = RNA  length = 22
FEATURE                 Location/Qualifiers
source                  1..22
                        mol_type = other RNA
                        organism = synthetic construct
SEQUENCE: 146
taagtggtag ttggaggaag cc                                            22

SEQ ID NO: 147          moltype = RNA  length = 22
FEATURE                 Location/Qualifiers
source                  1..22
                        mol_type = other RNA
                        organism = synthetic construct
SEQUENCE: 147
tcagagcttt gatatcctgt gc                                            22

SEQ ID NO: 148          moltype = RNA  length = 22
FEATURE                 Location/Qualifiers
source                  1..22
                        mol_type = other RNA
                        organism = synthetic construct
```

-continued

```
SEQUENCE: 148
taacagagct ttgatatcct gt                                          22

SEQ ID NO: 149          moltype = RNA  length = 22
FEATURE                 Location/Qualifiers
source                  1..22
                        mol_type = other RNA
                        organism = synthetic construct
SEQUENCE: 149
taaacagagc tttgatatcc tg                                          22

SEQ ID NO: 150          moltype = RNA  length = 22
FEATURE                 Location/Qualifiers
source                  1..22
                        mol_type = other RNA
                        organism = synthetic construct
SEQUENCE: 150
tcaaacagag ctttgatatc ct                                          22

SEQ ID NO: 151          moltype = RNA  length = 22
FEATURE                 Location/Qualifiers
source                  1..22
                        mol_type = other RNA
                        organism = synthetic construct
SEQUENCE: 151
tcagacacaa acagagcttt ga                                          22

SEQ ID NO: 152          moltype = RNA  length = 22
FEATURE                 Location/Qualifiers
source                  1..22
                        mol_type = other RNA
                        organism = synthetic construct
SEQUENCE: 152
tcttgatgta gacctccttc cg                                          22

SEQ ID NO: 153          moltype = RNA  length = 22
FEATURE                 Location/Qualifiers
source                  1..22
                        mol_type = other RNA
                        organism = synthetic construct
SEQUENCE: 153
tcattcttga tgtagacctc ct                                          22

SEQ ID NO: 154          moltype = RNA  length = 22
FEATURE                 Location/Qualifiers
source                  1..22
                        mol_type = other RNA
                        organism = synthetic construct
SEQUENCE: 154
tctttcttat ccccattctt ga                                          22

SEQ ID NO: 155          moltype = RNA  length = 22
FEATURE                 Location/Qualifiers
source                  1..22
                        mol_type = other RNA
                        organism = synthetic construct
SEQUENCE: 155
tctctctcac agctgccttt ct                                          22

SEQ ID NO: 156          moltype = RNA  length = 22
FEATURE                 Location/Qualifiers
source                  1..22
                        mol_type = other RNA
                        organism = synthetic construct
SEQUENCE: 156
tgagcatctc tctcacagct gc                                          22

SEQ ID NO: 157          moltype = RNA  length = 22
FEATURE                 Location/Qualifiers
source                  1..22
                        mol_type = other RNA
                        organism = synthetic construct
SEQUENCE: 157
tttgagcatc tctctcacag ct                                          22

SEQ ID NO: 158          moltype = RNA  length = 22
FEATURE                 Location/Qualifiers
```

-continued

```
source                  1..22
                        mol_type = other RNA
                        organism = synthetic construct
SEQUENCE: 158
tattgagcat ctctctcaca gc                                            22

SEQ ID NO: 159          moltype = RNA  length = 22
FEATURE                 Location/Qualifiers
source                  1..22
                        mol_type = other RNA
                        organism = synthetic construct
SEQUENCE: 159
tatattgagc atctctctca ca                                            22

SEQ ID NO: 160          moltype = RNA  length = 22
FEATURE                 Location/Qualifiers
source                  1..22
                        mol_type = other RNA
                        organism = synthetic construct
SEQUENCE: 160
tcatattgag catctctctc ac                                            22

SEQ ID NO: 161          moltype = RNA  length = 22
FEATURE                 Location/Qualifiers
source                  1..22
                        mol_type = other RNA
                        organism = synthetic construct
SEQUENCE: 161
tcttgacttt gtcatagcct gg                                            22

SEQ ID NO: 162          moltype = RNA  length = 22
FEATURE                 Location/Qualifiers
source                  1..22
                        mol_type = other RNA
                        organism = synthetic construct
SEQUENCE: 162
tgagatgtcc ttgactttgt ca                                            22

SEQ ID NO: 163          moltype = RNA  length = 22
FEATURE                 Location/Qualifiers
source                  1..22
                        mol_type = other RNA
                        organism = synthetic construct
SEQUENCE: 163
tgtcagcata gggactcact cc                                            22

SEQ ID NO: 164          moltype = RNA  length = 22
FEATURE                 Location/Qualifiers
source                  1..22
                        mol_type = other RNA
                        organism = synthetic construct
SEQUENCE: 164
tgtattgggg tcagcatagg ga                                            22

SEQ ID NO: 165          moltype = RNA  length = 22
FEATURE                 Location/Qualifiers
source                  1..22
                        mol_type = other RNA
                        organism = synthetic construct
SEQUENCE: 165
tatcacctct gcaagtattg gg                                            22

SEQ ID NO: 166          moltype = RNA  length = 22
FEATURE                 Location/Qualifiers
source                  1..22
                        mol_type = other RNA
                        organism = synthetic construct
SEQUENCE: 166
taactatcaa ggggccgcca ga                                            22

SEQ ID NO: 167          moltype = RNA  length = 22
FEATURE                 Location/Qualifiers
source                  1..22
                        mol_type = other RNA
                        organism = synthetic construct
SEQUENCE: 167
tgtgaactat caaggggccg cc                                            22

SEQ ID NO: 168          moltype = RNA  length = 22
```

```
FEATURE                Location/Qualifiers
source                 1..22
                       mol_type = other RNA
                       organism = synthetic construct
SEQUENCE: 168
tttgtgaact atcaaggggc cg                                          22

SEQ ID NO: 169         moltype = RNA  length = 22
FEATURE                Location/Qualifiers
source                 1..22
                       mol_type = other RNA
                       organism = synthetic construct
SEQUENCE: 169
tctcttgtga actatcaagg gg                                          22

SEQ ID NO: 170         moltype = RNA  length = 22
FEATURE                Location/Qualifiers
source                 1..22
                       mol_type = other RNA
                       organism = synthetic construct
SEQUENCE: 170
tgacttctct tgtgaactat ca                                          22

SEQ ID NO: 171         moltype = RNA  length = 22
FEATURE                Location/Qualifiers
source                 1..22
                       mol_type = other RNA
                       organism = synthetic construct
SEQUENCE: 171
tatgaaacga cttctcttgt ga                                          22

SEQ ID NO: 172         moltype = RNA  length = 22
FEATURE                Location/Qualifiers
source                 1..22
                       mol_type = other RNA
                       organism = synthetic construct
SEQUENCE: 172
tttttgcaga catccactac tc                                          22

SEQ ID NO: 173         moltype = RNA  length = 22
FEATURE                Location/Qualifiers
source                 1..22
                       mol_type = other RNA
                       organism = synthetic construct
SEQUENCE: 173
tgtttttgca gacatccact ac                                          22

SEQ ID NO: 174         moltype = RNA  length = 22
FEATURE                Location/Qualifiers
source                 1..22
                       mol_type = other RNA
                       organism = synthetic construct
SEQUENCE: 174
tttctggttt ttgcagacat cc                                          22

SEQ ID NO: 175         moltype = RNA  length = 22
FEATURE                Location/Qualifiers
source                 1..22
                       mol_type = other RNA
                       organism = synthetic construct
SEQUENCE: 175
tttggagttt ctccttcagc ca                                          22

SEQ ID NO: 176         moltype = RNA  length = 22
FEATURE                Location/Qualifiers
source                 1..22
                       mol_type = other RNA
                       organism = synthetic construct
SEQUENCE: 176
tatcttggag tttctccttc ag                                          22

SEQ ID NO: 177         moltype = RNA  length = 22
FEATURE                Location/Qualifiers
source                 1..22
                       mol_type = other RNA
                       organism = synthetic construct
SEQUENCE: 177
tctcatcttg gagtttctcc tt                                          22
```

```
SEQ ID NO: 178          moltype = RNA  length = 22
FEATURE                 Location/Qualifiers
source                  1..22
                        mol_type = other RNA
                        organism = synthetic construct
SEQUENCE: 178
taatcctcat cttggagttt ct                                              22

SEQ ID NO: 179          moltype = RNA  length = 22
FEATURE                 Location/Qualifiers
source                  1..22
                        mol_type = other RNA
                        organism = synthetic construct
SEQUENCE: 179
tgaaaaccca aatcctcatc tt                                              22

SEQ ID NO: 180          moltype = RNA  length = 20
FEATURE                 Location/Qualifiers
source                  1..20
                        mol_type = other RNA
                        organism = synthetic construct
SEQUENCE: 180
ggaatgtgac caggtctaga                                                 20

SEQ ID NO: 181          moltype = RNA  length = 20
FEATURE                 Location/Qualifiers
source                  1..20
                        mol_type = other RNA
                        organism = synthetic construct
SEQUENCE: 181
caggtctagg tctggagtta                                                 20

SEQ ID NO: 182          moltype = RNA  length = 20
FEATURE                 Location/Qualifiers
source                  1..20
                        mol_type = other RNA
                        organism = synthetic construct
SEQUENCE: 182
aggtctaggt ctggagttta                                                 20

SEQ ID NO: 183          moltype = RNA  length = 20
FEATURE                 Location/Qualifiers
source                  1..20
                        mol_type = other RNA
                        organism = synthetic construct
SEQUENCE: 183
ggtctaggtc tggagtttca                                                 20

SEQ ID NO: 184          moltype = RNA  length = 20
FEATURE                 Location/Qualifiers
source                  1..20
                        mol_type = other RNA
                        organism = synthetic construct
SEQUENCE: 184
gtctaggtct ggagtttcaa                                                 20

SEQ ID NO: 185          moltype = RNA  length = 20
FEATURE                 Location/Qualifiers
source                  1..20
                        mol_type = other RNA
                        organism = synthetic construct
SEQUENCE: 185
agacacgtac ctgcagatca                                                 20

SEQ ID NO: 186          moltype = RNA  length = 20
FEATURE                 Location/Qualifiers
source                  1..20
                        mol_type = other RNA
                        organism = synthetic construct
SEQUENCE: 186
gcagagtgca gagcaatcca                                                 20

SEQ ID NO: 187          moltype = RNA  length = 20
FEATURE                 Location/Qualifiers
source                  1..20
                        mol_type = other RNA
                        organism = synthetic construct
SEQUENCE: 187
ctccctacta caatgtgaga                                                 20
```

```
SEQ ID NO: 188          moltype = RNA  length = 20
FEATURE                 Location/Qualifiers
source                  1..20
                        mol_type = other RNA
                        organism = synthetic construct
SEQUENCE: 188
ctactacaat gtgagtgata                                              20

SEQ ID NO: 189          moltype = RNA  length = 20
FEATURE                 Location/Qualifiers
source                  1..20
                        mol_type = other RNA
                        organism = synthetic construct
SEQUENCE: 189
tactacaatg tgagtgatga                                              20

SEQ ID NO: 190          moltype = RNA  length = 20
FEATURE                 Location/Qualifiers
source                  1..20
                        mol_type = other RNA
                        organism = synthetic construct
SEQUENCE: 190
gagtgatgag atctctttca                                              20

SEQ ID NO: 191          moltype = RNA  length = 20
FEATURE                 Location/Qualifiers
source                  1..20
                        mol_type = other RNA
                        organism = synthetic construct
SEQUENCE: 191
tgatgagatc tctttccaca                                              20

SEQ ID NO: 192          moltype = RNA  length = 20
FEATURE                 Location/Qualifiers
source                  1..20
                        mol_type = other RNA
                        organism = synthetic construct
SEQUENCE: 192
atctctttcc actgctatga                                              20

SEQ ID NO: 193          moltype = RNA  length = 20
FEATURE                 Location/Qualifiers
source                  1..20
                        mol_type = other RNA
                        organism = synthetic construct
SEQUENCE: 193
tgctatgacg gttacactca                                              20

SEQ ID NO: 194          moltype = RNA  length = 20
FEATURE                 Location/Qualifiers
source                  1..20
                        mol_type = other RNA
                        organism = synthetic construct
SEQUENCE: 194
ctatgacggt tacactctca                                              20

SEQ ID NO: 195          moltype = RNA  length = 20
FEATURE                 Location/Qualifiers
source                  1..20
                        mol_type = other RNA
                        organism = synthetic construct
SEQUENCE: 195
agacagcgat ctgtgacaaa                                              20

SEQ ID NO: 196          moltype = RNA  length = 20
FEATURE                 Location/Qualifiers
source                  1..20
                        mol_type = other RNA
                        organism = synthetic construct
SEQUENCE: 196
ctgccaagac tccttcatga                                              20

SEQ ID NO: 197          moltype = RNA  length = 20
FEATURE                 Location/Qualifiers
source                  1..20
                        mol_type = other RNA
                        organism = synthetic construct
```

```
SEQUENCE: 197
ccaagactcc ttcatgtaca                                              20

SEQ ID NO: 198          moltype = RNA  length = 20
FEATURE                 Location/Qualifiers
source                  1..20
                        mol_type = other RNA
                        organism = synthetic construct
SEQUENCE: 198
caagactcct tcatgtacga                                              20

SEQ ID NO: 199          moltype = RNA  length = 20
FEATURE                 Location/Qualifiers
source                  1..20
                        mol_type = other RNA
                        organism = synthetic construct
SEQUENCE: 199
agactccttc atgtacgaca                                              20

SEQ ID NO: 200          moltype = RNA  length = 20
FEATURE                 Location/Qualifiers
source                  1..20
                        mol_type = other RNA
                        organism = synthetic construct
SEQUENCE: 200
aagaggtggc cgaagcttta                                              20

SEQ ID NO: 201          moltype = RNA  length = 20
FEATURE                 Location/Qualifiers
source                  1..20
                        mol_type = other RNA
                        organism = synthetic construct
SEQUENCE: 201
tacctggtgc tagatggata                                              20

SEQ ID NO: 202          moltype = RNA  length = 20
FEATURE                 Location/Qualifiers
source                  1..20
                        mol_type = other RNA
                        organism = synthetic construct
SEQUENCE: 202
tgctagatgg atcagacaga                                              20

SEQ ID NO: 203          moltype = RNA  length = 20
FEATURE                 Location/Qualifiers
source                  1..20
                        mol_type = other RNA
                        organism = synthetic construct
SEQUENCE: 203
cttcacagga gccaaaaaga                                              20

SEQ ID NO: 204          moltype = RNA  length = 20
FEATURE                 Location/Qualifiers
source                  1..20
                        mol_type = other RNA
                        organism = synthetic construct
SEQUENCE: 204
acaggagcca aaaagtgtca                                              20

SEQ ID NO: 205          moltype = RNA  length = 20
FEATURE                 Location/Qualifiers
source                  1..20
                        mol_type = other RNA
                        organism = synthetic construct
SEQUENCE: 205
agccaaaaag tgtctagtca                                              20

SEQ ID NO: 206          moltype = RNA  length = 20
FEATURE                 Location/Qualifiers
source                  1..20
                        mol_type = other RNA
                        organism = synthetic construct
SEQUENCE: 206
caaaaagtgt ctagtcaaca                                              20

SEQ ID NO: 207          moltype = RNA  length = 20
FEATURE                 Location/Qualifiers
```

```
source                  1..20
                        mol_type = other RNA
                        organism = synthetic construct
SEQUENCE: 207
aagtgtctag tcaacttaaa                                              20

SEQ ID NO: 208          moltype = RNA  length = 20
FEATURE                 Location/Qualifiers
source                  1..20
                        mol_type = other RNA
                        organism = synthetic construct
SEQUENCE: 208
tctagtcaac ttaattgaga                                              20

SEQ ID NO: 209          moltype = RNA  length = 20
FEATURE                 Location/Qualifiers
source                  1..20
                        mol_type = other RNA
                        organism = synthetic construct
SEQUENCE: 209
tagtcaactt aattgagaaa                                              20

SEQ ID NO: 210          moltype = RNA  length = 20
FEATURE                 Location/Qualifiers
source                  1..20
                        mol_type = other RNA
                        organism = synthetic construct
SEQUENCE: 210
tgagaaggtg gcaagttata                                              20

SEQ ID NO: 211          moltype = RNA  length = 20
FEATURE                 Location/Qualifiers
source                  1..20
                        mol_type = other RNA
                        organism = synthetic construct
SEQUENCE: 211
gagaaggtgg caagttatga                                              20

SEQ ID NO: 212          moltype = RNA  length = 20
FEATURE                 Location/Qualifiers
source                  1..20
                        mol_type = other RNA
                        organism = synthetic construct
SEQUENCE: 212
aaggtggcaa gttatggtga                                              20

SEQ ID NO: 213          moltype = RNA  length = 20
FEATURE                 Location/Qualifiers
source                  1..20
                        mol_type = other RNA
                        organism = synthetic construct
SEQUENCE: 213
tggcaagtta tggtgtgaaa                                              20

SEQ ID NO: 214          moltype = RNA  length = 20
FEATURE                 Location/Qualifiers
source                  1..20
                        mol_type = other RNA
                        organism = synthetic construct
SEQUENCE: 214
tgaagaccac aagttgaaga                                              20

SEQ ID NO: 215          moltype = RNA  length = 20
FEATURE                 Location/Qualifiers
source                  1..20
                        mol_type = other RNA
                        organism = synthetic construct
SEQUENCE: 215
aagaccacaa gttgaagtca                                              20

SEQ ID NO: 216          moltype = RNA  length = 20
FEATURE                 Location/Qualifiers
source                  1..20
                        mol_type = other RNA
                        organism = synthetic construct
SEQUENCE: 216
cagtgtacag catgatgaga                                              20

SEQ ID NO: 217          moltype = RNA  length = 20
```

```
FEATURE                Location/Qualifiers
source                 1..20
                       mol_type = other RNA
                       organism = synthetic construct
SEQUENCE: 217
atgggcgggg acccaattaa                                              20

SEQ ID NO: 218         moltype = RNA  length = 20
FEATURE                Location/Qualifiers
source                 1..20
                       mol_type = other RNA
                       organism = synthetic construct
SEQUENCE: 218
gggacccaat tactgtcata                                              20

SEQ ID NO: 219         moltype = RNA  length = 20
FEATURE                Location/Qualifiers
source                 1..20
                       mol_type = other RNA
                       organism = synthetic construct
SEQUENCE: 219
ggacccaatt actgtcatta                                              20

SEQ ID NO: 220         moltype = RNA  length = 20
FEATURE                Location/Qualifiers
source                 1..20
                       mol_type = other RNA
                       organism = synthetic construct
SEQUENCE: 220
gacccaatta ctgtcattga                                              20

SEQ ID NO: 221         moltype = RNA  length = 20
FEATURE                Location/Qualifiers
source                 1..20
                       mol_type = other RNA
                       organism = synthetic construct
SEQUENCE: 221
cccaattact gtcattgata                                              20

SEQ ID NO: 222         moltype = RNA  length = 20
FEATURE                Location/Qualifiers
source                 1..20
                       mol_type = other RNA
                       organism = synthetic construct
SEQUENCE: 222
ccaattactg tcattgatga                                              20

SEQ ID NO: 223         moltype = RNA  length = 20
FEATURE                Location/Qualifiers
source                 1..20
                       mol_type = other RNA
                       organism = synthetic construct
SEQUENCE: 223
aattactgtc attgatgaga                                              20

SEQ ID NO: 224         moltype = RNA  length = 20
FEATURE                Location/Qualifiers
source                 1..20
                       mol_type = other RNA
                       organism = synthetic construct
SEQUENCE: 224
ggattatctg gatgtctata                                              20

SEQ ID NO: 225         moltype = RNA  length = 20
FEATURE                Location/Qualifiers
source                 1..20
                       mol_type = other RNA
                       organism = synthetic construct
SEQUENCE: 225
gattatctgg atgtctatga                                              20

SEQ ID NO: 226         moltype = RNA  length = 20
FEATURE                Location/Qualifiers
source                 1..20
                       mol_type = other RNA
                       organism = synthetic construct
SEQUENCE: 226
agtgaacatc aatgctttga                                              20
```

-continued

```
SEQ ID NO: 227          moltype = RNA  length = 20
FEATURE                 Location/Qualifiers
source                  1..20
                        mol_type = other RNA
                        organism = synthetic construct
SEQUENCE: 227
aacatcaatg ctttggctta                                              20

SEQ ID NO: 228          moltype = RNA  length = 20
FEATURE                 Location/Qualifiers
source                  1..20
                        mol_type = other RNA
                        organism = synthetic construct
SEQUENCE: 228
tgctttggct tccaagaaaa                                              20

SEQ ID NO: 229          moltype = RNA  length = 20
FEATURE                 Location/Qualifiers
source                  1..20
                        mol_type = other RNA
                        organism = synthetic construct
SEQUENCE: 229
gctttggctt ccaagaaaga                                              20

SEQ ID NO: 230          moltype = RNA  length = 20
FEATURE                 Location/Qualifiers
source                  1..20
                        mol_type = other RNA
                        organism = synthetic construct
SEQUENCE: 230
tttggcttcc aagaaagaca                                              20

SEQ ID NO: 231          moltype = RNA  length = 20
FEATURE                 Location/Qualifiers
source                  1..20
                        mol_type = other RNA
                        organism = synthetic construct
SEQUENCE: 231
ttccaagaaa gacaatgaga                                              20

SEQ ID NO: 232          moltype = RNA  length = 20
FEATURE                 Location/Qualifiers
source                  1..20
                        mol_type = other RNA
                        organism = synthetic construct
SEQUENCE: 232
caagaaagac aatgagcaaa                                              20

SEQ ID NO: 233          moltype = RNA  length = 20
FEATURE                 Location/Qualifiers
source                  1..20
                        mol_type = other RNA
                        organism = synthetic construct
SEQUENCE: 233
aagaaagaca atgagcaaca                                              20

SEQ ID NO: 234          moltype = RNA  length = 20
FEATURE                 Location/Qualifiers
source                  1..20
                        mol_type = other RNA
                        organism = synthetic construct
SEQUENCE: 234
gaaagacaat gagcaacata                                              20

SEQ ID NO: 235          moltype = RNA  length = 20
FEATURE                 Location/Qualifiers
source                  1..20
                        mol_type = other RNA
                        organism = synthetic construct
SEQUENCE: 235
aaagacaatg agcaacatga                                              20

SEQ ID NO: 236          moltype = RNA  length = 20
FEATURE                 Location/Qualifiers
source                  1..20
                        mol_type = other RNA
                        organism = synthetic construct
SEQUENCE: 236
tgagcaacat gtgttcaaaa                                              20
```

```
SEQ ID NO: 237          moltype = RNA  length = 20
FEATURE                 Location/Qualifiers
source                  1..20
                        mol_type = other RNA
                        organism = synthetic construct
SEQUENCE: 237
gagcaacatg tgttcaaaga                                              20

SEQ ID NO: 238          moltype = RNA  length = 20
FEATURE                 Location/Qualifiers
source                  1..20
                        mol_type = other RNA
                        organism = synthetic construct
SEQUENCE: 238
gcaacatgtg ttcaaagtca                                              20

SEQ ID NO: 239          moltype = RNA  length = 20
FEATURE                 Location/Qualifiers
source                  1..20
                        mol_type = other RNA
                        organism = synthetic construct
SEQUENCE: 239
aaagtcaagg atatggaaaa                                              20

SEQ ID NO: 240          moltype = RNA  length = 20
FEATURE                 Location/Qualifiers
source                  1..20
                        mol_type = other RNA
                        organism = synthetic construct
SEQUENCE: 240
caaggatatg gaaaacctga                                              20

SEQ ID NO: 241          moltype = RNA  length = 20
FEATURE                 Location/Qualifiers
source                  1..20
                        mol_type = other RNA
                        organism = synthetic construct
SEQUENCE: 241
cagtctctga gtctctgtga                                              20

SEQ ID NO: 242          moltype = RNA  length = 20
FEATURE                 Location/Qualifiers
source                  1..20
                        mol_type = other RNA
                        organism = synthetic construct
SEQUENCE: 242
taccgattac cacaagcaaa                                              20

SEQ ID NO: 243          moltype = RNA  length = 20
FEATURE                 Location/Qualifiers
source                  1..20
                        mol_type = other RNA
                        organism = synthetic construct
SEQUENCE: 243
tgtggtgtct gagtacttta                                              20

SEQ ID NO: 244          moltype = RNA  length = 20
FEATURE                 Location/Qualifiers
source                  1..20
                        mol_type = other RNA
                        organism = synthetic construct
SEQUENCE: 244
ctgacagcag cacattgtta                                              20

SEQ ID NO: 245          moltype = RNA  length = 20
FEATURE                 Location/Qualifiers
source                  1..20
                        mol_type = other RNA
                        organism = synthetic construct
SEQUENCE: 245
caaggaacac tcaatcaaga                                              20

SEQ ID NO: 246          moltype = RNA  length = 20
FEATURE                 Location/Qualifiers
source                  1..20
                        mol_type = other RNA
                        organism = synthetic construct
```

```
SEQUENCE: 246
aacactcaat caaggtcaga                                              20

SEQ ID NO: 247          moltype = RNA  length = 20
FEATURE                 Location/Qualifiers
source                  1..20
                        mol_type = other RNA
                        organism = synthetic construct
SEQUENCE: 247
aaaaaagaag caggaattca                                              20

SEQ ID NO: 248          moltype = RNA  length = 20
FEATURE                 Location/Qualifiers
source                  1..20
                        mol_type = other RNA
                        organism = synthetic construct
SEQUENCE: 248
ggaattcctg aattttatga                                              20

SEQ ID NO: 249          moltype = RNA  length = 20
FEATURE                 Location/Qualifiers
source                  1..20
                        mol_type = other RNA
                        organism = synthetic construct
SEQUENCE: 249
cctgaatttt atgactatga                                              20

SEQ ID NO: 250          moltype = RNA  length = 20
FEATURE                 Location/Qualifiers
source                  1..20
                        mol_type = other RNA
                        organism = synthetic construct
SEQUENCE: 250
tgaattttat gactatgaca                                              20

SEQ ID NO: 251          moltype = RNA  length = 20
FEATURE                 Location/Qualifiers
source                  1..20
                        mol_type = other RNA
                        organism = synthetic construct
SEQUENCE: 251
tgacgttgcc ctgatcaaga                                              20

SEQ ID NO: 252          moltype = RNA  length = 20
FEATURE                 Location/Qualifiers
source                  1..20
                        mol_type = other RNA
                        organism = synthetic construct
SEQUENCE: 252
ccctgatcaa gctcaagaaa                                              20

SEQ ID NO: 253          moltype = RNA  length = 20
FEATURE                 Location/Qualifiers
source                  1..20
                        mol_type = other RNA
                        organism = synthetic construct
SEQUENCE: 253
cctgatcaag ctcaagaata                                              20

SEQ ID NO: 254          moltype = RNA  length = 20
FEATURE                 Location/Qualifiers
source                  1..20
                        mol_type = other RNA
                        organism = synthetic construct
SEQUENCE: 254
gatcaagctc aagaataaga                                              20

SEQ ID NO: 255          moltype = RNA  length = 20
FEATURE                 Location/Qualifiers
source                  1..20
                        mol_type = other RNA
                        organism = synthetic construct
SEQUENCE: 255
tatcaggccc atttgtctca                                              20

SEQ ID NO: 256          moltype = RNA  length = 20
FEATURE                 Location/Qualifiers
```

```
source                  1..20
                        mol_type = other RNA
                        organism = synthetic construct
SEQUENCE: 256
cttcctccaa ctaccactta                                                    20

SEQ ID NO: 257          moltype = RNA  length = 20
FEATURE                 Location/Qualifiers
source                  1..20
                        mol_type = other RNA
                        organism = synthetic construct
SEQUENCE: 257
acaggatatc aaagctctga                                                    20

SEQ ID NO: 258          moltype = RNA  length = 20
FEATURE                 Location/Qualifiers
source                  1..20
                        mol_type = other RNA
                        organism = synthetic construct
SEQUENCE: 258
aggatatcaa agctctgtta                                                    20

SEQ ID NO: 259          moltype = RNA  length = 20
FEATURE                 Location/Qualifiers
source                  1..20
                        mol_type = other RNA
                        organism = synthetic construct
SEQUENCE: 259
ggatatcaaa gctctgttta                                                    20

SEQ ID NO: 260          moltype = RNA  length = 20
FEATURE                 Location/Qualifiers
source                  1..20
                        mol_type = other RNA
                        organism = synthetic construct
SEQUENCE: 260
gatatcaaag ctctgtttga                                                    20

SEQ ID NO: 261          moltype = RNA  length = 20
FEATURE                 Location/Qualifiers
source                  1..20
                        mol_type = other RNA
                        organism = synthetic construct
SEQUENCE: 261
aaagctctgt ttgtgtctga                                                    20

SEQ ID NO: 262          moltype = RNA  length = 20
FEATURE                 Location/Qualifiers
source                  1..20
                        mol_type = other RNA
                        organism = synthetic construct
SEQUENCE: 262
gaaggaggtc tacatcaaga                                                    20

SEQ ID NO: 263          moltype = RNA  length = 20
FEATURE                 Location/Qualifiers
source                  1..20
                        mol_type = other RNA
                        organism = synthetic construct
SEQUENCE: 263
gaggtctaca tcaagaatga                                                    20

SEQ ID NO: 264          moltype = RNA  length = 20
FEATURE                 Location/Qualifiers
source                  1..20
                        mol_type = other RNA
                        organism = synthetic construct
SEQUENCE: 264
aagaatgggg ataagaaaga                                                    20

SEQ ID NO: 265          moltype = RNA  length = 20
FEATURE                 Location/Qualifiers
source                  1..20
                        mol_type = other RNA
                        organism = synthetic construct
SEQUENCE: 265
aaaggcagct gtgagagaga                                                    20

SEQ ID NO: 266          moltype = RNA  length = 20
```

```
FEATURE                Location/Qualifiers
source                 1..20
                       mol_type = other RNA
                       organism = synthetic construct
SEQUENCE: 266
agctgtgaga gagatgctca                                              20

SEQ ID NO: 267         moltype = RNA  length = 20
FEATURE                Location/Qualifiers
source                 1..20
                       mol_type = other RNA
                       organism = synthetic construct
SEQUENCE: 267
ctgtgagaga gatgctcaaa                                              20

SEQ ID NO: 268         moltype = RNA  length = 20
FEATURE                Location/Qualifiers
source                 1..20
                       mol_type = other RNA
                       organism = synthetic construct
SEQUENCE: 268
tgtgagagag atgctcaata                                              20

SEQ ID NO: 269         moltype = RNA  length = 20
FEATURE                Location/Qualifiers
source                 1..20
                       mol_type = other RNA
                       organism = synthetic construct
SEQUENCE: 269
tgagagagat gctcaatata                                              20

SEQ ID NO: 270         moltype = RNA  length = 20
FEATURE                Location/Qualifiers
source                 1..20
                       mol_type = other RNA
                       organism = synthetic construct
SEQUENCE: 270
gagagagatg ctcaatatga                                              20

SEQ ID NO: 271         moltype = RNA  length = 20
FEATURE                Location/Qualifiers
source                 1..20
                       mol_type = other RNA
                       organism = synthetic construct
SEQUENCE: 271
aggctatgac aaagtcaaga                                              20

SEQ ID NO: 272         moltype = RNA  length = 20
FEATURE                Location/Qualifiers
source                 1..20
                       mol_type = other RNA
                       organism = synthetic construct
SEQUENCE: 272
acaaagtcaa ggacatctca                                              20

SEQ ID NO: 273         moltype = RNA  length = 20
FEATURE                Location/Qualifiers
source                 1..20
                       mol_type = other RNA
                       organism = synthetic construct
SEQUENCE: 273
agtgagtccc tatgctgaca                                              20

SEQ ID NO: 274         moltype = RNA  length = 20
FEATURE                Location/Qualifiers
source                 1..20
                       mol_type = other RNA
                       organism = synthetic construct
SEQUENCE: 274
cctatgctga ccccaataca                                              20

SEQ ID NO: 275         moltype = RNA  length = 20
FEATURE                Location/Qualifiers
source                 1..20
                       mol_type = other RNA
                       organism = synthetic construct
SEQUENCE: 275
caatacttgc agaggtgata                                              20
```

```
SEQ ID NO: 276          moltype = RNA  length = 20
FEATURE                 Location/Qualifiers
source                  1..20
                        mol_type = other RNA
                        organism = synthetic construct
SEQUENCE: 276
tggcggcccc ttgatagtta                                              20

SEQ ID NO: 277          moltype = RNA  length = 20
FEATURE                 Location/Qualifiers
source                  1..20
                        mol_type = other RNA
                        organism = synthetic construct
SEQUENCE: 277
cggccccttg atagttcaca                                              20

SEQ ID NO: 278          moltype = RNA  length = 20
FEATURE                 Location/Qualifiers
source                  1..20
                        mol_type = other RNA
                        organism = synthetic construct
SEQUENCE: 278
gccccttgat agttcacaaa                                              20

SEQ ID NO: 279          moltype = RNA  length = 20
FEATURE                 Location/Qualifiers
source                  1..20
                        mol_type = other RNA
                        organism = synthetic construct
SEQUENCE: 279
ccttgatagt tcacaagaga                                              20

SEQ ID NO: 280          moltype = RNA  length = 20
FEATURE                 Location/Qualifiers
source                  1..20
                        mol_type = other RNA
                        organism = synthetic construct
SEQUENCE: 280
atagttcaca agagaagtca                                              20

SEQ ID NO: 281          moltype = RNA  length = 20
FEATURE                 Location/Qualifiers
source                  1..20
                        mol_type = other RNA
                        organism = synthetic construct
SEQUENCE: 281
acaagagaag tcgtttcata                                              20

SEQ ID NO: 282          moltype = RNA  length = 20
FEATURE                 Location/Qualifiers
source                  1..20
                        mol_type = other RNA
                        organism = synthetic construct
SEQUENCE: 282
gtagtggatg tctgcaaaaa                                              20

SEQ ID NO: 283          moltype = RNA  length = 20
FEATURE                 Location/Qualifiers
source                  1..20
                        mol_type = other RNA
                        organism = synthetic construct
SEQUENCE: 283
agtggatgtc tgcaaaaaca                                              20

SEQ ID NO: 284          moltype = RNA  length = 20
FEATURE                 Location/Qualifiers
source                  1..20
                        mol_type = other RNA
                        organism = synthetic construct
SEQUENCE: 284
atgtctgcaa aaaccagaaa                                              20

SEQ ID NO: 285          moltype = RNA  length = 20
FEATURE                 Location/Qualifiers
source                  1..20
                        mol_type = other RNA
                        organism = synthetic construct
SEQUENCE: 285
gctgaaggag aaactccaaa                                              20
```

```
SEQ ID NO: 286          moltype = RNA  length = 20
FEATURE                 Location/Qualifiers
source                  1..20
                        mol_type = other RNA
                        organism = synthetic construct
SEQUENCE: 286
gaaggagaaa ctccaagata                                            20

SEQ ID NO: 287          moltype = RNA  length = 20
FEATURE                 Location/Qualifiers
source                  1..20
                        mol_type = other RNA
                        organism = synthetic construct
SEQUENCE: 287
ggagaaactc caagatgaga                                            20

SEQ ID NO: 288          moltype = RNA  length = 20
FEATURE                 Location/Qualifiers
source                  1..20
                        mol_type = other RNA
                        organism = synthetic construct
SEQUENCE: 288
aaactccaag atgaggatta                                            20

SEQ ID NO: 289          moltype = RNA  length = 20
FEATURE                 Location/Qualifiers
source                  1..20
                        mol_type = other RNA
                        organism = synthetic construct
SEQUENCE: 289
gatgaggatt tgggttttca                                            20

SEQ ID NO: 290          moltype = RNA  length = 22
FEATURE                 Location/Qualifiers
source                  1..22
                        mol_type = other RNA
                        organism = synthetic construct
SEQUENCE: 290
tctgaaactc cagacctaga cc                                         22

SEQ ID NO: 291          moltype = RNA  length = 22
FEATURE                 Location/Qualifiers
source                  1..22
                        mol_type = other RNA
                        organism = synthetic construct
SEQUENCE: 291
tctcagtgtc caagctgaaa ct                                         22

SEQ ID NO: 292          moltype = RNA  length = 22
FEATURE                 Location/Qualifiers
source                  1..22
                        mol_type = other RNA
                        organism = synthetic construct
SEQUENCE: 292
tgatctctac cccctccaga ga                                         22

SEQ ID NO: 293          moltype = RNA  length = 22
FEATURE                 Location/Qualifiers
source                  1..22
                        mol_type = other RNA
                        organism = synthetic construct
SEQUENCE: 293
tttggagaag tcggaaggag cc                                         22

SEQ ID NO: 294          moltype = RNA  length = 22
FEATURE                 Location/Qualifiers
source                  1..22
                        mol_type = other RNA
                        organism = synthetic construct
SEQUENCE: 294
tctcttggag aagtcggaag ga                                         22

SEQ ID NO: 295          moltype = RNA  length = 22
FEATURE                 Location/Qualifiers
source                  1..22
                        mol_type = other RNA
                        organism = synthetic construct
```

```
SEQUENCE: 295
tcacagggta cgggtagaag cc                                          22

SEQ ID NO: 296          moltype = RNA  length = 22
FEATURE                 Location/Qualifiers
source                  1..22
                        mol_type = other RNA
                        organism = synthetic construct
SEQUENCE: 296
tcacttggca ggtgcgattg gc                                          22

SEQ ID NO: 297          moltype = RNA  length = 22
FEATURE                 Location/Qualifiers
source                  1..22
                        mol_type = other RNA
                        organism = synthetic construct
SEQUENCE: 297
tttcacttgg caggtgcgat tg                                          22

SEQ ID NO: 298          moltype = RNA  length = 22
FEATURE                 Location/Qualifiers
source                  1..22
                        mol_type = other RNA
                        organism = synthetic construct
SEQUENCE: 298
tctccaagag ccaccttcct ga                                          22

SEQ ID NO: 299          moltype = RNA  length = 22
FEATURE                 Location/Qualifiers
source                  1..22
                        mol_type = other RNA
                        organism = synthetic construct
SEQUENCE: 299
tgagtcttgg caggaaggct cc                                          22

SEQ ID NO: 300          moltype = RNA  length = 22
FEATURE                 Location/Qualifiers
source                  1..22
                        mol_type = other RNA
                        organism = synthetic construct
SEQUENCE: 300
tgtgtcgtac atgaaggagt ct                                          22

SEQ ID NO: 301          moltype = RNA  length = 22
FEATURE                 Location/Qualifiers
source                  1..22
                        mol_type = other RNA
                        organism = synthetic construct
SEQUENCE: 301
tggaagacag gaaagcttcg gc                                          22

SEQ ID NO: 302          moltype = RNA  length = 22
FEATURE                 Location/Qualifiers
source                  1..22
                        mol_type = other RNA
                        organism = synthetic construct
SEQUENCE: 302
tgtcagggaa gacaggaaag ct                                          22

SEQ ID NO: 303          moltype = RNA  length = 22
FEATURE                 Location/Qualifiers
source                  1..22
                        mol_type = other RNA
                        organism = synthetic construct
SEQUENCE: 303
tcatcgactc cttctatggt ct                                          22

SEQ ID NO: 304          moltype = RNA  length = 22
FEATURE                 Location/Qualifiers
source                  1..22
                        mol_type = other RNA
                        organism = synthetic construct
SEQUENCE: 304
tgttcatgga gcctgaaggg tc                                          22

SEQ ID NO: 305          moltype = RNA  length = 22
FEATURE                 Location/Qualifiers
```

```
source                 1..22
                       mol_type = other RNA
                       organism = synthetic construct
SEQUENCE: 305
ttgttcatgg agcctgaagg gt                                              22

SEQ ID NO: 306         moltype = RNA  length = 22
FEATURE                Location/Qualifiers
source                 1..22
                       mol_type = other RNA
                       organism = synthetic construct
SEQUENCE: 306
tatgttcatg gagcctgaag gg                                              22

SEQ ID NO: 307         moltype = RNA  length = 22
FEATURE                Location/Qualifiers
source                 1..22
                       mol_type = other RNA
                       organism = synthetic construct
SEQUENCE: 307
tcaggtagat gttcatggag cc                                              22

SEQ ID NO: 308         moltype = RNA  length = 22
FEATURE                Location/Qualifiers
source                 1..22
                       mol_type = other RNA
                       organism = synthetic construct
SEQUENCE: 308
tcaccaggta gatgttcatg ga                                              22

SEQ ID NO: 309         moltype = RNA  length = 22
FEATURE                Location/Qualifiers
source                 1..22
                       mol_type = other RNA
                       organism = synthetic construct
SEQUENCE: 309
tatctagcac caggtagatg tt                                              22

SEQ ID NO: 310         moltype = RNA  length = 22
FEATURE                Location/Qualifiers
source                 1..22
                       mol_type = other RNA
                       organism = synthetic construct
SEQUENCE: 310
tcatctagca ccaggtagat gt                                              22

SEQ ID NO: 311         moltype = RNA  length = 22
FEATURE                Location/Qualifiers
source                 1..22
                       mol_type = other RNA
                       organism = synthetic construct
SEQUENCE: 311
tgtgttagtc cctgacttca ac                                              22

SEQ ID NO: 312         moltype = RNA  length = 22
FEATURE                Location/Qualifiers
source                 1..22
                       mol_type = other RNA
                       organism = synthetic construct
SEQUENCE: 312
tcatgaggat gatgacatgg cg                                              22

SEQ ID NO: 313         moltype = RNA  length = 22
FEATURE                Location/Qualifiers
source                 1..22
                       mol_type = other RNA
                       organism = synthetic construct
SEQUENCE: 313
tgtcatgagg atgatgacat gg                                              22

SEQ ID NO: 314         moltype = RNA  length = 22
FEATURE                Location/Qualifiers
source                 1..22
                       mol_type = other RNA
                       organism = synthetic construct
SEQUENCE: 314
tgtaattggg tccccgccca tg                                              22

SEQ ID NO: 315         moltype = RNA  length = 22
```

```
FEATURE                Location/Qualifiers
source                 1..22
                       mol_type = other RNA
                       organism = synthetic construct
SEQUENCE: 315
tcagtaattg ggtccccgcc ca                                          22

SEQ ID NO: 316         moltype = RNA  length = 22
FEATURE                Location/Qualifiers
source                 1..22
                       mol_type = other RNA
                       organism = synthetic construct
SEQUENCE: 316
tgacagtaat tgggtccccg cc                                          22

SEQ ID NO: 317         moltype = RNA  length = 22
FEATURE                Location/Qualifiers
source                 1..22
                       mol_type = other RNA
                       organism = synthetic construct
SEQUENCE: 317
ttgacagtaa ttgggtcccc gc                                          22

SEQ ID NO: 318         moltype = RNA  length = 22
FEATURE                Location/Qualifiers
source                 1..22
                       mol_type = other RNA
                       organism = synthetic construct
SEQUENCE: 318
tttccatatc cttgactttg aa                                          22

SEQ ID NO: 319         moltype = RNA  length = 22
FEATURE                Location/Qualifiers
source                 1..22
                       mol_type = other RNA
                       organism = synthetic construct
SEQUENCE: 319
tgttttccat atccttgact tt                                          22

SEQ ID NO: 320         moltype = RNA  length = 22
FEATURE                Location/Qualifiers
source                 1..22
                       mol_type = other RNA
                       organism = synthetic construct
SEQUENCE: 320
tctcaaagct cgagttgttc cc                                          22

SEQ ID NO: 321         moltype = RNA  length = 22
FEATURE                Location/Qualifiers
source                 1..22
                       mol_type = other RNA
                       organism = synthetic construct
SEQUENCE: 321
tctcagacac aaacagagct tt                                          22

SEQ ID NO: 322         moltype = RNA  length = 22
FEATURE                Location/Qualifiers
source                 1..22
                       mol_type = other RNA
                       organism = synthetic construct
SEQUENCE: 322
tgatgtagac ctccttccga gt                                          22

SEQ ID NO: 323         moltype = RNA  length = 22
FEATURE                Location/Qualifiers
source                 1..22
                       mol_type = other RNA
                       organism = synthetic construct
SEQUENCE: 323
ttttcttatc cccattcttg at                                          22

SEQ ID NO: 324         moltype = RNA  length = 22
FEATURE                Location/Qualifiers
source                 1..22
                       mol_type = other RNA
                       organism = synthetic construct
SEQUENCE: 324
tgtccttgac tttgtcatag cc                                          22
```

-continued

```
SEQ ID NO: 325          moltype = RNA  length = 22
FEATURE                 Location/Qualifiers
source                  1..22
                        mol_type = other RNA
                        organism = synthetic construct
SEQUENCE: 325
ttgaactatc aaggggccgc ca                                              22

SEQ ID NO: 326          moltype = RNA  length = 22
FEATURE                 Location/Qualifiers
source                  1..22
                        mol_type = other RNA
                        organism = synthetic construct
SEQUENCE: 326
tcttgtgaac tatcaagggg cc                                              22

SEQ ID NO: 327          moltype = RNA  length = 22
FEATURE                 Location/Qualifiers
source                  1..22
                        mol_type = other RNA
                        organism = synthetic construct
SEQUENCE: 327
tcttttgccg cttctggttt tt                                              22

SEQ ID NO: 328          moltype = RNA  length = 22
FEATURE                 Location/Qualifiers
source                  1..22
                        mol_type = other RNA
                        organism = synthetic construct
SEQUENCE: 328
tagcaggtac ctgcttttgc cg                                              22

SEQ ID NO: 329          moltype = RNA  length = 22
FEATURE                 Location/Qualifiers
source                  1..22
                        mol_type = other RNA
                        organism = synthetic construct
SEQUENCE: 329
tcttggagtt tctccttcag cc                                              22

SEQ ID NO: 330          moltype = RNA  length = 20
FEATURE                 Location/Qualifiers
source                  1..20
                        mol_type = other RNA
                        organism = synthetic construct
SEQUENCE: 330
tctaggtctg gagtttcaga                                                 20

SEQ ID NO: 331          moltype = RNA  length = 20
FEATURE                 Location/Qualifiers
source                  1..20
                        mol_type = other RNA
                        organism = synthetic construct
SEQUENCE: 331
tttcagcttg gacactgaga                                                 20

SEQ ID NO: 332          moltype = RNA  length = 20
FEATURE                 Location/Qualifiers
source                  1..20
                        mol_type = other RNA
                        organism = synthetic construct
SEQUENCE: 332
tctggagggg gtagagatca                                                 20

SEQ ID NO: 333          moltype = RNA  length = 20
FEATURE                 Location/Qualifiers
source                  1..20
                        mol_type = other RNA
                        organism = synthetic construct
SEQUENCE: 333
ctccttccga cttctccaaa                                                 20

SEQ ID NO: 334          moltype = RNA  length = 20
FEATURE                 Location/Qualifiers
source                  1..20
                        mol_type = other RNA
                        organism = synthetic construct
SEQUENCE: 334
cttccgactt ctccaagaga                                                 20
```

```
SEQ ID NO: 335          moltype = RNA  length = 20
FEATURE                 Location/Qualifiers
source                  1..20
                        mol_type = other RNA
                        organism = synthetic construct
SEQUENCE: 335
cttctacccg taccctgtga                                              20

SEQ ID NO: 336          moltype = RNA  length = 20
FEATURE                 Location/Qualifiers
source                  1..20
                        mol_type = other RNA
                        organism = synthetic construct
SEQUENCE: 336
caatcgcacc tgccaagtga                                              20

SEQ ID NO: 337          moltype = RNA  length = 20
FEATURE                 Location/Qualifiers
source                  1..20
                        mol_type = other RNA
                        organism = synthetic construct
SEQUENCE: 337
atcgcacctg ccaagtgaaa                                              20

SEQ ID NO: 338          moltype = RNA  length = 20
FEATURE                 Location/Qualifiers
source                  1..20
                        mol_type = other RNA
                        organism = synthetic construct
SEQUENCE: 338
aggaaggtgg ctcttggaga                                              20

SEQ ID NO: 339          moltype = RNA  length = 20
FEATURE                 Location/Qualifiers
source                  1..20
                        mol_type = other RNA
                        organism = synthetic construct
SEQUENCE: 339
agccttcctg ccaagactca                                              20

SEQ ID NO: 340          moltype = RNA  length = 20
FEATURE                 Location/Qualifiers
source                  1..20
                        mol_type = other RNA
                        organism = synthetic construct
SEQUENCE: 340
actccttcat gtacgacaca                                              20

SEQ ID NO: 341          moltype = RNA  length = 20
FEATURE                 Location/Qualifiers
source                  1..20
                        mol_type = other RNA
                        organism = synthetic construct
SEQUENCE: 341
cgaagctttc ctgtcttcca                                              20

SEQ ID NO: 342          moltype = RNA  length = 20
FEATURE                 Location/Qualifiers
source                  1..20
                        mol_type = other RNA
                        organism = synthetic construct
SEQUENCE: 342
ctttcctgtc ttccctgaca                                              20

SEQ ID NO: 343          moltype = RNA  length = 20
FEATURE                 Location/Qualifiers
source                  1..20
                        mol_type = other RNA
                        organism = synthetic construct
SEQUENCE: 343
accatagaag gagtcgatga                                              20

SEQ ID NO: 344          moltype = RNA  length = 20
FEATURE                 Location/Qualifiers
source                  1..20
                        mol_type = other RNA
                        organism = synthetic construct
SEQUENCE: 344
```

```
cccttcaggc tccatgaaca                                         20

SEQ ID NO: 345          moltype = RNA  length = 20
FEATURE                 Location/Qualifiers
source                  1..20
                        mol_type = other RNA
                        organism = synthetic construct
SEQUENCE: 345
ccttcaggct ccatgaacaa                                         20

SEQ ID NO: 346          moltype = RNA  length = 20
FEATURE                 Location/Qualifiers
source                  1..20
                        mol_type = other RNA
                        organism = synthetic construct
SEQUENCE: 346
cttcaggctc catgaacata                                         20

SEQ ID NO: 347          moltype = RNA  length = 20
FEATURE                 Location/Qualifiers
source                  1..20
                        mol_type = other RNA
                        organism = synthetic construct
SEQUENCE: 347
ctccatgaac atctacctga                                         20

SEQ ID NO: 348          moltype = RNA  length = 20
FEATURE                 Location/Qualifiers
source                  1..20
                        mol_type = other RNA
                        organism = synthetic construct
SEQUENCE: 348
catgaacatc tacctggtga                                         20

SEQ ID NO: 349          moltype = RNA  length = 20
FEATURE                 Location/Qualifiers
source                  1..20
                        mol_type = other RNA
                        organism = synthetic construct
SEQUENCE: 349
catctacctg gtgctagata                                         20

SEQ ID NO: 350          moltype = RNA  length = 20
FEATURE                 Location/Qualifiers
source                  1..20
                        mol_type = other RNA
                        organism = synthetic construct
SEQUENCE: 350
atctacctgg tgctagatga                                         20

SEQ ID NO: 351          moltype = RNA  length = 20
FEATURE                 Location/Qualifiers
source                  1..20
                        mol_type = other RNA
                        organism = synthetic construct
SEQUENCE: 351
tgaagtcagg gactaacaca                                         20

SEQ ID NO: 352          moltype = RNA  length = 20
FEATURE                 Location/Qualifiers
source                  1..20
                        mol_type = other RNA
                        organism = synthetic construct
SEQUENCE: 352
ccatgtcatc atcctcatga                                         20

SEQ ID NO: 353          moltype = RNA  length = 20
FEATURE                 Location/Qualifiers
source                  1..20
                        mol_type = other RNA
                        organism = synthetic construct
SEQUENCE: 353
atgtcatcat cctcatgaca                                         20

SEQ ID NO: 354          moltype = RNA  length = 20
FEATURE                 Location/Qualifiers
source                  1..20
                        mol_type = other RNA
                        organism = synthetic construct
```

```
SEQUENCE: 354
tgggcgggga cccaattaca                                             20

SEQ ID NO: 355          moltype = RNA  length = 20
FEATURE                 Location/Qualifiers
source                  1..20
                        mol_type = other RNA
                        organism = synthetic construct
SEQUENCE: 355
ggcggggacc caattactga                                             20

SEQ ID NO: 356          moltype = RNA  length = 20
FEATURE                 Location/Qualifiers
source                  1..20
                        mol_type = other RNA
                        organism = synthetic construct
SEQUENCE: 356
cggggaccca attactgtca                                             20

SEQ ID NO: 357          moltype = RNA  length = 20
FEATURE                 Location/Qualifiers
source                  1..20
                        mol_type = other RNA
                        organism = synthetic construct
SEQUENCE: 357
ggggacccaa ttactgtcaa                                             20

SEQ ID NO: 358          moltype = RNA  length = 20
FEATURE                 Location/Qualifiers
source                  1..20
                        mol_type = other RNA
                        organism = synthetic construct
SEQUENCE: 358
caaagtcaag gatatggaaa                                             20

SEQ ID NO: 359          moltype = RNA  length = 20
FEATURE                 Location/Qualifiers
source                  1..20
                        mol_type = other RNA
                        organism = synthetic construct
SEQUENCE: 359
agtcaaggat atggaaaaca                                             20

SEQ ID NO: 360          moltype = RNA  length = 20
FEATURE                 Location/Qualifiers
source                  1..20
                        mol_type = other RNA
                        organism = synthetic construct
SEQUENCE: 360
gaacaactcg agctttgaga                                             20

SEQ ID NO: 361          moltype = RNA  length = 20
FEATURE                 Location/Qualifiers
source                  1..20
                        mol_type = other RNA
                        organism = synthetic construct
SEQUENCE: 361
agctctgttt gtgtctgaga                                             20

SEQ ID NO: 362          moltype = RNA  length = 20
FEATURE                 Location/Qualifiers
source                  1..20
                        mol_type = other RNA
                        organism = synthetic construct
SEQUENCE: 362
tcggaaggag gtctacatca                                             20

SEQ ID NO: 363          moltype = RNA  length = 20
FEATURE                 Location/Qualifiers
source                  1..20
                        mol_type = other RNA
                        organism = synthetic construct
SEQUENCE: 363
caagaatggg gataagaaaa                                             20

SEQ ID NO: 364          moltype = RNA  length = 20
FEATURE                 Location/Qualifiers
```

-continued

```
source                  1..20
                        mol_type = other RNA
                        organism = synthetic construct
SEQUENCE: 364
ctatgacaaa gtcaaggaca                                         20

SEQ ID NO: 365          moltype = RNA  length = 20
FEATURE                 Location/Qualifiers
source                  1..20
                        mol_type = other RNA
                        organism = synthetic construct
SEQUENCE: 365
gcggcccctt gatagttcaa                                         20

SEQ ID NO: 366          moltype = RNA  length = 20
FEATURE                 Location/Qualifiers
source                  1..20
                        mol_type = other RNA
                        organism = synthetic construct
SEQUENCE: 366
cccccttgata gttcacaaga                                         20

SEQ ID NO: 367          moltype = RNA  length = 20
FEATURE                 Location/Qualifiers
source                  1..20
                        mol_type = other RNA
                        organism = synthetic construct
SEQUENCE: 367
aaaccagaag cggcaaaaga                                         20

SEQ ID NO: 368          moltype = RNA  length = 20
FEATURE                 Location/Qualifiers
source                  1..20
                        mol_type = other RNA
                        organism = synthetic construct
SEQUENCE: 368
gcaaaagcag gtacctgcta                                         20

SEQ ID NO: 369          moltype = RNA  length = 20
FEATURE                 Location/Qualifiers
source                  1..20
                        mol_type = other RNA
                        organism = synthetic construct
SEQUENCE: 369
ctgaaggaga aactccaaga                                         20

SEQ ID NO: 370          moltype = RNA  length = 22
FEATURE                 Location/Qualifiers
modified_base           1..3
                        mod_base = OTHER
                        note = linked via phosphorothioate bond
modified_base           1
                        mod_base = OTHER
                        note = mono methyl protected phosphate mimic linked uridine
modified_base           2
                        mod_base = OTHER
                        note = 2'-fluoro-guanosine
modified_base           3
                        mod_base = OTHER
                        note = 2'-fluoro-uridine
modified_base           4
                        mod_base = cm
modified_base           5
                        mod_base = OTHER
                        note = 2'-fluoro-adenosine
modified_base           6
                        mod_base = um
modified_base           7
                        mod_base = OTHER
                        note = 2'-fluoro-adenosine
modified_base           8
                        mod_base = OTHER
                        note = 2'-O-methyl-adenosine
modified_base           9
                        mod_base = OTHER
                        note = 2'-O-methyl-adenosine
modified_base           10
                        mod_base = OTHER
                        note = 2'-fluoro-adenosine
```

```
modified_base         11
                      mod_base = um
modified_base         12
                      mod_base = um
modified_base         13
                      mod_base = cm
modified_base         14
                      mod_base = OTHER
                      note = 2'-fluoro-adenosine
modified_base         15
                      mod_base = gm
modified_base         16
                      mod_base = OTHER
                      note = 2'-fluoro-guanosine
modified_base         17
                      mod_base = OTHER
                      note = 2'-O-methyl-adenosine
modified_base         18
                      mod_base = OTHER
                      note = 2'-O-methyl-adenosine
modified_base         19
                      mod_base = um
modified_base         20..22
                      mod_base = OTHER
                      note = linked via phosphorothioate bond
modified_base         20
                      mod_base = um
modified_base         21
                      mod_base = cm
modified_base         22
                      mod_base = cm
source                1..22
                      mol_type = other RNA
                      organism = synthetic construct
SEQUENCE: 370
tgtcataaaa ttcaggaatt cc                                              22

SEQ ID NO: 371        moltype = RNA  length = 22
FEATURE               Location/Qualifiers
modified_base         1..3
                      mod_base = OTHER
                      note = linked via phosphorothioate bond
modified_base         1
                      mod_base = OTHER
                      note = mono methyl protected phosphate mimic linked uridine
modified_base         2
                      mod_base = OTHER
                      note = 2'-fluoro-uridine
modified_base         3
                      mod_base = OTHER
                      note = 2'-fluoro-adenosine
modified_base         4
                      mod_base = OTHER
                      note = 2'-O-methyl-adenosine
modified_base         5
                      mod_base = OTHER
                      note = 2'-fluoro-adenosine
modified_base         6
                      mod_base = OTHER
                      note = 2'-O-methyl-adenosine
modified_base         7
                      mod_base = OTHER
                      note = 2'-fluoro-uridine
modified_base         8
                      mod_base = um
modified_base         9
                      mod_base = cm
modified_base         10
                      mod_base = OTHER
                      note = 2'-fluoro-adenosine
modified_base         11
                      mod_base = gm
modified_base         12
                      mod_base = gm
modified_base         13
                      mod_base = OTHER
                      note = 2'-O-methyl-adenosine
```

-continued

```
modified_base          14
                       mod_base = OTHER
                       note = 2'-fluoro-adenosine
modified_base          15
                       mod_base = um
modified_base          16
                       mod_base = OTHER
                       note = 2'-fluoro-uridine
modified_base          17
                       mod_base = cm
modified_base          18
                       mod_base = cm
modified_base          19
                       mod_base = um
modified_base          20..22
                       mod_base = OTHER
                       note = linked via phosphorothioate bond
modified_base          20
                       mod_base = gm
modified_base          21
                       mod_base = cm
modified_base          22
                       mod_base = um
source                 1..22
                       mol_type = other RNA
                       organism = synthetic construct
SEQUENCE: 371
ttaaaattca ggaattcctg ct                                            22

SEQ ID NO: 372         moltype = RNA  length = 22
FEATURE                Location/Qualifiers
modified_base          1..3
                       mod_base = OTHER
                       note = linked via phosphorothioate bond
modified_base          1
                       mod_base = OTHER
                       note = mono methyl protected phosphate mimic linked uridine
modified_base          2
                       mod_base = OTHER
                       note = 2'-fluoro-guanosine
modified_base          3
                       mod_base = OTHER
                       note = 2'-fluoro-guanosine
modified_base          4
                       mod_base = OTHER
                       note = 2'-O-methyl-adenosine
modified_base          5
                       mod_base = OTHER
                       note = 2'-fluoro-adenosine
modified_base          6
                       mod_base = OTHER
                       note = 2'-O-methyl-adenosine
modified_base          7
                       mod_base = OTHER
                       note = 2'-fluoro-guanosine
modified_base          8
                       mod_base = OTHER
                       note = 2'-O-methyl-adenosine
modified_base          9
                       mod_base = gm
modified_base          10
                       mod_base = OTHER
                       note = 2'-fluoro-adenosine
modified_base          11
                       mod_base = um
modified_base          12
                       mod_base = cm
modified_base          13
                       mod_base = um
modified_base          14
                       mod_base = OTHER
                       note = 2'-fluoro-cytidine
modified_base          15
                       mod_base = OTHER
                       note = 2'-O-methyl-adenosine
modified_base          16
                       mod_base = OTHER
                       note = 2'-fluoro-uridine
```

-continued

```
modified_base          17
                       mod_base = cm
modified_base          18
                       mod_base = OTHER
                       note = 2'-O-methyl-adenosine
modified_base          19
                       mod_base = cm
modified_base          20..22
                       mod_base = OTHER
                       note = linked via phosphorothioate bond
modified_base          20
                       mod_base = um
modified_base          21
                       mod_base = cm
modified_base          22
                       mod_base = OTHER
                       note = 2'-O-methyl-adenosine
source                 1..22
                       mol_type = other RNA
                       organism = synthetic construct
SEQUENCE: 372
tggaaagaga tctcatcact ca                                            22

SEQ ID NO: 373         moltype = RNA  length = 22
FEATURE                Location/Qualifiers
modified_base          1..3
                       mod_base = OTHER
                       note = linked via phosphorothioate bond
modified_base          1
                       mod_base = OTHER
                       note = mono methyl protected phosphate mimic linked uridine
modified_base          2
                       mod_base = OTHER
                       note = 2'-fluoro-adenosine
modified_base          3
                       mod_base = OTHER
                       note = 2'-fluoro-adenosine
modified_base          4
                       mod_base = um
modified_base          5
                       mod_base = OTHER
                       note = 2'-fluoro-uridine
modified_base          6
                       mod_base = cm
modified_base          7
                       mod_base = OTHER
                       note = 2'-fluoro-adenosine
modified_base          8
                       mod_base = gm
modified_base          9
                       mod_base = gm
modified_base          10
                       mod_base = OTHER
                       note = 2'-fluoro-adenosine
modified_base          11
                       mod_base = OTHER
                       note = 2'-O-methyl-adenosine
modified_base          12
                       mod_base = um
modified_base          13
                       mod_base = um
modified_base          14
                       mod_base = OTHER
                       note = 2'-fluoro-cytidine
modified_base          15
                       mod_base = cm
modified_base          16
                       mod_base = OTHER
                       note = 2'-fluoro-uridine
modified_base          17
                       mod_base = gm
modified_base          18
                       mod_base = cm
modified_base          19
                       mod_base = um
modified_base          20..22
                       mod_base = OTHER
                       note = linked via phosphorothioate bond
```

```
modified_base          20
                       mod_base = um
modified_base          21
                       mod_base = cm
modified_base          22
                       mod_base = um
source                 1..22
                       mol_type = other RNA
                       organism = synthetic construct
SEQUENCE: 373
taattcagga attcctgctt ct                                          22

SEQ ID NO: 374         moltype = RNA  length = 22
FEATURE                Location/Qualifiers
modified_base          1..3
                       mod_base = OTHER
                       note = linked via phosphorothioate bond
modified_base          1
                       mod_base = OTHER
                       note = mono methyl protected phosphate mimic linked uridine
modified_base          2
                       mod_base = OTHER
                       note = 2'-fluoro-adenosine
modified_base          3
                       mod_base = OTHER
                       note = 2'-fluoro-adenosine
modified_base          4
                       mod_base = cm
modified_base          5
                       mod_base = OTHER
                       note = 2'-fluoro-adenosine
modified_base          6
                       mod_base = cm
modified_base          7
                       mod_base = OTHER
                       note = 2'-fluoro-adenosine
modified_base          8
                       mod_base = um
modified_base          9
                       mod_base = gm
modified_base          10
                       mod_base = OTHER
                       note = 2'-fluoro-uridine
modified_base          11
                       mod_base = um
modified_base          12
                       mod_base = gm
modified_base          13
                       mod_base = cm
modified_base          14
                       mod_base = OTHER
                       note = 2'-fluoro-uridine
modified_base          15
                       mod_base = cm
modified_base          16
                       mod_base = OTHER
                       note = 2'-fluoro-adenosine
modified_base          17
                       mod_base = um
modified_base          18
                       mod_base = um
modified_base          19
                       mod_base = gm
modified_base          20..22
                       mod_base = OTHER
                       note = linked via phosphorothioate bond
modified_base          20
                       mod_base = um
modified_base          21
                       mod_base = cm
modified_base          22
                       mod_base = um
source                 1..22
                       mol_type = other RNA
                       organism = synthetic construct
SEQUENCE: 374
taacacatgt tgctcattgt ct                                          22

SEQ ID NO: 375         moltype = RNA  length = 22
```

-continued

```
FEATURE                 Location/Qualifiers
modified_base           1..3
                        mod_base = OTHER
                        note = linked via phosphorothioate bond
modified_base           1
                        mod_base = OTHER
                        note = mono methyl protected phosphate mimic linked uridine
modified_base           2
                        mod_base = OTHER
                        note = 2'-fluoro-guanosine
modified_base           3
                        mod_base = OTHER
                        note = 2'-fluoro-uridine
modified_base           4
                        mod_base = gm
modified_base           5
                        mod_base = OTHER
                        note = 2'-fluoro-uridine
modified_base           6
                        mod_base = OTHER
                        note = 2'-O-methyl-adenosine
modified_base           7
                        mod_base = OTHER
                        note = 2'-fluoro-adenosine
modified_base           8
                        mod_base = cm
modified_base           9
                        mod_base = cm
modified_base           10
                        mod_base = OTHER
                        note = 2'-fluoro-guanosine
modified_base           11
                        mod_base = um
modified_base           12
                        mod_base = cm
modified_base           13
                        mod_base = OTHER
                        note = 2'-O-methyl-adenosine
modified_base           14
                        mod_base = OTHER
                        note = 2'-fluoro-uridine
modified_base           15
                        mod_base = OTHER
                        note = 2'-O-methyl-adenosine
modified_base           16
                        mod_base = OTHER
                        note = 2'-fluoro-guanosine
modified_base           17
                        mod_base = cm
modified_base           18
                        mod_base = OTHER
                        note = 2'-O-methyl-adenosine
modified_base           19
                        mod_base = gm
modified_base           20..22
                        mod_base = OTHER
                        note = linked via phosphorothioate bond
modified_base           20
                        mod_base = um
modified_base           21
                        mod_base = gm
modified_base           22
                        mod_base = gm
source                  1..22
                        mol_type = other RNA
                        organism = synthetic construct
SEQUENCE: 375
tgtgtaaccg tcatagcagt gg                                            22

SEQ ID NO: 376          moltype = RNA  length = 22
FEATURE                 Location/Qualifiers
modified_base           1..3
                        mod_base = OTHER
                        note = linked via phosphorothioate bond
modified_base           1
                        mod_base = OTHER
                        note = mono methyl protected phosphate mimic linked uridine
```

```
modified_base          2
                       mod_base = OTHER
                       note = 2'-fluoro-adenosine
modified_base          3
                       mod_base = OTHER
                       note = 2'-fluoro-uridine
modified_base          4
                       mod_base = OTHER
                       note = 2'-O-methyl-adenosine
modified_base          5
                       mod_base = OTHER
                       note = 2'-fluoro-guanosine
modified_base          6
                       mod_base = cm
modified_base          7
                       mod_base = OTHER
                       note = 2'-fluoro-adenosine
modified_base          8
                       mod_base = gm
modified_base          9
                       mod_base = um
modified_base          10
                       mod_base = OTHER
                       note = 2'-fluoro-guanosine
modified_base          11
                       mod_base = gm
modified_base          12
                       mod_base = OTHER
                       note = 2'-O-methyl-adenosine
modified_base          13
                       mod_base = OTHER
                       note = 2'-O-methyl-adenosine
modified_base          14
                       mod_base = OTHER
                       note = 2'-fluoro-adenosine
modified_base          15
                       mod_base = gm
modified_base          16
                       mod_base = OTHER
                       note = 2'-fluoro-adenosine
modified_base          17
                       mod_base = gm
modified_base          18
                       mod_base = OTHER
                       note = 2'-O-methyl-adenosine
modified_base          19
                       mod_base = um
modified_base          20..22
                       mod_base = OTHER
                       note = linked via phosphorothioate bond
modified_base          20
                       mod_base = cm
modified_base          21
                       mod_base = um
modified_base          22
                       mod_base = cm
source                 1..22
                       mol_type = other RNA
                       organism = synthetic construct
SEQUENCE: 376
tatagcagtg gaaagagatc tc                                            22

SEQ ID NO: 377         moltype = RNA  length = 22
FEATURE                Location/Qualifiers
modified_base          1..3
                       mod_base = OTHER
                       note = linked via phosphorothioate bond
modified_base          1
                       mod_base = um
modified_base          2
                       mod_base = OTHER
                       note = 2'-fluoro-guanosine
modified_base          3
                       mod_base = OTHER
                       note = 2'-fluoro-uridine
modified_base          4
                       mod_base = cm
```

```
modified_base         5
                      mod_base = OTHER
                      note = 2'-fluoro-adenosine
modified_base         6
                      mod_base = um
modified_base         7
                      mod_base = OTHER
                      note = 2'-fluoro-adenosine
modified_base         8
                      mod_base = OTHER
                      note = 2'-O-methyl-adenosine
modified_base         9
                      mod_base = OTHER
                      note = 2'-O-methyl-adenosine
modified_base         10
                      mod_base = OTHER
                      note = 2'-fluoro-adenosine
modified_base         11
                      mod_base = um
modified_base         12
                      mod_base = um
modified_base         13
                      mod_base = cm
modified_base         14
                      mod_base = OTHER
                      note = 2'-fluoro-adenosine
modified_base         15
                      mod_base = gm
modified_base         16
                      mod_base = OTHER
                      note = 2'-fluoro-guanosine
modified_base         17
                      mod_base = OTHER
                      note = 2'-O-methyl-adenosine
modified_base         18
                      mod_base = OTHER
                      note = 2'-O-methyl-adenosine
modified_base         19
                      mod_base = um
modified_base         20..22
                      mod_base = OTHER
                      note = linked via phosphorothioate bond
modified_base         20
                      mod_base = um
modified_base         21
                      mod_base = cm
modified_base         22
                      mod_base = cm
source                1..22
                      mol_type = other RNA
                      organism = synthetic construct
SEQUENCE: 377
tgtcataaaa ttcaggaatt cc                                        22

SEQ ID NO: 378        moltype = RNA  length = 22
FEATURE               Location/Qualifiers
modified_base         1..3
                      mod_base = OTHER
                      note = linked via phosphorothioate bond
modified_base         1
                      mod_base = um
modified_base         2
                      mod_base = OTHER
                      note = 2'-fluoro-uridine
modified_base         3
                      mod_base = OTHER
                      note = 2'-fluoro-adenosine
modified_base         4
                      mod_base = OTHER
                      note = 2'-O-methyl-adenosine
modified_base         5
                      mod_base = OTHER
                      note = 2'-fluoro-adenosine
modified_base         6
                      mod_base = OTHER
                      note = 2'-O-methyl-adenosine
modified_base         7
                      mod_base = OTHER
                      note = 2'-fluoro-uridine
```

```
modified_base          8
                       mod_base = um
modified_base          9
                       mod_base = cm
modified_base          10
                       mod_base = OTHER
                       note = 2'-fluoro-adenosine
modified_base          11
                       mod_base = gm
modified_base          12
                       mod_base = gm
modified_base          13
                       mod_base = OTHER
                       note = 2'-O-methyl-adenosine
modified_base          14
                       mod_base = OTHER
                       note = 2'-fluoro-adenosine
modified_base          15
                       mod_base = um
modified_base          16
                       mod_base = OTHER
                       note = 2'-fluoro-uridine
modified_base          17
                       mod_base = cm
modified_base          18
                       mod_base = cm
modified_base          19
                       mod_base = um
modified_base          20..22
                       mod_base = OTHER
                       note = linked via phosphorothioate bond
modified_base          20
                       mod_base = gm
modified_base          21
                       mod_base = cm
modified_base          22
                       mod_base = um
source                 1..22
                       mol_type = other RNA
                       organism = synthetic construct
SEQUENCE: 378
ttaaaattca ggaattcctg ct                                           22

SEQ ID NO: 379         moltype = RNA  length = 22
FEATURE                Location/Qualifiers
modified_base          1..3
                       mod_base = OTHER
                       note = linked via phosphorothioate bond
modified_base          1
                       mod_base = um
modified_base          2
                       mod_base = OTHER
                       note = 2'-fluoro-guanosine
modified_base          3
                       mod_base = OTHER
                       note = 2'-fluoro-guanosine
modified_base          4
                       mod_base = OTHER
                       note = 2'-O-methyl-adenosine
modified_base          5
                       mod_base = OTHER
                       note = 2'-fluoro-adenosine
modified_base          6
                       mod_base = OTHER
                       note = 2'-O-methyl-adenosine
modified_base          7
                       mod_base = OTHER
                       note = 2'-fluoro-guanosine
modified_base          8
                       mod_base = OTHER
                       note = 2'-O-methyl-adenosine
modified_base          9
                       mod_base = gm
modified_base          10
                       mod_base = OTHER
                       note = 2'-fluoro-adenosine
modified_base          11
                       mod_base = um
```

```
modified_base          12
                       mod_base = cm
modified_base          13
                       mod_base = um
modified_base          14
                       mod_base = OTHER
                       note = 2'-fluoro-cytidine
modified_base          15
                       mod_base = OTHER
                       note = 2'-O-methyl-adenosine
modified_base          16
                       mod_base = OTHER
                       note = 2'-fluoro-uridine
modified_base          17
                       mod_base = cm
modified_base          18
                       mod_base = OTHER
                       note = 2'-O-methyl-adenosine
modified_base          19
                       mod_base = cm
modified_base          20..22
                       mod_base = OTHER
                       note = linked via phosphorothioate bond
modified_base          20
                       mod_base = um
modified_base          21
                       mod_base = cm
modified_base          22
                       mod_base = OTHER
                       note = 2'-O-methyl-adenosine
source                 1..22
                       mol_type = other RNA
                       organism = synthetic construct
SEQUENCE: 379
tggaaagaga tctcatcact ca                                          22

SEQ ID NO: 380         moltype =   length =
SEQUENCE: 380
000

SEQ ID NO: 381         moltype = RNA  length = 20
FEATURE                Location/Qualifiers
modified_base          1..3
                       mod_base = OTHER
                       note = linked via phosphorothioate bond
modified_base          1
                       mod_base = OTHER
                       note = 2'-O-methyl-adenosine
modified_base          2
                       mod_base = OTHER
                       note = 2'-O-methyl-adenosine
modified_base          3
                       mod_base = um
modified_base          4
                       mod_base = um
modified_base          5
                       mod_base = cm
modified_base          6
                       mod_base = OTHER
                       note = 2'-fluoro-cytidine
modified_base          7
                       mod_base = um
modified_base          8
                       mod_base = OTHER
                       note = 2'-fluoro-guanosine
modified_base          9
                       mod_base = OTHER
                       note = 2'-fluoro-adenosine
modified_base          10
                       mod_base = OTHER
                       note = 2'-fluoro-adenosine
modified_base          11
                       mod_base = OTHER
                       note = 2'-fluoro-uridine
modified_base          12
                       mod_base = um
modified_base          13
                       mod_base = um
```

-continued

```
modified_base          14
                       mod_base = um
modified_base          15
                       mod_base = OTHER
                       note = 2'-O-methyl-adenosine
modified_base          16
                       mod_base = um
modified_base          17
                       mod_base = gm
modified_base          18..20
                       mod_base = OTHER
                       note = linked via phosphorothioate bond
modified_base          18
                       mod_base = OTHER
                       note = 2'-O-methyl-adenosine
modified_base          19
                       mod_base = cm
modified_base          20
                       mod_base = OTHER
                       note = 2'-O-methyl-adenosine
modified_base          20
                       mod_base = OTHER
                       note = conjugated to 3 iterations of
                        (2R,3R,4R,5S)-5-(3-(5-(((2R,3R,4R,5R,6R)-3-acetamido-
                        4,5-dihydroxy-6-(hydroxymethyl)tetrahydro-2H-pyran-2-yl)oxy
                        )pentanamido)propyl)-2-
                        ((hydroxyl)methyl)-4-methoxytetrahydrofuran-3-oxyl
source                 1..20
                       mol_type = other RNA
                       organism = synthetic construct
SEQUENCE: 381
aattcctgaa ttttatgaca                                                  20

SEQ ID NO: 382         moltype = RNA  length = 20
FEATURE                Location/Qualifiers
modified_base          1..3
                       mod_base = OTHER
                       note = linked via phosphorothioate bond
modified_base          1
                       mod_base = cm
modified_base          2
                       mod_base = OTHER
                       note = 2'-O-methyl-adenosine
modified_base          3
                       mod_base = gm
modified_base          4
                       mod_base = gm
modified_base          5
                       mod_base = OTHER
                       note = 2'-O-methyl-adenosine
modified_base          6
                       mod_base = OTHER
                       note = 2'-fluoro-adenosine
modified_base          7
                       mod_base = um
modified_base          8
                       mod_base = OTHER
                       note = 2'-fluoro-uridine
modified_base          9
                       mod_base = OTHER
                       note = 2'-fluoro-cytidine
modified_base          10
                       mod_base = OTHER
                       note = 2'-fluoro-cytidine
modified_base          11
                       mod_base = OTHER
                       note = 2'-fluoro-uridine
modified_base          12
                       mod_base = gm
modified_base          13
                       mod_base = OTHER
                       note = 2'-O-methyl-adenosine
modified_base          14
                       mod_base = OTHER
                       note = 2'-O-methyl-adenosine
modified_base          15
                       mod_base = um
modified_base          16
                       mod_base = um
```

```
modified_base          17
                       mod_base = um
modified_base          18..20
                       mod_base = OTHER
                       note = linked via phosphorothioate bond
modified_base          18
                       mod_base = um
modified_base          19
                       mod_base = OTHER
                       note = 2'-O-methyl-adenosine
modified_base          20
                       mod_base = OTHER
                       note = 2'-O-methyl-adenosine
modified_base          20
                       mod_base = OTHER
                       note = conjugated to 3 iterations of
                        (2R,3R,4R,5S)-5-(3-(5-(((2R,3R,4R,5R,6R)-3-acetamido-
                        4,5-dihydroxy-6-(hydroxymethyl)tetrahydro-2H-pyran-2-yl)oxy
                        )pentanamido)propyl)-2-
                        ((hydroxyl)methyl)-4-methoxytetrahydrofuran-3-oxyl
source                 1..20
                       mol_type = other RNA
                       organism = synthetic construct
SEQUENCE: 382
caggaattcc tgaattttaa                                              20

SEQ ID NO: 383         moltype = RNA  length = 20
FEATURE                Location/Qualifiers
modified_base          1..3
                       mod_base = OTHER
                       note = linked via phosphorothioate bond
modified_base          1
                       mod_base = OTHER
                       note = 2'-O-methyl-adenosine
modified_base          2
                       mod_base = gm
modified_base          3
                       mod_base = um
modified_base          4
                       mod_base = gm
modified_base          5
                       mod_base = OTHER
                       note = 2'-O-methyl-adenosine
modified_base          6
                       mod_base = OTHER
                       note = 2'-fluoro-uridine
modified_base          7
                       mod_base = gm
modified_base          8
                       mod_base = OTHER
                       note = 2'-fluoro-adenosine
modified_base          9
                       mod_base = OTHER
                       note = 2'-fluoro-guanosine
modified_base          10
                       mod_base = OTHER
                       note = 2'-fluoro-adenosine
modified_base          11
                       mod_base = OTHER
                       note = 2'-fluoro-uridine
modified_base          12
                       mod_base = cm
modified_base          13
                       mod_base = um
modified_base          14
                       mod_base = cm
modified_base          15
                       mod_base = um
modified_base          16
                       mod_base = um
modified_base          17
                       mod_base = um
modified_base          18..20
                       mod_base = OTHER
                       note = linked via phosphorothioate bond
modified_base          18
                       mod_base = cm
modified_base          19
                       mod_base = cm
```

```
modified_base          20
                       mod_base = OTHER
                       note = 2'-O-methyl-adenosine
modified_base          20
                       mod_base = OTHER
                       note = conjugated to 3 iterations of
                        (2R,3R,4R,5S)-5-(3-(5-(((2R,3R,4R,5R,6R)-3-acetamido-
                        4,5-dihydroxy-6-(hydroxymethyl)tetrahydro-2H-pyran-2-yl)oxy
                        )pentanamido)propyl)-2-
                        ((hydroxyl)methyl)-4-methoxytetrahydrofuran-3-oxyl
source                 1..20
                       mol_type = other RNA
                       organism = synthetic construct
SEQUENCE: 383
agtgatgaga tctctttcca                                              20

SEQ ID NO: 384         moltype = RNA  length = 20
FEATURE                Location/Qualifiers
modified_base          1..3
                       mod_base = OTHER
                       note = linked via phosphorothioate bond
modified_base          1
                       mod_base = OTHER
                       note = 2'-O-methyl-adenosine
modified_base          2
                       mod_base = OTHER
                       note = 2'-O-methyl-adenosine
modified_base          3
                       mod_base = gm
modified_base          4
                       mod_base = cm
modified_base          5
                       mod_base = OTHER
                       note = 2'-O-methyl-adenosine
modified_base          6
                       mod_base = OTHER
                       note = 2'-fluoro-guanosine
modified_base          7
                       mod_base = gm
modified_base          8
                       mod_base = OTHER
                       note = 2'-fluoro-adenosine
modified_base          9
                       mod_base = OTHER
                       note = 2'-fluoro-adenosine
modified_base          10
                       mod_base = OTHER
                       note = 2'-fluoro-uridine
modified_base          11
                       mod_base = OTHER
                       note = 2'-fluoro-uridine
modified_base          12
                       mod_base = cm
modified_base          13
                       mod_base = cm
modified_base          14
                       mod_base = um
modified_base          15
                       mod_base = gm
modified_base          16
                       mod_base = OTHER
                       note = 2'-O-methyl-adenosine
modified_base          17
                       mod_base = OTHER
                       note = 2'-O-methyl-adenosine
modified_base          18..20
                       mod_base = OTHER
                       note = linked via phosphorothioate bond
modified_base          18
                       mod_base = um
modified_base          19
                       mod_base = um
modified_base          20
                       mod_base = OTHER
                       note = 2'-O-methyl-adenosine
```

```
modified_base          20
                       mod_base = OTHER
                       note = conjugated to 3 iterations of
                        (2R,3R,4R,5S)-5-(3-(5-(((2R,3R,4R,5R,6R)-3-acetamido-
                        4,5-dihydroxy-6-(hydroxymethyl)tetrahydro-2H-pyran-2-yl)oxy
                        )pentanamido)propyl)-2-
                        ((hydroxyl)methyl)-4-methoxytetrahydrofuran-3-oxyl
source                 1..20
                       mol_type = other RNA
                       organism = synthetic construct
SEQUENCE: 384
aagcaggaat tcctgaatta                                            20

SEQ ID NO: 385         moltype = RNA  length = 20
FEATURE                Location/Qualifiers
modified_base          1..3
                       mod_base = OTHER
                       note = linked via phosphorothioate bond
modified_base          1
                       mod_base = OTHER
                       note = 2'-O-methyl-adenosine
modified_base          2
                       mod_base = cm
modified_base          3
                       mod_base = OTHER
                       note = 2'-O-methyl-adenosine
modified_base          4
                       mod_base = OTHER
                       note = 2'-O-methyl-adenosine
modified_base          5
                       mod_base = um
modified_base          6
                       mod_base = OTHER
                       note = 2'-fluoro-guanosine
modified_base          7
                       mod_base = OTHER
                       note = 2'-O-methyl-adenosine
modified_base          8
                       mod_base = OTHER
                       note = 2'-fluoro-guanosine
modified_base          9
                       mod_base = OTHER
                       note = 2'-fluoro-cytidine
modified_base          10
                       mod_base = OTHER
                       note = 2'-fluoro-adenosine
modified_base          11
                       mod_base = OTHER
                       note = 2'-fluoro-adenosine
modified_base          12
                       mod_base = cm
modified_base          13
                       mod_base = OTHER
                       note = 2'-O-methyl-adenosine
modified_base          14
                       mod_base = um
modified_base          15
                       mod_base = gm
modified_base          16
                       mod_base = um
modified_base          17
                       mod_base = gm
modified_base          18..20
                       mod_base = OTHER
                       note = linked via phosphorothioate bond
modified_base          18
                       mod_base = um
modified_base          19
                       mod_base = um
modified_base          20
                       mod_base = OTHER
                       note = 2'-O-methyl-adenosine
modified_base          20
                       mod_base = OTHER
                       note = conjugated to 3 iterations of
                        (2R,3R,4R,5S)-5-(3-(5-(((2R,3R,4R,5R,6R)-3-acetamido-
                        4,5-dihydroxy-6-(hydroxymethyl)tetrahydro-2H-pyran-2-yl)oxy
                        )pentanamido)propyl)-2-
                        ((hydroxyl)methyl)-4-methoxytetrahydrofuran-3-oxyl
```

```
source                  1..20
                        mol_type = other RNA
                        organism = synthetic construct
SEQUENCE: 385
acaatgagca acatgtgtta                                              20

SEQ ID NO: 386          moltype = RNA  length = 20
FEATURE                 Location/Qualifiers
modified_base           1..3
                        mod_base = OTHER
                        note = linked via phosphorothioate bond
modified_base           1
                        mod_base = OTHER
                        note = 2'-O-methyl-adenosine
modified_base           2
                        mod_base = cm
modified_base           3
                        mod_base = um
modified_base           4
                        mod_base = gm
modified_base           5
                        mod_base = cm
modified_base           6
                        mod_base = OTHER
                        note = 2'-fluoro-uridine
modified_base           7
                        mod_base = OTHER
                        note = 2'-O-methyl-adenosine
modified_base           8
                        mod_base = OTHER
                        note = 2'-fluoro-uridine
modified_base           9
                        mod_base = OTHER
                        note = 2'-fluoro-guanosine
modified_base           10
                        mod_base = OTHER
                        note = 2'-fluoro-adenosine
modified_base           11
                        mod_base = OTHER
                        note = 2'-fluoro-cytidine
modified_base           12
                        mod_base = gm
modified_base           13
                        mod_base = gm
modified_base           14
                        mod_base = um
modified_base           15
                        mod_base = um
modified_base           16
                        mod_base = OTHER
                        note = 2'-O-methyl-adenosine
modified_base           17
                        mod_base = cm
modified_base           18..20
                        mod_base = OTHER
                        note = linked via phosphorothioate bond
modified_base           18
                        mod_base = OTHER
                        note = 2'-O-methyl-adenosine
modified_base           19
                        mod_base = cm
modified_base           20
                        mod_base = OTHER
                        note = 2'-O-methyl-adenosine
modified_base           20
                        mod_base = OTHER
                        note = conjugated to 3 iterations of
                         (2R,3R,4R,5S)-5-(3-(5-(((2R,3R,4R,5R,6R)-3-acetamido-
                         4,5-dihydroxy-6-(hydroxymethyl)tetrahydro-2H-pyran-2-yl)oxy
                         )pentanamido)propyl)-2-
                         ((hydroxyl)methyl)-4-methoxytetrahydrofuran-3-oxyl
source                  1..20
                        mol_type = other RNA
                        organism = synthetic construct
SEQUENCE: 386
actgctatga cggttacaca                                              20

SEQ ID NO: 387          moltype = RNA  length = 20
FEATURE                 Location/Qualifiers
```

-continued

```
modified_base          1..3
                       mod_base = OTHER
                       note = linked via phosphorothioate bond
modified_base          1
                       mod_base = gm
modified_base          2
                       mod_base = OTHER
                       note = 2'-O-methyl-adenosine
modified_base          3
                       mod_base = um
modified_base          4
                       mod_base = cm
modified_base          5
                       mod_base = um
modified_base          6
                       mod_base = OTHER
                       note = 2'-fluoro-cytidine
modified_base          7
                       mod_base = um
modified_base          8
                       mod_base = OTHER
                       note = 2'-fluoro-uridine
modified_base          9
                       mod_base = OTHER
                       note = 2'-fluoro-uridine
modified_base          10
                       mod_base = OTHER
                       note = 2'-fluoro-cytidine
modified_base          11
                       mod_base = OTHER
                       note = 2'-fluoro-cytidine
modified_base          12
                       mod_base = OTHER
                       note = 2'-O-methyl-adenosine
modified_base          13
                       mod_base = cm
modified_base          14
                       mod_base = um
modified_base          15
                       mod_base = gm
modified_base          16
                       mod_base = cm
modified_base          17
                       mod_base = um
modified_base          18..20
                       mod_base = OTHER
                       note = linked via phosphorothioate bond
modified_base          18
                       mod_base = OTHER
                       note = 2'-O-methyl-adenosine
modified_base          19
                       mod_base = um
modified_base          20
                       mod_base = OTHER
                       note = 2'-O-methyl-adenosine
modified_base          20
                       mod_base = OTHER
                       note = conjugated to 3 iterations of
                        (2R,3R,4R,5S)-5-(3-(5-(((2R,3R,4R,5R,6R)-3-acetamido-
                        4,5-dihydroxy-6-(hydroxymethyl)tetrahydro-2H-pyran-2-yl)oxy
                        )pentanamido)propyl)-2-
                        ((hydroxyl)methyl)-4-methoxytetrahydrofuran-3-oxyl
source                 1..20
                       mol_type = other RNA
                       organism = synthetic construct
SEQUENCE: 387
gatctctttc cactgctata                                              20

SEQ ID NO: 388         moltype = RNA  length = 20
FEATURE                Location/Qualifiers
modified_base          1..3
                       mod_base = OTHER
                       note = linked via phosphorothioate bond
modified_base          1
                       mod_base = OTHER
                       note = 2'-O-methyl-adenosine
modified_base          2
                       mod_base = OTHER
                       note = 2'-O-methyl-adenosine
```

-continued

```
modified_base          3
                       mod_base = um
modified_base          4
                       mod_base = um
modified_base          5
                       mod_base = cm
modified_base          6
                       mod_base = OTHER
                       note = 2'-fluoro-cytidine
modified_base          7
                       mod_base = um
modified_base          8
                       mod_base = OTHER
                       note = 2'-fluoro-guanosine
modified_base          9
                       mod_base = OTHER
                       note = 2'-fluoro-adenosine
modified_base          10
                       mod_base = OTHER
                       note = 2'-fluoro-adenosine
modified_base          11
                       mod_base = OTHER
                       note = 2'-fluoro-uridine
modified_base          12
                       mod_base = um
modified_base          13
                       mod_base = um
modified_base          14
                       mod_base = um
modified_base          15
                       mod_base = OTHER
                       note = 2'-O-methyl-adenosine
modified_base          16
                       mod_base = um
modified_base          17
                       mod_base = gm
modified_base          18
                       mod_base = OTHER
                       note = 2'-O-methyl-adenosine
modified_base          19
                       mod_base = cm
modified_base          20
                       mod_base = OTHER
                       note = 2'-O-methyl-adenosine
modified_base          20
                       mod_base = OTHER
                       note = conjugated to 3 iterations of
                        (2R,3R,4R,5S)-5-(3-(5-(((2R,3R,4R,5R,6R)-3-acetamido-
                        4,5-dihydroxy-6-(hydroxymethyl)tetrahydro-2H-pyran-2-yl)oxy
                        )pentanamido)propyl)-2-
                        ((hydroxyl)methyl)-4-methoxytetrahydrofuran-3-oxyl
source                 1..20
                       mol_type = other RNA
                       organism = synthetic construct
SEQUENCE: 388
aattcctgaa ttttatgaca                                          20

SEQ ID NO: 389         moltype = RNA  length = 20
FEATURE                Location/Qualifiers
source                 1..20
                       mol_type = other RNA
                       organism = synthetic construct
SEQUENCE: 389
actgctatga cggttacaca                                          20

SEQ ID NO: 390         moltype =   length =
SEQUENCE: 390
000

SEQ ID NO: 391         moltype = RNA  length = 20
FEATURE                Location/Qualifiers
source                 1..20
                       mol_type = other RNA
                       organism = synthetic construct
SEQUENCE: 391
actgctatga cggttacaca                                          20
```